(12) United States Patent
Simard

(10) Patent No.: US 9,375,438 B2
(45) Date of Patent: *Jun. 28, 2016

(54) INHIBITORS OF $NC_{Ca-ATP}$ CHANNELS FOR THERAPY

(71) Applicants: University of Maryland, Baltimore, Baltimore, MD (US); The United States of America as Represented by the Department of Veterans Affairs, Washington, DC (US)

(72) Inventor: J. Marc Simard, Baltimore, MD (US)

(73) Assignees: University of Maryland, Baltimore, Baltimore, MD (US); The United States of America as Represented by the Dept. of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/040,104

(22) Filed: Sep. 27, 2013

(65) Prior Publication Data

US 2014/0171467 A1 Jun. 19, 2014

Related U.S. Application Data

(63) Continuation of application No. 12/665,853, filed as application No. PCT/US2008/067640 on Jun. 20, 2008, now Pat. No. 8,557,867.

(60) Provisional application No. 60/945,825, filed on Jun. 22, 2007, provisional application No. 60/945,811, filed on Jun. 22, 2007, provisional application No. 60/945,636, filed on Jun. 22, 2007.

(51) Int. Cl.
| | | |
|---|---|---|
| A61K 31/64 | (2006.01) | |
| A61K 31/00 | (2006.01) | |
| A61K 31/195 | (2006.01) | |
| A61K 31/198 | (2006.01) | |
| A61K 31/4453 | (2006.01) | |
| A61K 31/454 | (2006.01) | |
| A61K 45/06 | (2006.01) | |
| A61K 31/451 | (2006.01) | |

(52) U.S. Cl.
CPC ............. *A61K 31/64* (2013.01); *A61K 31/00* (2013.01); *A61K 31/195* (2013.01); *A61K 31/198* (2013.01); *A61K 31/4453* (2013.01); *A61K 31/451* (2013.01); *A61K 31/454* (2013.01); *A61K 45/06* (2013.01)

(58) Field of Classification Search
CPC ..... A61K 31/64; A61K 31/00; A61K 31/195; A61K 31/198; A61K 31/44453; A61K 31/454; A61K 45/06; A61K 31/451
See application file for complete search history.

(56) References Cited

U.S. PATENT DOCUMENTS

| | | | |
|---|---|---|---|
| 5,047,429 | A | 9/1991 | Nye |
| 5,166,162 | A | 11/1992 | Masereel et al. |
| 5,215,985 | A | 6/1993 | Murphy et al. |
| 5,236,932 | A | 8/1993 | Greenfield et al. |
| 5,281,599 | A | 1/1994 | Murphy et al. |
| 5,451,580 | A | 9/1995 | Murphy et al. |
| 5,545,656 | A | 8/1996 | Loose et al. |
| 5,677,344 | A | 10/1997 | Greenfield et al. |
| 5,811,393 | A | 9/1998 | Klagsbrun et al. |
| 5,849,796 | A | 12/1998 | Gericke et al. |
| 5,916,871 | A | 6/1999 | Johnson |
| 5,929,082 | A | 7/1999 | Chambers et al. |
| 5,962,645 | A | 10/1999 | Keay et al. |
| 6,043,224 | A | 3/2000 | Lee et al. |
| 6,056,977 | A | 5/2000 | Bhagwat et al. |
| 6,100,047 | A | 8/2000 | Wilkison et al. |
| 6,156,522 | A | 12/2000 | Keay et al. |
| 6,180,671 | B1 | 1/2001 | Freedman et al. |
| 6,184,248 | B1 | 2/2001 | Lee et al. |
| 6,187,756 | B1 | 2/2001 | Lee et al. |
| 6,232,289 | B1 | 5/2001 | Keay et al. |
| 6,242,200 | B1 | 6/2001 | Wilkison et al. |

(Continued)

FOREIGN PATENT DOCUMENTS

| | | | |
|---|---|---|---|
| AU | 2003222020 A1 | | 10/2003 |
| EP | 0338415 A3 | | 3/1991 |

(Continued)

OTHER PUBLICATIONS

Terrie Inder & Joseph Volpe, Mechanisms of Perinatal Brain Injury, 5 Semin. Neonatol. 3 (2000).*
Charles Tator & Michael Fehlings, Review of the Secondary Injury Theory of Acute Spinal Cord Trauma with Emphasis on Vascular Mechanisms, 75 J Neurosurg. 15 (1991).*
Bo Siesjo, et al, Mechanisms of Secondary Brain Damage in Global and Focal Ischemia: A Speculative Synthesis, 12 J Neurotrauma 943 (1995).*
K. Valentino, et al, A Selective N-type Calcium Channel Antagonist Protects Against Neuronal Loss After Global Cerebral Ischemia, 90 Proc. Natl. Acad. Sci. 7894 (1993).*

*Primary Examiner* — Sean Basquill
(74) *Attorney, Agent, or Firm* — Norton Rose Fulbright US LLP

(57) ABSTRACT

Methods and compositions are provided that are utilized for treatment and/or prevention of intraventricular hemorrhage or progressive hemorrhagic necrosis (PHN), particularly following spinal cord injury. In particular, the methods and compositions are inhibitors of a particular NCca-ATP channel and include, for example, inhibitors of SUR1 and/or inhibitors of TRPM4. Kits for treatment and/or prevention of intraventricular hemorrhage or progressive hemorrhagic necrosis (PHN), particularly following spinal cord injury, are also provided. The present invention also concerns treatment and/or prevention of intraventricular hemorrhage in infants, including premature infants utilizing one or more inhibitors of the channel is provided to the infant, for example to brain cells of the infant.

1 Claim, 30 Drawing Sheets

(56) References Cited

U.S. PATENT DOCUMENTS

| | | | |
|---|---|---|---|
| 6,365,577 | B1 | 4/2002 | Iversen |
| 6,372,743 | B1 | 4/2002 | Darrow et al. |
| 6,376,197 | B1 | 4/2002 | Keay et al. |
| 6,469,055 | B2 | 10/2002 | Lee et al. |
| 6,492,130 | B1 | 12/2002 | Wilkison et al. |
| 6,492,339 | B1 | 12/2002 | Sleevi et al. |
| 6,511,989 | B2 | 1/2003 | Heitsch et al. |
| 6,569,633 | B1 | 5/2003 | Wilkison et al. |
| 6,569,845 | B1 | 5/2003 | Futamura et al. |
| 6,596,751 | B2 | 7/2003 | Fujita et al. |
| 6,610,746 | B2 | 8/2003 | Fryburg et al. |
| 6,613,785 | B2 | 9/2003 | Bril et al. |
| 6,679,859 | B1 | 1/2004 | Keipert et al. |
| 7,285,574 | B2 | 10/2007 | Simard et al. |
| 7,877,048 | B2 | 1/2011 | Kitagawa |
| 8,318,810 | B2 | 11/2012 | Simard et al. |
| 8,557,867 | B2 * | 10/2013 | Simard ............ 514/563 |
| 2001/0003751 | A1 | 6/2001 | Terashita et al. |
| 2001/0016586 | A1 | 8/2001 | Guitard et al. |
| 2002/0013268 | A1 | 1/2002 | Fryburg et al. |
| 2002/0016443 | A1 | 2/2002 | Keay et al. |
| 2002/0016643 | A1 | 2/2002 | Sakata |
| 2002/0037928 | A1 | 3/2002 | Jaen et al. |
| 2002/0065315 | A1 | 5/2002 | Jensen et al. |
| 2002/0081306 | A1 | 6/2002 | Elliott et al. |
| 2002/0094977 | A1 | 7/2002 | Robl et al. |
| 2002/0166443 | A1 | 11/2002 | Haerr et al. |
| 2003/0215889 | A1 | 11/2003 | Simard et al. |
| 2003/0216294 | A1 | 11/2003 | Fryburg et al. |
| 2005/0009733 | A1 | 1/2005 | Stephenson et al. |
| 2005/0054659 | A1 | 3/2005 | Ellsworth et al. |
| 2006/0100183 | A1 | 5/2006 | Simard |
| 2006/0276411 | A1 | 12/2006 | Simard et al. |
| 2007/0203239 | A1 | 8/2007 | Gehenne et al. |
| 2009/0130083 | A1 * | 5/2009 | Simard et al. ............ 424/94.63 |
| 2010/0092469 | A1 * | 4/2010 | Simard et al. ............ 424/133.1 |
| 2010/0311639 | A1 | 12/2010 | Simard |
| 2011/0026347 | A1 | 2/2011 | Fort et al. |
| 2011/0263478 | A1 * | 10/2011 | Simard ............ 514/1.1 |
| 2012/0237449 | A1 | 9/2012 | Simard et al. |

FOREIGN PATENT DOCUMENTS

| | | | |
|---|---|---|---|
| EP | 0467709 | A3 | 7/1992 |
| EP | 1782815 | A1 | 5/2007 |
| ES | P200401628 | | 6/2004 |
| JP | H09208562 | A | 8/1997 |
| JP | 2004-516236 | A | 6/2004 |
| WO | 97/41857 | A1 | 11/1997 |
| WO | 01/10430 | A2 | 2/2001 |
| WO | 01/54771 | | 8/2001 |
| WO | 02/070499 | A2 | 9/2002 |
| WO | 03057843 | A2 | 7/2003 |
| WO | 03075933 | | 9/2003 |
| WO | 03/079987 | A2 | 10/2003 |
| WO | 03079987 | | 10/2003 |
| WO | 2005/041877 | A2 | 5/2005 |
| WO | 2006/000608 | A1 | 1/2006 |
| WO | 2006/034048 | A2 | 3/2006 |
| WO | 2006/036278 | A2 | 4/2006 |
| WO | WO 2006/036278 | * | 4/2006 |
| WO | 2007/011595 | A2 | 1/2007 |
| WO | 2007011926 | A2 | 1/2007 |
| WO | WO 2007/011926 | * | 1/2007 ............ A61K 31/56 |
| WO | 2006/036278 | A8 | 5/2007 |
| WO | 2007058902 | | 5/2007 |
| WO | 2008/089103 | A2 | 7/2008 |
| WO | 2008/098160 | A1 | 8/2008 |
| WO | 2009/002832 | A2 | 12/2008 |
| WO | 2008/089103 | A8 | 10/2009 |

OTHER PUBLICATIONS

Ahmad et al., "Mouse cortical collecting duct cells show nonselective cation channel activity and express a gene related to the cGMP-gated rod photoreceptor channel," Proc. Natl. Acad. Sci. USA, 89: 10262-10266, 1992.

Angel et al., "The binding site for [3H]glibenclamide in the rat cerebral cortex does not recognize K-channel agonists or antagonists other than sulphonylureas," Fundam. Clin. Pharmacol, 5(2): 107-15, 1991.

Armijo, "Advances in the physiopathology of epilegtogenesis: molecular aspects," Rev. Neurol., 34(5): 409-29, 2002.

Ballerini, "Glial cells express multiple ATP binding cassette proteins which are involved in ATP release," Neuroreport, 13(14): 1789-92, 2002.

Baudelet et al., "Evidence for a Neuroprotective Effect of Pyrid-3-yl-sulphonyl-urea in Photochemically Induced Focal Ischaemia in Rats: Magnetic Resonance Imaging Evaluation," J. Pharm. Pharmacol., 51: 967-970, 1999.

Bevan et al, "Voltage Gasted Ionic Channels in Rat Cultured Astrocytes, Reactive Astrocytes and an Astrocyte-oligodendrocyte Progenitor Cell, " J. Physiol vol. 82, 1987, pp. 327-335.

Champigny et al., "A voltage, calcium, and ATP sensitive non selective cation channel in human colonic tumor cells," Biochem. Biophys. Res. Commun., 176: 1196-1203, 1991.

Chen et al., "Cell Swelling and a Nonselective Cation Channel Regulated by Internal Ca2+ and ATP in Native Reactive Astrocytes from Adult Rat Brain," J. Neurosci., 21(17): 6512-6521, 2001.

Davies, "Insulin secretagogues," Curr. Med. Res. Opin. 18 Suppl., 1: ss22-30, 2002 (abstract only).

Gopalakrishnan et al., "Pharmacological characterization of a 1,4-dihydropyridine analogue, 9-(3,4-dichorophenyl)-3,3,6,6-tetramethyl-3,4,6,7,9,10-hexahydro-1,8(2H,5H)-acridinedione (A-184209) as a novelK(ATP) channel inhibitor," Br. J. Pharmacol., 138(2): 393-99, 2003 (abstract only).

Gray et al., "Non-selective cation channel on pancreatic duct cells," Biochem. Biophys. Acta, 1029:33-42, 1990.

Gribble et al., "Differential selectivity of insulin secretagogues. Mechanisms, clinical implications, and drug interactions," J. Diabetes Complications, 17(2 Suppl): 11-5, 2003.

Cribble et al., "Tissue Specificity of Sulfonylureas: Studies on Cloned Cardiac and B-Cells K-ATP Channels," Diabetes, 47: 1412-1418, 1998.

Hambrock et al., "Four novel splice variants of sulfonylurea receptor 1," Am. J. Physiol. Cell Physiol., 283: C587-C598, 2002.

Hernandez-Sanchez et al., "Mice transgenically overexpressing sulfonylurea receptor 1 in forebrain resist seizure induction and excitotoxic neuron death," PNAS, 98(6): 3549-3554, 2001.

Jarvis et al., "Purinergic Mechanisms in the Nervous System Function and Disease States," Psychopharmacology: The Fourth Generation of Progress, (Kupfer, David J. et al., Lippincott 2000), found at www.acnp.org/g4/GN401000063/CH.html.

Kimelberg et al., "Astrocytic swelling in traumatic-hypoxic brain injury. Beneficial effects of an inhibitor of anion exchange transport and glutamate uptake in glial cells," Mol. Chem. Neuropathol., 11(1): 1-31, 1989.

Koch et al., "Mechanism of shrinkage activation of nonselective cation channels in M-1 mouse cortical collecting duct cells," J. Membr. Biol., 177(3): 231-42, 2000.

Koch et al., "Osmotic shrinkage activates nonselective cation (NSC) channels in various cell types," J. Membr. Biol., 168(2): 131-39, 1999.

Lauritzen et al., "The potassium channel opener (−)-cromakalim prevents glutamate-induced cell death in hippocampal neurons," J. Neurochem., 69(4): 1570-79, 1997.

Lee et al., "Direct demonstration of sulphonylurea-sensitive KATP channels on nerve terminals of the rat motor cortex," Br. J. Pharmacol., 115(3): 385-87, 1995.

Lee et al., "The high-affinity sulphonylurea receptor regulates KATP channels in nerve terminals of the rat motor cortex," J. Neurochem., 66(6): 2562-71, 1996.

Lee et al, "Upregulation of Phospholipase D in Astrocytes in Response to Transient Forebrain Ischemia," GLIA vol. 30, 2000, pp. 311-317.

Liu et al., "Tenidap, a novel anti-inflammatory agent, is an opener of the inwardly rectifying K+ channel hKir2.3," Eur. J. Pharmacol., 435(2-3): 153-60, 2002.

(56) References Cited

OTHER PUBLICATIONS

Mest et al., "Glucose-induced insulin secretion is potentiated by a new imidazoline compound," Naunyn Schmledebergs Arch. Pharmacol., 364(1): 47-52, 2001.
Ono et al., "ATP and calcium modulation of nonselective cation channels in IMCD cells," Am. J. Physiol., 267: F558-F565, 1994.
Perillan et al., "Inward Rectifier K+ Channel Kir2.3 (IRK3) in Reactive Astrocytes from Adult Rat Brain," GLIA, 31: 181-192, 2000.
Perillan et al., "K+ Inward Rectifier Currents in Reactive Astrocytes from Adult Rat Brain," GLIA, 27: 213:225, 1999.
Perillan et al., "Transforming Growth Factor-B1 Regulates Kir2.3 Inward Rectifier K+ Channels via Phospholipase C and Protein Kinase C-d in Reactive Astrocytes from Adult Rat Brain," J. Biol. Chem., 277: 1974-1980, 2002.
Popp et al, "A Calcium and ATP Sensitive Nonselective Cation Channel in the Antiluminal Membrane of Rat Cerebral Capillary Endothelial Cells," Biochimica et Biophysica Acta vol. 1108, 1992, pp. 59-66.
Proks et al., "Sulfonylurea stimulation of insulin secretion," Diabetes, 51(Suppl. 3): S368-76, 2002.
Rae et al., "A non-selective Cation Channel in Rabbit Corneal Endothelium Activated by Internal Calcium and Inhibited by Internal ATP," Exp. Eye. Res., 50: 373-384, 1990.
Schroder et al., "AMPA receptor-mediated modulation of inward rectifier K+ channels in astrocytes of couse hippocampus," Mol. Cell Neurosci., 19(3): 447-8, 2002 (abstract only).
Schubert et al., "Cascading glia reactions: a common pathomechanism and its differentiated control by cyclic nucleotide signaling," Ann. N.Y. Acad. Sci., 903: 24-33, 2000 (abstract only).
Sturgess et al., "Calcium and ATP regulate the activity of a non-selective cation channel in a rat insulinoma cell line," Pflugers Arch., 409: 607-615, 1987.
Verkhratsky et al., "Ion channels in glial cells," Brain Res. Rev., 32: 380-412, 2000.
Auger, G. et al; Purification and Partial Characterization of a Hepatocyte Antiproliferative Glycopeptide, Journal of Cellular Biochemistry, (1989) vol. 40, pp. 439-451.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression asscoiated with interstitial cystitis or antiproliferative factor treatment, Physiol. Genomics (2003) vol. 14, pp. 107-115.
Keay, S., et al.; Current and future directions in diagnostic markers in interstitial cystitis, Intern'l J. of Urology (2003) vol. 10, pp. S27-S230.
Keay, S., et al.; Decreased In Vitro Proliferation of Bladder Epithelial Cells from Patients with Interstitial Cystitis, The Journal of Urology (2003) vol. 61, pp. 1278-1284.
Rashid, H., et al; Interstitial cystitis antiproliferative factor (APF) as a cell-cycle modulator, BMC Urology (2004) 4:3, pp. 1-5.
Zhang, C., et al; Comparison of APF Activity and Epithelial Growth Factor Levels in Urine from Chinese, African-American, and White American Patients with Intestitial Cystitis, Urology (2003) vol. 61, pp. 897-901.
Parson, C.L., et al., "Role of Toxic Urine in Interstitial Cystitis", Journal of Urology (1990) vol. 143, p. 373A.
Beier-Holgersen, R., "The in vitro cytotoxicity of urine from patients with interstitial cystitis", Journal of Urology (Jan. 1994), vol. 151, pp. 206-207.
Nishimura, M., et al., "Cerebral ATM-Sensitive Potassium Channels During Acute Reduction of Carotid Blood Flow", American Heart Assoc., (1995), vol. 25, 1069-1074.
Simard, J., et. al., "Molecular pathophysiology of brains edema in focal ischemia—a focused review" (Apr. 8, 2006) pp. 1-42.
Hambrock, A., et al., "Mg2+ and ATP dependence of KATP Channel Modulator Binding to the Recombinant Sulphonylurea Receptor, SUR2B", British Journal of Pharm. 1998) vol. 125, pp. 577-583.
Torsemide Tablets Package Insert, pp. 1-2.

Torsemide advanced consumer drug information, pp. 1-10. http://www.drugs.com/MMX/Torsemide.html. (May 2006).
Proks ey al., "Inhibition of recombinant K(ATP) channels by the antidiabetic agents midaglizole, LY397364 and LY389382", Eur. J. Pharmacol.; 2002; 11-9, vol. 452(1).
Phillips, "The challenge of gene therapy and DNA delivery", Journal of Pharmacy and Pharmacology; 2001; 1169-1174; vol. 53(9).
Weith et al., Stroke, 2001; 2029-3032; vol. 32.
Gribble et al., "The interaction of nucleotides with the tolbutamide block of cloned ATP-sensitive K+ channel currents expressed in Xenopus oocytes: a reinterpretation", J Physiol.; 1997; 35-45; vol. 504(Pt 1).
Plangger, "Effect of Torasemide on Intracranial Pressure, Mean Systemic Arterial Pressure, and Cerebral Perfusion Pressure in Experimental Brain Edema of the Rat", Acta Neurochir Suppl (Wien), 1994; 519-20; vol. 60.
Loffler-Walz et al., "Interaction of the diuretics torasemide and U-37883A with the K(ATP) channel in rat isolated aorta", Naunyn Schmiedebergs Arch Pharmacol.; 1998; 230-7; vol. 358(2).
Gribble, "Sulphonylurea action revisited: the post-cloning era", Diabetologia, 2003; 875-91. vol. 46(7).
Kempski, "Cerebral Edema", Semin Nephol; 2001; 303-307; vol. 21 (3); abstract only.
Unterberg, et al., "Edema and Brain Trauma", Neuroscience, 2004; 1021-1029; vol. 129.
Kaal, et al., "The Management of Brain Edema in Brain Tumors", Curr. Opin. Oncol.; 2004; 593-600; vol. 16.
Eriksson, "Preparation of liver microsomes with high recovery of endoplasmic reticulum and a low grade of contamination", Biochim Biophys Acta; 1978; 155-64; vol. 508(1).
Mersel et al., "Plasma membrane isolated from astrocytes in primary cultures. Its acceptor oxidoreductase properties", Biochim Biophys Acta; 1984; 144-54; vol. 778(1).
Heinemann et al., Frontiers in Bioscience 3, d483-493, May 1, 1998, printed out from the bioscience.org website as pp. 1-24.
Benos, "Methods to study CFTR protein in vitro", Journal of Cystic Fibrosis; 2004; 79-83; vol. 3.
Dubyak, "Ion homeostasis, channels, and transporters: an update on cellular mechanisms", Adv Physiol Educ; 2004; 143-154, vol. 28.
Hambrock et al., Mg2+ and ATP dependence of K(ATP) channel modulator binding to the recombinant sulphonylurea receptor, SUR2B, Br J Pharmacol. Oct. 1998;125(3):577-83.
Heinemann et al., Isolation and structural analysis of microsomal membrane proteins, Front Biosci. May 1, 1998;3: d483-93.
Simard, et al., "Brain Oedema in Focal Ischaemia: Molecular Pathophysiology and Theoretical Implications," Lancet Neurol. Mar. 2007;6(3):258-68.
Tank, D., et al., "Isolated-patch recording from liposomes containing functionally reconstituted chloride channels from Torpedo electroplax", Proc Nati Acad Sci U S A. Dec. 1982;79(24):7749-53.
Vidal, et al., "Making sense of antisense", Eur J Cancer. Dec. 2005;41(18):2812-8. Epub Nov. 9, 2005.
Haider et al., "Identification of the PIP2-binding site on Kir6.2 by molecular modelling and functional analysis," EMBO J. Aug. 22, 2007;26(16):3749-59. Epub Aug. 2, 2007.
Simard et al., "Endothelial sulfonylurea receptor 1-regulated NC Ca-ATP channels mediate progressive hemorrhagic necrosis following spinal cord injury," J Clin Invest. Aug. 2007;117(8):2105-13.
Grijalva et al., "Efficacy and Safety of 4-aminopyridine in Patients with Long-term Spinal Cord Injury: A Randomized, Double-blind, Placebo-controlled trial," Pharmacotherapy, 23(7):823-834, 2003.
Hozumi, et al., "Biochemical and Immunocytochemical Changes in Glial Fibrillary Acidic Protein After Stab Wounds," Brain Research, 524:64-71, 1990.
Yokoshiki, et al., "Antisense Oligodeoxynucleotides of Sulfonlurea Recepters Inhibit ATP-sensitive K+ Channels in Cultured Neonatal Rat Ventricular Cells," Pflugers Arcch—Eur J Physiol, 437:400-408, 1999.
Mizognchi et al., "Inhibition of Carbonic Anydrases Enhanced the Recovery from Acute Experimental colitis by Controlling Epithelial Registration", Abstract In: Elsevier Health Journals, p. 821, 2003.

(56) References Cited

OTHER PUBLICATIONS

Kawaguchi et al., "A case of hemorrhagic colitis associated with flufenamic acid aluminium", Japanese Journal of National Medical Services, 47(12):999-1003, 1993.

Gunal et al., "Estradiol Treatment Ameliorates Acetic Acid-Induced Gastric and Colonic Injuries in Rats", Inflammation, 27(6):351-359, 2003.

Jin et al., "Altered gene expression and increased bursting activity of colonic smooth muscle ATP-sensitive K+ channels in experimental colitis", Am. J. Physiol. Gastrointest. Liver Physiol., 287:G274-G285, 2004.

Daneshmand et al., "Chronic lithium administration ameliorates 2,4,6-trinitrobenzene sulfonic acid-induced colitis in rats; potential role for adenosine triphosphate sensitive potassium channels", Gastroenterology and Hepatology, 26:1174-1181, 2011.

Nieuwenhuijs et al., "Hepatic ischemia-reperfusion injury: roles of Ca2+ and other intracellular mediators of impaired bile flow and hepatocyte damage"; Digestive Diseases and Sciences, Jun. 2006, vol. 51(6); 1087-102.

Pompermayer et al.; "The ATP-sensitive potassium channel blocker glibenclamide prevents renal ischemia/reperfusion injury in rats"; Kidney International, May 2005, vol. 67(5); 1785-96.

Kim, H.J., et al.; "Anthocyanins from soybean seed coat inhibit the expression of TNF-alpha-induced genes associated with ischemia/reperfusion in endothelial cell by NF-kappaB-dependent pathway and reduce rat myocardial damages incurred by ischemia and reperfusion in vivo"; FEBS Letters 580, Jan. 20, 2006; pp. 1391-1397.

Fagan et al., "Targets for vascular protection after acute ischemic stroke"; Stroke. Sep. 2004;35(9):2220-5. Epub Jul. 29, 2004.

Gürsoy-Özdemir et al., "Role of Endothelial Nitric Oxide Generation and Peroxynitrite Formation in Reperfusion Injury After Focal Cerebral Ischemia"; Stroke. 2000;31:1974.

Manley et al., "Aquaporin-4 deletion in mice reduces brain edema after acute water intoxication and ischemic stroke"; Nature Medicine 6, 159-163 (2000).

Morris et al., "Extension of the Therapeutic Window for Recombinant Tissue Plasminogen Activator With Argatroban in a Rat Model of Embolic Stroke"; Stroke. 2001;32:2635-2640.

Nilius et al., "Transient Receptor Potential Cation Channels in Disease"; Physiol. Rev. 87: 165-217, 2007.

Pisano et al., "Undersulfated, low-molecular-weight glycol-split heparin as an antiangiogenic VEGF antagonist"; Glycobiology 2005 15(2):1C-6C.

Rosenberg et al., "TIMP-2 reduces proteolytic opening of blood-brain barrier by type IV collagenase" Brain Res—Apr. 3, 1992; 576(2): 203-7.

Ullrich et al., "Comparison of functional properties of the Ca2+-activated cation channels TRPM4 and TRPM5 from mice"; Cell Calcium. Mar. 2005; 37(3):267-78.

Grand, T., et al; "9-Phenanthrol Inhibits Human TRPM4 But Not TRPM5 Cationic Channels"; British Journal of Pharmacology; 2008, vol. 153, vol. 1697-1705.

Matsuo, Michinori, et al; "Different Binding Properties and Affinities for ATP and ADP Among Sulfonylurea Receptor Subtypes, SUR1, SUR2A, and SUR2B*"; The Journal of Biological Chemistry; Sep. 15, 2000; vol. 275, No. 37, pp. 28757-28763.

Nilius, Bernd, et al; "Intracellular Nucleotides and Polyamines Inhibit the Ca2+—Activated Cation Channel TRPM4b"; Pfulgers Arch—Eur. J. Physiol., 2004, vol. 448; pp. 70-75.

Babenko; Audrey P., et al; "Pharmaco-topology of Sulfonylurea Receptors"; The Journal of Biological Chemistry (Accelerated Publication); vol. 275, No. 2, Jan. 14, 2000, pp. 717-720.

Earley, Scott, et al; "Protein Kinase C Regulates Vascular Myogenic Tone Through Activation of TRPM4"; American Physiological Society; Feb. 9, 2007; vol. 292; pp. H2613-H2622.

Woo, Seung Kyoon, et al; "The Sulfonylurea Receptor 1 (Sur1)-Transcient Receptor Potential Melastatin 4 (Trpm4) Channel"; The Journal of Biological Chemistry, Feb. 1, 2013, vol. 288, No. 5, pp. 3655-3667.

Pfeiffer et al., "Controlled extension of oral antidiabetic therapy on former insulin dependent diabetics by means of the combined i.v.. Glibenclamide-glucose-response test", Diabetologia, 8:41-47, 1972.

Wise, "New clinical guidelines for stroke published", BMJ, 320:823, 2000.

Bereczki et al., "Mannitol for acute stroke (Review)", Cochrane Database of Systematic Reviews, Issue 3, p. 1-20, 2009.

Chen et al., "Fenamates protect neurons against ischemic and exitotoxic injury in chick embryo retina", Neuroscience Letters, 242(3):163-166, 1998.

Riddle, "Editorial: sulfonylureas differ in effects on ischemic preconditioning—is it time to retire glyburide?", The Journal of Clincial Endocrinology & Metabolism, 2003, 88(2):528-530.

Gurke et al., "Mechanisms of ischemic preconditionin in skeletal muscle", Journal of Surgical Research, 2000, 94:18-27.

Greenwood et al., "Comparison of the effects of fenamates on Ca-activated chloride and potassium currents in rabbit portal vein smooth muscle cells" Biritish Journal of Pharmacology, 116:2939-2948, 1995.

Schmidt et al., "Endocrine and metabolic consequences of spinal injuries", Chapter 18, Sprinal Coard Medicine; Principles and Practices, pp. 221-235, 2002.

Launary et al., "TRPM4 Regulates Calcium Oscillations After T Cell Activation", Science, 306(5700):1374-1377, 2004.

Definition of "infusion" from www.merriam-webster.com, printed on Apr. 10, 2013, 1 pages as printed.

Heurteaux et al., "Alpha-Linolenic Acid and Riluzole Treatment Confer Cerebral Protection and Improce Survival After Focal Brain Ischemia", Neuroscience, 137:241-251, 2006.

Simard et al., Comparative effects of glibenclamide and riluzole in a rat model of severe cervical spinal cord injury, Experimental Neurology, 233:566-574, 2012.

Demion et al., "TRPM4, a Ca2+-activated nonselective cation channel in mouse sino-atrial nod cells", Cardiovasuclar Research, 73:531-538, 2007.

Khansari, "An investigation of the neuroprotective properties of fenamate NSAIDs, against experimental models of ischemic stroke", Dissertation Abstracts International, 68:11B, 197 pages, 2007.

Khansari and Halliwell, "Evidence for neuroprotection by the fenamate NSAID, mefenamic acid", Neurochemistry International, 55:683-688, 2009.

Klose et al., "Fenamates as TRP channel blockers: mefenamic acid selectively blocks TrPM3", British Journal of Pharmacology, 162:1757-1769, 2011.

Pirollo and Chang, "Targeted Delivery of Small Interfering RNA: Approaching Effetive Cancer Therapies", Cancer Res., 68(5):1247-1250, 2008.

Hausmann, "Post-traumatic inflammation following spinal cord injury", Spinal Cord, 41:369-378, 2003.

Woodcock, "The role of markers of inflammation in traumatic brain injury", Frontiers in Neurology, 4:1-18, 2013.

Hugelshofer, "Neuroinflammation after Subarachnoid Hemorrhage: The Role of Microglia", UniversitatsSpital Zurich Institut fur Neuropathologie & Klinik fur Neurochirurgie, p. 1-18, 2013.

Hallevi, "Inflammatory response to intraventricular hemorrage: Time course, magnitude and effect of t-PA," Journal of the Nurological Science, 315:93-95, 2012.

Kunte et al., "Sulfonylureas Improve Outcome in Patients With Type 2 Diabetes and Acute Ischemic Stroke", Stroke, 38(9):2526-2530, 2007.

Liang et al., "Cytotoxic edema: mechanisms of pathological cell swelling", Neurosurg Focus, 22(5):E2, pp. 1-16, 2007.

Gavin, "Management of Diabetes Mellitus During Surgery", West J M. 151:525-529, 1989.

Vestergaard et al., "Relative fracture risk in patients with diabetes melitus, and the impact of insulin and oral antidiabetic medication on relative fracture risk", Diabetologia, 48:1292-1299, 2005.

Inder and Volpe, "Mechanisms of Perinatal Brain Injury", 5 Semin, Neonatol. 3, 2000.

Wright et al., Evidence from Multicenter Networks on the Current Use and Effectiveness of Antenatal Corticosteroids in Low Birth Weight Infants, Am. J Obstet. Gynecol., 173:263, 1995.

(56) References Cited

OTHER PUBLICATIONS

Egarter et al., "Antibiotic Treatment in Preterm Premature Rupture of Membranes and Neonatal Morbidity: A Metaanalysis", Am. J. Obstet. Gynecol., 174:589, 1996.
Huss et al., "Differentiation of canine bone marrow cells with hemopoietic characteristics from an adherent stromal cell precursor", Proc natl. Acad. Sci USA, 92:748-752, 1995.
Zhu, Q., et al., "Modulation by Nucleotides of Binding Sites for [3H]Glibenclamide in Rat Aorta and Cardiac Ventricular Membranes", J. of Cardivascular Pharm., (2001), vol. 37, pp. 522-531.
Walaas et al., PCPP-260, A Purkinje Cell-Specific Cyclic AMP-Regulated Membrane Phosphoprotein of MR 260,000, J Neurosci. Apr. 1986;6(4):954-61.
Favre, I., et al., "Reconstitution of Native and Cloned Channels into Planar Bilayers", Methods in Enzymology, (1999) vol. 294, pp. 287-304.
Jamme, I., et al., "Focal cerebral ischaemia induces a decrease in activity and a shift in ouabain affinity of Na +, K +—ATPase isoforms without modifications in mRNA and protein expression", Brain Research (1999) vol. 810, pp. 132-142.
Chen, M., et al., "Glial and Other Non-Neuronal Cell Specification and Differentiation IV", Society for Neuroscience, (2000) vol. 26, pp. 791.1.
Rosenberg, "Ischemic brain edema." Prog Cardiovasc Dis. Nov.-Dec. 1999; vol. 42(3):209-16.
Apo-Glibenclamide Data Sheet, Medsafe (New Zealand Medicines and Medical Devices Safety Authority), published Jun. 16, 1999, 6 pages; online http://www.medsafe.govt.nz/Profs/DataSheet/a/Apoglibenclamidetab.htm.
Slikker et al., "Session IV: Models of Neurotoxicity and Neuroprotection, Questions for Dr. Banik", Ann NY Acad Sci; 2003; 993; 159-160.
Sribnick et al., "Estrogen as a Neuroprotective Agent in the Treatment of Spinal Cord Injury", Ann. N.Y. Acad. Sci., vol. 993;. 2003;125-133.
Weih et al., "Sulfonylurea Drugs Do Not Influence Initial Stroke Severity and In-Hospital Outcome in Stroke Patients With Diabetes", Stroke. 2001; vol. 32(9):2029-2032.
Lee et al., "In vitro Antitumor Activity of Cromakalim in Human Brain Tumor Cells," Pharmacology 1994; vol. 49:69-74.
Gagliardino, J.J. et al.; Inhibitory effect of sulfonylureas on protein phosphatase activity in rat pancreatic islets; Acta Diabetol (1997) 34:6-9; Springer-Verlang 1997.
Medline Plus® Merriam Webster Medical Dictionary, main entry: par.en.ter.al, online <http://www2.merriam-webster.com/cgi-bin/mwmednlm>; 2005; 1 page.
Rothstein et al, "Neuroprotective strategies in a model of chronic glutamate-mediated motor neuron toxicity," J Neurochem. Aug. 1995;65(2):643-51.
Sang et al., "ATP sensitive potassium channels are involved in the protective effect of ischemic preconditioning on spinal cord in rabbits"; Chinese Pharmacological Bulletin, 2003, Issue 12, 1362-1365.
Khan Hussein Hamed, et al.; "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Verkhratsky, et al., "Ion channels in glial cells," Brain Res. Rev., 32: 380-412, 2000.
Aguilar-Bryan et al., "Cloning of the beta cell high-affinity sulfonylurea receptor: a regulator of insulin secretion," Science, 268: 423-426, 1995.
Bareyre et al., "Inflammation, degeneration and regeneration in the injured spinal cord: insights from DNA microarrays," Trends Neurosci., 26(10): 555-563, 2003.
Bartholdi et al., "Expression of pro-inflammatory cytokine and chemokine mRNA upon experimental spinal cord injury in mouse: an in situ hybridization study," Eur. J. Neurosci., 9(7): 1422-1438, 1997.

Csanady et al., "Ca(2+)- and voltage-dependent gating of Ca(2+)- and ATP-sensitive cationic channels in brain capillary endothelium," Biophys. J., 85: 313-327, 2003.
Copin et al., "70-kDa heat shock protein expression in cultured rat astrocytes after hypoxia: regulatory effect of almitrine," Neurochem. Res., 20(1): 11-15, 1995.
Currie et al., "Benign focal ischemic preconditioning induces neuronal Hsp70 and prolonged astrogliosis with expression of Hsp27," Brain Res., 863(1-2): 169-181, 2000.
Fujita et al., "Molecular aspects of ATP-sensitive K+ channels in the cardiovascular system and K+ channel openers," Pharmacol. Ther., 85: 39-53, 2000.
Inagaki et al., "A family of sulfonylurea receptors determines the pharmacological properties of ATP-sensitive K+ channels," Neuron, 16: 1011-1017, 1996.
Isomoto et al., "A novel sulfonylurea receptor forms with BIR (Kir6.2) a smooth muscle type ATP-sensitive K+ channel," J. Biol. Chem., 271: 24321-24324, 1996.
Kakimura et al., "Microglial activation and amyloid-beta clearance induced by exogenous heat-shock proteins," FASEB J., 16(6): 601-603, 2002.
Lee et al., "Differential neuroprotection from human heat shock protein 70 overexpression in in vitro and in vivo models of ischemia and ischemia-like conditions," Exp. Neurol., 170(1): 129-139, 2001.
Matz et al., "Heme-oxygenase-1 induction in glia throughout rat brain following experimental subarachnoid hemorrhage," Brain Res., 713(1-2): 211-222.
Mautes et al., "Co-induction of HSP70 and heme oxygenase-1 in macrophages and glia after spinal cord contusion in the rat," Brain Res., 883(2): 233-237, 2000.
Mautes et al., "Sustained induction of heme oxygenase-1 in the traumatized spinal cord," Exp. Neurol., 166(2): 254-265, 2000.
Nichols et al., "Adenosine diphosphate as an intracellular regulator of insulin secretion," Science, 272: 1785-1787, 1996.
Papadopoulos et al., "Over-expression of HSP-70 protects astrocytes from combined oxygen-glucose deprivation," Neuroreport, 7(2): 429-432, 1996.
Regan et al., "Heme oxygenase-1 induction protects murine cortical astrocytes from hemoglobin toxicity," Neurosci. Lett, 282(1-2): 1-4, 2000.
Shyng et al., "Regulation of KATP channel activity by diazoxide and MgADP. Distinct functions of the two nucleotide binding folds of the sulfonylurea receptor," J. Gen. Physiol., 110: 643-654, 1997.
Song et al., "GeneChip analysis after acute spinal cord injury in rat," J. Neurochem., 79(4): 804-815, 2001.
Xu et al., "HSP70 protects murine astrocytes from glucose deprivation injury," Neurosci. Lett., 224(1): 9-12, 1997.
Chen et al., "A Calcium-Activated Nonspecific Cation Channel in Reactive Astrocytes from Adult Rat Brain," Society for Neuroscience Abstracts, vol. 26, No. 1-2, Abstract No. 791.1, 2000 [abstract].
Suarez-Isla, B., et al. "Single-Channel Recordings from Purified Acetylcholine Receptors Reconstitute in Bilayers Formed at the Tip of Patch Pipets," American Chemical Society (1983) pp. 2319-2323.
Salvail, Dany, et al., "Direct modulation of tracheal C1—channel activity by 5,6- and 11, 12-EET," Amer. Physio. Soc. (1998) pp. L432-L441.
Eriksson, Biochimica et Biophysica ACTA, Biomembranes, vol. 508 (1978) pp. 155-164.
Sharma, R.V., et al., "Isolation and characterization of plasma membranes from bovine carotid arteries." Amer. Physio. Soc. (1996) pp. C65-C75.
Eben-Brunnen, J., et al., "Lentil Lectin Enriched Microsomes from the Plasma Membrane of the Human B-Lymphocyte Cell Line H2LCL Carry a Heavy Load of Type-1 Porin", Biol. Chem., vol. 379, (1998) pp. 1419-1426.
Garcia, Ann Maria, et al., "Channel-mediated monovalent cation fluxes in isolated sarcoplasmic reticulum vesicles," J. Gen. Physiol., vol. 83, (Jun. 1984) pp. 819-839.
Nelson, N., et al., "Reconstitution of purified acetylcholine receptors with functional ion channels in planar lipid bilayers", Proc. Natl. Acad. Sci., Sci. USA, vol. 77, No. 5 (May 1990) pp. 3057-3061.

(56) References Cited

OTHER PUBLICATIONS

Suarez-Isla, B., et al, "Single calcium channels in native sarcoplasmic reticulum membranes from skeletal muscle." Proc. Nat'l. Acad. Sci., USA, vol. 83, (Oct. 1986) pp. 7741-7745.
Schindler, H. et al., "Functional acetylcholine receptor from Torpedo marmorata in planar membranes," Proc. Nat'l. Acad. Sci. USA, vol. 77, No. 5, (May 1980) pp. 3052-3056.
Garty, H. et al, "A simple and sensitive procedure for measuring isotope fluxes through ion-specific channels in heterogenous populations of membrane vesicles," The Jol. of Bio. Chem., vol. 256, No. 21 (1983) pp. 13094-13099.
Lee et al., "In vitro Antitumor Activity of Cromakalim in Human Brain Tumor Cells," Pharmacology, 49: 69-74, 1994.
Ren, et. al. "Altered mRNA Expression of ATP-Sensitive and Inward Rectifier Potassium Channel Subunits in Streptozotocin-Induced Diabetics Rat Herat and Aorta", J. Pharmacol Sci., 2003, vol. 93, pp. 478-483.
Chen, et al., "Functional Coupling between Sulfonylurea Receptor Type 1 and a Nonselective Cation Channel in Reactive Astrocytes from Adult Rat Brain," J. Neurosci., 23: 8568-8577, 2003.
Crepel, et al., "Glibenclamide depresses the slowly inactivating outward current (ID) in Hippocampal Neurons," Canadian Journal of Physiology and Pahrmacology, 70(2):306-307, 1992.
Elliott, Byron D., et al; "Comparative Placental Transport of Oral Hypoglycemic Agents in Humans: A Model of Human Placental Drug Transfer"; Am. J. Obstet. Gynecol., Sep. 1994, vol. 171, No. 3, pp. 653-660.
Elliott, Byron D., et al; "Insignificant Transfer of Glyburide Occurs Across the Human Placenta"; Oct. 1991; Am. J. Obstet. Gynecol., vol. 165, No. 4, Part 1, pp. 807-812.
Gribble and Ashcroft, "Sulfonylurea Sensitivity of Adenosine Triposphate-sensitive Potassium Channels from b Cells and Extrapancreatic Tissues," Metabolism, 49(10Supp2):3-6, 2000.
Grijalva, et al., "Efficacy and Safety of 4-aminopyridine in Patients with Long-term Spinal Cord Injury: A Randomized, Double-blind, Placebo-controlled Trial," Pharmacotherapy, 23(7):823-834, 2003.
Kawanabe, Yoshifumi, et al., "Effects of the Ca++-permeable Nonselective Cation Channel Blocker LOE 908 on Subarachnoid Hemorrhage-induced Vasospasm in the Basilar Artery in Rabbits", Experimental Biology and Medicine, Mar. 2003, XP008150600.
Khan Hussein Hamed, et al., "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Koltz, Michael T., et al; "Tandem Insults of Prenatal Ischemia Plus Postnatal Raised Intrathoracic Pressure in a Novel Rat Model of Encephalopathy of Prematurity"; J. Neurosurg. Pediatrics, Dec. 2011, vol. 8, pp. 628-639.
Kraemer, Jennifer, et al; "Perfusion Studies of Glyburide Transfer Across the Human Placenta: Implications for Fetal Safety"; American Journal of Obstetrics and Gynecology, 2006, vol. 195, pp. 270-274.
Koren, Gideon; "Glyburide and Fetal Safety; Transplacental Pharmacokinetic Considerations"; Reproductive Toxicology, 2001, vol. 15, pp. 227-229.
Lin, et al., "17b-Estradiol Inhibits Endothelin-1 Production and Attenuates Cerebral Vasospasm After Expreimental Subarachnoid Hemorrhage", Experimental Biology and Medicine, Jun. 1, 2006, pp. 1054-1057, XP55024011, URL: http://ebm.rsmjournals.com/content/231/6/1054.full.pdf#page=1&view=FitH [retrieved Apr. 5, 2012].
Liu, et al., "Suppression of Hippocampus Fos Expression and Activator Protein-1 (AP-1) Activity During Focal Cerebral Ischemia Using Antisense Strategy," Stroke, 26(1):182, 1995.
Maeda, Yoshihisa, et al. "Endothelial Dysfunction and Altered Bradykinin Response Due to Oxidative Stress Induced by Serum Deprivation in the Bovine Cerebral Artery", European Journal of Pharmacology, Elsevier Science, NL, vol. 491, No. 1, Apr. 26, 2004, pp. 53-60, XP008150602, ISSN 0014-2999.

Maybaur, D.M., et al, "The ATP-sensitive Potassium-channel Inhibitor Glibenclamide Improves Outcome in an Ovine Model of Hemorragic Shock," Shock, vol. 22(4), 2004, pp. 387-391.
Proks, et al., "Inhibition of Recombinant K(ATP) Channels by the Antidiabetic Agents Midaglizole, LY397364 and LY389382," Eur J Pharmacol. Sep. 27, 2002;452(1):11-9.
Proks, et al., "Sulfonylurea Stimulation of Insulin Secretion," Diabetes, 51(Suppl. 3): S368-76, 2002 (abstract only).
Simard, et al., "Regulation by Sulfanylurea Receptor Type 1 of a Non-selective Cation Channel Involved in Cytotoxic Edema of Reactive Astrocytes," J. Neurosurg. Anesthesiol., 16(1): 98-9, 2004.
Simard, J. M., et al.; "Endothelial Sulfonylurea Receptor 1-Regulated NC Ca-ATP Channels Mediate Progressive Hemorrhagic Necrosis Following Spinal Cord Injury"; J Clin Invest., Aug. 2007;117(8), pp. 2105-2113.
Simard, J. M., et al.; "Glibenclamide Reduces Inflammation, Vasogenic Edema, and Caspase-3 Activation After Subarachnoid Hemorrhage"; Journal of Cerebral Blood Flow & Metabolism (2008), 29(2) pp. 317-330.
Simard, J. M., et al., "Newly Expressed SUR1-regulated NCca-ATP Channel Mediates Cerebral Edema after Ischemic Stroke", Nature Medicine (Apr. 2006) vol. 12, No. 4, pp. 433-440.
Simard, J. M., et al.; "Sulfonylurea Receptor 1 in the Germinal Matrix of Premature Infants"; Pediatr Res.; Dec. 2008; 64(6), pp. 648-652.
Sribnick, E.A., et al., "Estrogen as a Neuroprotective Agent in the Treatment of Spinal Cord Injury", Annals of New York Academy Science, vol. 993, pp. 125-133; 2003.
Tosun, Cigdem, et al; "The Protective Effect of Glibenclamide in a Model of Hemorrhagic Encephalopathy of Prematurity"; Brain Sciences, 2013, vol. 3, pp. 215-238.
Wang, H., et al., "Targeting Ischemic Stroke with a Novel Opener of ATP-Sensitive Potassium Channels in the Brain", Molecular Pharmacology, vol. 66(5), 2004, pp. 1160-1168.
White, R. P., et al., "Cerebral Arterial Contractions Induced by Human and Bovine Thrombin", Stroke, vol. 11, No. 4, Jul. 1, 1980, pp. 363-368, XP55024008, ISSN: 0039-2499.
White, R. P., et al., "Comparison of Piroxicam, Meclofenamate, Ibuprofen, Aspirin, and Prostcyclin Efficacy in a Chronic Model of Cerebral Vasospasm", Neurosurgery, Williams & Wilkens, Baltimore, MD, vol. 12, No. 1, Jan. 1, 1983, pp. 40-46, XP000614038, ISSN 0148-396X.
Wickelgren, "Animal Studies Raise Hopes for Spinal Cord Repair," Science, 297:178-181, 2002.
Yokoshiki, et al., "Antisense Oligodeoxynucleotides of Sulfonlurea Recepters Inhibit ATP-sensitive K+ Channels in Cultured Neonatal Rat Ventricular Cells," Eur J Physiol, 437:400-408, 1999.
Yang, Shao-Hua, "17-beta Estradiol Can Reduce Secondary Ischemic Damage and Mortality of Subarachnoid Hemorrhage", Journal of Cerebral Blood Folw and Metabolism, 2001, pp. 174-181, XP055024012.
Yune et al., "Systemic Administration of 17?-Estradiol Reduces Apoptotic Cell Death and Improves Functional Recovery following Traumatic Spinal Cord Injury in Rats", Journal of Neurotrauma. Mar. 1, 2004, 21(3): 293-306.
European Office Action, issued in European Application No. 08 771 576.9, mailed Aug. 8, 2011.
Partial European Search Report issued in European Application No. 10010753.1, mailed Jul. 22, 2011.
International Search Report, issued Jan. 2, 2009 (published Jan. 2, 2009) during the prosecution of International Application No. PCT/US2008/067640.
International Search Report, issued Jul. 26, 2010 (published Jul. 20, 2010) during the prosecution of International Application No. PCT/US2008/06740.
International Preliminary Report on Patentability, issued Jan. 7, 2010 (published Jan. 7, 2010) during the prosecution of International Application No. PCT/US2008/067640.
International Preliminary Report on Patentability, issued Mar. 31, 2011, during prosection of International Application No. PCT/US2009/057111.
Japanese Office Action, issued in Japanese Patent Application No. 2007-5232321, mailed Apr. 22, 2011.

(56) References Cited

OTHER PUBLICATIONS

Japanese Office Action, issued in Japanese Patent Application No. 2007-532507, mailed Jun. 20, 2011.

Japanese Office Action, issued in Japanese Patent Application No. 2007-532321, mailed Apr. 22, 2011.

Koltz, Michael T., et al; "Tandem Insults of Prenatal Ischemia Plus Postnatal Raised Intrathoracic Pressure in a Novel Rat Model of Encephalopathy of Prematurity"; J. Neurosurg. Pediatrics, 2011, vol. 8, pp. 628-639.

Koren, Gideon; Glyburide and Fetal Safety; Transplacental Pharmacokinetic Considerations; Reproductivie Toxicology 15 (2001) 227-229.

Elliott, Byron D., et al; Insignificant Transfer of Glyburide Occurs Across the Human Placenta; Department of Obstetrics and Gynecology, University of Texas Health Science Cnter at San Antoino, vol. 165; No. 4, Part 1; 1991.

Kraemer, Jennifer; et al, Perfusion Studies of Glyburide Transfer Across the Human Placenta: Implications of Fetal Safety; Am. Journal of Obstetrics & Gynecology; (2006) 195, 270-4.

Elliott, Byron D.; Comparative Placental Transport of Oral Hypoglycemic Agents n Humans: A Model of Human Placental Drug Transfer; Department of Obsetrics and Gynecology; University of Texas Health Science Center at San Antonio; 1994.

Declaration under 37 CFR 1.132 of Dr. J. Marc Simard, filed on May 13, 2013 in U.S. Appl. No. 12/665,853, now U.S. Pat. No. 8,557,867.

\* cited by examiner

SEQUENCE LISTING

```
<160> NUMBER OF SEQ ID NOS: 15

<210> SEQ ID NO 1
<211> LENGTH: 18
<212> TYPE: DNA
<213> ORGANISM: Artificial Sequence
<220> FEATURE:
<223> OTHER INFORMATION: Artificial Primer

<400> SEQUENCE: 1
tgcctgaggc gtggctgt                                                 18

<210> SEQ ID NO 2
<211> LENGTH: 18
<212> TYPE: DNA
<213> ORGANISM: Artificial Sequence
<220> FEATURE:
<223> OTHER INFORMATION: Artificial Primer

<400> SEQUENCE: 2
ggccgagtgg ttctcggt                                                 18

<210> SEQ ID NO 3
<211> LENGTH: 48
<212> TYPE: DNA
<213> ORGANISM: Artificial Sequence
<220> FEATURE:
<223> OTHER INFORMATION: Artificial Primer

<400> SEQUENCE: 3
gcccgggcac cctgctggct ctgtgtgtcc ttccgcgcct gggcatcg                 48
```

<210> SEQ ID NO 4
<211> LENGTH: 48
<212> TYPE: DNA
<213> ORGANISM: Artificial Sequence
<220> FEATURE:
<223> OTHER INFORMATION: Artificial Primer

<400> SEQUENCE: 4
tgcaggggtc agggtcaggg cgctgtcggt ccacttggcc agccagta                48

<210> SEQ ID NO 5
<211> LENGTH: 20
<212> TYPE: DNA
<213> ORGANISM: Artificial Sequence
<220> FEATURE:
<223> OTHER INFORMATION: Artificial Primer

<400> SEQUENCE: 5
cggaccaccc caagtattca                                               20

<210> SEQ ID NO 6
<211> LENGTH: 17
<212> TYPE: DNA
<213> ORGANISM: Artificial Sequence
<220> FEATURE:
<223> OTHER INFORMATION: Artificial Primer

<400> SEQUENCE: 6
gccggcacgg ttcttct                                                  17

<210> SEQ ID NO 7
<211> LENGTH: 25
<212> TYPE: DNA
<213> ORGANISM: Artificial Sequence
<220> FEATURE:
<223> OTHER INFORMATION: Artificial Primer

<400> SEQUENCE: 7
catgatcgtg gctgctatcc aggca                                         25

<210> SEQ ID NO 8
<211> LENGTH: 19
<212> TYPE: DNA
<213> ORGANISM: Artificial Sequence
<220> FEATURE:
<223> OTHER INFORMATION: Artificial Primer

<400> SEQUENCE: 8
gagtcggact tctcgccct                                                19

<210> SEQ ID NO 9
<211> LENGTH: 20
<212> TYPE: DNA
<213> ORGANISM: Artificial Sequence
<220> FEATURE:
<223> OTHER INFORMATION: Artificial Primer

<400> SEQUENCE: 9
ccttgacagt ggaccgaacc                                               20

<210> SEQ ID NO 10
<211> LENGTH: 25
<212> TYPE: DNA
<213> ORGANISM: Artificial Sequence
<220> FEATURE:
<223> OTHER INFORMATION: Artificial Primer

```
<400> SEQUENCE: 10
ttccacatcc tggtcacacc gctgt                                            25

<210> SEQ ID NO 11
<211> LENGTH: 20
<212> TYPE: DNA
<213> ORGANISM: Artificial Sequence
<220> FEATURE:
<223> OTHER INFORMATION: Artificial Primer

<400> SEQUENCE: 11
agttgagttc cccctggact                                                  20

<210> SEQ ID NO 12
<211> LENGTH: 20
<212> TYPE: DNA
<213> ORGANISM: Artificial Sequence
<220> FEATURE:
<223> OTHER INFORMATION: Artificial Primer

<400> SEQUENCE: 12
aattccagtc cctcccactc                                                  20

<210> SEQ ID NO 13
<211> LENGTH: 48
<212> TYPE: DNA
<213> ORGANISM: Artificial Sequence
<220> FEATURE:
<223> OTHER INFORMATION: Artificial Primer

<400> SEQUENCE: 13
gcccgggcac cctgctggct ctgtgtgtcc ttccgcgcct gggcatcg                   48

<210> SEQ ID NO 14
<211> LENGTH: 48
<212> TYPE: DNA
<213> ORGANISM: Artificial Sequence
<220> FEATURE:
<223> OTHER INFORMATION: Artificial Primer

<400> SEQUENCE: 14
ccagggcagg ccgcgaatgg aattcccgga tgaggctgta gcgctgcg                   48

<210> SEQ ID NO 15
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 15

Cys Thr Thr His Trp Gly Phe Thr Leu Cys
1               5                   10
```

INHIBITORS OF NC$_{Ca-ATP}$ CHANNELS FOR THERAPY

This application claims priority to U.S. patent application No. 12/665,853, filed Dec. 21, 2009, which was a U.S. 0371 national phase application of PCT International Patent Application PCT/US2008/067640, filed Jun. 20, 2008, which claims priority to U.S. Provisional Patent Application Ser. No. 60/945,825, filed Jun. 22, 2007; and to U.S. Provisional Patent Application Ser. No. 60/945,811, filed Jun. 22, 2007; and to U.S. Provisional Patent Application Ser. No. 60/945,636, filed Jun. 22, 2007, all of which applications are incorporated by reference herein in their entirety.

STATEMENT REGARDING FEDERALLY SPONSORED RESEARCH OR DEVELOPMENT

This invention was made with government support under Grant Numbers NS048260 and HL082517 awarded by the National Institutes of Health. The government has certain rights in the invention.

FIELD OF THE INVENTION

The present invention concerns at least the fields of cell biology, molecular biology, and medicine. In particular aspects, the present invention concerns the fields of treatment and/or prevention of intraventricular hemorrhage or spinal cord injury, particularly related to progressive hemorrhagic necrosis, for example.

BACKGROUND OF THE INVENTION

The present invention concerns therapy for a variety of maladies, including at least spinal cord injury and intraventricular hemorrhage.
Spinal Cord Injury
Acute spinal cord injury (SCI) results in physical disruption of spinal cord neurons and axons leading to deficits in motor, sensory, and autonomic function. SCI is a debilitating neurological disorder common in young adults that often requires life-long therapy and rehabilitative care, placing significant burdens on healthcare systems. Although many patients exhibit neuropathologically and clinically complete cord injuries following SCI, many others have neuropathologically incomplete lesions (Hayes and Kakulas, 1997; Tator and Fehlinds, 1991) giving hope that proper treatment to minimize "secondary injury" may reduce the functional impact.

The concept of secondary injury in SCI arises from the observation that the lesion expands and evolves over time (Tator and Fehlings, 1991; Kwon et al., 2004). Whereas primary injured tissues are irrevocably damaged at the time of impact, tissues that are destined to become "secondarily" injured are considered to be potentially salvageable. Older observations based on histological studies that gave rise to the concept of lesion-evolution have been confirmed with non-invasive MRI (Bilgen et al., 2000).

Several mechanisms of secondary injury have been postulated, including ischemia/hypoxia, oxidative stress and inflammation, all of which have been considered to be responsible for the devastating process termed "progressive hemorrhagic necrosis" (PHN) (Tator and Fehlings, 1991; Nelson et al., 1977; Tator, 1991; Fitch et al., 1999; Tator and Koyanagi, 1997). PHN is a mysterious condition, first recognized over three decades ago, that has thus far eluded understanding and treatment. Shortly after injury (10-15 min), a small hemorrhagic lesion involving primarily the capillary-rich central gray matter is observed, but over the following 3-24 h, petechial hemorrhages emerge in more distant tissues, eventually coalescing into the characteristic lesion of hemorrhagic necrosis (Balentine, 1978; Kawata et al., 1993). The white matter surrounding the hemorrhagic gray matter shows a variety of abnormalities, including decreased hematoxylin and eosin staining, disrupted myelin, and axonal and periaxonal swelling. White matter lesions extend far from the injury site, especially in the posterior columns (Tator and Koyanagi, 1997). The evolution of hemorrhage and necrosis has been referred to as "autodestruction". PHN results in loss of vital spinal cord tissue and, in some species including humans, leads to post-traumatic cystic cavitation surrounded by glial scar tissue.

The mechanism responsible for PHN is not known. Tator and Koyanagi (1997) speculated that obstruction of small intramedullary vessels by the initial mechanical stress or secondary injury might be responsible for PHN, whereas Kawata and colleagues (Kawata et al., 1993) attributed the progressive changes to leukocyte infiltration around the injured area leading to plugging of capillaries. Given that petechial hemorrhages, the pathognomonic feature of PHN, form as a result of catastrophic failure of vascular integrity, damage to the endothelium of spinal cord capillaries and postcapillary venules has long been regarded as a major factor in the pathogenesis of PHN (Nelson et al., 1977; Griffiths et al., 1978; Kapadia, 1984). However, no molecular mechanism for progressive dysfunction of endothelium has been identified.

The sulfonylurea receptor-1 (SUR1)-regulated NC$_{Ca-ATP}$ channel is a non-selective cation channel that is not constitutively expressed, but is transcriptionally up-regulated in astrocytes and neurons following an hypoxic or ischemic insult (Chen and Simard, 2001; Chen et al., 2003; Simard et al., 2006). The channel is inactive when expressed, but becomes activated when intracellular ATP is depleted, with activation leading to cell depolarization, cytotoxic edema and oncotic cell death. Block of the channel in vitro by the sulfonylurea, glibenclamide, prevents cell depolarization, cytotoxic edema and oncotic cell death induced by ATP depletion. In rodent models of ischemic stroke, treatment with glibenclamide results in significant improvements in edema, lesion volume and mortality (Simard et al., 2006). In humans with diabetes mellitus, use of sulfonylureas before and during hospitalization for stroke is associated with significantly better stroke outcomes (Kunte et al., 2007).
Intra-Axial Hemorrhage Intra-axial hemorrhage is characterized by bleeding within the brain itself. Intraparenchymal or intraventricular hemorrhages are types of intra-axial hemorrhage.
Intraventricular Hemorrhage (IVH)

Intraventricular Hemorrhage (IVH), a bleeding from fragile blood vessels in the brain, is a significant cause of morbidity and mortality in premature infants and may have include, for example, death, shunt-dependent hydrocephalus, and life-long neurological consequences such as cerebral palsy, seizures, mental retardation, and other neurodevelopmental disabilities. Neurological sequelae include shunt-dependent hydrocephalus, seizures, neurodevelopmental disabilities, and cerebral palsy. The vasculature is especially fragile in preterm infants, particularly those born more than 8 weeks early, i.e., before 32 weeks of gestation. IVH is more commonly seen in extremely premature infants; its incidence is over 50% in preterm infants with birth weight less than 750 grams, and up to 25% in infants with birth weight less than 1000 to 1500 grams.

IVH encompasses a wide spectrum of intra-cranial vascular injuries with bleeding into the brain ventricles, a pair of C-shaped reservoirs, located in each half of the brain near its center, that contain cerebrospinal fluid. Bleeding occur in the subependymal germinal matrix, a region of the developing brain located in close proximity to the ventricles. Within the germinal matrix, during fetal development, there is intense neuronal proliferation as neuroblasts divide and migrate into the cerebral parenchyma. This migration is about complete by about the 24th week of gestation, although glial cells can still be found within the germinal matrix until term. The germinal matrix undergoes rapid involution from the 26th to the 32nd week of gestation, at which time regression is nearly complete, as glial precursors migrate out to populate the cerebral hemispheres.

Supporting this intense cell differentiation and proliferation activity there is a primitive and fragile capillary network. These vessels have thin walls for their relatively large size, lack a muscularis layer, have immature interendothelial junctions and basal laminae, and often lack direct contact with perivascular glial structures, suggesting diminished extravascular support. It is in this fragile capillary network where IVH originates. When a fetus is born prematurely, the infant is suddenly thrust from a well-controlled, protective environment into a stimulating, hostile one. Because of this physiologic stress and shock, the infant may lose the ability to regulate cerebral blood flow and may suffer alterations in blood flow and pressure and in the amounts of substances dissolved in the blood such as oxygen, glucose and sodium. The fragile capillaries may, and often do, rupture.

The severity of the condition depends on the extent of the vascular injury. There are four grades, or stages, of IVH as can be seen using ultrasound or brain computer tomography. Grade I IVH, the less severe stage, involves bleeding in the subependymal germinal matrix, with less than 10% involvement of the adjacent ventricles. Grade II IVH results when 10 to 40% of the ventricles are filled with blood, but without enlargement of the ventricles. Grade III IVH involves filling of over 50% of the ventricles with blood, with significant ventricular enlargement. In Grade IV IVH, the bleeding extends beyond the intraventricular area into the brain parenchyma (intraparenchymal hemorrhage).

The major complications of IVH relate to the destruction of the cerebral parenchyma and the development of posthemorrhagic hydrocephalus. Following parenchymal hemorrhages (Grade IV IVH), necrotic areas may form cysts that can become contiguous with the ventricles. Cerebral palsy is the primary neurological disorder observed in those cases, although mental retardation and seizures may also occur. In addition, infants affected with Grade III to IV IVH may develop posthemorrhagic hydrocephalus, a condition characterized by rapid growth of the lateral ventricles and excessive head growth within two weeks of the hemorrhage. Likely causes are obstruction of the cerebrospinal fluid conduits by blood clots or debris, impaired absorption of the cerebrospinal fluid at the arachnoid villi, or both. Another form of the hydrocephalus condition may develop weeks after the injury. In this case the likely cause is obstruction of the cerebrospinal fluid flow due to an obliterative arachnoiditis in the posterior fossa.

Several trials were conducted in the 1980s and 1990s to evaluate prophylactic use of phenobarbitone in preterm infants to reduce the risk of IVH, however, no statistical significance was observed (Postnatal phenobarbitone for the prevention of intraventricular hemorrhage in preterm infants, Whitelaw et al., 2000; and Bedard M P, Shankaran S, Slovis T L, Pantoja A, Dayal B. Poland R L. Effect of prophylactic phenobarbital on intraventricular hemorrhage in high-risk infants. Pediatrics 1984; 73:435-9.). Other pharmacological interventions have been assessed, such as indomethacin (Fowlie 1999), but without substantial clinical impact and IVH remains a problem. (Whitelaw A, Placzek M, Dubowitz L, Lary S, Levene M. Phenobarbitone for prevention of periventricular haemorrhage in very low birth-weight infants. A randomised double-blind trial. Lancet 1983; ii:1168-70.).

Extra-Axial Hemorrhage

Extra-axial hemorrhage is characterized by bleeding that occurs within the skull but outside of the brain tissue. Epidural hemorrhage, subdural hemorrhage and subarachnoid hemorrhage are types of extra-axial hemorrhage.

Subarachnoid hemorrhage (SAH)

SAH, like intraparenchymal hemorrhage, may result from trauma (physical or physiological) or from ruptures of aneurysms or arteriovenous malformations, or a combination thereof. SAH often indicates the presence of blood within the subarachnoid space, blood layering/layered into the brain along sulci and fissures, or blood filling cisterns (such as the suprasellar cistern because of the presence of the vessels of the circle of Willis and their branchpoints within that space). The classic presentation of subarachnoid hemorrhage is the sudden onset of a severe headache. This can be a very dangerous entity, and requires emergent neurosurgical evaluation, and sometimes urgent intervention. In the United States, the annual incidence of nontraumatic SAH is about 6-25 per 100,000. Internationally, incidences have been reported but vary to 2-49 per 100,000.

Unlike ischemic stroke, in SAH the entire cortex bathed in blood is at risk from hemotoxicity-related inflammation. Also, hemotoxicity-related inflammation is potentially more amenable to treatment than ischemic stroke because it develops relatively slowly, compared to rapid loss of penumbral tissues in ischemia. At present, treatments for edema are limited because underlying molecular mechanics are not well understood, and treatments aimed at mechanism that have been implicated (Park et al., 2004) are not yet available. Therefore, the present invention fulfills a long-standing need in the art by providing a treatment for SAH predicated on ameliorating (or otherwise inhibiting) post-SAH hemotoxicity-related inflammation.

The present invention provides a solution for a long-felt need in the art to treat progressive hemorrhagic necrosis following spinal cord injury and to treat IVH, traumatic brain injury, and subarachnoid hemorrhage. for example.

SUMMARY OF THE INVENTION

The present invention is directed to systems, methods, and compositions that concern multiple conditions, including progressive hemorrhagic necrosis following spinal cord injury, traumatic brain injury, subarachnoid hemorrhage, and intraventricular hemorrhage, for example.

In particular embodiments, the present invention concerns a specific channel, the $NC_{Ca\text{-}ATP}$ channel. The $NC_{Ca\text{-}ATP}$ channel is a unique non-selective cation channel that is activated by intracellular calcium and blocked by intracellular ATP. In particular aspects, the $NC_{Ca\text{-}ATP}$ channel of the present invention has a single-channel conductance to potassium ion (K+) between 20 and 50 pS. The $NC_{Ca\text{-}ATP}$ channel is also stimulated by $Ca^{2+}$ on the cytoplasmic side of the cell membrane in a physiological concentration range, (from about $10^{-8}$ to about $10^{-5}$ M). The $NC_{Ca\text{-}ATP}$ channel is also inhibited by cytoplasmic ATP in a physiological concentration range (from about 0.1 mM to about 10 mM, or more particularly about 0.2 mM to about 5 mM). The $NC_{Ca\text{-}ATP}$ channel is also permeable at least to the following cations: $K^+$, $Cs^+$, $Li^+$, $Na^+$; with the permeability ratio between any two of the cations typically being greater than about 0.5 and less than about 2, for example.

The $NC_{Ca\text{-}ATP}$ channel includes at least a pore-forming component (pore-forming subunit) and a regulatory component (regulatory subunit); the regulatory subunit includes sulfonylurea type 1 receptor (SUR1) and the pore-forming subunit includes a non-selective cation channel subunit that is, or closely resembles, a transient receptor potential melastatin 4 (TRPM4) pore. In some embodiments, pathological diseases and conditions may be treated or prevented by inhibition of the $NC_{Ca\text{-}ATP}$ channel. The $NC_{Ca\text{-}ATP}$ channel may be inhibited by reducing its activity, by reducing the numbers of such channels present in cell membranes, and by other means. For example, the $NC_{Ca\text{-}ATP}$ channel may be inhibited by administration of SUR1 antagonists; by administration of TRPM4 antagonists; by administration of a combination of drugs including a SUR1 antagonist and a TRPM4 antagonist; by reducing or antagonizing the expression, transcription, or translation of genetic message encoding the $NC_{Ca\text{-}ATP}$ channel; by reducing or antagonizing the insertion of $NC_{Ca\text{-}ATP}$ channels into cell membranes; and by other means.

In particular embodiments the $NC_{Ca\text{-}ATP}$ channel is regulated by sulfonylurea receptor 1 (SUR1): e.g., it is opened by ATP depletion. SUR1-regulated $NC_{Ca\text{-}ATP}$ channels have been shown to play an important role in cytotoxic edema, oncotic cell death, and hemorrhagic conversion in ischemic stroke and CNS trauma. Moreover, SUR1 is blocked by SUR1 antagonists such as, for example, glibenclamide and tolbutamide, providing an exemplary avenue for treatment. TRPM4 pores may be blocked by TRPM4 antagonists (e.g., TRPM4 blockers such as, for example, pinkolant, rimonabant, or a fenamate). In one aspect, the hypoxic-ischemic environment in prematurity leads to transcriptional activation of SUR1 and opening of $NC_{Ca\text{-}ATP}$ channels, initiating a cascade of events culminating in acute hemorrhage in parallel with ischemic stroke. Thus, hypoxic, ischemic, or hemorrhagic injury may be treated by inhibition of the $NC_{Ca\text{-}ATP}$ channel, e.g., by administration of a SUR1 antagonist, a TRPM4 antagonist, or both.

In certain embodiments related at least to spinal cord injury, for example, the channel is expressed in neural, glial, and vascular cells and tissues, among others, including in capillary endothelium, cells in the core near the spinal cord injury impact site, and in reactive astrocytes although in alternative cases the channel is expressed in neurons, glia and neural endothelial cells after brain trauma, for example.

More particularly, the present invention relates to the regulation and/or modulation of this $NC_{Ca\text{-}ATP}$ channel and how its modulation can be used to prevent, ameliorate, or treat intraventricular hemorrhage and/or spinal cord injury and/or progressive hemorrhagic necrosis and/or traumatic brain injury and/or subarachnoid hemorrhage or other hypoxic or ischemic injury, disease, or condition. Administration of an antagonist or inhibitor of the $NC_{Ca\text{-}ATP}$ channel is effective to modulate and/or regulate the channel and to prevent or treat such injury, disease, or condition in specific embodiments. Thus, depending upon the disease, a composition (an antagonist, which may also be referred to as an inhibitor) is administered to block or inhibit at least in part the channel, for example to prevent cell death and/or to prevent or reduce or modulate depolarization of the cells. Administration of an antagonist or inhibitor of the $NC_{Ca\text{-}ATP}$ channel includes administration of a SUR1 antagonist, a TRPM4 antagonist, or both, and may include such administration in combination with administration of other agents as well.

The invention encompasses antagonists of the $NC_{Ca\text{-}ATP}$ channel, including small molecules, large molecules, proteins, (including antibodies), as well as nucleotide sequences that can be used to inhibit $NC_{Ca\text{-}ATP}$ channel gene expression (e.g., antisense and ribozyme molecules). In certain cases, an antagonist of the $NC_{Ca\text{-}ATP}$ channel includes one or more compounds capable of one or more of the following: (1) blocking the channel; (2) preventing channel opening; (3) inhibiting the channel; (4) reducing the magnitude of membrane current through the channel; (5) inhibiting transcriptional expression of the channel; and/or (6) inhibiting post-translational assembly and/or trafficking of channel subunits.

Another aspect of the present invention for the treatment of ischemic, hypoxic, or other injury, including IVH or spinal cord injury or progressive hemorrhagic conversion comprises administration of an effective amount of a SUR1 antagonist and/or a TRPM4 antagonist and administration of glucose. Glucose administration may be by intravenous, or intraperitoneal, or other suitable route and means of delivery. Additional glucose allows administration of higher doses of an antagonist of the $NC_{Ca\text{-}ATP}$ channel than might otherwise be possible, so that combined glucose with an antagonist of the $NC_{Ca\text{-}ATP}$ channel provides greater protection, and may allow treatment at later times, than with an antagonist of the $NC_{Ca\text{-}ATP}$ channel alone. Greater amounts of glucose are administered where larger doses of an antagonist of the $NC_{Ca\text{-}ATP}$ channel are administered.

In certain aspects, antagonists of one or more proteins that comprise the channel and/or antagonists for proteins that modulate activity of the channel are utilized in methods and compositions of the invention. The channel is expressed on neuronal cells, neuroglia cells, neural epithelial cells, neural endothelial cells, vascular cells, or a combination thereof, for example. In specific embodiments, an inhibitor of the channel directly or indirectly inhibits the channel, for example by the influx of cations, such as $Na+$, into the cells, thereby preventing depolarization of the cells. Inhibition of the influx of $Na+$ into the cells thereby at least prevents or reduces cytotoxic edema and/or ionic edema, and/or vasogenic edema and prevents or reduces hemorrhagic conversion. Thus, this treatment reduces cell death or necrotic death of at least neuronal, glial, vascular, endothelial, and/or neural endothelial cells.

The $NC_{Ca\text{-}ATP}$ channel can be inhibited by an $NC_{Ca\text{-}ATP}$ channel inhibitor, an $NC_{Ca\text{-}ATP}$ channel blocker, a type 1 sulfonylurea receptor (SUR1) antagonist, SUR1 inhibitor, a TRPM4 inhibitor, or a compound capable of reducing the magnitude of membrane current through the channel, or a combination or mixture thereof. In further specific embodiments, the SUR1 inhibitor is a sulfonylurea compound or a benzamido derivative. A SUR1 inhibitor such as iptakalim may be used. More specifically, the exemplary SUR1 antagonist may be selected from the group consisting of glibenclamide, tolbutamide, repaglinide, nateglinide, meglitinide, midaglizole, LY397364, LY389382, glyclazide, glimepiride, estrogen, estrogen related-compounds (estradiol, estrone, estriol, genistein, non-steroidal estrogen (e.g., diethylstilbestrol), phytoestrogen (e.g., coumestrol), zearalenone, etc.), and compounds known to inhibit or block $K_{ATP}$ channels. MgADP can also be used to inhibit the channel. Other compounds that can be used to block or inhibit $K_{ATP}$ channels include, but are not limited to tolbutamide, glyburide (1[p-2 [5-chloro-O-anisamido)ethyl]phenyl]sulfonyl]-3-cyclohexyl-3-urea); chlorpropamide(1-[[(p-chlorophenyl)sulfonyl]-3-propylurea; glipizide (1-cyclohexyl-3[[p-[2(5-methylpyrazine carboxamido)ethyl]phenyl]sulfonyl]urea); or tolazamide(benzenesulfonamide-N-[[(hexahydro-1H-azepin-1yl)amino]carbonyl]-4-methyl). In a specific embodiment, the cation channel blocker is selected from the group consisting of pinkolant, rimonabant, a fenamate (such as flufenamic acid, mefenamic acid, meclofenamic acid, or niflumic acid), 1-(beta-[3-(4-methoxy-phenyl)propoxy]-4-methoxyphenethyl)-1H-imidazole hydrochloride, and a biologically active derivative thereof. In additional embodiments, non-sulfonyl urea compounds, such as 2,3-butanedione and 5-hydroxydecanoic acid, quinine, and therapeutically equivalent salts and derivatives thereof, may be employed in the invention. The benzamido derivative may be selected from the group consisting of repaglinide, nateglinide, and meglitinide. The inhibitor may comprise a protein, a peptide, a nucleic acid (such as an RNAi molecule or antisense RNA, including siRNA), or a small molecule. In specific aspects, the inhibitor is provided intravenously, subcutaneously, intramuscularly, intracutaneously, intragastrically, or orally. In an additional embodiment, the method further comprises administering MgADP to the individual.

In one embodiment of the invention, $NC_{Ca-ATP}$ channels are involved in progressive hemorrhagic necrosis (PHN) in SCI. Although endothelial dysfunction has been implicated in PHN, SUR1-regulated $NC_{Ca-ATP}$ channels have not previously been shown in capillary endothelium. Here, development of the present invention utilized a rodent model of unilateral cervical SCI and endothelial cell cultures, wherein SUR1 was prominently up-regulated in capillaries in the region of SCI, endothelial cells subjected to hypoxic conditions express SUR1-regulated $NC_{Ca-ATP}$ channels, and inhibition of SUR1 by a variety of molecularly distinct mechanisms largely eliminated the progressive extravasation of blood characteristic of PHN, reduced lesion size, and was associated with marked neurobehavioral functional improvement, consistent with a critical role for SUR1-regulated $NC_{Ca-ATP}$ channels in PHN following SCI.

Thus, in one embodiment of the invention, there is a method of treating and/or preventing progressive hemorrhagic necrosis in an individual, comprising the step of providing to the individual an effective amount of an inhibitor of a $NC_{Ca-ATP}$ channel. In a specific embodiment, the progressive hemorrhagic necrosis is a direct or indirect result of spinal cord injury. In another specific embodiment, the inhibitor of the channel is a SUR1 inhibitor, a TRPM4 inhibitor, or a combination or mixture thereof. The inhibitor may be provided intravenously, subcutaneously, intramuscularly, intracutaneously, intragastrically, or orally. In an additional specific embodiment, the method further comprises administering MgADP to the individual.

An individual provided the methods of the invention may be an individual that suffers from a spinal cord injury or that is at risk for having a spinal cord injury, for example. Individuals at risk for having spinal cord injuries may be of any kind, and in certain cases the spinal cord injury is the result of an unexpected accident. Still, some groups of the population have a higher risk of sustaining a spinal cord injury, including at least, for example, men; African-Americans; young adults; seniors; motor vehicle accident victims; fall victims; victims of violence, for example, gunshot wounds, stabbings and assaults; athletes, including those who partake in football, rugby, wrestling, gymnastics, diving, surfing, swimming, ice hockey, equestrian activities, or downhill skiing, for example; individuals participating in recreational activities, such as horseback riding, swimming; and individuals with predisposing conditions, such as conditions that affect the bones or joints, including arthritis or osteoporosis.

The present invention is also directed to a system and method that concern treatment and/or prevention of intraventricular hemorrhage in an individual, and, in specific embodiments, in a premature infant. In particular aspects, a premature infant is defined as any infant that is recognized in the art to be premature, although in specific aspects a premature infant is an infant that is born before the 37th week of pregnancy.

The present invention relates to a novel ion channel whose function underlies the swelling of a cell, for example, such as in response to ATP depletion. Treatment methods are provided that exploit the differential expression of such channels in response to trauma, including but not limited to the use of inhibitors of the channel function to prevent the cell swelling response. Several adverse effects are associated with such physiological phenomenon, including hemorrhagic stroke, intracranial hemorrhage, and further, IVH and SAH.

In certain embodiments, the invention is drawn to methods of treating intracranial hemorrhage, including but not limited to intra-axial hemorrhage such as IVH and extra-axial hemorrhage such as SAH. In specific embodiments, the methods comprise the administration of an inhibitor of an $NC_{Ca-ATP}$ channel to a cell and/or subject in need thereof.

In an exemplary embodiment of the present invention, the treatment methods are effective for therapeutic and/or preventative compositions and methods of the invention may be provided to the premature infant following birth, the mother of the premature infant during pregnancy, or the infant in utero. In a specific embodiment, the inhibitor is provided to the mother prior to 37 weeks of gestation. In another specific embodiment, the mother is at risk for premature labor. In a further specific embodiment, the pregnancy is less than 37 weeks in gestation and the mother has one or more symptoms of labor.

Thus, in one non-limiting embodiment, there is a method of treating intraventricular hemorrhage in the brain of an infant or preventing intraventricular hemorrhage in the brain of an infant at risk for developing intraventricular hemorrhage, comprising administering an effective amount of an inhibitor of $NC_{Ca-ATP}$ channel to the infant following birth and/or the mother prior to birth of the infant. In a specific embodiment, the infant is a premature infant. In further specific embodiments, the infant weighs less than 1500 grams at birth or weighs less than 1000 grams at birth. In particular aspects, the infant is a premature infant born at 36, 35, 34, 33, 32, 31, 30, 29, 28, 27, 26, 25, 24, or at or prior to 23 weeks of gestation.

In an additional embodiment, there is a kit for treating and/or preventing intraventricular hemorrhage or spinal cord injury (including related to PHN), comprising an inhibitor of $NC_{Ca-ATP}$ channel, including an inhibitor of TRPM4 and/or SUR1. The channel inhibitor is a SUR1 inhibitor, a TRPM4 inhibitor, or a mixture or combination thereof, in specific embodiments. The kit may further comprise an additional compound for treating spinal cord. The kit may further comprise an additional compound for treating intraventricular hemorrhage, either for delivery to the infant and/or to the mother. In some embodiments of the kit, the kit comprises methylprednisone, one or more of a cation channel blocker, and/or an antagonist of VEGF, MMP, NOS, or thrombin, for example. The kit may also comprise suitable tools to administer compositions of the invention to an individual. The inhibitor is formulated for administration in utero, in specific embodiments for intraventricular hemorrhage.

In yet another exemplary embodiment of the present invention, the compositions and methods of the present invention are predicated on the concept that cortical dysfunction is due to hemotoxcity-related inflammation, which activates an immune response cascade events, such as production of cytokines such as TNFalpha and/or NF-kappaB, resulting in upregulation of SUR1-regulated $NC_{Ca-ATP}$ channels, thereby predisposing the cell/subject to edema and/or cell death. Thus, in a non-limiting embodiment, the invention includes methods of treating and/or preventing SAH comprising administration of an effective amount of an inhibitor of an $NC_{Ca-ATP}$ channel to a cell and/or subject in need thereof.

In specific embodiments, the methods of treating or preventing SAH are useful in any subject at risk for SAH, such as hypertensive patients, individuals at risk to trauma both physical and physiological, and the like.

The methods of the present invention may include combination therapies, such as co-administration of dexamethasone, glucose, an antiinflammatory agent, an anticholesterol agent, an antihyperlipoproteinemic agent, or other agent or combination of agents, for example. In certain embodiments, methods of the present invention may include combination therapies including antithrombotic and or antifibrinolytic agents, such as co-administration of tPA, for example to help remove a blood clot from the ventricle or any condition that would not be contra-indicated for co-administration of tPA. In fact, one of skill in the art recognizes that at least some of the conditions that are treatable with the methods of the present invention (intraventricular hemorrhage, subarachnoid hemorrhage, progressive secondary hemorrhage and progressive hemorrhagic necrosis, for example) are all situations with excess bleeding, and tPA, anti-platelet agents and anticoagulants are contraindicated, because they could worsen the bleeding. Such compounds would not be utilized in cases where there is bleeding or where bleeding is suspected.

The present invention provides compounds that inhibit the $NC_{Ca-ATP}$ channel for the treatment and/or prevention of intraventricular hemorrhage in an individual, wherein the individual is provided one or more inhibitors of the channel. The inhibitor(s) may be of any kind, but in specific embodiments it is an inhibitor of a regulatory subunit of the channel and/or a pore-forming subunit of the channel. In certain aspects a combination or mixture of an antagonist of a regulatory subunit of the channel and an antagonist of a pore-forming subunit of the channel are provided to the individual.

The therapeutic and/or preventative compositions and methods of the invention may be provided to the premature infant following birth, the mother of the premature infant during pregnancy, or the infant in utero. In a specific embodiment, the inhibitor is provided to the mother prior to 37 weeks of gestation. In another specific embodiment, the mother is at risk for premature labor. In a further specific embodiment, the pregnancy is less than 37 weeks in gestation and the mother has one or more symptoms of labor.

Thus, in one embodiment, there is a method of treating intraventricular hemorrhage in the brain of an infant or preventing intraventricular hemorrhage in the brain of an infant at risk for developing intraventricular hemorrhage, comprising administering an effective amount of an inhibitor of $NC_{Ca-ATP}$ channel to the infant following birth and/or the mother prior to birth. In a specific embodiment, the infant is a premature infant. In further specific embodiments, the infant weighs less than 1500 grams at birth or weighs less than 1000 grams at birth. In particular aspects, the infant was born at 36, 35, 34, 33, 32, 31, 30, 29, 28, 27, 26, 25, 24, or at or prior to 23 weeks of gestation.

In one aspect, the present invention provides novel methods of treating a patient comprising administering at least a therapeutic compound that targets the $NC_{Ca-ATP}$ channel, either alone or in combination with an additional therapeutic compound, and in specific embodiments the additional therapeutic compound is methylprednisolone, cation channel blockers and antagonists of VEGF, MMP, NOS, and/or thrombin, for example.

In one embodiment, the therapeutic combinatorial composition can be administered to and/or into the spinal cord injury site, for example. Such administration to the site includes injection directly into the site, for example, particularly in the case where the site has been rendered accessible to injection due to trauma to the spine, for example.

Any compound(s) of the invention can be administered alimentarily (e.g., orally, buccally, rectally or sublingually); parenterally (e.g., intravenously, intradermally, intramuscularly, intraarterially, intrathecally, subcutaneously, intraperitoneally, intraventricularly); by intracavity; intravesically; intrapleurally; and/or topically (e.g., transdermally), mucosally, or by direct injection into the brain parenchyma.

In further embodiments, the compound that inhibits the $NC_{Ca-ATP}$ channel can be administered in combination with, for example, statins, diuretics, vasodilators (e.g., nitroglycerin), mannitol, diazoxide and/or similar compounds that ameliorate ischemic conditions. Yet further, another embodiment of the present invention comprises a pharmaceutical composition comprising statins, diuretics, vasodilators, mannitol, diazoxide or similar compounds that ameliorate ischemic conditions or a pharmaceutically acceptable salt thereof and a compound that inhibits a $NC_{Ca-ATP}$ channel or a pharmaceutically acceptable salt thereof. This pharmaceutical composition can be considered neuroprotective, in specific embodiments. In only certain embodiments of the invention, there are methods and compounds (including pharmaceutical conditions) that concern administration in combination with a compound that inhibits the $NC_{Ca-ATP}$ channel, such as a thrombolytic agent (e.g., tissue plasminogen activator (tPA), urokinase, prourokinase, streptokinase, antistreplase, reteplase, tenecteplase), an anticoagulant or antiplatelet (e.g., aspirin, warfarin or coumadin) may be employed, wherein such compounds would not be contraindicated. For example, the pharmaceutical composition comprising a combination of the thrombolytic agent and a compound that inhibits a $NC_{Ca-ATP}$ channel is therapeutic, because it increases the therapeutic window for the administration of the thrombolytic agent by several hours; for example, the therapeutic window for administration of thrombolytic agents may be increased by several hours (e.g. about 4-about 8 hrs) by co-administering one or more antagonists of the NCCa-ATP channel.

An effective amount of an antagonist of the $NC_{Ca-ATP}$ channel or related-compounds thereof as treatment and/or prevention varies depending upon the host treated and the particular mode of administration. In one embodiment of the invention, the dose range of the therapeutic combinatorial composition of the invention, including an antagonist of $NC_{Ca-ATP}$ channel and/or the additional therapeutic compound, will be about 0.01 µg/kg body weight to about 20,000 µg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg.

An effective amount of an inhibitor of $NC_{Ca-ATP}$ channel that may be administered to an individual or a cell in a tissue or organ thereof includes a dose of about 0.0001 nM to about 2000 µM, for example. More specifically, doses of an antagonist to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 µM to about 500 µM; about 500 µM to about 1000 µM; about 1000 µM to about 1500 µM and about 1500 µM to about 2000 µM, for example. Of course, all of these amounts are exemplary, and any amount in-between these dosages is also expected to be of use in the invention.

An effective amount of an inhibitor of the $NC_{Ca-ATP}$ channel or related-compounds thereof as a treatment varies depending upon the host treated and the particular mode of administration. In one embodiment of the invention the dose range of the agonist or antagonist of the $NC_{Ca-ATP}$ channel or related-compounds thereof will be about 0.01 µg/kg body weight to about 20,000 µg/kg body weight.

In specific embodiments, the dosage is less than 0.8 mg/kg. In particular aspects, the dosage range may be from 0.005 mg/kg to 0.8 mg/kg body weight, 0.006 mg/kg to 0.8 mg/kg body weight, 0.075 mg/kg to 0.8 mg/kg body weight, 0.08 mg/kg to 0.8 mg/kg body weight, 0.09 mg/kg to 0.8 mg/kg body weight, 0.005 mg/kg to 0.75 mg/kg body weight, 0.005 mg/kg to 0.7 mg/kg body weight, 0.005 mg/kg to 0.65 mg/kg body weight, 0.005 mg/kg to 0.5 mg/kg body weight, 0.09 mg/kg to 0.8 mg/kg body weight, 0.1 mg/kg to 0.75 mg/kg body weight, 0.1 mg/kg to 0.70 mg/kg body weight, 0.1 mg/kg to 0.65 mg/kg body weight, 0.1 mg/kg to 0.6 mg/kg body weight, 0.1 mg/kg to 0.55 mg/kg body weight, 0.1 mg/kg to 0.5 mg/kg body weight, 0.1 mg/kg to 0.45 mg/kg body weight, 0.1 mg/kg to 0.4 mg/kg body weight, 0.1 mg/kg to 0.35 mg/kg body weight, 0.1 mg/kg to 0.3 mg/kg body weight, 0.1 mg/kg to 0.25 mg/kg body weight, 0.1 mg/kg to 0.2 mg/kg body weight, or 0.1 mg/kg to 0.15 mg/kg body weight, for example.

In specific embodiments, the dosage range may be from 0.2 mg/kg to 0.8 mg/kg body weight, 0.2 mg/kg to 0.75 mg/kg body weight, 0.2 mg/kg to 0.70 mg/kg body weight, 0.2 mg/kg to 0.65 mg/kg body weight, 0.2 mg/kg to 0.6 mg/kg body weight, 0.2 mg/kg to 0.55 mg/kg body weight, 0.2 mg/kg to 0.5 mg/kg body weight, 0.2 mg/kg to 0.45 mg/kg body weight, 0.2 mg/kg to 0.4 mg/kg body weight, 0.2 mg/kg to 0.35 mg/kg body weight, 0.2 mg/kg to 0.3 mg/kg body weight, or 0.2 mg/kg to 0.25 mg/kg body weight, for example.

In further specific embodiments, the dosage range may be from 0.3 mg/kg to 0.8 mg/kg body weight, 0.3 mg/kg to 0.75 mg/kg body weight, 0.3 mg/kg to 0.70 mg/kg body weight, 0.3 mg/kg to 0.65 mg/kg body weight, 0.3 mg/kg to 0.6 mg/kg body weight, 0.3 mg/kg to 0.55 mg/kg body weight, 0.3 mg/kg to 0.5 mg/kg body weight, 0.3 mg/kg to 0.45 mg/kg body weight, 0.3 mg/kg to 0.4 mg/kg body weight, or 0.3 mg/kg to 0.35 mg/kg body weight, for example.

In specific embodiments, the dosage range may be from 0.4 mg/kg to 0.8 mg/kg body weight, 0.4 mg/kg to 0.75 mg/kg body weight, 0.4 mg/kg to 0.70 mg/kg body weight, 0.4 mg/kg to 0.65 mg/kg body weight, 0.4 mg/kg to 0.6 mg/kg body weight, 0.4 mg/kg to 0.55 mg/kg body weight, 0.4 mg/kg to 0.5 mg/kg body weight, or 0.4 mg/kg to 0.45 mg/kg body weight, for example.

In specific embodiments, the dosage range may be from 0.5 mg/kg to 0.8 mg/kg body weight, 0.5 mg/kg to 0.75 mg/kg body weight, 0.5 mg/kg to 0.70 mg/kg body weight, 0.5 mg/kg to 0.65 mg/kg body weight, 0.5 mg/kg to 0.6 mg/kg body weight, or 0.5 mg/kg to 0.55 mg/kg body weight, for example. In specific embodiments, the dosage range may be from 0.6 mg/kg to 0.8 mg/kg body weight, 0.6 mg/kg to 0.75 mg/kg body weight, 0.6 mg/kg to 0.70 mg/kg body weight, or 0.6 mg/kg to 0.65 mg/kg body weight, for example. In specific embodiments, the dosage range may be from 0.7 mg/kg to 0.8 mg/kg body weight or 0.7 mg/kg to 0.75 mg/kg body weight, for example. In specific embodiments the dose range may be from 0.001 mg/day to 3.5 mg/day. In other embodiments, the dose range may be from 0.001 mg/day to 10 mg/day. In other embodiments, the dose range may be from 0.001 mg/day to 20 mg/day.

Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg. In particular embodiments, there may be dosing of from very low ranges (e.g. 1 mg/kg/day or less; 5 mg/kg bolus; or 1 mg/kg/day) to moderate doses (e.g. 2 mg bolus, 15 mg/day) to high doses (e.g. 5 mg bolus, 30-40 mg/day; and even higher). Of course, all of these dosages are exemplary, and any dosage in-between these dosages is also expected to be of use in the invention. Any of the above dosage ranges or dosage levels may be employed for an agonist or antagonist, or both, of $NC_{Ca-ATP}$ channel or related-compounds thereof.

An effective amount of a therapeutic composition of the invention, including an antagonist of $NC_{Ca-ATP}$ channel and/or the additional therapeutic compound, that may be administered to a cell includes a dose of about 0.0001 nM to about 2000 µM, for example. More specifically, doses to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 µM to about 500 µM; about 500 µM to about 1000

µM; about 1000 µM to about 1500 µM and about 1500 µM to about 2000 µM, for example. Of course, all of these amounts are exemplary, and any amount in-between these dosages is also expected to be of use in the invention.

In particular embodiments, there may be dosing of from very low ranges (e.g. for glyburide 1 mg/day or less) to moderate doses (e.g. 3.5 mg/day) to high doses (e.g. 10-40 mg/day; and even higher). Of course, all of these dosages are exemplary, and any dosage in-between these dosages is also expected to be of use in the invention. Any of the above dosage ranges or dosage levels may be employed for an agonist or antagonist, or both, of $NC_{Ca-ATP}$ channel or related-compounds thereof.

In a particular embodiment, the dosage is about 0.5 mg/day too about 10 mg/day.

In certain embodiments, the amount of the combinatorial therapeutic composition administered to the subject is in the range of about 0.0001 µg/kg/day to about 20 mg/kg/day, about 0.01 µg/kg/day to about 100 µg/kg/day, or about 100 µg/kg/day to about 20 mg/kg/day. Still further, the combinatorial therapeutic composition may be administered to the subject in the form of a treatment in which the treatment may comprise the amount of the combinatorial therapeutic composition or the dose of the combinatorial therapeutic composition that is administered per day (1, 2, 3, 4, etc.), week (1, 2, 3, 4, 5, etc.), month (1, 2, 3, 4, 5, etc.), etc. Treatments may be administered such that the amount of combinatorial therapeutic composition administered to the subject is in the range of about 0.0001 µg/kg/treatment to about 20 mg/kg/treatment, about 0.01 µg/kg/treatment to about 100 µg/kg/treatment, or about 100 µg/kg/treatment to about 20 mg/kg/treatment.

A typical dosing regime consists of a loading dose designed to reach a target agent plasma level followed by an infusion of up to 7 days to maintain that target level. One skilled in the art will recognize that the pharmacokinetics of each agent will determine the relationship between the load dose and infusion rate for a targeted agent plasma level. In one example, for intravenous glyburide administration, a 15.7 µg bolus (also called a loading dose) is followed by a maintenance dose of 0.3 µg/min (432 µg/day) for 120 hours (5 days). This dose regime is predicted to result in a steady-state plasma concentration of 4.07 ng/mL. In another example for intravenous glyburide, a 117 µg bolus dose is followed by a maintenance dose of 2.1 µg/min (3 mg/day) for 3 days. This dose is predicted to result in a steady-state plasma concentration of 28.3 ng/mL. In yet another example for glyburide, a 665 µg bolus dose is followed by a maintenance dose of 11.8 µg/min (17 mg/day) for 120 hours (5 days). This dose is predicted to result in a steady-state plasma concentration of 160.2 ng/mL. Once the pharmacokinetic parameters for an agent are known, loading dose and infusion dose for any specified targeted plasma level can be calculated. As an illustrative case for glyburide, the bolus is generally 30-90 times, for example 40-80 times, such as 50-60 times, the amount of the maintenance dose, and one of skill in the art can determine such parameters for other compounds based on the guidance herein.

In cases where combination therapies are utilized, the components of the combination may be of any kind. In specific embodiments, the components are provided to an individual substantially concomitantly, whereas in other cases the components are provided at separate times. The ratio of the components may be determined empirically, as is routine in the art. Exemplary ratios include at least about the following: 1:1, 1:2, 1:3, 1:4, 1:5, 1:6, 1:7, 1:8, 1:9, 1:10, 1:20, 1:25, 1:30, 1:40, 1:50, 1:60, 1:70, 1:80, 1:90, 1:100, 1:500, 1:750, 1:1000, 1:10000, and so forth.

In particular embodiments, there may be dosing of from very low ranges (e.g. 1 mg/kg/day or less; 5 mg/kg bolus; or 1 mg/kg/day) to moderate doses (e.g. 2 mg bolus, 15 mg/day) to high doses (e.g. 5 mg bolus, 30-40 mg/day; and even higher). Of course, all of these dosages are exemplary, and any dosage between these points is also expected to be of use in the invention. Any of the above dosage ranges or dosage levels may be employed for an antagonist of $NC_{Ca-ATP}$ channel or related-compounds thereof and, in appropriate cases, of an additional compound.

In certain embodiments, the amount of the singular or combinatorial therapeutic composition administered to the subject is in the range of about 0.0001 µg/kg/day to about 20 mg/kg/day, about 0.01 µg/kg/day to about 100 µg/kg/day, or about 100 µg/kg/day to about 20 mg/kg/day. Still further, the combinatorial therapeutic composition may be administered to the subject in the form of a treatment in which the treatment may comprise the amount of the combinatorial therapeutic composition or the dose of the combinatorial therapeutic composition that is administered per day (1, 2, 3, 4, etc.), week (1, 2, 3, 4, 5, etc.), month (1, 2, 3, 4, 5, etc.), etc. Treatments may be administered such that the amount of combinatorial therapeutic composition administered to the subject is in the range of about 0.0001 µg/kg/treatment to about 20 mg/kg/treatment, about 0.01 µg/kg/treatment to about 100 µg/kg/treatment, or about 100 µg/kg/treatment to about 20 mg/kg/treatment.

In those cases wherein more than one compound is provided to an individual to treat intraventricular hemorrhage or spinal cord injury and, in particular, progressive hemorrhagic necrosis, the compounds may be provided in a mixture, may be provided simultaneously, or may be provided sequentially. In cases where more than one composition is provided to the individual, they may be provided in a particular ratio including, for example, in a 1:1 ratio, a 1:2 ratio, a 1:3 ratio, a 1:4 ratio, and so forth.

In one embodiment of the invention, there is a composition, comprising a compound that inhibits a $NC_{Ca-ATP}$ channel and an additional therapeutic compound, wherein the additional therapeutic compound is selected from the group consisting of: a) one or more cation channel blockers; and b) one or more of a compound selected from the group consisting of one or more antagonists of vascular endothelial growth factor (VEGF), one or more antagonists of matrix metalloprotease (MMP), one or more antagonists of nitric oxide synthase (NOS), one or more antagonists of thrombin, aquaporin, or a biologically active derivative thereof, wherein the $NC_{Ca-ATP}$ channel has the following characteristics: 1) it is a non-selective monovalent cation channel; 2) it is activated by an increase in intracellular calcium or by a decrease in intracellular ATP, or both; and 3) it is regulated by a SUR1.

In a further specific embodiment, one or more antagonists of vascular endothelial growth factor (VEGF) are soluble neuropilin 1 (NRP-1), undersulfated LMW glycol-split heparin, VEGF TrapR1R2, Bevacizumab, HuMV833, s-Flt-1, s-Flk-1, s-Flt-1/Flk-1, NM-3, GFB 116, or a combination or mixture thereof. In an additional specific embodiment, the undersulfated, LMW glycol-split heparin comprises ST2184. In an additional specific embodiment, the one or more antagonists of matrix metalloprotease (MMP) are (2R)-2-[(4-biphenylsulfonyl)amino]-3-phenylproprionic acid, GM-6001, TIMP-1, TIMP-2, RS 132908, batimastat, marimastat, a peptide inhibitor that comprises the amino acid sequence HWGF, or a mixture or combination thereof.

In one aspect of the invention, the one or more antagonists of nitric oxide synthase (NOS) are aminoguanidine (AG), 2-amino-5,6-dihydro-6-methyl-4H-1,3 thiazine (AMT), S-ethylisothiourea (EIT), asymmetric dimethylarginine (ADMA), N-nitro-L-arginine methylester (L-NAME), nitro-L-arginine (L-NA), N-(3-aminomethyl)benzylacetamidine dihydrochloride (1400W), NG-monomethyl-L-arginine (L-NMMA), 7-nitroindazole (7-NINA), N-nitro-L-arginine (L-NNA), or a mixture or combination thereof. In another aspect of the invention, the one or more antagonists of thrombin are ivalirudi, hirudin, SSR182289, antithrombin III, thrombomodulin, lepirudin, P-PACK II (d-Phenylalanyl-L-Phenylalanylarginine-chloro-methyl ketone 2HCl), (BNas-Gly-(pAM)Phe-Pip), Argatroban, and mixtures or combinations thereof.

In a specific embodiment wherein an additional compound other than the channel inhibitor is employed, the compound that inhibits the $NC_{Ca-ATP}$ channel and the additional therapeutic compound are delivered to the individual successively. In another specific embodiment, the compound that inhibits the $NC_{Ca-ATP}$ channel is delivered to the individual prior to delivery of the additional therapeutic compound. In a further specific embodiment, the compound that inhibits the $NC_{Ca-ATP}$ channel is delivered to the individual subsequent to delivery of the additional therapeutic compound. In another aspect, the compound that inhibits the $NC_{Ca-ATP}$ channel and the additional therapeutic compound are delivered to the individual concomitantly. In an additional aspect, the compound that inhibits the $NC_{Ca-ATP}$ channel and the additional therapeutic compound being delivered as a mixture. In an additional embodiment, the compound that inhibits the $NC_{Ca-ATP}$ channel and the additional therapeutic compound act synergistically in the individual. In a particular case, the compound that inhibits the $NC_{Ca-ATP}$ channel and/or the additional therapeutic compound is delivered to the individual at a certain dosage or range thereof, such as is provided in exemplary disclosure elsewhere herein.

In particular embodiments, the methods of the invention are employed within a certain amount of time of a spinal cord injury or intraventricular hemorrhage, for example. In specific embodiments, the composition(s) is delivered to the individual within minutes, hours, days, or months of the injury. In further specific embodiments, the composition(s) are delivered to the individual within 10 minutes, within 15 minutes, within 30 minutes, within 45 minutes, within 60 minutes, within 75 minutes, within 90 minutes, within 2 hours, within 2.5 hours, within 3 hours, within 3.5 hours, within 4 hours, within 4.5 hours, within 5 hours, within 5.5 hours, within 6 hours, within 6.5 hours, within 7 hours, within 7.5 hours, within 8 hours, within 8.5 hours, within 9 hours, within 9.5 hours, within 10 hours, within 10.5 hours, within 11 hours, within 11.5 hours, within 12 hours, within 13 hours, within 14 hours, within 15 hours, within 16 hours, within 17 hours, within 18 hours, within 20 hours, within 22 hours, within 24 hours, and so on, of the time of the spinal cord injury. In specific cases, the composition(s) of the invention are present at places where spinal cord injury may occur (swimming pools, stables, ski resorts, gymnasiums, nursing homes, sports arenas or fields, schools, etc.), are present in first aid kits, are present in emergency vehicles, are present in hospitals, including emergency rooms, and/or are present in doctors' offices.

In a specific embodiment of the invention, the compound that inhibits the $NC_{Ca-ATP}$ channel is glibenclamide, and the maximum dosage of glibenclamide for the individual is about 20 mg/day. In a further specific embodiment, the compound that inhibits the $NC_{Ca-ATP}$ channel is glibenclamide, and the dosage of glibenclamide for the individual is between about 2.5 mg/day and about 20 mg/day. In an additional specific embodiment, the compound that inhibits the $NC_{Ca-ATP}$ channel is glibenclamide, and the dosage of glibenclamide for the individual is between about 5 mg/day and about 15 mg/day. In another specific embodiment, the compound that inhibits the $NC_{Ca-ATP}$ channel is glibenclamide, and the dosage of glibenclamide for the individual is between about 5 mg/day and about 10 mg/day. In a still further specific embodiment, the compound that inhibits the $NC_{Ca-ATP}$ channel is glibenclamide, and the dosage of glibenclamide for the individual is about 7 mg/day.

In one exemplary embodiment concerning singular therapeutic compositions of the invention, there is a method of inhibiting neural cell swelling in an individual having traumatic brain injury, cerebral ischemic, central nervous system (CNS) damage, peripheral nervous system (PNS) damage, cerebral hypoxia, or edema, comprising delivering to the individual a therapeutically effective amount of an antagonist of TRMP4. In specific embodiments, the antagonist of TRMP4 is a nucleic acid (such as a TRMP4 siRNA, for example), a protein, a small molecule, or a combination thereof. In particular aspects, the method further comprises delivering to the individual a therapeutically effective amount of an additional therapeutic compound selected from the group consisting of: a) a SUR1 antagonist; b) one or more cation channel blockers; b) one or more of a compound selected from the group consisting of one or more antagonists of vascular endothelial growth factor (VEGF), one or more antagonists of matrix metalloprotease (MMP), one or more antagonists of nitric oxide synthase (NOS), one or more antagonists of thrombin, aquaporin, a biologically active derivative thereof, and a combination thereof; and d) a combination thereof.

In one embodiment of the invention, there is a method for processing an insurance claim for treatment of a medical condition of the invention using a composition(s) of the invention. In a specific embodiment, the method employs a computer for said processing. In further specific embodiments, the dosage for the composition may be any suitable dosage for treatment of the medical condition.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIGS. 14A-4B show that a percussion TBI model produces deep contusion injury. A,B: Unprocessed (A) and Niss1 stained (B) coronal sections from two different rats 24 hr following moderate-to-severe percussion injury (2.5-3 atm) to the posterior parasagittal parietal cortex; note extensive hemorrhagic contusion involving cortex, corpus callosum and underlying hippocampus.

DETAILED DESCRIPTION OF THE INVENTION

Figure 1:
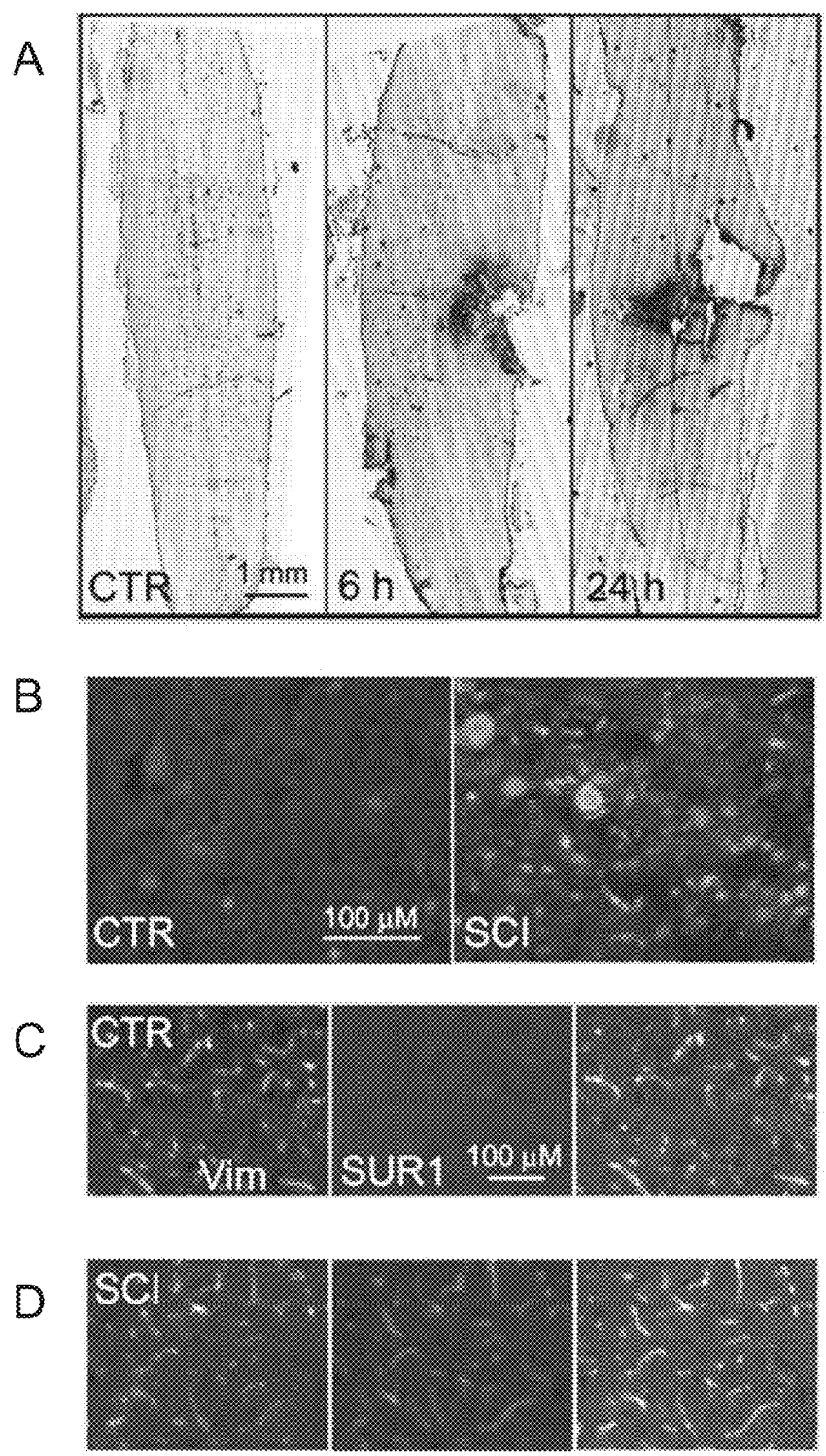
FIG. 1 shows that SUR1 is up-regulated in SCI. a: Immunohistochemical localization of SUR1 in control and at different times post-SCI, as indicated, with montages constructed from multiple individual images, and positive labeling shown in black pseudocolor. b: Magnified views of SUR1 immunolabeled sections taken from control and from the "core" (heavily labeled area in a, 6 h). c,d: Immunolabeling of capillaries with vimentin and co-labeling with SUR1 in control (c), and from the "penumbra" (tissue adjacent to the heavily labeled core in a, 6 h) (d). e: Western blots for SUR1 of spinal cord tissue from control (lanes 1, 2), 6 h post-SCI (lanes 3, 4) and from an equivalent amount of blood (BL) as is present in the injured cord (lane 5); 50 μg protein in lanes 1-4, 2 μl blood in lane 5; blots representative of 5-6 CTR and SCI rats. f,g: In situ hybridization for SUR1 in controls and in whole cords (f) or in the penumbra (g) 6 h post-SCI using antisense (AS) and sense (SE), as indicated. Images of immunohistochemistry and in situ hybridization representative of findings in 3-5 rats/group.
Figure 1:
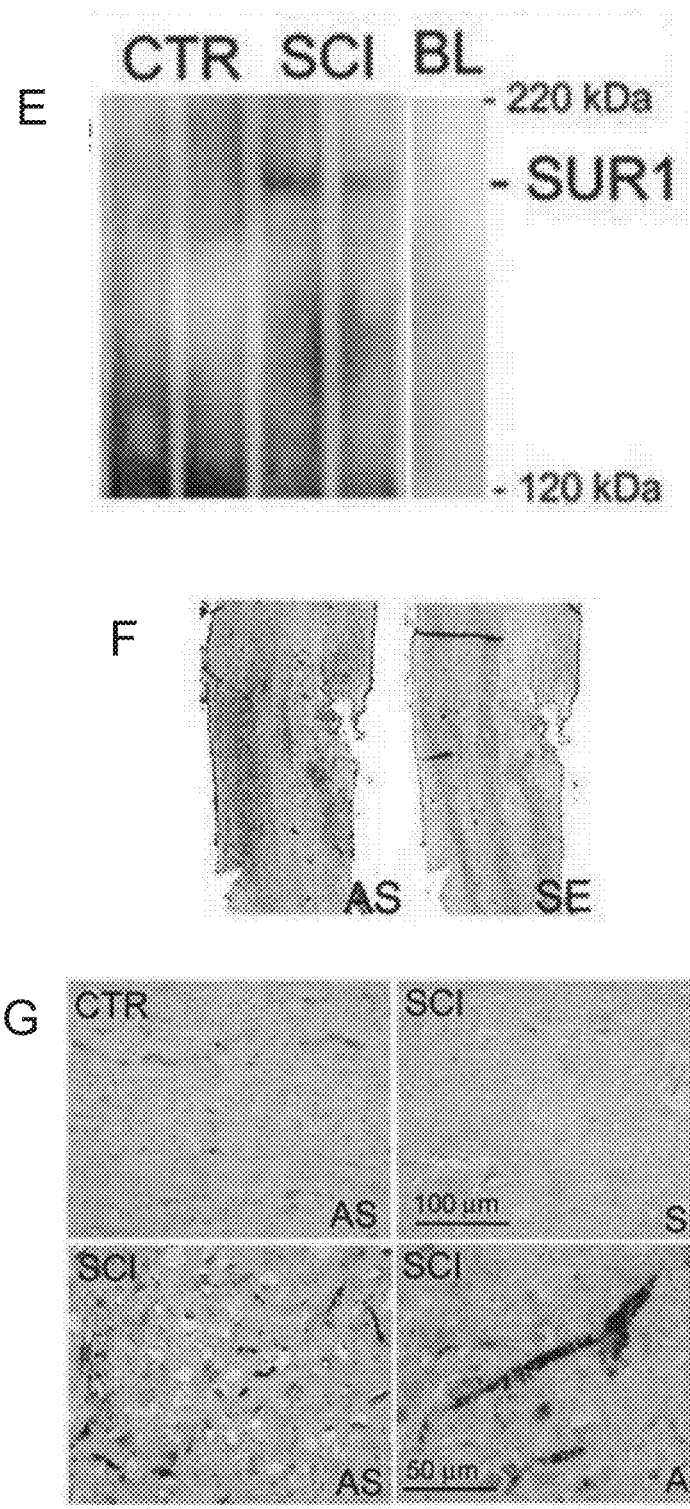

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references, for example.

As used herein the specification, "a" or "an" may mean one or more. As used herein in the claim(s), when used in conjunction with the word "comprising", the words "a" or "an" may mean one or more than one. As used herein "another"

may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein.

The present application incorporates by reference herein in their entirety the following applications: U.S. patent application Ser. No. 11/099,332, filed Apr. 5, 2005; U.S. patent application Ser. No. 11/359,946, filed Feb. 22, 2006; U.S. patent application Ser. No. 11/229,236, filed Sep. 16, 2005; U.S. patent application Ser. No. 11/574,793, filed Jul. 25, 2005; U.S. Patent Application Ser. No. 60/880,119, filed Jan. 12, 2007; and U.S. Patent Application Ser. No. 60/889,065, filed Feb. 9, 2007.

I. Exemplary Definitions

As used herein, "about" refers to a numeric value, including, for example, whole numbers, fractions, and percentages, whether or not explicitly indicated. The term "about" generally refers to a range of numerical values (e.g., +/−5-10% of the recited value) that one would consider equivalent to the recited value (e.g., having the same function or result). In some instances, the term "about" may include numerical values that are rounded to the nearest significant figure.

As used herein, the term "antagonist" refers to a biological or chemical agent that acts within the body to reduce the physiological activity of another chemical or biological substance. In the present invention, the antagonist blocks, inhibits, reduces and/or decreases the activity of a $NC_{Ca-ATP}$ channel of any cell. In the present invention, the antagonist combines, binds, associates with a $NC_{Ca-ATP}$ channel of a cell, such as an endothelial cell, including cells in capillary endothelium, neurons or neuron-like cells, or reactive astrocytes, for example, such that the $NC_{Ca-ATP}$ channel is closed (deactivated), meaning reduced biological activity with respect to the biological activity in the diseased state. In certain embodiments, the antagonist combines, binds and/or associates with a regulatory subunit of the $NC_{Ca-ATP}$ channel, particularly a SUR1: combines, binds, and/or associates with a pore-forming subunit of the $NC_{Ca-ATP}$ ATP channel, such as TRPM4; or both. The terms antagonist or inhibitor can be used interchangeably.

As used herein, antagonists, inhibitors, and blockers of the $NC_{Ca-ATP}$ channel are those agents that reduce the activity or expression of the $NC_{Ca-ATP}$ channel, and may include (but are not limited to) SUR1 antagonists, TRPM4 antagonists, antisense molecules that inhibit expression of the $NC_{Ca-ATP}$ channel, MgADP, blockers of $K_{ATP}$ channel, agents that inhibit incorporation of the $NC_{Ca-ATP}$ channel into the cell membrane, and other compounds and agents that prevent or reduce the activity of the $NC_{Ca-ATP}$ channel. For example, non-sulfonyl urea compounds, such as 2,3-butanedione and 5-hydroxydecanoic acid, quinine, and therapeutically equivalent salts and derivatives thereof, may be employed as antagonists, inhibitors, and blockers of the $NC_{Ca-ATP}$ channel. An inhibitor may comprise a protein, a peptide, a nucleic acid (such as an RNAi molecule or antisense RNA, including siRNA), or a small molecule.

As used herein, the term "depolarization" refers to a change in the electrical potential difference across the cell membrane (between the inside of the cell and the outside of the cell, with outside taken as ground potential), where that electrical potential difference is reduced, eliminated, or reversed in polarity. Activation of a non-selective channel, such as the $NC_{Ca-ATP}$ channel, will typically increase in the permeability of the cell membrane to sodium and other ions effective to reduce the magnitude, and may nearly or completely eliminate, the electrical potential difference across a cell membrane.

As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition, but may not be a complete cure of the disease and/or condition.

As used herein, the term "endothelium" refers to a layer of cells that line the inside surfaces of body cavities, blood vessels, and lymph vessels or that form capillaries.

As used herein, the term "endothelial cell" refers to a cell of the endothelium or a cell that lines the surfaces of body cavities, for example, blood or lymph vessels or capillaries. In certain embodiments, the term endothelial cell refers to a neural endothelial cell or an endothelial cell that is part of the nervous system, for example the central nervous system or the brain or spinal cord.

As used herein, the term "inhibit" refers to the ability of the compound to block, partially block, interfere, decrease, reduce or deactivate a channel such as the $NC_{Ca-ATP}$ channel. Thus, one of skill in the art understands that the term inhibit encompasses a complete and/or partial loss of activity of a channel, such as the $NC_{Ca-ATP}$ channel. Channel activity may be inhibited by channel block (occlusion or closure of the pore region, preventing ionic current flow through the channel), by changes in an opening rate or in the mean open time, changes in a closing rate or in the mean closed time, or by other means. For example, a complete and/or partial loss of activity of the $NC_{Ca-ATP}$ channel as may be indicated by a reduction in cell depolarization, reduction in sodium ion influx or any other monovalent ion influx, reduction in an influx of water, reduction in extravasation of blood, reduction in cell death, as well as an improvement in cellular survival following an ischemic challenge.

As used herein, the term "inhibits the $NC_{Ca-ATP}$ channel" refers to a reduction in, cessation of, or blocking of, the activity of the $NC_{Ca-ATP}$ channel, including inhibition of current flow through the channel, inhibition of opening of the channel, inhibition of activation of the channel, inhibition or reduction of the expression of the channel, including inhibition or reduction of genetic message encoding the channel and inhibition or reduction of the production channel proteins, inhibition or reduction of insertion of the channel into the plasma membrane of a cell, or other forms of reducing the physiologic activity of the $NC_{Ca-ATP}$ channel.

The term "morbidity" as used herein is the state of being diseased. Yet further, morbidity can also refer to the disease rate or the ratio of sick subjects or cases of disease in to a given population.

The term "mortality" as used herein is the state of being mortal or causing death. Yet further, mortality can also refer to the death rate or the ratio of number of deaths to a given population.

The term "preventing" as used herein refers to minimizing, reducing or suppressing the risk of developing a disease state or parameters relating to the disease state or progression or other abnormal or deleterious conditions.

As used herein, the term "reduces" refers to a decrease in cell death, inflammatory response, hemorrhagic conversion, extravasation of blood, etc. as compared to no treatment with the compound of the present invention. Thus, one of skill in the art is able to determine the scope of the reduction of any of the symptoms and/or conditions associated with a spinal cord injury in which the subject has received the treatment of the present invention compared to no treatment and/or what would otherwise have occurred without intervention.

As used herein, the terms "SUR1 antagonist," "SUR1 inhibitor," and "SUR1 blocker" and their grammatical variants may be used interchangeably and each refers to compounds that reduce the activity or effect of the receptors SUR1, and include (but are not limited to) such compounds as, for example, glibenclamide (also known as glyburide), tolbutamide, repaglinide, nateglinide, meglitinide, midaglizole, LY397364, LY389382, glyclazide, glimepiride, estrogen, estrogen related-compounds (estradiol, estrone, estriol, genistein, non-steroidal estrogen (e.g., diethylstilbestrol), phytoestrogen (e.g., coumestrol), zearalenone, etc.) and combinations thereof. Chemical names of some SUR1 antagonists include: glibenclamide (1 [p-2[5-chloro-O-anisamido) ethyl]phenyl]sulfonyl]-3-cyclohexyl-3-urea); chlorpropamide(1-[[(p-chlorophenyl)sulfonyl]-3-propylurea; glipizide (1-cyclohexyl-3 [[p-[2(5-methylpyrazine carboxamido)ethyl]phenyl]sulfonyl]urea); and tolazamide(benzenesulfonamide-N-[[(hexahydro-1H-azepin-1yl)amino] carbonyl]-4-methyl)

As used herein, the terms "TRPM4 antagonist," "TRPM4 inhibitor," and "TRPM4 blocker" and their grammatical variants may be used interchangeably and each refers to compounds that reduce the activity or effect of the TRPM4 channel, e.g. by reducing or blocking the flow of ions through the TRPM4 pore, and include (but are not limited to) such compounds as, for example, pinkolant, rimonabant, a fenamate (such as flufenamic acid, mefenamic acid, meclofenamic acid, or niflumic acid), 1-(beta-[3-(4-methoxy-phenyl)propoxy]-4-methoxyphenethyl)-1H-imidazole hydrochloride, and a biologically active derivatives thereof.

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

II. Exemplary Embodiments of the Invention

In particular cases of the invention, there are methods and/or compositions for the treatment and/or prevention of spinal cord injury, brain injury, and other damage to the nervous system, such as, e.g., injury related to progressive hemorrhagic necrosis, and intraventricular hemorrhage.

A. Intraventricular Hemorrhage

In exemplary embodiments of the invention, there are methods and compositions and kits for the treatment and/or prevention of intraventricular hemorrhage in an individual. The present invention concerns a specific channel, the $NC_{Ca\text{-}ATP}$ channel, which is expressed, for example, in the vasculature endothelium and germinal matrix following intraventricular hemorrhage (IVH). This unique non-selective cation channel is activated by intracellular calcium and blocked by intracellular ATP ($NC_{Ca\text{-}ATP}$ channel), and can be also be expressed in, for example, neural cells, such as neuronal cells, neuroglia cells (also termed glia, or glial cells, e.g., astrocyte, ependymal cell, oligodendrocyte and microglia) or endothelial cells (e.g., capillary endothelial cells) in which the cells have been or are exposed to a traumatic insult, for example, an acute insult (e.g., hypoxia, ischemia, tissue compression, mechanical distortion, cerebral edema or cell swelling), toxic compounds or metabolites, an acute injury, cancer, and brain abscess.

Without being bound by theory, it is believed that the hypoxic-ischemic environment in prematurity leads to transcriptional activation of SUR1 and opening of NC(Ca-ATP) channels in IVH, initiating a cascade of events culminating in acute hemorrhage in parallel with ischemic stroke.

Intraventricular hemorrhage is bleeding into ventricular spaces, which are spaces in the brain that carry cerebrospinal fluid. Following birth, the premature infant's brain is exposed to changes in blood flow and oxygen levels, which may cause the many tiny, fragile blood vessels of the infant's brain to break and bleeding to occur. Such an event happens usually in babies who are extremely premature or who have medical problems during or after birth. Intraventricular hemorrhage often occurs in very low birthweight babies weighing less than 1,500 grams. Almost all IVH occurs within the first week of life.

Babies with respiratory problems such as hyaline membrane disease, or other complications of prematurity, are at greater risk to have IVH. The smaller and more premature the baby, the more likely IVH will occur. Although many babies have no symptoms at the time that bleeding occurs, some infants do have symptoms, including apnea, bradycardia, poor muscle tone, decreased activity, anemia, seizures, high-pitched cry, weak suck, cyanosis, and/or bulging fontanel.

Infants at risk for IVH may have an ultrasound of the head to look for bleeding in the first days following birth. IVH is graded on a scale of one to four, with grade IV being most severe. Grade 1 is considered when bleeding occurs just in a small area of the ventricles; in Grade 2, bleeding also occurs inside the ventricles; in Grade 3, ventricles are enlarged by the blood; and in Grade 4, there is bleeding into the brain tissues around the ventricles.

More than half of babies born weighing less than 1,000 grams have intraventricular hemorrhages, although most of these bleeds are mild (Grade I or II), and many resolve with few or no problems, wherein, for example, the body absorbs the blood. In more severe cases (Grade III or IV), however, as blood absorbs there can be damage to the brain tissue, and these cases (especially Grade IV) can result in additional problems, such as enlarged ventricles, hydrocephalus, cerebral palsy, hearing loss, vision problems, and/or learning disabilities, for example.

In some cases, the infant develops hydrocephalus, which may be treated by medicines to decrease the amount of spinal fluid that the brain makes, frequent lumbar punctures (LPs), reservoir, or shunt.

Long-term abnormalities that may occur following intraventricular hemorrhage include at least motor (movement) problems (tight or stiff muscles; slow to crawl, stand, or walk; abnormal crawling, toe walking; moving one side more than the other; frequent arching of the back (not just when angry or at play); slow mental development (does not listen to the parent voice by age 3-4 months after hospital discharge; does not make different sounds by 8-9 months after discharge; does not seem to understand or say any words by 12-13 months after discharge); seizure; deafness; blindness; poor coordination or balance; specific learning disabilities (math or reading); very short attention span; behavioral problems; difficulty with activities that require coordination of the eyes and hands, for example, catching a ball or copying a simple drawing; and vision correction, for example.

Prior to the present invention, there was no treatment for intraventricular hemorrhage itself, although mother's between 24 and 34 weeks of gestation and may be at risk for early delivery may be provided corticosteroids before delivery, which has been shown to lower the risk of IVH in the baby.

In other embodiments, the present invention is drawn to the regulation and/or modulation of this $NC_{Ca-ATP}$ channel and how its modulation can be used to treat various diseases and/or conditions, for example, IVH. In specific embodiments, the modulation and/or regulation of the channel results from administration of an antagonist or inhibitor of the channel. Thus, depending upon the disease state or progression, a composition (an antagonist or inhibitor) is administered to block or inhibit at least in part the channel to prevent cell death, for example, that results from IVH. In these instances, the channel is blocked to prevent or reduce or modulate, for example, depolarization of the cells or other pathological conditions associated with IVH.

In one aspect, the present invention provides novel methods of treating a patient comprising administering at least a therapeutic compound that targets a unique non-selective cation channel activated by intracellular calcium and blocked by intracellular ATP ($NC_{Ca-ATP}$ channel), in combination with an additional therapeutic compound. In specific embodiments, the therapeutic compound that targets the channel may be an antagonist (such as a SUR1 inhibitor or a TRPM4 inhibitor, for example) that is employed in therapies, such as treatment of IVH, whereby blocking and/or inhibiting the $NC_{Ca-ATP}$ channel ameliorates pathological conditions associated with IVH.

In certain embodiments, additional compounds for the compositions of the invention include cation channel blockers and antagonists of VEGF, MMP, NOS, and/or thrombin, for example.

Further embodiments comprises a method of treating a subject at risk of IVH comprising administering to the subject a combinatorial therapeutic composition effective at least in part to inhibit a $NC_{Ca-ATP}$ channel in a cell, such as, for example, an endothelial cell, germinal matrix tissue, or a combination thereof.

The invention also encompasses the use of such compounds in combinatorial compositions that at least in part modulate $NC_{Ca-ATP}$ channel activity to treat, for example, IVH. In certain embodiments, IVH causes cell swelling resulting in cellular damage (including, for example, cell death). Further provided by the invention is a method of preventing cellular swelling and the resulting cellular damage through the therapeutic use of antagonists to the $NC_{Ca-ATP}$ channel, in combination with an additional therapeutic compound. In one embodiment, the therapeutic combinatorial composition can be administered to a premature infant subject to or undergoing IVH. The invention further provides the therapeutic use of sulfonylurea compounds as antagonists to the $NC_{Ca-ATP}$ channel to treat IVH. In one embodiment the sulfonylurea compound is glibenclamide. In another embodiment, the sulfonylurea compound is tolbutamide, or any of the other compounds that have been found to promote insulin secretion by acting on KATP channels in pancreatic $\beta$ cells, as listed elsewhere herein.

In certain embodiments, $NC_{Ca-ATP}$ channel is blocked, inhibited, or otherwise is decreased in activity. In such examples, an antagonist of the $NC_{Ca-ATP}$ channel is administered and/or applied. The antagonist modulates the $NC_{Ca-ATP}$ channel such that flux (ion and/or water) through the channel is reduced, ceased, decreased and/or stopped. The antagonist may have a reversible or an irreversible activity with respect to the activity of the $NC_{Ca-ATP}$ channel IVH. Thus, inhibition of the $NC_{Ca-ATP}$ channel can reduce cytotoxic edema and death of endothelial cells which are associated IVH.

Accordingly, the present invention is useful in the treatment or prevention of IVH. According to a specific embodiment of the present invention the administration of effective amounts of the active compound can block the channel, which if remained open leads to cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen related-compounds and combinations thereof. In a preferred embodiment of the invention the SUR1 antagonists is selected from the group consisting of glibenclamide and tolbutamide. Another antagonist that can be used is MgADP. Still other therapeutic "strategies" for preventing cell swelling and cell death can be adopted including, but not limited to methods that maintain the cell in a polarized state and methods that prevent strong depolarization.

In certain embodiments, the invention encompasses antagonists of the $NC_{Ca-ATP}$ channel, including small molecules, large molecules, and antibodies, as well as nucleotide sequences that can be used to inhibit $NC_{Ca-ATP}$ channel gene expression (e.g., antisense and ribozyme molecules). An antagonist of the $NC_{Ca-ATP}$ channel includes one or more compounds capable of (1) blocking the channel; (2) preventing channel opening; (3) reducing the magnitude of membrane current through the channel; (4) inhibiting transcriptional expression of the channel; and/or (5) inhibiting post-translational assembly and/or trafficking of channel subunits.

In certain embodiments of the invention, several pathways to cell death are involved in IVH, which require monovalent or divalent cation influx, implicating non-selective cation (NC) channels. In specific embodiments, NC channels are also likely to be involved in the dysfunction of vascular endothelial cells that leads to formation of edema IVH. In other specific embodiments, blockers of NC channels, including pinokalant (LOE 908 MS) and rimonabant (SR141716A) can be administered to treat IVH.

In other embodiments of the invention, IVH causes capillary dysfunction, resulting in edema formation and hemorrhagic conversion. In specific embodiments, the invention generally concerns the central role of Starling's principle, which states that edema formation is determined by the "driving force" and capillary "permeability pore." In particular aspects related to the invention, movements of fluids are driven largely without new expenditure of energy. In one embodiment, the progressive changes in osmotic and hydrostatic conductivity of abnormal capillaries is organized into 3 phases: formation of ionic edema, formation of vasogenic edema, and catastrophic failure with hemorrhagic conversion. In certain embodiments, IVH capillary dysfunction is attributed to de novo synthesis of a specific ensemble of proteins that determine the terms for osmotic and hydraulic conductivity in Starling's equation, and whose expression is driven by a distinct transcriptional program.

Another embodiment of the present invention comprises a method of reducing morbidity and morality of a subject suffering from IVH comprising administering to the subject a therapeutic composition comprising a single $NC_{Ca-ATP}$ channel inhibitor or a combinatorial therapeutic composition effective to inhibit $NC_{Ca-ATP}$ channels in a cell, including, for example, an endothelial cell, germinal matrix tissue, or a combination thereof. In specific embodiments, morbidity and mortality includes, for example, death, shunt-dependent hydrocephalus, and life-long neurological consequences such as cerebral palsy, seizures, mental retardation, and other neurodevelopmental disabilities.

In specific embodiments, the individual is an infant, including a premature infant, although in alternative embodiments the individual is a child or adult. The treatment and/or prevention may occur prior and/or following birth of the infant, and the treatment and/or prevention may be directed to the mother during pregnancy, in specific embodiments. In particular cases, the pregnant mother is at risk for delivery prematurely and may be provided methods and compositions of the invention to treat and/or prevent intraventricular hemorrhage in the infant following birth. Women at risk for preterm delivery include at least if they have one or more of the following conditions or situations: pregnant with multiples; have had a previous premature birth; have certain uterine or cervical abnormalities; recurring bladder and/or kidney infections; urinary tract infections, vaginal infections, and sexually transmitted infections; infection with fever (greater than 101 degrees F.) during pregnancy; unexplained vaginal bleeding after 20 weeks of pregnancy; chronic illness such as high blood pressure, kidney disease or diabetes; multiple first trimester abortions or one or more second trimester abortions; underweight or overweight before pregnancy; clotting Disorder (thrombophilia); being Pregnant with a single fetus after in vitro fertilization (IVF); short time between pregnancies (less than 6-9 months between birth and beginning of the next pregnancy); little or no prenatal care; smoking; drinking alcohol; using illegal drugs; victim of domestic violence, including physical, sexual or emotional abuse; lack of social support; high levels of stress; low income; and/or long working hours with long periods of standing.

Thus, in women at risk for preterm delivery, the mother or infant (in utero) may be provided methods and/or compositions of the invention, including women at risk for developing premature labor or who have symptoms of having premature labor, such as having labor symptoms prior to 37 weeks of gestation. Alternatively, or in addition, the inventive methods and/or compositions may be provided to the infant following birth.

The treatment and/or prevention of intraventricular hemorrhage utilizes inhibitors of a $NC_{Ca-ATP}$ channel, and in particular cases this channel is upregulated in brain tissues prior to and/or during onset of intraventricular hemorrhage. In certain aspects, the channel is upregulated in endothelial cells in the brain, neural cells, including neuronal cells, and so forth. In specific embodiments, the inhibitors are directed to a regulatory component of the channel and/or a pore-forming subunit of the channel, although other components of the channel may be targeted, or example. The inhibitors, in particular cases, are directed to SUR1, a regulatory subunit of the channel, TRPM4, a pore-forming subunit of the channel, or they may be mixtures or combinations thereof. SUR1 inhibitors include sulfonylurea compounds, benzamido derivatives, or mixtures thereof.

In a specific embodiment, the inhibitor is provided to the mother prior to 37 weeks of gestation. In another specific embodiment, the mother is at risk for premature labor. In a further specific embodiment, the pregnancy is less than 37 weeks in gestation and the mother has one or more symptoms of labor. Symptoms of labor are known in the art, although in specific embodiments they include one or more of the following: a contraction every 10 minutes, or more frequently within one hour (five or more uterine contractions in an hour); watery fluid leaking from the vagina, which could signal that the bag of water has broken; menstrual-like cramps felt in the lower abdomen that may be transient or constant; low, dull backache experienced below the waistline that may be transient or constant; pelvic pressure; abdominal cramps that may occur with or without diarrhea; and/or increase or change in vaginal discharge.

B. Spinal Cord Injury and Progressive Hemorrhagic Necrosis

Acute spinal cord injury (SCI) results in progressive hemorrhagic necrosis (PHN), a poorly understood pathological process characterized by hemorrhage and necrosis that leads to devastating loss of spinal cord tissue, cyctic cavitation of the cord, and debilitating neurological dysfunction. Using a rodent model of severe cervical SCI, SUR1-regulated $NC_{Ca-ATP}$ channels were characterized for involvement in PHN. In controls, SCI caused a progressively expansive lesion with fragmentation of capillaries, hemorrhage that doubled in volume over 12 h, tissue necrosis and severe neurological dysfunction. Necrotic lesions were surrounded by widespread up-regulation of SUR1 in capillaries and neurons. Patch clamp of cultured endothelial cells exposed to hypoxia showed that up-regulation of SUR1 was associated with expression of functional SUR1-regulated $NC_{Ca-ATP}$ channels. Following SCI, block of SUR1 by glibenclamide or repaglinide, or gene suppression of SUR1 by phosphorothioated antisense oligodeoxynucleotide, essentially eliminated capillary fragmentation and progressive accumulation of blood, was associated with significant sparing of white matter tracts and a 3-fold reduction in lesion volume, and resulted in marked neurobehavioral functional improvement compared to controls. Therefore, SUR1-regulated $NC_{Ca-ATP}$ channels in capillary endothelium are critical to development of PHN and constitute a major novel target for therapy in SCI.

1. Spinal Cord Injury—the Clinical Problem

Acute spinal cord injury (SCI) results in physical disruption of spinal cord neurons and axons leading to deficits in motor, sensory, and autonomic function. This is a debilitating neurological disorder common in young adults that often requires life-long therapy and rehabilitative care, placing a significant burden on healthcare systems. The fact that SCI impacts mostly young people makes the tragedy all the more horrific, and the cost to society in terms of lost "person-years" all the more enormous. Sadly, many patients exhibit neuropathologically and clinically complete cord injuries following SCI. However, many others have neuropathologically incomplete lesions (Hayes and Kakulas, 1997; Tator and Fehlings, 1991). giving hope that proper treatment to minimize secondary injury may reduce the functional impact.

2. Secondary Injury—progressive Hemorrhagic Necrosis (PHN)

The concept of secondary injury in SCI arises from the observation that the volume of injured tissue increases with time after injury, i.e., the lesion itself expands and evolves over time. Whereas primary injured tissues are irrevocably damaged from the very beginning, right after impact, tissues that are destined to become "secondarily" injured are considered to be potentially salvageable. Secondary injury in SCI has been reviewed in a classic paper by Tator (1991), as well as in more recent reviews (Kwon et al., 2004), wherein the overall concept of secondary injury is validated. Older observations based on histological studies that gave rise to the concept of lesion-evolution have been confirmed with non-invasive MRI (Bilgen et al., 2000; Ohta et al., 1999; Sasaki et al., 1978; Weirich et al., 1990).

Numerous mechanisms of secondary injury are recognized, including edema, ischemia, oxidative stress and inflammation. In SCI, however, one pathological entity in particular is recognized that is relatively unique to the spinal cord and that has especially devastating consequences—progressive hemorrhagic necrosis (PHN) (Fitch et al., 1999; Kraus, 1996; nelson et al., 1977; Tator, 1991; Tator and Fehlings, 1991; Tator and Koyanagi, 1997).

PHN is a rather mysterious condition, first recognized over 3 decades ago, that has previously eluded understanding and treatment. As disclosed herein, the present invention provides treatment for this condition. Following impact, petechial hemorrhages form in surrounding tissues and later emerge in more distant tissues, eventually coalescing into the characteristic lesion of hemorrhagic necrosis. The specific time course and magnitude of these changes remain to be determined, but papers by Khan et al. (1985) and Kawata et al. (1993) nicely describe the progressive increase in hemorrhage in the cord. After injury, a small hemorrhagic lesion involving primarily the capillary-rich central gray matter is observed at 15 min, but hemorrhage, necrosis and edema in the central gray matter enlarge progressively over a period of 3-24 h (Balentine, 1978; Iizuka et al., 1987; Kawata et al., 1993). The white matter surrounding the hemorrhagic gray matter shows a variety of abnormalities, including decreased H&E staining, disrupted myelin, and axonal and periaxonal swelling. Tator and Koyanagi (1997) noted that white matter lesions extend far from the injury site, especially in the posterior columns. The evolution of hemorrhage and necrosis has been referred to as "autodestruction", and it is this that forms the key observation that defines PHN. PHN eventually causes loss of vital spinal cord tissue and, in some species including humans, leads to post-traumatic cystic cavitation surrounded by glial scar tissue.

3. Mechanisms of Delayed Hemorrhage and PHN

Tator and Koyanagi (1997) expressed the view that obstruction of small intramedullary vessels by the initial mechanical stress or secondary injury may be responsible for PHN. Kawata and colleagues (1993) attributed the progressive changes to leukocyte infiltration around the injured area leading to plugging of capillaries. Most importantly, damage to the endothelium of spinal cord capillaries and postcapillary venules has been regarded as a major factor in the pathogenesis of PHN (Griffiths et al., 1978; Kapadia, 1984; Nelson et al., 1977). That endothelium is involved is essentially certain, given that petechial hemorrhages, the primary characteristic of PHN, arise from nothing less than catastrophic failure of capillary or venular integrity. However, no molecular mechanism for progressive dysfunction of endothelium has heretofore been identified.

"Hemorrhagic conversion" is a term familiar to many from the stroke literature, but not from the SCI literature. Hemorrhagic conversion describes the process of conversion from a bland infarct into a hemorrhagic infarct, and is typically associated with post-ischemic reperfusion, either spontaneous or induced by thrombolytic therapy. The molecular pathology involved in hemorrhagic conversion has yet to be fully elucidated, but considerable work has implicated enzymatic destruction of capillaries by matrix-metalloproteinases (MMP) released by invading neutrophils (Gidday et al., 2005; Justicia et al., 2003; Lorenzl et al., 2003; Romanic et al., 1998). Maladaptive activation of MMP compromises the structural integrity of capillaries, leading to formation of petechial hemorrhages. In ischemic stroke, MMP inhibitors reduce hemorrhagic conversion following thrombolytic-induced reperfusion. MMPs are also implicated in spinal cord injury (de et al., 2000; Duchossoy et al., 2001; Duchossoy et al., 2001; Goussev et al., 2003; Hsu et al., 2006; Noble et al., 2002; Wells et al., 2003). In SCI, however, their role has been studied predominantly in the context of delayed tissue healing, and no evidence has been put forth to suggest their involvement in PHN.

Expression and activation of $NC_{Ca-ATP}$ channels (see Simard et al., 2007) gives rise to PHN. The data demonstrate that cells that express the $NC_{Ca-ATP}$ channel following an ischemic or other injury-stimulus, later undergo oncotic (necrotic) cell death when ATP is depleted. This is shown explicitly for astrocytes (Simard et al., 2006), and in specific embodiments it also occurs with capillary endothelial cells that express the channel. It follows that if capillary endothelial cells undergo this process leading to necrotic death, capillary integrity would be lost, leading to extravasation of blood and formation of petechial hemorrhages. Applicants disclose herein that inhibition of $NC_{Ca-ATP}$ channels is useful to prevent and to treat PHN and SCI.

4. Therapies in SCI

No cure exists for the primary injury in SCI, but research has identified various pharmacological compounds that specifically antagonize secondary injury mechanisms responsible for worsened outcome in SCI. Several compounds including methylprednisolone, GM-1 ganglioside, thyrotropin releasing hormone, nimodipine, and gacyclidine have been tested in prospective randomized clinical trials of SCI, with only methylprednisolone and GM-1 ganglioside showing evidence of a modest benefit (Fehlings and Baptiste, 2005). At present, high dose methylprednisolone steroid therapy is the only pharmacological therapy shown to have efficacy in a Phase Three randomized trial when it can be administered within eight hours of injury (Bracken, 2002; Bracken et al., 1997; Bracken et al., 1998).

Of the numerous treatments assessed in SCI, very few have been shown to actually decrease the hemorrhage and tissue loss associated with PHN. Methylprednisolone, the only approved therapy for SCI, improves edema, but does not alter the development of PHN (Merola et al., 2002). A number of compounds have shown beneficial effects related to sparing of white matter, including the NMDA antagonist, MK801 (Faden et al., 1988), the AMPA antagonist, GYKI 52466 (Colak et al., 2003), $Na^+$ channel blockers (Schwartz and Fehlings, 2001; Teng and Wrathall, 1997), minocycline (Teng et al., 2004), and estrogen (Chaovipoch et al., 2006).

However, no treatment has been previously reported that reduces PHN and lesion volume, and that improves neurobehavioral function to the extent that is disclosed herein in which the highly selective but exemplary SUR1 antagonists, glibenclamide and repaglinide, as well as with antisense-oligodeoxynucleotide (AS-ODN) directed against SUR1, are able to treat PHN. It is useful that the molecular mechanisms targeted by these 3 agents—SUR1 and the SUR1-regulated $NC_{Ca-ATP}$ channel, are characterized to further elucidate their role in PHN.

III. $NC_{Ca-ATP}$ Channel

A unique non-selective monovalent cationic ATP-sensitive channel ($NC_{Ca-ATP}$ channel) was identified first in native reactive astrocytes (NRAs) and later in neurons and capillary endothelial cells after stroke or traumatic brain or spinal cord injury (see International application WO 03/079987 to Simard et al., and Chen and Simard, 2001, each incorporated by reference herein in its entirety). As with the $K_{ATP}$ channel in pancreatic β cells, the $NC_{Ca-ATP}$ channel is considered to be a heteromultimer structure comprised of sulfonylurea receptor type 1 (SUR1) regulatory subunits and pore-forming subunits (Chen et al., 2003), which include TRPM4 pore subunits.

The invention is based, in part, on the discovery of a specific channel, the $NC_{Ca-ATP}$ channel, defined as a channel on astrocytes in U.S. Application Publication No. 20030215889, which is incorporated herein by reference in its entirety. More specifically, the present invention has further defined that this channel is not only expressed on astrocytes, it is expressed at least on neural cells, neuroglial cells, and/or neural endothelial cells after brain and spinal cord trauma, for example, an hypoxic event, an ischemic event, or other secondary neuronal injuries relating to these events.

The $NC_{Ca\text{-}ATP}$ channel is activated by calcium ions ($Ca^{2+}$) and is sensitive to ATP. Thus, this channel is a non-selective cation channel activated by intracellular $Ca^{2+}$ and blocked by intracellular ATP. When opened by depletion of intracellular ATP, this channel is responsible for complete depolarization due to massive $Na^+$ influx, which creates an electrical gradient for $Cl^-$ and an osmotic gradient for $H_2O$, resulting in cytotoxic edema and cell death. When the channel is blocked or inhibited, massive $Na^+$ does not occur, thereby preventing cytotoxic edema.

Certain functional characteristics distinguish the $NC_{Ca\text{-}ATP}$ channel from other known ion channels. These characteristics can include, but are not limited to, at least some of the following: 1) it is a non-selective cation channel that readily allows passage of $Na^+$, $K^+$ and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic 13 cells.

More specifically, the $NC_{Ca\text{-}ATP}$ channel of the present invention has a single-channel conductance to potassium ion ($K^+$) between 20 and 50 pS. The $NC_{Ca\text{-}ATP}$ channel is also stimulated by $Ca^{2+}$ on the cytoplasmic side of the cell membrane in a physiological concentration range, where concentration range is from $10^{-8}$ to $10^{-5}$ M. The $NC_{Ca\text{-}ATP}$ channel is also inhibited by cytoplasmic ATP in a physiological concentration range, where the concentration range is about 0.1 mM to about 10 mM, or more particularly about 0.2 mM to about 5 mM. The $NC_{Ca\text{-}ATP}$ channel is also permeable to the following cations; $K^+$, $Cs^+$, $Li^+$, $Na^+$; to the extent that the permeability ratio between any two of the cations is greater than 0.5 and less than 2.

SUR imparts sensitivity to antidiabetic sulfonylureas such as glibenclamide and tolbutamide and is responsible for activation by a chemically diverse group of agents termed "$K^+$ channel openers" such as diazoxide, pinacidil and cromakalin (Aguilar-Bryan et al., 1995; Inagaki et al., 1996; Isomoto et al., 1996; Nichols et al., 1996; Shyng et al., 1997). In various tissues, molecularly distinct SURs are coupled to distinct pore-forming subunits to form different $K_{ATP}$ channels with distinguishable physiological and pharmacological characteristics. The $K_{ATP}$ channel in pancreatic β cells is formed from SUR1 linked with Kir6.2, whereas the cardiac and smooth muscle $K_{ATP}$ channels are formed from SUR2A and SUR2B linked with Kir6.2 and Kir6.1, respectively (Fujita et al., 2000). Despite being made up of distinctly different pore-forming subunits, the $NC_{Ca\text{-}ATP}$ channel is also sensitive to sulfonylurea compounds.

Also, unlike the $K_{ATP}$ channel, the $NC_{Ca\text{-}ATP}$ channel conducts sodium ions, potassium ions, cesium ions and other monovalent cations with near equal facility (Chen and Simard, 2001) suggesting further that the characterization, and consequently the affinity to certain compounds, of the $NC_{Ca\text{-}ATP}$ channel differs from the $K_{ATP}$ channel.

Other nonselective cation channels that are activated by intracellular $Ca^{2+}$ and inhibited by intracellular ATP have been identified by others but not in astrocytes or neurons as disclosed herein. Further, the $NC_{Ca\text{-}ATP}$ channel expressed and found in astrocytes differs physiologically from the other channels with respect to calcium sensitivity and adenine nucleotide sensitivity (Chen et al., 2001).

The $NC_{Ca\text{-}ATP}$ channel can be inhibited by an $NC_{Ca\text{-}ATP}$ channel inhibitor, an $NC_{Ca\text{-}ATP}$ channel blocker, a type 1 sulfonylurea receptor (SUR1) antagonist, SUR1 inhibitor, or a compound capable of reducing the magnitude of membrane current through the channel. More specifically, the exemplary SUR1 antagonist may be selected from the group consisting of glibenclamide, tolbutamide, repaglinide, nateglinide, meglitinide, midaglizole, LY397364, LY389382, glyclazide, glimepiride, estrogen, estrogen related-compounds (estradiol, estrone, estriol, genistein, non-steroidal estrogen (e.g., diethylstilbestrol), phytoestrogen (e.g., coumestrol), and zearalenone), and compounds known to inhibit or block $K_{ATP}$ channels. MgADP can also be used to inhibit the channel. Other compounds that can be used to block or inhibit $K_{ATP}$ channels include, but are not limited to tolbutamide, glyburide (1[p-2[5-chloro-O-anisamido)ethyl]phenyl]sulfonyl]-3-cyclohexyl-3-urea); chlopropamide(1-[[(p-chlorophenyl)sulfonyl]-3-propylurea; glipizide (1-cyclohexyl-3 [[p-[2(5-methylpyrazine carboxamido)ethyl]phenyl]sulfonyl]urea); or tolazamide(benzenesulfonamide-N-[[(hexahydro-1H-azepin-1yl)amino]carbonyl]-4-methyl). In additional embodiments, non-sulfonyl urea compounds, such as 2,3-butanedione and 5-hydroxydecanoic acid, quinine, and therapeutically equivalent salts and derivatives thereof, may be employed in the invention.

The channel is expressed on cells, including, for example, vascular endothelial cells and germinal matrix tissue. In specific embodiments, the inhibitor of the channel blocks the influx of Na+ into the cells thereby preventing depolarization or other deleterious effects caused by the altered ionic concentration of the cells. Inhibition of the influx of Na+ into the cells, thereby at least prevents or reduces cytotoxic edema and/or ionic edema. Thus, this treatment reduces cell death, including, for example, necrotic cell death. In specific embodiments, the invention reduces cell death of endothelial cells.

The compound can be administered alimentarily (e.g., orally, buccally, rectally or sublingually); parenterally (e.g., intravenously, intradermally, intramuscularly, intraarterially, intrathecally, subcutaneously, intraperitoneally, intraventricularly); by intracavity; intravesically; intrapleurally; and/or topically (e.g., transdermally), mucosally, or by direct injection into the brain parenchyma.

Another embodiment of the present invention comprises a method of treating a subject at risk for developing edema comprising administering to the subject a therapeutic composition effective to inhibit a $NC_{Ca\text{-}ATP}$ channel in at least an endothelial cell, germinal matrix tissue, or combination thereof. In specific embodiments, the composition is effective to inhibit a $NC_{Ca\text{-}ATP}$ channel in an endothelial cell.

In further embodiments, the compound that inhibits the $NC_{Ca\text{-}ATP}$ channel can be administered in combination with one or more statins, diuretics, vasodilators (e.g., nitroglycerin), mannitol, diazoxide or similar compounds that stimulate or promote ischemic preconditioning.

Yet further, another embodiment of the present invention comprises a pharmaceutical composition comprising or more statins, diuretics, vasodilators, mannitol, diazoxide or similar compounds that stimulate or promote ischemic preconditioning or a pharmaceutically acceptable salt thereof and a compound that inhibits a $NC_{Ca\text{-}ATP}$ channel or a pharmaceutically acceptable salt thereof. This pharmaceutical composition can be considered neuroprotective, in specific embodiments. For example, the pharmaceutical composition comprising a combination of the second agent and a compound that inhibits a $NC_{Ca\text{-}ATP}$ channel is therapeutic or protective because it increases the therapeutic window for the administration of the second agent by several hours; for example the therapeutic window for administration of second agents may be increased by several hours (e.g. about 4 to about 8 hrs) by co-administering antagonist of the $NC_{Ca\text{-}ATP}$ channel.

An effective amount of a therapeutic composition of the invention, including an antagonist of $NC_{Ca\text{-}ATP}$ channel and/or the additional therapeutic compound, that may be administered to a cell includes a dose of about 0.0001 nM to about 2000 µM, for example. More specifically, doses to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 about 300 to about 500 µM; about 500 to about 1000 µM; about 1000 µM to about 1500 µM and about 1500 µM to about 2000 µM, for example. Of course, all of these amounts are exemplary, and any amount in-between these points is also expected to be of use in the invention.

An effective amount of an antagonist of the $NC_{Ca\text{-}ATP}$ channel or related-compounds thereof as a treatment varies depending upon the host treated and the particular mode of administration. In one embodiment of the invention, the dose range of the therapeutic combinatorial composition of the invention, including an antagonist of $NC_{Ca\text{-}ATP}$ channel and/or the additional therapeutic compound, will be about 0.01 µg/kg body weight to about 20,000 ÿg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 ÿg/kg, 900 ÿg/kg, 1 mg/kg, 5 mg/kg, 10 mg/kg, 12 mg/kg, 15 mg/kg, 20 mg/kg, and/or 30 mg/kg.

In certain embodiments, there may be dosing of from very low ranges (e.g. 1 mg/kg/day or less; 5 mg/kg bolus; or 1 mg/kg/day) to moderate doses (e.g. 2 mg bolus, 15 mg/day) to high doses (e.g. 5 mg bolus, 30-40 mg/day; and even higher). Of course, all of these dosages are exemplary, and any dosage in-between these points is also expected to be of use in the invention. Any of the above dosage ranges or dosage levels may be employed for an agonist or antagonist, or both, of $NC_{Ca\text{-}ATP}$ channel or related-compounds thereof.

In certain embodiments, the amount of the combinatorial therapeutic composition administered to the subject is in the range of about 0.0001 µg/kg/day to about 20 mg/kg/day, about 0.01 µg/kg/day to about 100 µg/kg/day, or about 100 µg/kg/day to about 20 mg/kg/day. Still further, the combinatorial therapeutic composition may be administered to the subject in the form of a treatment in which the treatment may comprise the amount of the combinatorial therapeutic composition or the dose of the combinatorial therapeutic composition that is administered per day (1, 2, 3, 4, etc.), week (1, 2, 3, 4, 5, etc.), month (1, 2, 3, 4, 5, etc.), etc. Treatments may be administered such that the amount of combinatorial therapeutic composition administered to the subject is in the range of about 0.0001 µg/kg/treatment to about 20 mg/kg/treatment, about 0.01 µg/kg/treatment to about 100 µg/kg/treatment, or about 100 µg/kg/treatment to about 20 mg/kg/treatment.

In another embodiment of the invention, there is a kit, housed in a suitable container, that comprises an inhibitor of $NC_{Ca\text{-}ATP}$ channel. In another embodiment of the invention, the kit comprises an inhibitor of $NC_{Ca\text{-}ATP}$ channel and, for example, one or more of a cation channel blocker and/or an antagonist of VEGF, MMP, NOS, or thrombin. The kit may also comprise suitable tools to administer compositions of the invention to an individual.

The $NC_{Ca\text{-}ATP}$ channel of the present invention is distinguished by certain functional characteristics, the combination of which distinguishes it from known ion channels. The characteristics that distinguish the $NC_{Ca\text{-}ATP}$ channel of the present invention include, but are not necessarily limited to, the following: 1) it is a non-selective cation channel that readily allows passage of Na, K and other monovalent cations; 2) it is activated by an increase in intracellular calcium, and/or by a decrease in intracellular ATP; 3) it is regulated by sulfonylurea receptor type 1 (SUR1), which heretofore had been considered to be associated exclusively with $K_{ATP}$ channels such as those found in pancreatic y cells, for example.

More specifically, the $NC_{Ca\text{-}ATP}$ channel of the present invention has a single-channel conductance to potassium ion ($K^+$) between 20 and 50 pS. The $NC_{Ca\text{-}ATP}$ channel is also stimulated by $Ca^{2+}$ on the cytoplasmic side of the cell membrane in a physiological concentration range, where said concentration range is from $10^{-8}$ to $10^{-5}$ M. The $NC_{Ca\text{-}ATP}$ channel is also inhibited by cytoplasmic ATP in a physiological concentration range, where said concentration range is from about $10^{-1}$ mM to about 5 mM. The $NC_{Ca\text{-}ATP}$ channel is also permeable to the following cations; $K^+$, $Cs^+$, $Li^+$, $Na^+$; to the extent that the permeability ratio between any two of said cations is greater than 0.5 and less than 2.

IV. Exemplary Therapeutic and Preventative Embodiments

Treatment methods may involve treating an individual with an effective amount of a composition comprising an antagonist of $NC_{Ca\text{-}ATP}$ channel or related-compound thereof. An effective amount is described, generally, as that amount sufficient to detectably and repeatedly ameliorate, reduce, minimize, limit the extent of a medical condition or its symptoms or, to prevent a disease or its medical condition. More specifically, it is envisioned that the treatment and/or prevention with an antagonist of $NC_{Ca\text{-}ATP}$ channel or related-compounds thereof will inhibit cell depolarization, inhibit $Na^+$ influx, inhibit an osmotic gradient change, inhibit water influx into the cell, inhibit cytotoxic cell edema, decrease stroke size, inhibit hemorrhagic conversion, and/or decrease mortality of the subject, in specific embodiments The effective amount of an antagonist of $NC_{Ca\text{-}ATP}$ channel or related-compounds thereof to be used are those amounts effective to produce beneficial results, for example, with respect to spinal cord injury or progressive hemorrhagic necrosis treatment or prevention, in the recipient animal or patient. Such amounts may be initially determined by reviewing the published literature, by conducting in vitro tests and/or by conducting metabolic studies in healthy experimental animals, for example, as is routine in the art. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an antagonist of the $NC_{Ca\text{-}ATP}$ channel or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the effective amount of the antagonist or related-compound thereof can be the amount that is required to achieve the desired result: reduction in the risk of spinal cord injury or progressive hemorrhagic necrosis, reduction in the amount of damage following spinal cord injury or progressive hemorrhagic necrosis, reduction in cell death, and so forth In specific embodiments, this amount also is an amount that maintains a reasonable level of blood glucose in the patient, for example, the amount of the antagonist maintains a blood glucose level of at least 60 mmol/l, more preferably, the blood glucose level is maintained in the range of about 60 mmol/l to about 150 mmol/l. Thus, the amounts prevents the subject from becoming hypoglycemic. If glucose levels are not normal, then one of skill in the art would administer either insulin or glucose, depending upon if the patient is hypoglycemic or hyperglycemic.

Administration of the therapeutic antagonist of $NC_{Ca\text{-}ATP}$ channel composition of the present invention to a patient or subject will follow general protocols for the administration of therapies used in spinal cord injury or progressive hemorrhagic necrosis treatment, taking into account the toxicity, if any, of the antagonist of the $NC_{Ca\text{-}ATP}$ channel. It is expected that the treatment cycles would be repeated as necessary. It also is contemplated that various standard therapies, as well as surgical intervention, may be applied in combination with the described therapy.

Another aspect of the present invention for the treatment of IVH or spinal cord injury or progressive hemorrhagic conversion comprises administration of an effective amount of a SUR1 antagonist and/or a TRPM4 antagonist and administration of glucose. Glucose administration may precede the time of treatment with an antagonist of the $NC_{Ca\text{-}ATP}$ channel, may be at the time of treatment with an antagonist of the $NC_{Ca\text{-}ATP}$ channel, such as a SUR1 and/or TRPM4 antagonist, or may follow treatment with an antagonist of the $NC_{Ca\text{-}ATP}$ channel (e.g., at 15 minutes after treatment with an antagonist of the $NC_{Ca\text{-}ATP}$ channel, or at one half hour after treatment with an antagonist of the $NC_{Ca\text{-}ATP}$ channel, or at one hour after treatment with an antagonist of the $NC_{Ca\text{-}ATP}$ channel, or at two hours after treatment with an antagonist of the $NC_{Ca\text{-}ATP}$ channel, or at three hours after treatment with an antagonist of the $NC_{Ca\text{-}ATP}$ channel, for example). Glucose administration may be by intravenous, or intraperitoneal, or other suitable route and means of delivery. Additional glucose allows administration of higher doses of an antagonist of the $NC_{Ca\text{-}ATP}$ channel than might otherwise be possible, so that combined glucose with an antagonist of the $NC_{Ca\text{-}ATP}$ channel provides greater protection, and may allow treatment at later times, than with an antagonist of the $NC_{Ca\text{-}ATP}$ channel alone. Greater amounts of glucose are administered where larger doses of an antagonist of the $NC_{Ca\text{-}ATP}$ channel are administered.

Yet further, the compositions of the present invention can be used to produce neuroprotective kits that are used to treat subjects at risk or suffering from conditions that are associated with spinal cord injury, including progressive hemorrhagic necrosis, for example.

V. Combinatorial Therapeutic Compositions

In certain embodiments of the present invention includes a combinatorial therapeutic composition comprising an antagonist of the NCCa-ATP channel and another therapeutic compound, such as a cation channel blocker and/or an antagonist of a specific molecule, such as VEGF, MMP, NOS, thrombin, and so forth.

A. Inhibitors of $NC_{Ca\text{-}ATP}$ Channel

According to a specific embodiment of the present invention, the administration of effective amounts of the active compound can block the channel, which if it remained open would lead cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY3 89382, gliclazide, glimepiride, MgADP, and combinations thereof. In a preferred embodiment of the invention the SUR1 antagonists is selected from the group consisting of glibenclamide and tolbutamide. A variety of TRPM4 antagonists are suitable for blocking the channel. Examples of suitable TRPM4 antagonists include, but are not limited to, pinkolant, rimonabant, a fenamate (such as flufenamic acid, mefenamic acid, meclofenamic acid, or niflumic acid), 1-(beta-[3-(4-methoxy-phenyl)propoxy]-4-methoxyphenethyl)-1H-imidazole hydrochloride, and a biologically active derivative thereof. Still other therapeutic "strategies" for preventing cell swelling and cell death can be adopted including, but not limited to methods that maintain the cell in a polarized state and methods that prevent strong depolarization.

The present invention comprises modulators of the channel, for example one or more agonists and/or one or more antagonists of the channel. Examples of antagonists or agonists of the present invention may encompass respective antagonists and/or agonists identified in US Application Publication No. 20030215889, which is incorporated herein by reference in its entirety. One of skill in the art is aware that the NCCa-ATP channel is comprised of at least two subunits: the regulatory subunit, SUR1, and the pore forming subunit.

1. Exemplary SUR1 Inhibitors

In certain embodiments, antagonists to sulfonylurea receptor-1 (SUR1) are suitable for blocking the channel. Examples of suitable SUR1 antagonists include, but are not limited to glibenclamide, tolbutamide, repaglinide, nateglinide, meglitinide, midaglizole, LY397364, LY389382, glyclazide, glimepiride, estrogen, estrogen related-compounds estrogen related-compounds (estradiol, estrone, estriol, genistein, non-steroidal estrogen (e.g., diethylstilbestrol), phytoestrogen (e.g., coumestrol), zearalenone, etc.) and combinations thereof. In a preferred embodiment of the invention the SUR1 antagonists is selected from the group consisting of glibenclamide and tolbutamide. Yet further, another antagonist can be MgADP. Other antagonist include blockers of KATP channels, for example, but not limited to tolbutamide, glibenclamide (1 [p-2[5-chloro-O-anisamido)ethyl]phenyl]sulfonyl]-3-cyclohexyl-3-urea); chlopropamide(1-[[(p-chlorophenyl) sulfonyl]-3-propylurea; glipizide (1-cyclohexyl-3[[p-[2(5-methylpyrazine carboxamido)ethyl]phenyl]sulfonyl]urea); or tolazamide(benzenesulfonamide-N-[[(hexahydro-1H-azepin-1yl)amino]carbonyl]-4-methyl).

2. Modulators of SUR1 Transcription and/or Translation

In certain embodiments, the modulator can comprise a compound (protein, nucleic acid, siRNA, etc.) that modulates transcription and/or translation of SUR1 (regulatory subunit) and/or the molecular entities that comprise the pore-forming subunit.

3. Transcription Factors

Transcription factors are regulatory proteins that binds to a specific DNA sequence (e.g., promoters and enhancers) and regulate transcription of an encoding DNA region. Thus, transcription factors can be used to modulate the expression of SUR1. Typically, a transcription factor comprises a binding domain that binds to DNA (a DNA-binding domain) and a regulatory domain that controls transcription. Where a regulatory domain activates transcription, that regulatory domain is designated an activation domain. Where that regulatory domain inhibits transcription, that regulatory domain is designated a repression domain. More specifically, transcription factors such as Sp1, HIF1, and NFB can be used to modulate expression of SUR1.

In particular embodiments of the invention, a transcription factor may be targeted by a composition of the invention. The transcription factor may be one that is associated with a pathway in which SUR1 is involved. The transcription factor may be targeted with an antagonist of the invention, including siRNA to downregulate the transcription factor. Such antagonists can be identified by standard methods in the art, and in particular embodiments the antagonist is employed for treatment and or prevention of an individual in need thereof. In an additional embodiment, the antagonist is employed in conjunction with an additional compound, such as a composition that modulates the $NC_{Ca-ATP}$ channel of the invention. For example, the antagonist may be used in combination with an inhibitor of the channel of the invention. When employed in combination, the antagonist of a transcription factor of a SUR1-related pathway may be administered prior to, during, and/or subsequent to the additional compound.

4. Antisense and Ribozymes

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SUR1. Thus, it is contemplated that antisense, ribozyme, and double-stranded RNA, and RNA interference molecules are constructed and used to modulate SUR1 expression.

5. Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

6. RNA Interference

It is also contemplated in the present invention that double-stranded RNA is used as an interference molecule, e.g., RNA interference (RNAi). RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques (Giet, 2001; Hammond, 2001; Stein P, et al., 2002; Svoboda P, et al., 2001; Svoboda P, et al., 2000).

Another type of RNAi is often referred to as small interfering RNA (siRNA), which may also be utilized to inhibit SUR1. A siRNA may comprises a double stranded structure or a single stranded structure, the sequence of which is "substantially identical" to at least a portion of the target gene (See WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.,) and CLUSTAL (Higgins et al., 1992; Thompson, et al., 1994).

Thus, siRNA contains a nucleotide sequence that is essentially identical to at least a portion of the target gene, for example, SUR1, or any other molecular entity associated with the $NC_{Ca-ATP}$ channel such as the pore-forming subunit. One of skill in the art is aware that the nucleic acid sequences for SUR1 are readily available in GenBank, for example, GenBank accession L40624, which is incorporated herein by reference in its entirety. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SUR1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

7. Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al., 1991; Sarver et al., 1990; Sioud et al., 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis d virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in SUR1 targeted ribozymes is simply a matter of preparing and testing a given sequence, and is a routinely practiced screening method known to those of skill in the art.

8. Inhibition of Post-translational Assembly and Trafficking

Following expression of individual regulatory and pore-forming subunit proteins of the channel, and in particular aspects of the invention, these proteins are modified by glycosylation in the Golgi apparatus of the cell, assembled into functional heteromultimers that comprise the channel, and then transported to the plasmalemmal membrane where they are inserted to form functional channels. The last of these processes is referred to as "trafficking".

In specific embodiments of the invention, molecules that bind to any of the constituent proteins interfere with post-translational assembly and trafficking, and thereby interfere with expression of functional channels. One such example is with glibenclamide binding to SUR1 subunits. In additional embodiments, glibenclamide, which binds with femtomolar affinity to SUR1, interferes with post-translational assembly and trafficking required for functional channel expression.

B. Cation Channel Blockers

In some embodiments of the present invention, the combinatorial therapeutic composition comprises one or more cation channel blockers (including, for example, TRPM4 blockers, $Ca^{2+}$ channel blocker, $K^+$ channel blocker, $Na^+$ channel blocker, and non-specific cation channel blocker). Exemplary TRPM4 blockers include pinokalant (LOE 908 MS); rimonabant (SR141716A); fenamates (flufenamic acid, mefenamic acid, niflumic acid, for example); SKF 96365 (1-(beta-[3-(4-methoxy-phenyl)propoxy]-4-methoxyphenethyl)-1H-imidazole hydrochloride); and/or a combination or mixture thereof.

In certain embodiments a Ca2+ channel blocker includes, for example, Amlodipine besylate, (R)-(+)-Bay K, Cilnidipine, w-Conotoxin GVIA, w-Conotoxin MVIIC, Diltiazem hydrochloride, Gabapentin, Isradipine, Loperamide hydrochloride, Mibefradil dihydrochloride, Nifedipine, (R)-(−)-Niguldipine hydrochloride, (S)-(+)-Niguldipine hydrochloride, Nimodipine, Nitrendipine, NNC 55-0396 dihydrochloride, Ruthenium Red, SKF 96365 hydrochloride, SR 33805 oxalate, Verapamil hydrochloride.

In certain embodiments a K+ channel blocker includes, for example, Apamin, Charybdotoxin, Dequalinium dichloride, Iberiotoxin, Paxilline, UCL 1684, Tertiapin-Q, AM 92016 hydrochloride, Chromanol 293B, (−)-[3R,4S]-Chromanol 293B, CP 339818 hydrochloride, DPO-1, E-4031 dihydrochloride, KN-93, Linopirdine dihydrochloride, XE 991 dihydrochloride, 4-Aminopyridine, DMP 543, YS-035 hydrochloride.

In certain embodiments a Na+ channel blocker includes, for example, Ambroxol hydrochloride, Amiloride hydrochloride, Flecamide acetate, Flunarizine dihydrochloride, Mexiletine hydrochloride, QX 222, QX 314 bromide, QX 314 chloride, Riluzole hydrochloride, Tetrodotoxin, Vinpocetine.

In certain embodiments a non-specific cation channel blocker includes, for example, Lamotrigine or Zonisamide.

In other embodiments of the present invention, the combinatorial therapeutic composition comprises one or more glutamate receptor blockers including, for example, D-AP5, DL-AP5, L-AP5, D-AP7, DL-AP7, (R)-4-Carboxyphenylglycine, CGP 37849, CGP 39551, CGS 19755, (2R,3S)-Chlorpheg, Co 101244 hydrochloride, (R)-CPP, (RS)-CPP, D-CPP-ene, LY 235959, PMPA, PPDA, PPPA, Ro 04-5595 hydrochloride, Ro 25-6981 maleate, SDZ 220-040, SDZ 220-581, (±)-1-(1,2-Diphenylethyl)piperidine maleate, IEM 1460, Loperamide hydrochloride, Memantine hydrochloride, (−)-MK 801 maleate, (+)-MK 801 maleate, N20C hydrochloride, Norketamine hydrochloride, Remacemide hydrochloride, ACBC, CGP 78608 hydrochloride, 7-Chlorokynurenic acid, CNQX, 5,7-Dichlorokynurenic acid, Felbamate, Gavestinel, (S)-(−)-HA-966, L-689,560, L-701,252, L-701,324, Arcaine sulfate, Eliprodil, N-(4-Hydroxyphenylacetyl)spermine, N-(4-Hydroxyphenylpropanoyl)spermine trihydrochloride, Ifenprodil hemitartrate, Synthalin sulfate, CFM-2, GYKI 52466 hydrochloride, IEM 1460, ZK 200775, NS 3763, UBP 296, UBP 301, UBP 302, CNQX, DNQX, Evans Blue tetrasodium salt, NBQX, SYM 2206, UBP 282, and ZK 200775.

C. Antagonists of Specific Molecules

Antagonists of specific molecules may be employed, for example, those related to endothelial dysfunction.

1. Antagonists of VEGF

Antagonists of VEGF may be employed. The antagonists may be synthetic or natural, and they may antagonize directly or indirectly. VEGF TrapR1R2 (Regeneron Pharmaceuticals, Inc.); Undersulfated, low-molecular-weight glycol-split heparin (Pisano et al., 2005); soluble NRP-1 (sNRP-1); Avastin (Bevacizumab); HuMV833; s-Flt-1, s-Flk-1; s-Flt-1/Flk-1; NM-3; and/or GFB 116.

2. Antagonists of MMP

Antagonists of any MMP may be employed. The antagonists may be synthetic or natural, and they may antagonize directly or indirectly. Exemplary antagonists of MMPs include at least (2R)-2-[(4-biphenylsulfonyl)amino]-3-phenylproprionic acid (compound 5a), an organic inhibitor of MMP-2/MMP-9 (Nyormoi et al., 2003); broad-spectrum MMP antagonist GM-6001 (Galardy et al., 1994; Graesser et al., 1998); TIMP-1 and/or TIMP-2 (Rolli et al., 2003); hydroxamate-based matrix metalloproteinase inhibitor (RS 132908) (Moore et al., 1999); batimastat (Corbel et al., 2001); those identified in United States Application 20060177448 (which is incorporated by reference herein in its entirety); and/or marimastat (Millar et al., 1998); peptide inhibitors that comprise HWGF (including CTTHWGFTLC; SEQ ID NO:15) (Koivunen et al., 1999); and combinations thereof.

3. Antagonists of NOS

Antagonists of NOS may be employed. The antagonists may be synthetic or natural, and they may antagonize directly or indirectly. The antagonists may be antagonists of NOS I, NOS II, NOS III, or may be nonselective NOS antagonists. Exemplary antagonists include at least the following: aminoguanidine (AG); 2-amino-5,6-dihydro-6-methyl-4H-1,3 thiazine (AMT); 5-ethylisothiourea (EIT) (Rairigh et al., 1998); asymmetric dimethylarginine (ADMA) (Vallance et al., 1992); N-nitro-L-arginine methylester (L-NAME) (Papapetropoulos et al., 1997; Babaei et al., 1998); nitro-L-arginine (L-NA) (Abman et al., 1990; Abman et al., 1991; Cornfield et al., 1992; Fineman et al., 1994; McQueston et al., 1993; Storme et al., 1999); the exemplary selective NOS II antagonists, aminoguanidine (AG) and N-(3-aminomethyl)benzylacetamidine dihydrochloride (1400W); NG-monomethyl-L-arginine (L-NMMA); the exemplary selective NOS I antagonist, 7-nitroindazole (7-NINA), and a nonselective NOS antagonist, N-nitro-L-arginine (L-NNA), or a mixture or combination thereof.

4. Antagonists of Thrombin

Antagonists of thrombin may be employed. The antagonists may be synthetic or natural, and they may antagonize directly or indirectly. Exemplary thrombin antagonists include at least the following: ivalirudin (Kleiman et al., 2002); hirudin (Hoffman et al., 2000); SSR182289 (Duplantier et al., 2004); antithrombin III; thrombomodulin; Lepirudin (Refludan, a recombinant therapeutic hirudin); P-PACK II (d-Phenylalanyl-L-Phenylalanylarginine-chloro-methyl ketone 2HCl); Thromstop® (BNas-Gly-(pAM)Phe-Pip); Argatroban (Carr et al., 2003); and mixtures or combinations thereof.

D. Others

Non-limiting examples of an additional pharmacological therapeutic agent that may be used in the present invention include an antihyperlipoproteinemic agent, an antiarteriosclerotic agent, an anticholesterol agent, an antiinflammatory agent, an antithrombotic/fibrinolytic agent, antiplatelet, vasodilator, and/or diuretics. Anticholesterol agents include but are not limited to HMG-CoA Reductase inhibitors, cholesterol absorption inhibitors, bile acid sequestrants, nicotinic acid and derivatives thereof, fibric acid and derivatives thereof. HMG-CoA Reductase inhibitors include statins, for example, but not limited to atorvastatin calcium (Lipitor®), cerivastatin sodium (Baycol®), fluvastatin sodium (Lescol®), lovastatin (Advicor®), pravastatin sodium (Pravachol®), and simvastatin (Zocor®). Agents known to reduce the absorption of ingested cholesterol include, for example, Zetia®. Bile acid sequestrants include, but are not limited to cholestyramine, cholestipol and colesevalam. Other anticholesterol agents include fibric acids and derivatives thereof (e.g., gemfibrozil, fenofibrate and clofibrate); nicotinic acids and derivatives thereof (e.g., nician, lovastatin) and agents that extend the release of nicotinic acid, for example niaspan. Antiinflammatory agents include, but are not limited to non-sterodial anti-inflammatory agents (e.g., naproxen, ibuprofen, celeoxib) and sterodial anti-inflammatory agents (e.g., glucocorticoids). Diuretics include, but are not limited to such as furosemide (Lasix®), bumetanide (Bumex®), torsemide (Demadex®), thiazide & thiazide-like diuretics (e.g., chlorothiazide (Diuril®) and hydrochlorothiazide (Esidrix®), benzthiazide, cyclothiazide, indapamide, chlorthalidone, bendroflumethiazide, metolazone), amiloride, triamterene, and spironolacton. Vasodilators include, but are not limited to nitroglycerin.

In only certain embodiments that would not be contraindicated for co-administration with an inhibitor of the $NC_{Ca-ATP}$ channel, additional pharmacological therapeutic agents include antithrombotic/fibrinolytic agent, anticoagulant, antiplatelet, vasodilator, and/or diuretics. Thrombolytics that are used can include, but are not limited to prourokinase, streptokinase, and tissue plasminogen activator (tPA). Anticoagulants include, but are not limited to heparin, warfarin, and coumadin. Antiplatelets include, but are not limited to aspirin, and aspirin related-compounds, for example acetaminophen. Thus, in certain embodiments, the present invention comprises co-administration of an antagonist of the $NC_{Ca-ATP}$ channel with a thrombolytic agent. Co-administration of these two compounds will increase the therapeutic window of the thrombolytic agent. Examples of suitable thrombolytic agents that can be employed in the methods and pharmaceutical compositions of this invention are prourokinase, streptokinase, and tissue plasminogen activator (tPA).

In certain embodiments, the present invention comprises co-administration of an antagonist of the $NC_{Ca-ATP}$ channel with glucose or related carbohydrate to maintain appropriate levels of serum glucose. Appropriate levels of blood glucose are within the range of about 60 mmol/l to about 150 mmol/liter. Thus, glucose or a related carbohydrate is administered in combination to maintain the serum glucose within this range.

VI. Exemplary Pharmaceutical Formulations and Methods of Use

In particular embodiments, the invention employs pharmaceutical formulations comprising a singular or combinatorial composition that inhibits a $NC_{Ca-ATP}$ channel.

A. Exemplary Compositions of the Present Invention

The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

B. Dose Determinations

By a "therapeutically effective amount" or simply "effective amount" of an active compound, such as glibenclamide or tolbutamide, for example, is meant a sufficient amount of the compound to treat or alleviate the spinal cord injury at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the spinal cord injury; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

Toxicity and therapeutic efficacy of such compounds can be determined by standard pharmaceutical procedures in cell assays or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell based assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Such a fairly high dose may include a dose that is several times greater than its use in other indications. For example, the typical anti-diabetic dose of oral or IV glibenclamide is about 2.5 mg/kg to about 15 mg/kg per day; the typical anti-diabetic dose of oral or IV tolbutamide is about to 0.5 gm/kg to about 2.0 gm/kg per day; the typical anti-diabetic dose for oral gliclazide is about 30 mg/kg to about 120 mg/kg per day; however, much larger doses may be required to block spinal cord damage and/or PHN.

For example, in one embodiment of the present invention directed to a method of preventing neuronal cell swelling in the brain of a subject by administering to the subject a formulation containing an effective amount of a compound that blocks the $NC_{Ca-ATP}$ channel and a pharmaceutically acceptable carrier; such formulations may contain from about 0.1 to about 100 grams of tolbutamide or from about 0.5 to about 150 milligrams of glibenclamide. In another embodiment of the present invention directed to a method of alleviating the negative effects of traumatic brain injury or cerebral ischemia stemming from neural cell swelling in a subject by administering to the subject a formulation containing an effective amount of a compound that blocks the $NC_{Ca-ATP}$ channel and a pharmaceutically acceptable carrier.

In situations of spinal cord injury and/or PHN, it may be important to maintain a fairly high dose of the active agent to ensure delivery to the brain of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours. In situations of traumatic brain injury or cerebral ischemia (such as stroke), it may be important to maintain a fairly high dose of the active agent to ensure delivery to the brain of the patient, particularly early in the treatment.

C. Formulations and Administration

The compounds of the present invention may be administered alone or in combination or in concurrent therapy with other agents which affect the central or peripheral nervous system.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

As employed herein, the phrase "suitable dosage levels" refers to levels of compound sufficient to provide circulating concentrations high enough to effectively block the $NC_{Ca-ATP}$ channel and prevent or reduce spinal cord injury and/or PHN.

In accordance with a particular embodiment of the present invention, compositions comprising at least one SUR1 antagonist compound (as described above), and a pharmaceutically acceptable carrier are contemplated.

In accordance with a particular embodiment of the present invention, compositions comprising at least one TRPM4 antagonist compound (as described above), and a pharmaceutically acceptable carrier are contemplated.

In accordance with a particular embodiment of the present invention, compositions comprising a combination of at least one SUR1 antagonist compound and at least one TRPM4 antagonist compound (as described above), and a pharmaceutically acceptable carrier are contemplated.

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition (an antagonist of the $NC_{Ca-ATP}$ channel or its related-compounds thereof) calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

D. Formulations and Routes for Administration of Compounds

Pharmaceutical compositions of the present invention comprise an effective amount of one or more modulators of $NC_{Ca-ATP}$ channel (antagonist) or related-compounds or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one modulators of $NC_{Ca-ATP}$ channel (antagonist) or related-compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The modulators of $NC_{Ca-ATP}$ channel (antagonist) or related-compounds may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The modulators of $NC_{Ca\text{-}ATP}$ channel (antagonist) or related-compounds may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentarily administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include modulators of $NC_{Ca\text{-}ATP}$ channel (antagonist) or related-compounds, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the modulators of $NC_{Ca\text{-}ATP}$ channel (antagonist) or related-compounds may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylatic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Pharmaceutical formulations may be administered by any suitable route or means, including alimentarily, parenteral, topical, mucosal or other route or means of administration. Alimentary routes of administration include administration oral, buccal, rectal and sublingual routes. Parenteral routes of administration include administration include injection into the brain parenchyma, and intravenous, intradermal, intramuscular, intraarterial, intrathecal, subcutaneous, intraperitoneal, and intraventricular routes of administration. Topical routes of administration include transdermal administration.

E. Alimentary Compositions and Formulations

In preferred embodiments of the present invention, the modulators of $NC_{Ca-ATP}$ channel (antagonist) or related-compounds are formulated to be administered via an alimentarily route. Alimentarily routes include all possible routes of administration in which the composition is in direct contact with the alimentarily tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentarily administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

F. Parenteral Compositions and Formulations

In further embodiments, modulators of $NC_{Ca-ATP}$ channel (antagonist) or related-compounds may be administered via a parenteral route. As used herein, the term "parenteral" includes routes that bypass the alimentarily tract. Specifically, the pharmaceutical compositions disclosed herein may be administered for example, but not limited to intravenously, intradermally, intramuscularly, intraarterially, intraventricularly, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, DMSO, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

G. Miscellaneous Pharmaceutical Compositions and Formulations

In other preferred embodiments of the invention, the active compound modulators of $NC_{CaATP}$ channel (antagonist) or related-compounds may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804, 212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VII. Kits of the Invention

Any of the compositions described herein may be comprised in a kit, and the kit may be employed for therapeutic and/or preventative purposes, including for IVH, SCI, and/or PHN. Antagonists of the channel (regulatory subunit or pore-forming) that may be provided include but are not limited to sulfonylurea compounds, benzamido derivatives, antibodies (monoclonal or polyclonal, for example to SUR1 or TRPM4), SUR1 oligonucleotides, SUR1 polypeptides, TRPM4 oligonucleotides, TRPM4 polypeptides, small molecules or combinations thereof, antagonist, etc.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one components in the kit, the kit also may generally contain a second, third or other additional container into which additional components may be separately placed. However, various combinations of components may be comprised in a vial. The kits of the present invention also will typically include a means for containing the SUR1 inhibitor, lipid, additional agent, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The SUR1 antagonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. Examples of aqueous solutions include, but are not limited to ethanol, DMSO and/or Ringer's solution. In certain embodiments, the concentration of DMSO or ethanol that is used is no greater than 0.1% or (1 ml/1000 L).

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SUR1 antagonist or related-compounds thereof is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the composition(s) of the invention within the body of an animal. Such an instrument may be a syringe, pipette, forceps, and/or any such medically approved delivery vehicle.

In addition to the SUR1 antagonist or related-compounds thereof, the kits may also include a second active ingredient. Examples of the second active ingredient include substances to prevent hypoglycemia (e.g., glucose, D5W, glucagon, etc.), statins, diuretics, vasodilators, etc. These second active ingredients may be combined in the same vial as the SUR1 antagonist or related-compounds thereof or they may be contained in a separate vial. In a specific embodiment, a combinatorial therapeutic composition is provided in a kit, and in some embodiments the two or more compounds that make up the composition are housed separately or as a mixture. Other second active ingredients may be employed so long as they are not contra-indicated and would not worsen bleeding, for example, such as thrombolytic agents, anticoagulants, and/or antiplatelets, for example.

Still further, the kits of the present invention can also include glucose-testing kits. Thus, the blood glucose of the patient is measured using the glucose testing kit, then the SUR1 antagonist or related-compounds thereof can be administered to the subject followed by measuring the blood glucose of the patient.

In addition to the above kits, the kits of the present invention can be assembled such that an IV bag comprises a septum or chamber which can be opened or broken to release the compound into the IV bag. Another type of kit may include a bolus kit in which the bolus kit comprises a pre-loaded syringe or similar easy to use, rapidly administrable device. An infusion kit may comprise the vials or ampoules and an IV solution (e.g., Ringer's solution) for the vials or ampoules to be added prior to infusion. The infusion kit may also comprise a bolus kit for a bolus/loading dose to be administered to the subject prior, during or after the infusion.

Any of the compositions described herein may be comprised in a kit. In a specific embodiment, a combinatorial therapeutic composition is provided in a kit, and in some embodiments the two or more compounds that make up the composition are housed separately or as a mixture. Antagonists of the channel that may be provided include but are not limited to antibodies (monoclonal or polyclonal), SUR1 oligonucleotides, SUR1 polypeptides, small molecules or combinations thereof, antagonist, etc.

Therapeutic kits of the present invention are kits comprising an antagonist or an related-compound thereof. Depending upon the condition and/or disease that is being treated, the kit may comprise an SUR1 antagonist or related-compound thereof to block and/or inhibit the $NC_{Ca-ATP}$ channel. The kit may comprise a TRPM4 antagonist or related-compound thereof to block and/or inhibit the $NC_{Ca-ATP}$ channel. The kit may comprise both a TRPM4 antagonist or related-compound thereof and a SUR1 antagonist or related compound thereof to block and/or inhibit the $NC_{Ca-ATP}$ channel. Such kits will generally contain, in suitable container means, a pharmaceutically acceptable formulation of SUR1 antagonist, TRPM4 antagonist, or related-compound thereof. The kit may have a single container means, and/or it may have distinct container means for each compound. For example, the therapeutic compound and solution may be contained within the same container; alternatively, the therapeutic compound and solution may each be contained within different containers. A kit may include a container with the therapeutic compound that is contained within a container of solution.

When the components of the kit are provided in one and/or more liquid solutions, the liquid solution is an aqueous solution, with a sterile aqueous solution being particularly preferred. The SUR1 antagonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

Examples of aqueous solutions include, but are not limited to ethanol, DMSO and/or Ringer's solution. In certain embodiments, the concentration of DMSO or ethanol that is used is no greater than 0.1% or (1 ml/1000 L). However, the components of the kit may be provided as dried powder(s). When reagents and/or components are provided as a dry powder, the powder can be reconstituted by the addition of a suitable solvent. It is envisioned that the solvent may also be provided in another container means.

VIII. Insurance Processing Embodiments

In one embodiment of the invention, there is provided a method for processing an insurance claim for diagnosis and/or treatment of a medical condition of the invention using a composition(s) of the invention as disclosed herein and/or using a treatment method as disclosed herein. In a specific embodiment, the method employs a computer for said processing of an insurance claim. In further specific embodiments, the dosage for the composition may be any suitable dosage for treatment of the medical condition.

In embodiments of the present invention, a subject, in particular a human subject, may be examined and/or may be diagnosed as suffering from, or being at risk of, a disease or condition selected from, for example, progressive hemorrhagic necrosis following spinal cord injury, traumatic brain injury, subarachnoid hemorrhage, and/or intraventricular hemorrhage. Such an examination may be performed by, for example, a physician, including a general practice physician or a specialist, such as an emergency room physician, a trauma specialist, an internist, a neurologist, a cardiologist, or other specialist; may be performed by a nurse, physician's assistant, medic, ambulance attendant, or other health professional. Examination and/or diagnosis may be performed anywhere, including at the scene of an accident or disaster; in an ambulance or other medial transport vehicle; in a clinic; in an examining room; in a hospital, including in any room or part of a hospital; in an extended care facility; or other health care facility. Such an examination may be an emergency examination, and/or a perfunctory examination, and or a minimally detailed examination, or may be an extended and detailed examination.

Such an examination may be performed without the use of clinical equipment or devices, or with some use of clinical equipment and devices, and may include the use of sophisticated clinical and/or diagnostic equipment and/or devices, which may include, for example, computer assisted tomography, magnetic resonance imaging, positron emission tomography, X-ray, ultrasound, or other imaging equipment; angiography, or other invasive procedures; and other medical equipment and procedures.

Such a diagnosis may be made as a result of an examination as discussed above, or may be made in the absence of an examination.

A medical practitioner, nurse, clinical or emergency technician or other person may provide medical assistance and diagnostic assistance in the course of providing routine, elective, or emergency medical care. In any case, all or part of the cost of such care, such procedures, such diagnostic work, and such diagnoses may be reimbursed by an insurance plan, employment agreement, government program, or other arrangement from which the subject may benefit. For example, a human subject may be covered by an insurance policy which pays for and/or reimburses ("covers") medical costs incurred by the subject.

As disclosed herein, a method for processing an insurance claim for diagnosis and/or treatment of a medical condition of the invention as disclosed herein, for a subject who has received medical treatment for progressive hemorrhagic necrosis following spinal cord injury, traumatic brain injury, subarachnoid hemorrhage, and/or intraventricular hemorrhage, includes the steps of:

I) receiving a claim for a medical treatment, procedure, and/or medicament for treating for progressive hemorrhagic necrosis following spinal cord injury, traumatic brain injury, subarachnoid hemorrhage, and/or intraventricular hemorrhage with a SUR1 antagonist, a TRPM4 antagonist, or combination thereof; and ii) providing reimbursement for the medical treatment, procedure, and/or medicament.

In a further embodiment, a method for processing an insurance claim for diagnosis and/or treatment of a medical condition of the invention as disclosed herein, for a subject who has received medical treatment for progressive hemorrhagic necrosis following spinal cord injury, traumatic brain injury, subarachnoid hemorrhage, and/or intraventricular hemorrhage, includes the steps of:

I) receiving a claim for a medical treatment, procedure, and/or medicament for treating for progressive hemorrhagic necrosis following spinal cord injury, traumatic brain injury, subarachnoid hemorrhage, and/or intraventricular hemorrhage with a SUR1 antagonist, a TRPM4 antagonist, or both;

ii) evaluating the claim for a medical treatment, procedure, and/or medicament; and ii) providing reimbursement for the medical treatment, procedure, and/or medicament.

In embodiments of these methods for processing an insurance claim, any one or more of the steps may involve the use of a computer; any one or more of the steps may involve the use of electronic data transfer; any one or more of the steps may involve the use of a telephone and/or facsimile device; any one or more of the steps may involve the use of mail and/or of a delivery service; and any one or more of the steps may involve the use of electronic fund transfer devices and/or methods.

In embodiments of these methods for processing an insurance claim, the treatment may include a treatment or medicament comprising any suitable dosage of a SUR1 antagonist, a TRPM4 antagonist, or combination thereof, for treatment of the medical condition.

In particular embodiments of the methods for processing an insurance claim, the treatment and/or medicament is directed to, or affects, the $NC_{Ca\text{-}ATP}$ channel.

In particular embodiments of the methods for processing an insurance claim, the treatment and/or medicament uses or includes a SUR1 antagonist such as, for example, glibenclamide and tolbutamide, repaglinide, nateglinide, meglitinide, midaglizole, LY397364, LY389382, glyclazide, glimepiride, estrogen, estrogen related-compounds (estradiol, estrone, estriol, genistein, non-steroidal estrogen (e.g., diethylstilbestrol), phytoestrogen (e.g., coumestrol), zearalenone, etc.), and compounds known to inhibit or block KATP channels.

In particular embodiments of the methods for processing an insurance claim, the treatment and/or medicament uses or includes a TRPM4 antagonist such as, for example, flufenamic acid, pinkolant, rimonabant, or a fenamate (such as flufenamic acid, mefenamic acid, meclofenamic acid, or niflumic acid), 1-(beta-[3-(4-methoxy-phenyl)propoxy]-4-methoxyphenethyl)-1H-imidazole hydrochloride, and a biologically active derivative thereof.

In particular embodiments of the methods for processing an insurance claim, the treatment and/or medicament uses or includes a SUR1 antagonist and a TRPM4 antagonist.

In further embodiments of the methods for processing an insurance claim, the treatment and/or medicament uses or includes a treatment and/or medicament is directed to, or affects, the $NC_{Ca\text{-}ATP}$ channel, where a treatment and/or medicament is directed to, or affects, the $NC_{Ca\text{-}ATP}$ channel includes or uses a non-sulfonyl urea compound, such as 2,3-butanedione and 5-hydroxydecanoic acid, quinine, and therapeutically equivalent salts and derivatives thereof; a protein, a peptide, a nucleic acid (such as an RNAi molecule or antisense RNA, including siRNA), or a small molecule that antagonizes or reduces the activity of the $NC_{Ca\text{-}ATP}$ channel; and/or includes or uses MgADP.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Up-Regulation of SUR1 in SCI

SUR1 expression was studied in spinal cords of uninjured rats and rats after "severe" SCI (10-gm weight dropped 25 mm; 3-5 rats/group) (Soblosky et al., 2001; Gensel et al., 2006). In controls, low levels of SUR1 expression were found in the dorsal horns (FIG. 1a), due to constitutively expressed KATP channels (Yamashita et al., 1994).

After unilateral SCI, the lesion itself as well as the pattern of SUR1 expression changed with time and distance from the impact site (FIG. 1a). Early post-SCI (¾ h), the lesion was small and was not immunolabeled by anti-SUR1 antibody (not shown). At 6 h, a necrotic lesion was apparent as a void in the ipsilateral cord, and SUR1 up-regulation was prominent in tissues surrounding the void. At 24 h, the necrotic lesion had enlarged (Nelson et al., 1977; Tator, 1995), SUR1 up-regulation was still apparent in the rim of the necrotic lesion, but now it extended to tissues more distant from the impact site, including into the contralateral hemi-cord. Immunolabeling for SUR2 was detected only in vascular smooth muscle cells of pial arterioles, both pre- and post-SCI.

Figure 6:
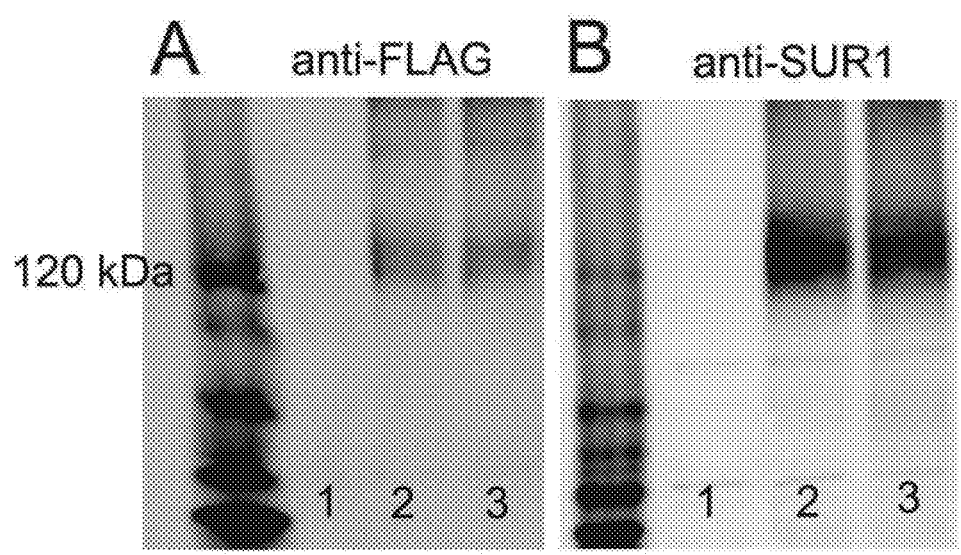
FIGS. 6A-6B demonstrate a western blot validating the specificity of the anti-SUR1 antibody (6B) compared to an anti-FLAG control (6A).

In the "core" of the lesion (heavily labeled area in FIG. 1a, 6 h), SUR1 up-regulation was present in various cells and structures, including large ballooned neuron-like cells and capillary-like elongated structures (FIG. 1b). In the "penumbra" (tissue adjacent to the heavily labeled core in FIG. 1a, 6 h), SUR1 up-regulation was associated predominantly with capillaries (FIG. 1 c,d).

Up-regulation of SUR1 was confirmed with immunoblots. With the amount of protein loaded, SUR1 was not detectable in normal cords, whereas a prominent, single band at ~190 kDa (Simard et al., 2006) was observed 6 h post-SCI (FIG. 1e). The blood introduced into the tissues by the injury did not account for the increase in SUR1 (FIG. 1e). In situ hybridization confirmed widespread expression of SUR1 after injury, especially in capillaries and post-capillary venules in the penumbra (FIG. 1f,g).

Example 2

SUR1 In Endothelium is Associated with $NC_{Ca-ATP}$ Channel

SUR1 forms the regulatory subunit of both $NC_{Ca-ATP}$ and some $K_{ATP}$ channels (Chen et al., 2003). Our previous work demonstrated that, following exposure to hypoxia or ischemia in vivo, up-regulation of SUR1 in astrocytes and neurons is associated with expression of functional $NC_{Ca-ATP}$ channels, not $K_{ATP}$ channels (Chen et al., 2003; Simard et al., 2006). The same reports also showed up-regulation of SUR1 in capillaries, as was found here with SCI, but the associated channel was not identified. Endothelial cells may normally express $K_{ATP}$ channels, but the regulatory subunit of cardiovascular $K_{ATP}$ channels is generally SUR2, not SUR1 (Jansen-Olesen et al., 2005). Nevertheless, it was important to determine which of the two channels, $K_{ATP}$ or $NC_{Ca-ATP}$, the newly expressed SUR1 was associated with in capillary endothelium.

Figure 2:
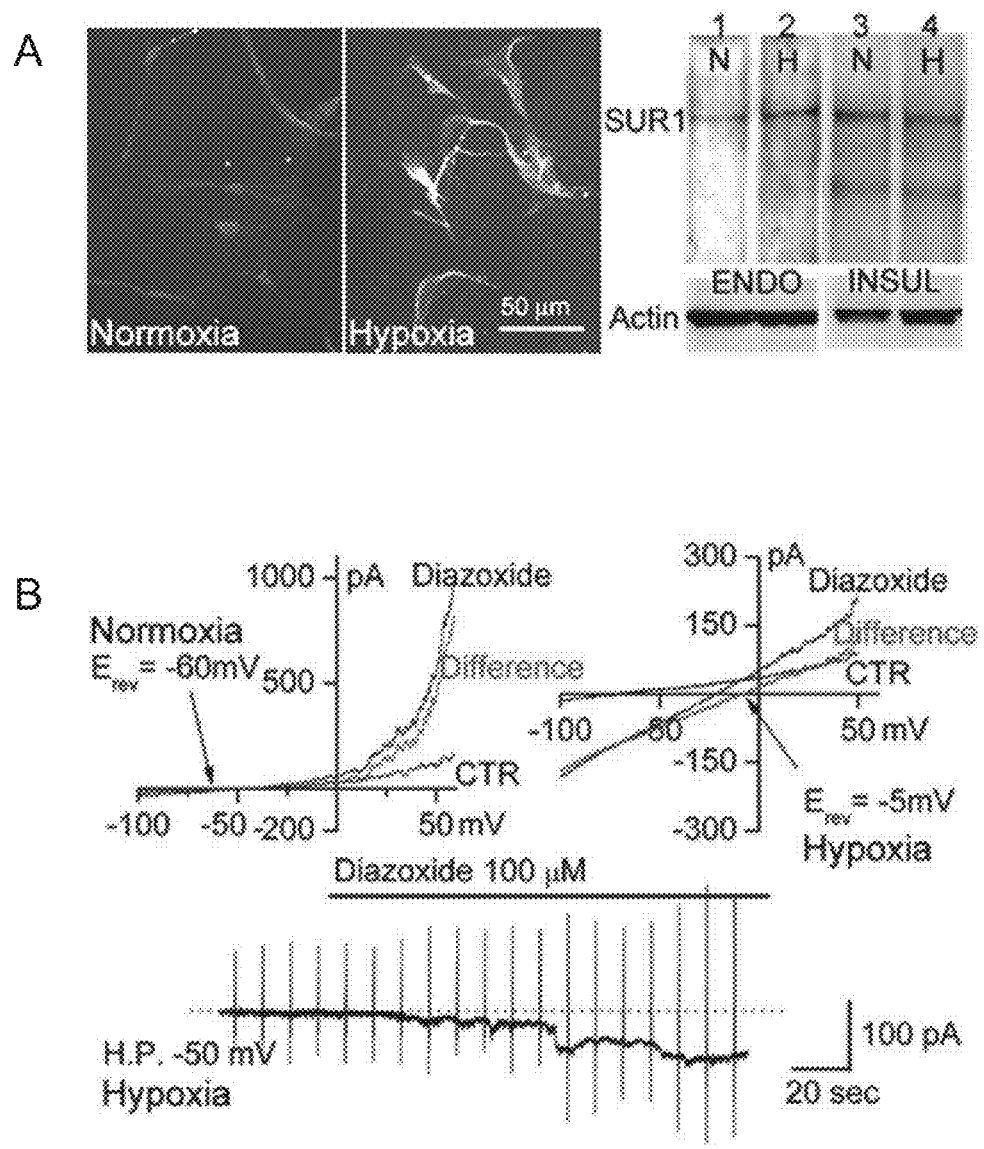
FIG. 2. SUR1-regulated $NC_{Ca\text{-}ATP}$ channel is up-regulated in endothelial cells by hypoxia. a: Immunolabeling and Western blots (lanes 1, 2) for SUR1 in human aortic endothelial cells (ENDO) cultured under normoxic (N) or hypoxic (H) conditions, as indicated; Western blots for SUR1 of rat insulinoma RIN-m5F cells (INSUL; lanes 3, 4) cultured under normoxic or hypoxic condition, with β-actin also shown. b,c: Whole-cell currents during ramp pulses (4/min; HP, −50 mV) or at the holding potential of −50 mV, before and after application of diazoxide (b) or Na azide (c), in endothelial cells exposed to normoxic or hypoxic conditions; the difference currents are also shown (red); data are representative of 7-15 recordings from human aortic endothelial cells (b) or bEnd.3 cells (c) for each condition. d: Single channel recordings of inside-out patches with $Cs^+$ as the principal cation, with channel openings inhibited by ATP on the cytoplasmic side; channel amplitude at various potentials indicated a slope conductance of 37 pS (data from 7 patches) from human brain microvascular endothelial cells.
Figure 2:
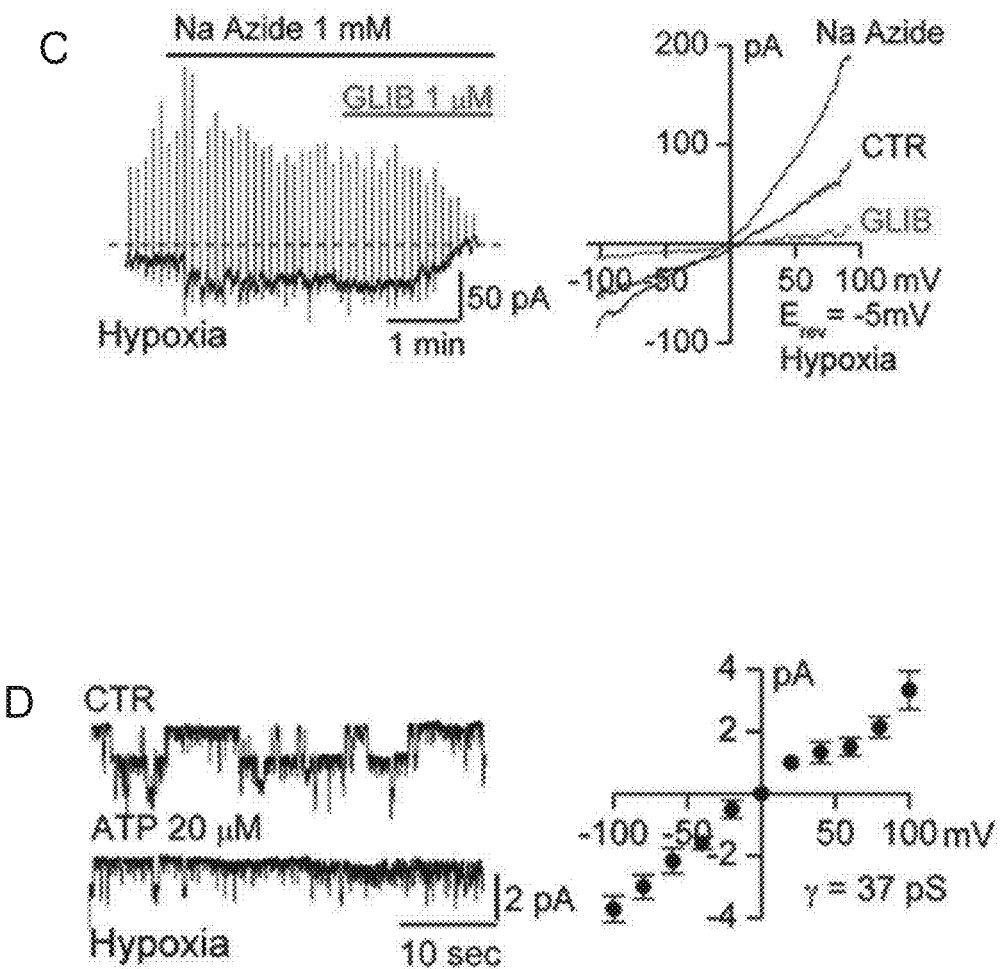

Endothelial cell cultures from 3 sources, human brain microvascular, human aorta, and murine brain microvascular, were used to assess SUR1 expression and characterize channel properties following exposure to hypoxia, with the same results observed with all 3. Control cultures showed little expression of SUR1, but exposure to hypoxia for 24 h resulted in significant up-regulation of SUR1 (FIG. 2a). Insulinoma cells, which constitutively express SUR1-regulated $K_{ATP}$ channels, showed no up-regulation of SUR1 when exposed to the same hypoxic conditions (FIG. 2a).

Patch clamp of endothelial cells was performed using a nystatin-perforated patch technique, to maintain the metabolic integrity of the cells. The identity of the activated channel can be assessed by measurement of the "reversal potential", the potential at which an ion channel current reverses from inward to outward. With physiologically relevant concentrations of ions intracellularly and extracellularly (high potassium inside, high sodium outside), the reversal potential can unambiguously distinguish between a $K^+$ channel current such as $K_{ATP}$, which reverses negative to −50 mV and a non-selective cation channel current such as $NC_{Ca-ATP}$, which reverses near 0 mV.

Channel activation by diazoxide was studied, which opens SUR-regulated channels without ATP depletion and, of SUR activators, is the most selective for SUR1 over SUR2 (Chen et al., 2003). Patch clamp of endothelial cells cultured under normoxic conditions showed that diazoxide either had no effect or, in half of the cells, activated an outwardly rectifying current that reversed at potentials more negative than −50 mV, consistent with a $K_{ATP}$ channel (FIG. 2b) (Seino, 1999). By contrast, in most endothelial cells cultured under hypoxic conditions, diazoxide activated an ohmic current that reversed near 0 mV and that was inward at −50 mV (FIG. 2b), which is incompatible with $K_{ATP}$, but consistent with $NC_{Ca-ATP}$ channels (Chen and Simard, 2001; Chen et al., 2003; Simard et al., 2006).

Channel activation induced by Na azide was also studied, which is a mitochondrial uncoupler that depletes cellular ATP (Chen and Simard, 2001). In most endothelial cells exposed to hypoxic conditions, Na azide-induced ATP depletion activated an ohmic current that was inward at −50 mV, that reversed near 0 mV, and that was blocked by 1 μM glibenclamide (FIG. 2c), again consistent with NCCa-ATP channels.

Single channel recordings were performed using inside-out patches, with $Cs^+$ as the only permeant cation. This confirmed the presence of a channel that was sensitive to block by ATP on the cytoplasmic side and that had a single channel conductance of 37 pS (FIG. 2d). These findings are incompatible with $K_{ATP}$ channels, which is not permeable to $Cs^+$ and which has a slope conductance of ~75 pS, but are consistent with $NC_{Ca-ATP}$ channels.

The characteristics of the channel identified in endothelial cells from both aorta and brain capillaries from 2 species, including expression only after exposure to hypoxia, activation by depletion of cellular ATP or diazoxide, a reversal potential near 0 mV, conductance of $Cs^+$, and single channel conductance of 37 pS, reproduce exactly our previous findings with $NC_{Ca-ATP}$ channels in astrocytes and neurons (Chen and Simard, 2001; Chen et al., 2003; Simard et al., 2006), and reaffirm that the $NC_{Ca-ATP}$ channel is not constitutively expressed, is up-regulated only with an appropriate insult, and when expressed, is inactive until intracellular ATP is depleted.

Example 3

Glibenclamide Block of SUR1-Extravasation of Blood

To assess the role of SUR1 in SCI, the effect of glibenclamide was studied, which is a sulfonylurea inhibitor that binds with subnanomolar or nanomolar affinity (0.4-4.0 nM) to SUR1 (24). Immediately after injury, animals were implanted with mini-osmotic pumps that delivered either vehicle or glibenclamide (200 ng/h) s.q. Constant infusion of a low-dose of drug was used to achieve sustained occupancy of only high-affinity receptors.

Figure 3:
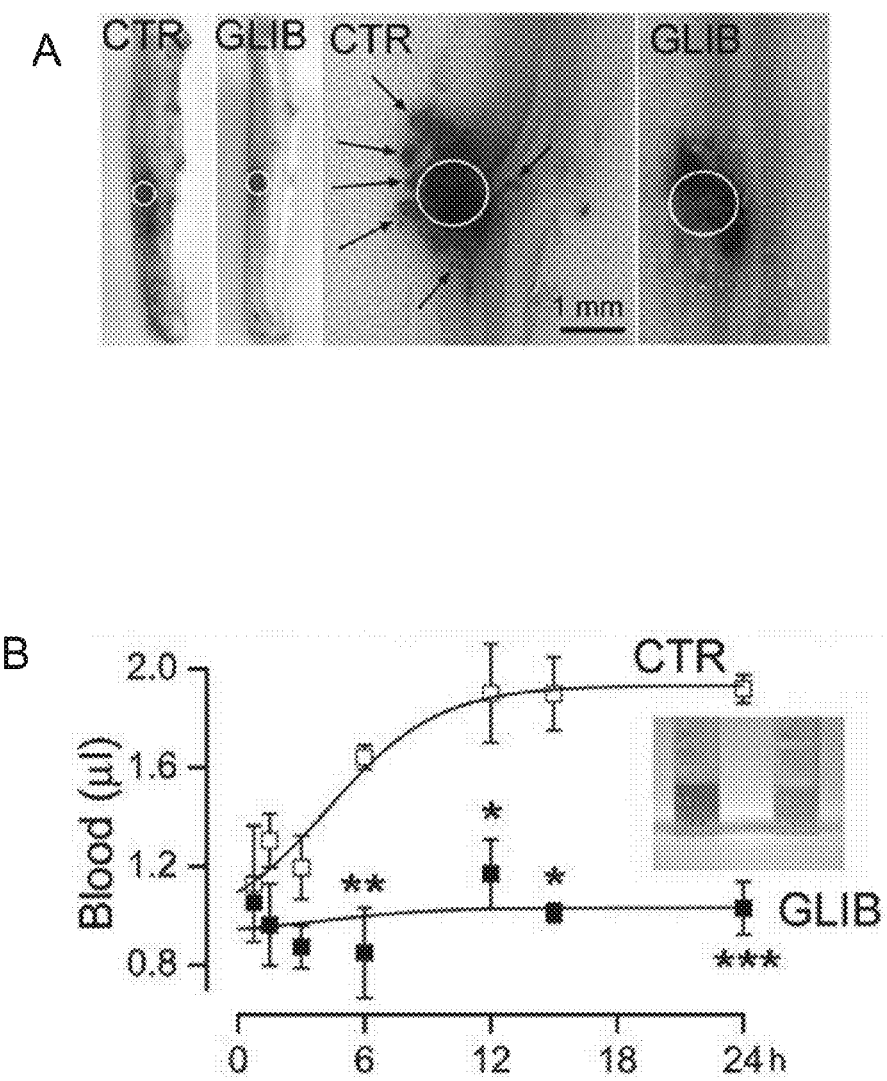
FIG. 3. Block of SUR1 reduces hemorrhage after SCI. a: whole cords and longitudinal sections of cords 24 h post-SCI, from vehicle-treated (CTR) and glibenclamide-treated (GLIB) rats; white circles indicate impact area. b: Cord homogenates in test tubes at 24 h, and spectrophotometric measurements of blood in cord homogenates at various times post-SCI, from vehicle-treated (CTR; n=66) and glibenclamide-treated (GLIB; n=62) rats; *, P<0.05; , P<0.01; *, P<0.001. c: Cord sections immunolabeled for vimentin to show capillaries, at two magnifications, from SCI rats treated with vehicle (CTR) or glibenclamide (GLIB); central canal marked by arrows; images representative of findings in 6 rats/group. d: Zymography of recombinant MMP-2 and MMP-9 performed under control conditions (CTR), in the presence of glibenclamide (10 μM; GLIB), and in the presence of MMP-inhibitor II (300 nM; Calbiochem). e: bleeding times in uninjured rats infused with vehicle (CTR) or glibenclamide (GLIB); 3 rats/group.
Figure 3:
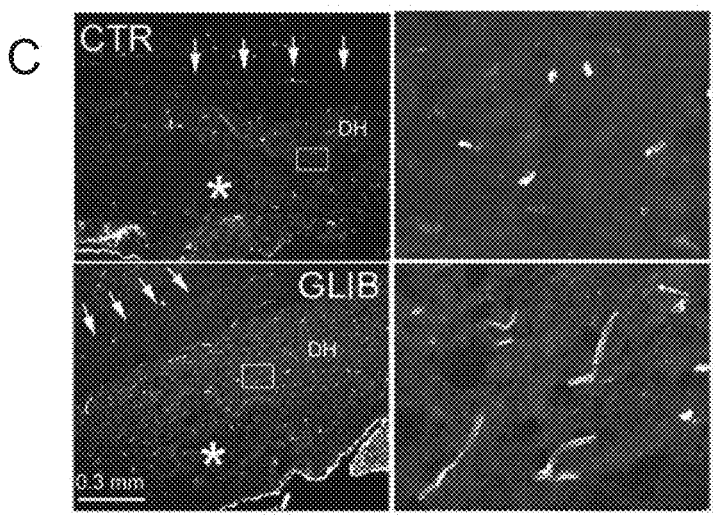
Figure 3:
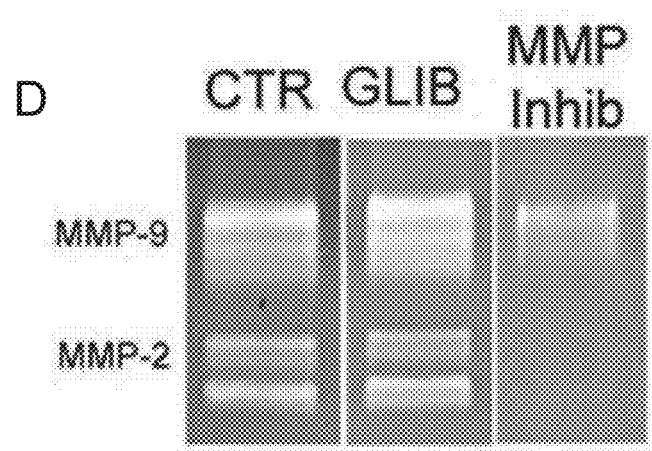
Figure 3:
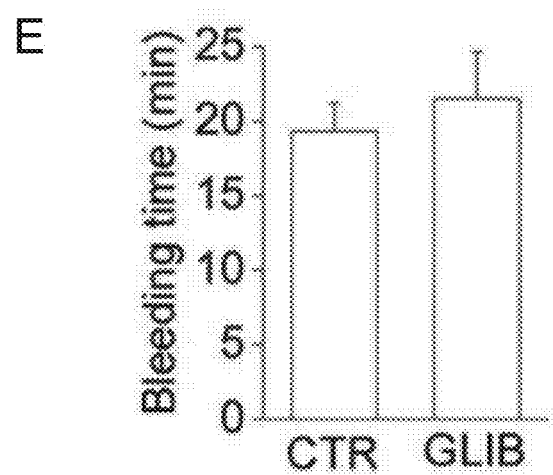

Cords of vehicle-treated animals examined 24 h post-SCI showed prominent bleeding at the surface and internally, with internal bleeding consisting of a central region of hemorrhage plus numerous distinct petechial hemorrhages at the periphery (FIG. 3a, arrows). By contrast, cords of glibenclamide-treated animals showed visibly less hemorrhage and it was largely confined to the site of impact, with fewer petechial hemorrhages in surrounding tissues (FIG. 3a).

The amount of extravasated blood in tissue homogenates was quantified at different times post-SCI, after first removing intravascular blood (FIG. 3b). In cords from vehicle-treated animals, measurements showed a progressive increase in the amount of blood, with a maximum reached ~12 h post-SCI (FIG. 3b). By contrast, cords from glibenclamide-treated animals showed little increase in extravasated blood during the 24 h after injury, with most of the blood present at 24 h being attributable to the initial impact (FIG. 3b).

Formation of petechial hemorrhages implies catastrophic failure of capillary integrity. Capillaries in the region of injury were examined by immunolabeling with vimentin, which is up-regulated in endothelium following injury (Haseloff et al., 2006). In controls, vimentin(+) capillaries appeared foreshortened or fragmented, whereas in glibenclamide-treated animals, the capillaries were elongated and appeared more normal (FIG. 3c).

In post-ischemic reperfusion of CNS tissues, catastrophic failure of capillary integrity has been attributed to the action of matrix metalloproteinases (MMP) (Wang et al., 2004). It was assessed whether glibenclamide might have an effect on MMP activity using zymography to measure gelatinase activity of recombinant MMP. Gelatinase activity was not affected by glibenclamide, although it was strongly inhibited by a specific MMP inhibitor (FIG. 3d), indicating that the reduction in hemorrhage with glibenclamide could not be attributed to MMP inhibition.

Glibenclamide did not affect bleeding time (FIG. 3e), suggesting that the reduction in hemorrhage with glibenclamide following SCI was unlikely to be due to an effect on coagulation or platelet function (Chan et al., 1982).

The dose of glibenclamide used resulted in a small decrease in serum glucose, from 236±15 to 201±20 (5 rats per group; p=0.19) measured 3 h after SCI.

Example 4

Glibenclamide Block of SUR1-Lesion Size

Figure 4:
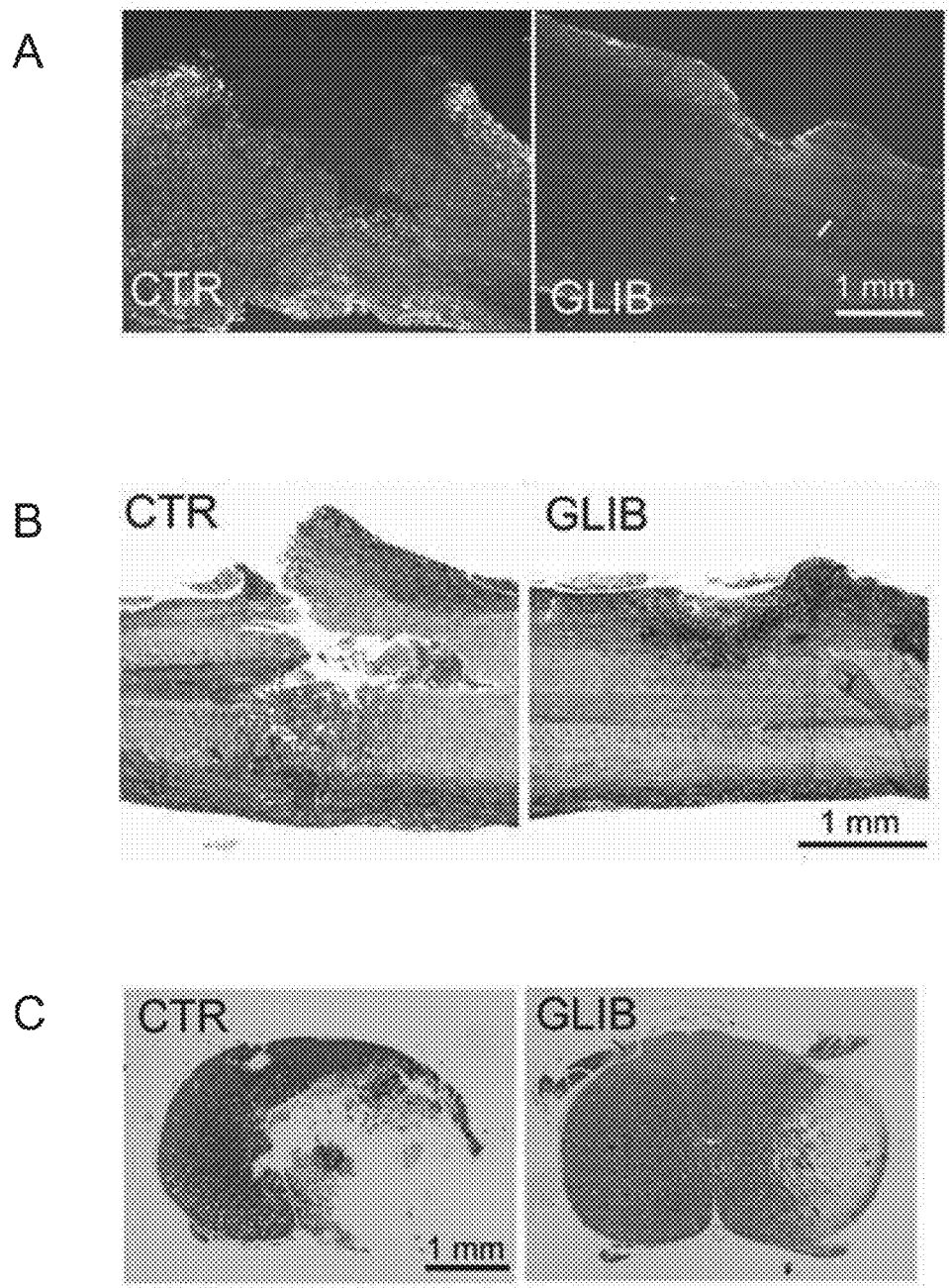
FIG. 4. Block of SUR1 reduces lesion size and improves neurobehavioral function after SCI. a-c: Cord sections immunolabeled for GFAP (a) or stained with Eriochrome cyanine-R (b) or hematoxylin and eosin (c), 1 d (a,b) or 7 d (c) post-SCI, from vehicle-treated (CTR) and glibenclamide-treated (GLIB) rats; images representative of findings in 3 rats/group. d: Cascaded outlines of lesion areas in serial sections 250 μm apart, 7 d post-SCI, from vehicle-treated (CTR) and glibenclamide-treated (GLIB) rats; lesion volumes from vehicle-treated (CTR) and glibenclamide-treated (GLIB) rats (n=4-6/group; excludes 2 CTR rats that died). e: Performance on inclined plane (head-up and head-down), ipsilateral paw placement and vertical exploration (rearing), at the times indicated post-SCI, in vehicle-treated (CTR) and glibenclamide-treated (GLIB) rats (same rats as in d); paw placement measured 1 d post-SCI; *, P<0.05; , P<0.01; *, P<0.001.
Figure 4:
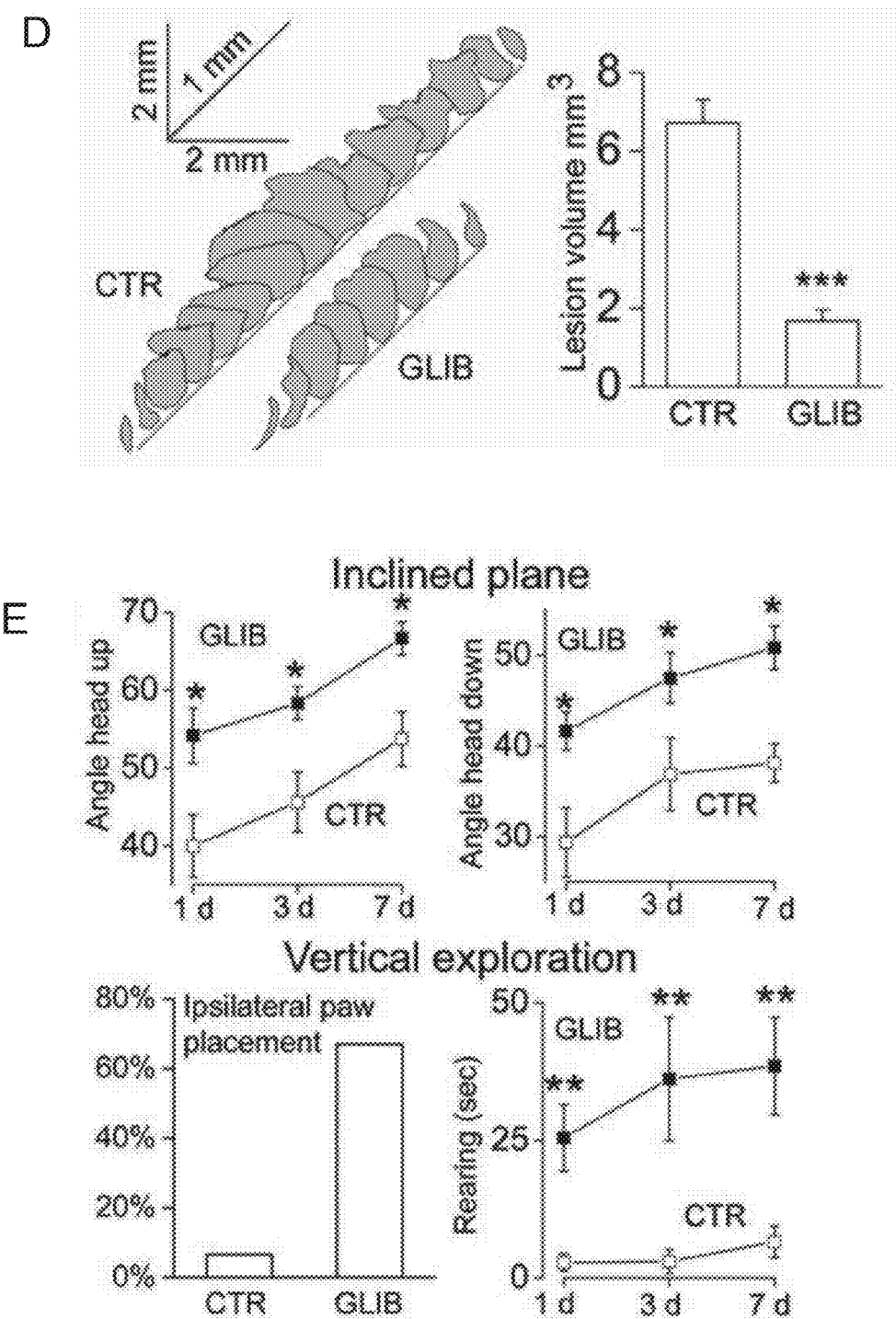

Labeling of longitudinal sections for the astrocyte-marker, glial fibrillary acidic protein (GFAP) and for myelin revealed that glibenclamide-treatment was associated with smaller lesions, less reactive gliosis and better myelin preservation 24 h post-SCI compared to controls (FIG. 4a,b). Similarly, hematoxylin and eosin staining of cross sections showed that glibenclamide-treatment was associated with smaller lesions 7 d post-SCI compared to controls (FIG. 4c). In vehicle-treated controls at both 1 and 7 d, the lesions incorporated large voids of necrotic tissue that involved most of the hemicord ipsilateral to the impact site and that typically extended to the contralateral hemicord. White matter tracts of the contralateral hemicord were typically disrupted. By contrast, lesions in glibenclamide-treated animals were smaller, typically did not cross the midline, and contralateral as well as portions of ipsilateral white matter tracts were spared. Lesion volumes at 7 d were ~3-fold smaller in glibenclamide-treated rats compared to controls (FIG. 4d). Notably, the lesion volumes we observed with glibenclamide following a "severe" impact (10 gm×25 mm) were comparable to those observed by other investigators in untreated rats using the same cervical contusion model following a "mild" impact (10 gm×6.25 mm) (Gensel et al., 2006).

Example 5

Glibenclamide Block of SUR1-Neurobehavioral Function

Vehicle-treated rats were generally not mobile (Soblosky et al., 2001), whereas glibenclamide-treated rats were typically ambulatory and often exhibited proficient exploratory behavior. When suspended by their tail, vehicle-treated rats hung passively with little or no flexion of the trunk, whereas glibenclamide-treated rats could typically flex their trunk, bringing the snout to the level of the thorax or hindquarters.

The same animals used to assess lesion size on an inclined plane were tested, which is a standard test that requires more-and-more dexterous function of the limbs and paws as the angle of the plane is increased (Rivlin and Tator, 1977). At 1, 3 and 7 d post-SCI, glibenclamide-treatment was associated with significantly better performance than vehicle-treatment (FIG. 4e).

Ipsilateral paw placement was quantified, which is characteristically lost following cervical hemicord transection (Nikulina et al., 2004). In the same animals tested 1 d post-SCI, glibenclamide-treatment was associated with significantly better performance than vehicle-treatment (FIG. 4e).

The BBB scale (Basso et al., 1995) is commonly used to evaluate neurobehavioral function in rodents post-SCI. However, it was designed for thoracic-level lesions, not cervical-level lesions, and the highest level of performance that it records is less than what our glibenclamide-treated rats could achieve. The vertical exploratory behavior ("rearing") was quantified, a complex exercise that requires balance, truncal stability, bilateral hindlimb dexterity and strength, and at least unilateral forelimb dexterity and strength, which together are excellent markers of cervical spinal cord function. Testing the same rats as above at 1, 3 and 7 d post-SCI showed that glibenclamide-treatment was associated with significantly better performance than vehicle-treatment (FIG. 4e). In additional groups of rats tested only at 1 d post-SCI, similar differences were observed (3±1 vs. 42±7 sec; P=0.001; 14-15 rats/group).

Example 6

Repaglinide Block of SUR1

Repaglinide is a member of a distinct class of insulin secretagogues that are structurally unrelated to sulphonylureas and whose binding site may differ from that of sulfonylureas (Hansen et al., 2002) Like glibenclamide, repaglinide produces high-affinity block of both native and recombinant β-cell $K_{ATP}$ channels ($IC_{50}$=0.9-7 nM), and shows higher potency in inhibiting pancreatic SUR1-regulated KATP channels than cardiovascular SUR2-regulated channels (Stephan et al., 2006).

The effect of repaglinide on PHN was examined, using the same treatment regimen as used for glibenclamide. As with glibenclamide, repaglinide treatment reduced blood in cord homogenates from 1.8±0.2 to 1.2±0.1 µl at 1 d post-SCI (P<0.01; 5-8 rats/group), and was associated with significantly better performance on the inclined plane (head up: 40±4 vs. 62±2 degrees; P=0.01; head down: 29±4 vs. 47±3 degrees; P=0.03; n=3-8/group) and in vertical exploration (3±2 vs. 27±6 sec; P=0.005; 5-6 rats/group) than vehicle-treated controls.

Example 7

Gene Suppression of SUR1

Gene suppression was used to confirm involvement of SUR1 in PHN, choosing an antisense-oligodeoxynucleotide strategy shown to be effective in vitro (Yokoshiki et al., 1999).

Figure 5:
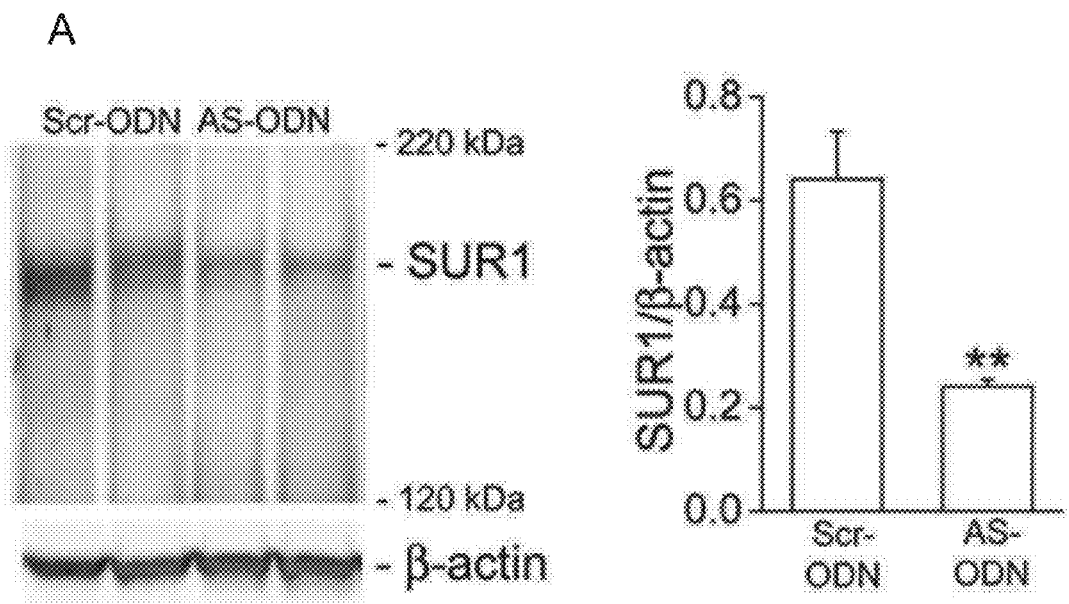
FIG. 5. Gene suppression of SUR1 blocks expression of functional $NCCa\text{-}ATP$ channels and improves outcome in SCI. a: Western blots for SUR1 in gliotic capsule from rats with infusion of Scr-ODN (lanes 1, 2) or AS-ODN (lanes 3, 4) directly into the brain injury site for 10-12 d prior to tissue harvest; densitometric analysis of Western blots from the same groups of rats (n=3/group). b: Membrane potential of astrocytes from gliotic capsules of the same groups of rats, during application of Na azide to deplete ATP; the average depolarization in the 2 groups is shown; 3 cells/group. c: Cord sections immunolabeled for SUR1, 1 d post-SCI, from rats treated with i.v. infusion of Scr-ODN or AS-ODN; quantitative immunofluorescence for the same groups of rats; (n=3/group). d: measurements of blood in cord homogenates, performance on angled plane, and vertical exploration, 1 d post-SCI, for rats treated with i.v. infusion of Scr-ODN or AS-ODN; *, P<0.05; **, P<0.01.
Figure 5:
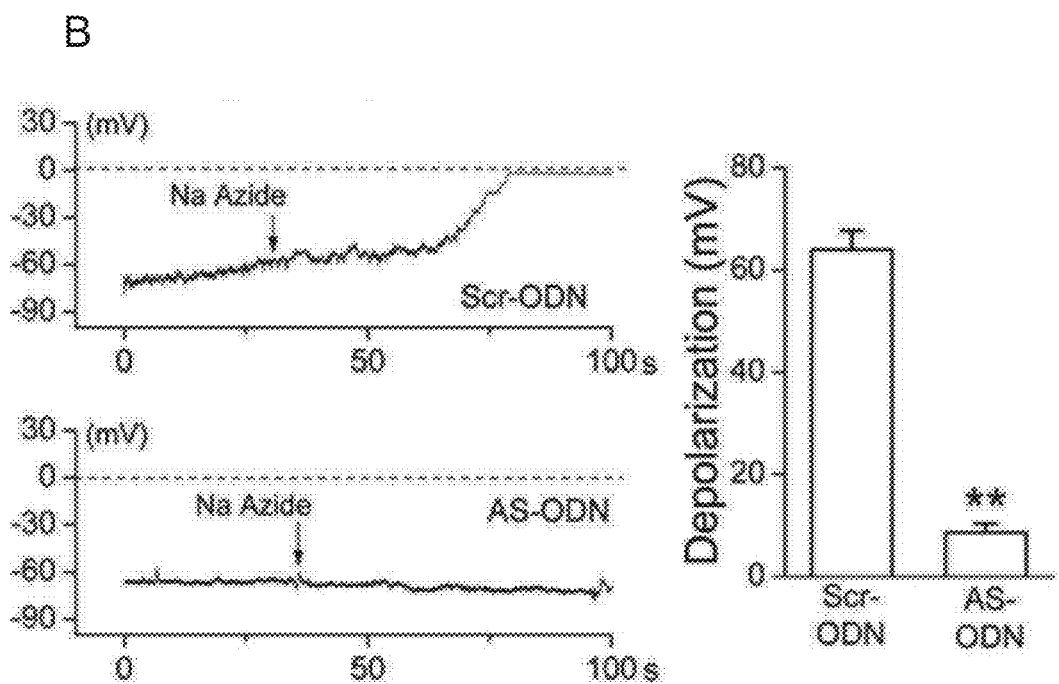
Figure 5:
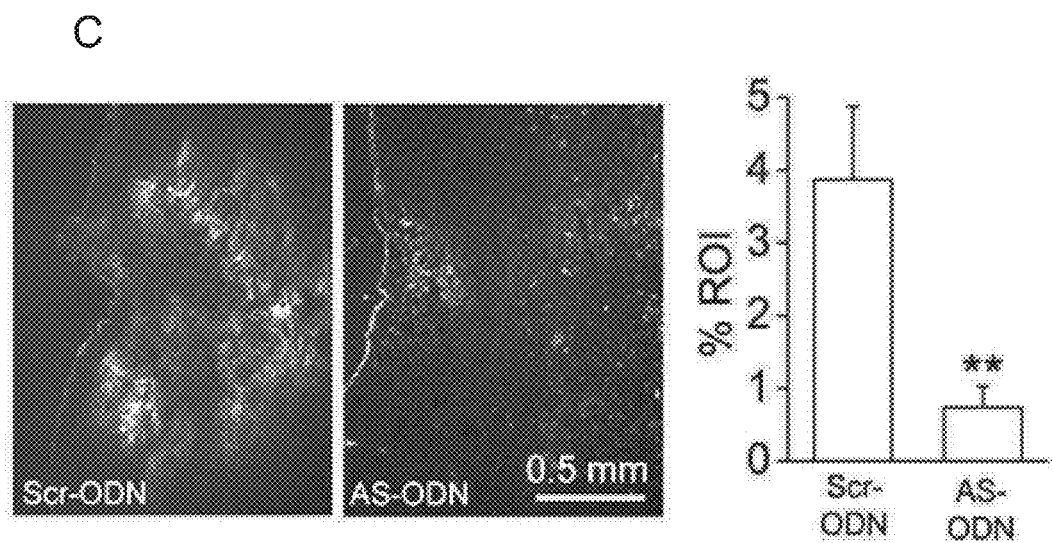
Figure 5:
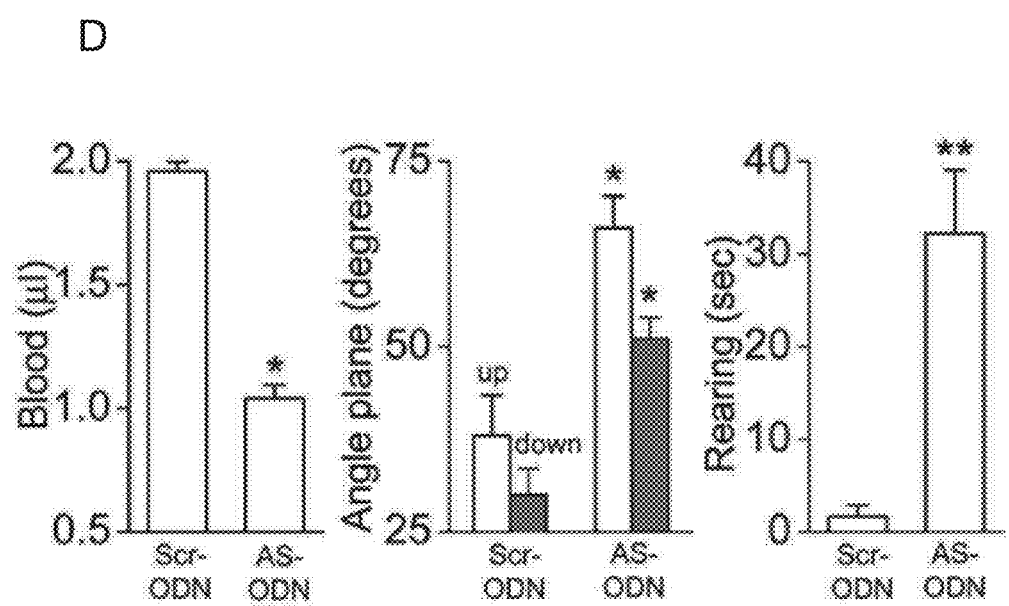

To validate the antisense strategy, it was first implemented in the model that was originally used for the discovery of the $NC_{Ca-ATP}$ channel, wherein a gelatin sponge is implanted into the parietal lobe to stimulate formation of a gliotic capsule (Chen and Simard, 2001). Here, animals were also fitted with mini-osmotic pumps that delivered oligodeoxynucleotides (ODN), either antisense (AS) or scrambled (Scr), continuously for 7 d into the injury site. Gliotic capsules from rats treated with AS-ODN showed a significant reduction in SUR1 protein, compared to Scr-ODN (FIG. 5a). Patch clamp of astrocytes from gliotic capsule of rats treated with Scr- ODN showed that they rapidly depolarized when cellular ATP was depleted by exposure to Na azide (FIG. 5b), an effect that was previously shown was due to opening of NCCa-ATP channels (Chen et al., 2003). By contrast, astrocytes from rats treated with AS-ODN depolarized only slightly or not at all (FIG. 5b), demonstrating that SUR1 is required for expression of functional $NC_{Ca\text{-}ATP}$ channels, just as with $K_{ATP}$ channels (Sharma et al., 1999).

For experiments with SCI, AS-ODN and Scr-ODN were used that were phosphorothioated at 4 distal bonds to protect against endogenous nucleases (Galderisi et al., 1999), with ODN's administered i.v. starting immediately after injury. At 6 h post-SCI, cords from rats treated with AS-ODN showed significantly less immunolabeling for SUR1 than controls (FIG. 5c). With Scr-ODN, the necrotic void beneath the impact site was surrounded by an SUR1-positive shell of tissue, similar to observations in untreated animals (FIG. 1a). With AS-ODN, however, only the small volume of tissue immediately beneath the impact site was labeled for SUR1, and no necrotic void was evident (FIG. 5c). AS-ODN did not affect normal expression of SUR1 in dorsal horn cells (FIG. 5c). At 1 d post-SCI, treatment with AS-ODN reduced blood in cord homogenates, and was associated with significantly better performance on the inclined plane and in vertical exploration compared to Scr-ODN (FIG. 5d).

Example 8

Significance of Certain Embodiments of the Invention

The present invention includes the novel finding that SUR1 is strongly up-regulated following SCI, and that block of SUR1 is associated with significant improvements in all of the characteristic manifestations of PHN, including hemorrhage, tissue necrosis, lesion evolution and neurological dysfunction. Although one embodiment focused on SUR1 and $NC_{Ca\text{-}ATP}$ channels in capillary endothelium, the data also showed early (<6 h) up-regulation of SUR1 in large neuron-like cells in the core near the impact site, and in other studies, late (12-24 h) up-regulation of SUR1 in reactive astrocytes was observed. These responses to SCI may be compared to findings previously reported for ischemic stroke, wherein there is early up-regulation of SUR1 in neurons and capillaries in the core, and later up-regulation of SUR1 in capillaries and astrocytes in penumbral tissues (Simard et al., 2006).

PHN has been linked to tissue ischemia (Nelson et al., 1977; Tator, 1995), but has not previously been characterized at a molecular level. PHN is probably a variant of "hemorrhagic conversion", a mechanism of secondary injury in the CNS, wherein capillaries or post-capillary venules undergo delayed catastrophic failure that allows extravasation of blood to form petechial hemorrhages, which in turn coalesce into a unified region of "hemorrhagic necrosis" or "hemorrhagic infarction" (Simard et al., 2007). Hemorrhagic conversion is common in traumatic brain injury (Oertel et al., 2002) and following post-ischemic reperfusion (Wang et al., 2004), with hypoxia and active perfusion being important antecedents (Simard et al., 2007). The molecular pathology involved in hemorrhagic conversion has not been fully elucidated, but work in ischemic stroke has implicated enzymatic destruction of capillaries by matrix-metalloproteinases (MMP) (Wang et al., 2004; Gidday et al., 2005). MMPs have been implicated in SCI (Noble et al., 2002; Pannu et al., 2007), but not in PHN.

The work reported here indicates that endothelial SUR1-regulated $NC_{Ca\text{-}ATP}$ channels are involved in PHN. The data show that PHN was associated with up-regulation of SUR1 in capillaries and post-capillary venules, structures long held to be responsible for PHN (Griffiths et al., 1978; Kapadia, 1984). Moreover, the data show that block of SUR1 by 3 molecularly distinct agents, glibenclamide, repaglinide and AS-ODN, significantly reduced PHN. The remarkably similar outcomes obtained with highly selective agents that act via distinct molecular mechanisms underscore the important role of SUR1. These data also provide evidence that de novo expression of SUR1 is necessary and sufficient for development of PHN. Use of a knock-down strategy employing AS-ODN appears to have been more informative than a gene knock-out strategy, since the latter would not have distinguished between constitutive and de novo expression of SUR1.

SUR1 forms the regulatory subunit of both $NC_{Ca\text{-}ATP}$ and some $K_{ATP}$ channels (Chen et al., 2003; Simard et al., 2006). Here, it is shown that up-regulation of SUR1 in endothelial cells was associated with expression of functional $NC_{Ca\text{-}ATP}$ channels, which was previously implicated in edema formation and cell death in CNS ischemia/hypoxia (Simard et al., 2006; Simard et al., 2007). Our patch clamp recordings confirmed the presence of non-selective cation channel that was activated by diazoxide and ATP-depletion, blocked by glibenclamide and cytoplasmic ATP, conducted $Cs^+$, and had a single channel conductance of ~35 pS, all of which are characteristic of the $NC_{Ca\text{-}ATP}$ channel (Chen and Simard, 2001; Chen et al., 2003). It was previously shown that this channel conducts only monovalent, not divalent cations (Chen and Simard, 2001). The studies reported here showing up-regulation of functional $NC_{Ca\text{-}ATP}$ channels were performed using endothelial cells from CNS as well as non-CNS sources from two species, suggesting a certain degree of generality of the phenomenon. In the patch clamp studies, endothelial cells from spinal cord were not explicitly studied, which could potentially differ from those in brain. However, it seems unlikely that the up-regulation of SUR1 in spinal cord capillaries that was observed was associated with a different channel, such as $K_{ATP}$. Sulfonylurea block of $K_{ATP}$ would not be expected to be neuroprotective (Sun et al., 2007), whereas block of $NC_{Ca\text{-}ATP}$ is highly neuroprotective in both rodents and humans (Simard et al., 2006; Kunte et al., 2007).

Of the numerous treatments assessed in SCI, very few have been shown to actually decrease the hemorrhage and tissue loss associated with PHN. Methylprednisolone, the only approved therapy for SCI, improves edema, but does not alter the development of PHN (Merola et al., 2002). A number of compounds have shown beneficial effects related to tissue sparing, including the NMDA antagonist, MK801 (Faden et al., 1988), the AMPA antagonist, GYKI 52466 (Colak et al., 2003), $Na^+$ channel blockers (Schwartz and Fehlings, 2001), and minocycline (Teng et al., 2004). Overall however, no treatment has been reported that reduces PHN and lesion volume, and that improves neurobehavioral function to the extent observed here with glibenclamide, repaglinide and AS-ODN.

There are 2 mechanisms by which glibenclamide can antagonizing SUR1-regulated $NC_{Ca\text{-}ATP}$ channels: (I) by block of the channel once it is expressed and subsequently opened by ATP depletion (Chen et al., 2003); (ii) by interfering with trafficking of SUR1 to the cell membrane, a process that is required for expression of functional channels (Partridge et al., 2001). Both block of open channels (Simard et al., 2006) and SUR1 binding (Nelson et al.,) needed to inhibit trafficking are increased an order of magnitude or more at the low pH of ischemic tissues. Either block of open channels or interference with trafficking or both, coupled with the augmented efficacy imparted by low pH, likely account for the high efficacy of glibenclamide found previously with stroke (Simard et al., 2006) and here with SCI.

Half of patients with SCI initially present with an incomplete lesion (Bracken et al., 1990), making it important to identify therapeutic strategies to inhibit secondary injury mechanisms. Glibenclamide has been used safely in humans for several decades for treatment of type 2 diabetes, with no untoward side-effects except hypoglycemia, and its continued use immediately post-stroke improves outcome in patients with type 2 diabetes (Kunte et al., 2007). The safety of glibenclamide, plus its unique mechanism of action in targeting the capillary failure that leads to PHN, indicate that this drug may be especially attractive for translational use in human SCI.

Example 9

Exemplary Materials and Methods

SCI injury model. This study was performed in accordance with the guidelines of the Institutional Animal Care and Use Committee. Adult female Long-Evans rats (275-350 gm) were anesthetized (Ketamine, 60 mg/kg plus Xylazine, 7.5 mg/kg, i.p.). The dura at C4-5 was exposed via a left hemilaminectomy. A hemi-cervical spinal cord contusion was created using a blunt force impactor (1.3-mm impactor head driven by a 10 gm weight dropped vertically 25 mm) (Soblosky et al., 2001; Gensel et al., 2006). After SCI, animals were given 10 ml of glucose-free normal saline s.q. Rectal temperature was maintained at ~37° C. using a servo-controlled warming blanket. Blood gases and serum glucose 10-15 min post-SCI were: $pO_2$, 95±6 mm Hg; $pCO_2$, 46±3 mm Hg; pH, 7.33±0.01; glucose 258±17 mg/dl in controls and $pO_2$, 96±7 mm Hg; $pCO_2$, 45±2 mm Hg; pH, 7.37±0.01; glucose 242±14 mg/dl in glibenclamide-treated animals.

Drug delivery. Within 2-3 min post-SCI, mini-osmotic pumps (Alzet 2002, 0.5 μl/h; Durect Corporation) were implanted that delivered either vehicle (saline plus DMSO), glibenclamide (Sigma) in vehicle, or repaglinide (Sigma) in vehicle subcutaneously. During the course of the project, slightly different formulations of drug were used, with the best results obtained using stock solutions made by placing 50 mg (or 25 mg) of drug into 10 ml DMSO, and infusion solutions made by placing 400 μl (or 800 μl) stock into 4.6 ml (or 4.2 ml) unbuffered saline (0.9% NaCl) and adjusting the pH to ~8.5 using 0.1 N NaOH. Infusion solutions of glibenclamide and repaglinide were delivered at 0.5 μl/h, yielding infusion doses of 200 ng/h.

For in vivo gene suppression of SUR1, we used oligodeoxynucleotides that were phosphorothioated at 4 distal bonds to protect against endogenous nucleases (35). Within a few min of SCI, mini-osmotic pumps (Alzet 2002, 0.5 μl/h; Durect Corporation) with jugular vein catheters were implanted that delivered either scrambled sequence ODN (Scr-ODN) (5'-TGCCTGAGGCGTGGCTGT-3'; SEQ ID NO:1) or antisense ODN (AS-ODN) (5'-GGCCGAGTGGT-TCTCGGT-3'; SEQ ID NO:2) (Yokoshiki et al., 1999) in PBS at a rate of 1 mg/rat/24 h.

Tissue blood. Rats were sacrificed at various times after SCI (n=5-11 rats/group), were perfused with heparinized saline to remove intravascular blood, and 5-mm segments of cord encompassing the lesion were homogenized and processed as described (Choudhri et al., 1997).

Lesion size. At 7 d post-SCI, cords were paraffin sectioned and stained with H&E. Lesion volumes were calculated from lesion areas measured on serial sections every 250 μm.

Neurobehavioral Assessment. All measurements were performed by blinded evaluators. Performance on the inclined plane was evaluated as described (Rivlin and Tator, 1977). To assess paw placement and vertical exploration (rearing) (Nikulina et al., 2004) animals were videotaped while in a translucent cylinder (19×20 cm). Rearing was quantified as the number of seconds spent with both front paws elevated above shoulder-height during a 3-min period of observation.

Bleeding times were measured using tail tip bleeding as described (Lorrain et al., 2003).

Zymography of recombinant MMP-2 and MMP-9 (Sigma) was performed as described (Sumii and Lo, 2002).

Cell culture. Endothelial cell cultures from human brain microvessels, human aorta (ScienCell Research Laboratories), and murine brain microvessels (bEnd.3; ATCC), were grown at low density using media and supplements recommended by suppliers.

SUR1 knock-down in astrocytes was performed in triplicates by implanting rats with gelatin sponges in the parietal lobe to induce formation of a gliotic capsule containing reactive astrocytes that express the SUR1-regulated $NC_{Ca\text{-}ATP}$ channel (Chen and Simard, 2001; Chen et al., 2003). At the same time, they were implanted with mini-osmotic pumps (Alzet, model 2002; 14-day pump) placed in the dorsal thoracolumbar region that contained ODN (711 μg/ml delivered @ 0.5 μl/h, yielding 1500 picomoles/day), with the delivery catheter placed directly into the site of the gelatin sponge implant in the brain. Animals were infused with Scr-ODN or AS-ODN, as above but not phosphorothioated. After 10-14 days, the gelatin sponge plus encapsulating gliotic tissues were harvested and processed either for Western immunoblots or to obtain fresh reactive astrocytes for patch clamp electrophysiology.

Patch clamp electrophysiology for the $NC_{Ca\text{-}ATP}$ channel in this lab has been described (Chen and Simard, 2001; Chen et al., 2003).

Immunohistochemistry. Cryosections were immunolabeled (Chen et al., 2003; Simard et al., 2006) using primary antibodies directed against SUR1 (Santa Cruz, C-16; 1:200; 1 h at RT, 48 h at 4° C.), SUR2 (Santa Cruz, H-80; 1:200; 1 h at RT, 48 h at 4° C.), GFAP (Sigma, C-9205; 1:500), and vimentin (Sigma, monoclonal CY3 conjugated; 1:100). Quantitative immunofluorescence was performed as described (Gerzanich et al., 2003).

Immunoblots were prepared using antibodies directed against SUR1. The specificity of the antibody (Chen and Simard, 2001; Chen et al., 2003; Simard et al., 2006) is demonstrated by the knock-down experiments of FIG. 5.

In situ hybridization. Fresh-frozen cord sections were fixed in 5% formaldehyde for 5 min. Digoxigenin-labeled probes (sense: '5-GCCCGGGCACCCTGCTGGCTCTGTGT-GTCCTTCCGCGCCTGGGCATCG-3'; SEQ ID NO:3) were designed and supplied by GeneDetect and hybridization was performed according to the manufacturer's protocol (see website for GeneDetect).

Example 10

Spinal Cord Injury, Progressive Hemorrhagic Necrosis and the NC(CA-ATP) Channel

Anti-SUR1 antibody. Because of the emerging importance of the SUR1-regulated $NC_{Ca\text{-}ATP}$ channel in SCI and other disorders (Simard et al., 2007), an antibody against SUR1 was developed. A part of the rat SUR1 cDNA (Protein Id, NP_037171; amino acid 598-965) was subcloned into pQE31 (Qiagen, Chatsworth, Calif.) to overexpress the protein in a hexa-histidine-tagged form in bacterial cells. The fusion protein was purified using a Ni+-agarose column and was used to raise antibodies in rabbits by a commercial service (Covance, Denver, Pa.). To validate the antibody, flag-tagged SUR1 was expressed in COS7 cells. Total lysates from COS7 cells transfected with a control empty vector (FIG. 6A lane 1, 6B lane 1) or with an expression vector encoding FLAG-tagged SUR1 (FIG. 6A lanes 2 and 3, 6B lanes 2 and 3) were examined by immunoblot using FLAG monoclonal M2 antibody (FIG. 6A) and the anti-SUR1 polyclonal antibody generated in this lab (FIG. 6B). Both antibodies detected the same band at ~160 kDa, as well as higher molecular weight products believed to be due to poly-ubiquitination of SUR1, as reported previously (Yan et al., 2005) Note that neither antibody detected any specific band from lysates from cells transfected with a control vector (FIG. 6A lane 1, 6B lane 1), consistent with a high specificity of the antibody.

Figure 7:
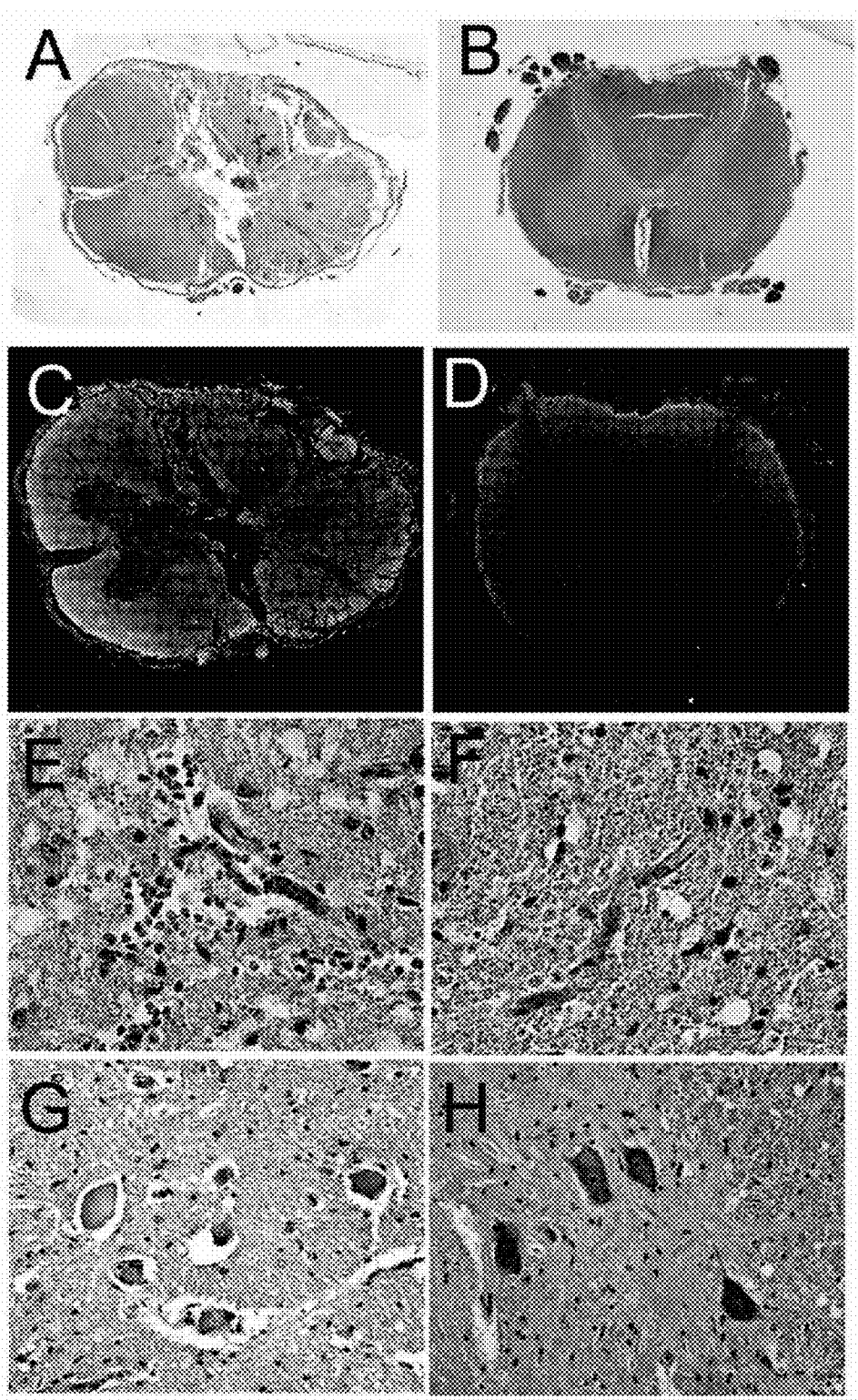
FIGS. 7A-7H show that SUR1 is upregulated in human SCI. A-H: Low power (A-D) and high power (E-H) views of cord sections stained with H&E (A,B,E-H) or immunolabeled for SUR1; sections from the core of the lesion (A,C,E, G) or from uninvolved cord (B,D,F,H).
Figure 8:
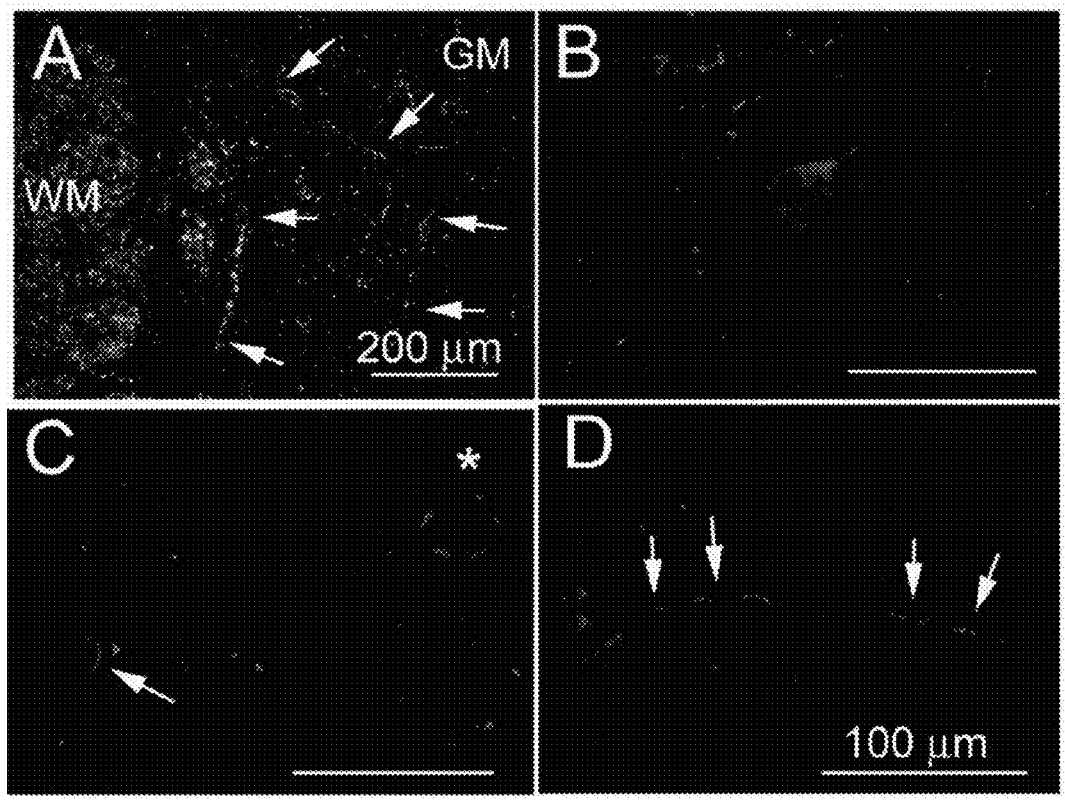
FIGS. 8A-8D demonstrate that SUR1 is upregulated in human SCI. A-D: Sections from core of the lesion immunolabeled for SUR1, showing expression in microvessels (A), in ballooned neuron (B), and in microvessels and arterioles (C,D).

Exemplary data on human SCI. Because of the emerging importance of the SUR1-regulated $NC_{Ca-ATP}$ channel in SCI and other disorders (Simard et al., 2007) the upregulation of the channel in human SCI was investigated. To date, SUR1 expression has been studied in 3 human cases using the antibody referred to above. The exemplary case illustrated here is that of a 59 yo male who sustained a C3 level injury and expired 3 days later. Low power views of H&E sections at the level of injury showed gross tissue disruption, which was not present in "uninvolved" cord (FIG. 7A vs. 7B). Immunolabeling of adjacent sections demonstrated diffuse upregulation of SUR1 throughout the area of involvement (FIG. 7C vs. 7D). High power views of H&E sections confirmed the presence of extravasated blood and fractured microvessels within the core of the lesion, but not in "uninvolved" cord (FIG. 7E vs. 7F), and confirmed the presence of dying neurons in the core but not in "uninvolved" cord (FIG. 7G vs. 7H). Sections from the core showed prominent expression of SUR1 in microvessels (FIG. 8A, arrows), in ballooned neurons (FIG. 8B), in microvascular endothelium (FIG. 8C, arrow) and in endothelium of arterioles (FIG. 8C, * and FIG. 8D, arrows). Each of these findings in humans duplicates exactly recent findings in rats (Simard et al., 2007). Notably, SUR1 is not normally expressed in CNS microvessels (Sullivan and Harik, 1993), making these findings in human microvessels post-SCI remarkably similar to the findings in rodents. In specific embodiments, double labeling of these tissues is employed to verify cellular identity and in situ hybridization to confirm SUR1 upregulation. Nevertheless, these exciting findings indicate that progressive secondary hemorrhage in humans may be ameliorated, as in rodents, by block of SUR1 with glibenclamide.

Figure 9:
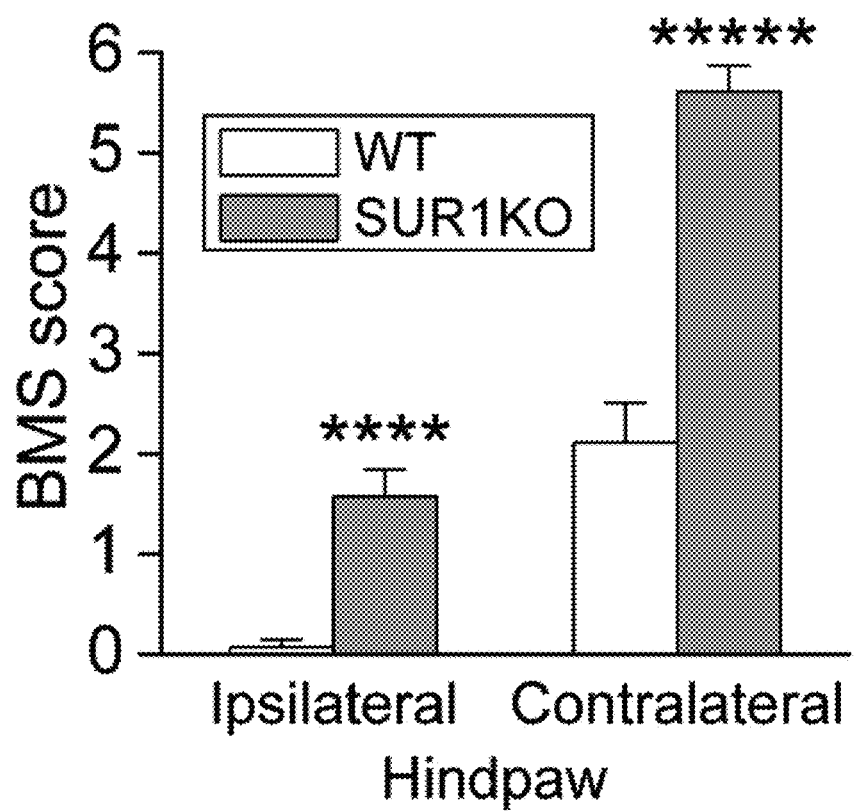
FIG. 9 demonstrates that a knockout of SUR1 gene is associated with significantly better short-term neurobehavioral outcome post-SCI. Spinal cord injury was produced by impact on the right side of the dura after laminectomy at T9. Hindpaw function was assessed 24 hr post-SCI using the Basso Mouse Scale for locomotion. In WT mice, function ipsilateral to the injury was absent whereas in SUR1-KO, function was preserved. In WT mice, function contralateral to the lesion was significantly more impaired than in SUR1-KO mice. An important element of the unilateral injury model is that it clearly demonstrates spread of progressive hemorrhagic necrosis and prevention of that spread by SUR1-KO.

Exemplary data on SCI in SUR1-KO mice. A colony of SUR1-KO mice is maintained to perform studies to demonstrate the beneficial effect of SUR1-KO in SCI. An active colony of >20 SUR1-KO mice that are successfully breeding now exists. Additional SCI experiments have been performed (unilateral T9 lesion). The behavioral response was evaluated at 24 hr in 14 WT and in 18 SUR1-KO mice using BMS, confirming that SUR1-KO is highly protective against progressive hemorrhagic necrosis (FIG. 9). In addition, longer term outcome in investigated, for example to assess durability of the protective effect. Data at 7 days continue to show highly significant differences between WT and SUR1-KO.

In certain embodiments of the invention, transfection of plasmids into endothelial cells, both bEnd.3 cells and primary cultured CNS microvascular endothelial cells, is employed. To improve transfection efficiencies, the Nucleofector 96-well shuttle system is utilized. Two experiments were performed with transfection of plasmids that encode GFP: 1) with primary cultured CNS microvascular cells, there was a survival rate of 30% at 24 hrs, with 90% of surviving cells showing fluorescent signal; 2) with bEnd.3 cells, there was a survival rate of 60% at 24 hrs, with >70% of surviving cells showing fluorescent signal. The transfection parameters to improve cell survival rates with this method were optimized.

Example 11

SUR1 Upregulation Predisposes Premature Infants to Intraventricular Hemorrhage

Brain tissues were obtained at autopsy from 6 premature infants with IVH and 3 controls without IVH. For routine histopathology, sections of germinal matrix in affected areas were dehydrated in graded ethanol and xylene solutions, embedded in paraffin, and sectioned at 6 microns. For immunofluorescence for SUR1, fixed and unprocessed tissues were suspended in sucrose and snap frozen. Six micron cryostat sections were obtained. Immunofluorescence for SUR1 was performed as previously described (Nature Medicine 2006; 12:433-40).

Significant increased expression of SUR1 was observed in vascular endothelium and germinal matrix tissue in one of the three non-IVH cases; the clinical course of this case was complicated by hypoxia necessitating intubation. A second non-IVH case showed an intermediate level of fluorescence in germinal matrix only; this infant expired of extreme prematurity shortly after delivery. The third non-IVH also expiring of extreme prematurity following delivery, showed no reactivity. The 6 IVH cases showed patchy increased fluorescence consistent with up-regulation followed by early ischemic necrosis.

These results indicate that SUR1 is increased in premature infant brains, and particularly in germinal matrix regions of infants who suffer hypoxia and IVH. This suggests that maladaptive opening of the $NC_{Ca-ATP}$ channels may result in endothelial injury and hemorrhage. Since SUR1 is blocked at least by glibenclamide, these data provide a useful therapeutic and/or preventative intervention in premature infants, including stressed premature infants prior to IVH.

Example 12

In Utero Ischemia Leads to the Upregulation of Sulfonylurea Receptor 1 in the Periventricular Zone in Rats Periventricular leukomalacia (PVL) is a form of cerebral palsy that involves deep white matter injury and that usually occurs during fetal development. In specific embodiments of the invention, hypoxic/ischemic insults during pregnancy induces the expression of sulfonylurea receptor 1(SUR1)-regulated NC(Ca-ATP) channels, which were recently implicated in programmed oncotic cell death in the central nervous system (CNS), and have been found to play an important role in cerebral ischemia and spinal cord injury. In this study, expression of the regulatory subunit of the channel, SUR1, was evaluated in a rodent model of prenatal ischemia/hypoxia. Transient (1 hr) unilateral uterine ischemia/reperfusion was induced in pregnant rats at embryonic day 17 by clamping the right uterine artery. Embryos in the left uterine horn, where blood flow was not interrupted, served as controls.

Embryos were delivered by cesarean section 24 hr after uterine ischemia/reperfusion. SUR1 was prominently upregulated in the brains of embryos that were subjected to ischemia/reperfusion, but not in controls.

Especially prominent upregulation of SUR1 was found in neural progenitor cells in the subventricular zone, which corresponds to the area of vulnerability that is affected in PVL. Additionally, neurons in the cortex of ischemic embryos exhibited increased SUR1 compared to control embryos. Thus, in certain aspects of the invention, SUR1 is upregulated following intra-uterine transient ischemia. In specific embodiments, it is determined whether the pore-forming subunit of the SUR1-regulated NC(Ca-ATP) is also upregulated, and whether this novel pathological mechanism accounts for PVL following intrauterine ischemia/hypoxia.

Example 13

In Utero Ischemia Upregulates SUR1- Links to Periventricular Leukomalacia and Germinal Matrix Hemorrhage Premature infants often suffer from cerebral palsy (CP), which leads to devastating lifelong disability. At present, there is no good prevention for CP. CP is believed to arise from periods of reduced blood flow to the brain in utero, which predisposes premature infants to white matter injury (periventricular leukomalacia) and bleeding in the brain (germinal matrix hemorrhage) during the early post-natal period. The experiments reported here were intended to model this condition in rats. Using pregnant rats, the uterine artery was temporarily clamped on one side to mimic placental insufficiency. The next day, the pups were delivered "prematurely" by C-section. Shortly after birth, saline was injected into the abdomen of the pups to raise central venous pressure, to mimic complications associated with mechanical ventilation often required in premature infants with "stiff" lungs. The pups were later euthanized, within 1 hr of birth. The pups from the opposite side, where the uterine artery was not clamped, were used as controls. The brains of the pups were studied to detect the regulatory subunit of the SUR1 regulated $NC_{Ca-ATP}$ channel. SUR1 was found to be significantly upregulated in periventricular progenitor cells and in veins, consistent with the embodiment that SUR1-regulated $NC_{Ca-ATP}$ channels may be causally linked to the brain damage in humans characterized as periventricular leukomalacia and germinal matrix hemorrhage.

Introduction

The neuropathology underlying cerebral palsy includes white matter injury, known as periventricular leukomalacia (PVL) and germinal matrix (GM) hemorrhage (GMH) (Vergani et al., 2004; Folkerth, 2005). Each has distinctive features, but both share important risk factors, including prematurity and hypoxia/ischemia, which may occur prenatally or may be due to post-natal ventilatory difficulties that are complicated by mild-to-moderate hypotension (Veragni et al., 2004; Kadri et al., 2006; Lou, 1993).

GMH is a common complication of prematurity, occurring in 20-45% of premature infants (Kadri et al., 2006). GMH may range in severity from subependymal hemorrhage (grade 1) to intraventricular hemorrhage without (grade 2) or with (grade 3) ventricular dilatation, to parenchymal extension and periventricular venous infarction (grade 4). In survivors, neurological sequelae, particularly with higher grade GMH, include cerebral palsy, hydrocephalus requiring ventricular shunting, learning disabilities, and seizures (Levy et al., 1997; Pikus et al., 1997). Numerous factors are believed to contribute to GMH, including innate weakness of GM veins, autoregulatory dysfunction, hypoxic/ischemic tissue damage, damage due to post-ischemic reperfusion and increased venous pressure (Lou, 1993; Nakamura et al., 1990; Wei et al., 2000; Anstrom et al., 2004; Berger et al., 2002; Ghazi-Birry et al., 1997). The incidence of GMH increases with the degree of prematurity (Kadri et al., 2006), suggesting that advances in perinatal care that yield concomitant increases in the number of extremely premature infants will continue to be hampered by complications of GMH. At present, no effective prevention is available.

Hypoxia/ischemia in human CNS, both in utero (Xia et al., 1993) and in adults (Xia et al., 1993; Simard et al., 2007) results in upregulation of sulfonylurea receptor 1 (SUR1). Under pathological conditions, SUR1 upregulation is associated with formation of SUR1-regulated $NC_{Ca-ATP}$ channels, not $K_{ATP}$ channels (Simard et al., 2006; Simar et al., 2007a; Simard et al., 2007b). Expression of SUR1-regulated $NC_{Ca-ATP}$ channels in capillary endothelium has been causally implicated in progressive secondary hemorrhage in CNS, with block of these channels by infusion of low-dose (non-hypoglycemogenic) glibenclamide (glyburide) completely preventing secondary hemorrhage (Simard et al., 2007b). In specific embodiments, this channel is induced in periventricular tissues, including the GM, by hypoxia/ischemia, and thereby predispose to PVL and GMH. To assess this, expression of the regulatory (SUR1) subunit of the channel in brain tissues was studied from a rat model of intrauterine ischemia.

Methods

Pregnant female Wistar rats were shipped to arrive on gestational day (GD) (Simard et al., 2006; Simard et al., 2007b; Simard et al., 2007b). They were acclimatized, then on GD 17, they underwent surgery for temporary clamping of the right uterine artery. An animal was anesthetized to a surgical level with 3% isoflurane in the mixture $N_2O/O_2$, 70%/30%, after which anesthesia is maintained with 1.5% isoflurane during surgery. Core temperature is maintained at 37° C. Transient unilateral uterine ischemia was induced as described (Nakai et al., 201; Tanaka et al., 1994). Two sterile microvascular clips were used to occlude the uterine vessels near the lower and upper ends of the right uterine horn. The clips were removed after 60 min of ischemia. For each experiment the fetuses in the right uterine horn served as the ischemia group and those in the left horn as the non-ischemia group.

24 hr after induction of uterine ischemia, the rats were re-anesthetized. The fetuses are delivered by cesarean section, after which the dam was euthanized. All the pups delivered from the left cornu (non-ischemic side) and half the pups delivered from the right cornu (ischemic side) underwent no further intervention. The other half of the pups from the right cornu (ischemic side) underwent a single intraperitoneal injection of sterile, USP grade normal saline (100 µl). One hr after birth, all pups were euthanized for tissue analysis.

Results

Figure 10:
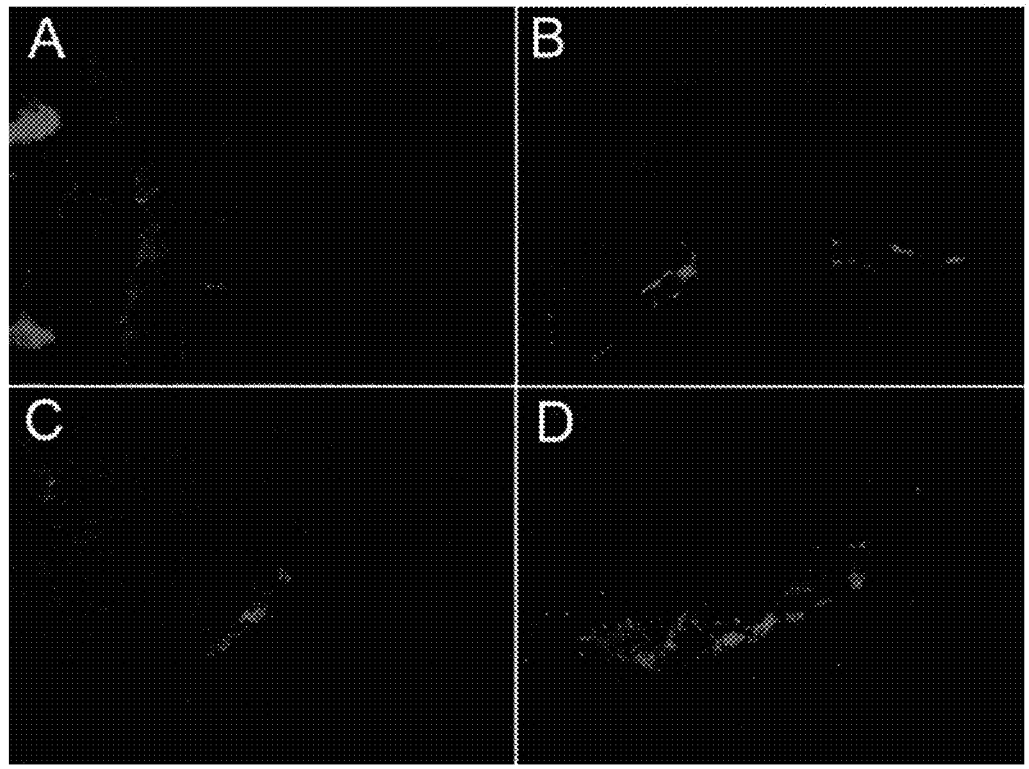
FIGS. 10A-10D show that SUR1 is upregulated by prenatal ischemia/hypoxia. A-D: Progenitor cells in periventricular zones (A) and veins scattered throughout the basal forebrain (B-D) showed prominent upregulation of SUR1 (red); nuclei labeled with DAPI (blue).

Immunolabeling of brains from control pups showed no appreciable SUR1. However, pups subjected to transient ischemia/hypoxia showed significant upregulation of SUR1, especially in the progenitor cells that were densely packed in periventricular regions (FIG. 10A). In pups exposed to transient ischemia/hypoxia plus an increase in central venous pressure, SUR1 was also found to be prominently upregulated in veins (FIG. 10B-D).

Conclusions

SUR1 is upregulated in periventricular progenitor cells in a rodent model of in utero ischemia/hypoxia and, when central venous pressure is increased, in veins as well. This pattern of SUR1 upregulation corresponds to the pattern observed in premature infants at risk for or who sustain germinal matrix hemorrhages. The known functions of the SUR1-regulated $NC_{Ca\text{-}ATP}$ indicate that SUR1 upregulation following in utero ischemic/hypoxic insults is causally linked to pathological disorders such as periventricular leukomalacia and germinal matrix hemorrhage, for example.

Example 14

Sulfonylurea Receptor 1 in the Germinal Matrix of Premature Infants

The present example concerns germinal matrix (GM) hemorrhage (GMH), which is a major cause of mortality and of life-long morbidity from cerebral palsy (CP). GMH is typically preceded by hypoxic/ischemic events and is believed to arise from rupture of weakened veins in the GM. In the CNS, hypoxia/ischemia upregulate sulfonylurea receptor 1 (SUR1)-regulated $NC_{Ca\text{-}ATP}$ channels in microvascular endothelium, with channel activation by depletion of ATP being responsible for progressive secondary hemorrhage. In specific embodiments of the invention, this channel is upregulated in the GM of preterm infants at risk for GMH. Here, the expression of the regulatory subunit of the channel, SUR1, and its transcriptional antecedent, hypoxia inducible factor 1 (HIF1), were examined in postmortem tissues of premature infants who either were at risk for or who sustained GMH. Regionally specific upregulation of HIF1 and of SUR1 protein and mRNA in GM tissues was identified, compared to remote cortical tissues. Upregulation was prominent in most progenitor cells, whereas in veins, SUR1 was found predominantly in infants who had sustained GMH compared to those without hemorrhage. The data indicate that the SUR1-regulated $NC_{Ca\text{-}ATP}$ channel is associated with GMH, in certain embodiments, and that pharmacological block of these channels reduces the incidence of this devastating complication of prematurity.

The neuropathology underlying cerebral palsy includes white matter injury, such as periventricular leukomalacia (PVL) and germinal matrix (GM) hemorrhage (GMH) (Vergani et al., 2004; Folkerth, 2005). Each has distinctive features, but both share important risk factors, including prematurity and hypoxia/ischemia, which may occur prenatally or may be due to post-natal ventilatory difficulties that are complicated by mild-to-moderate hypotension (Vergani et al., 2004; Kadri et al., 2006; Lou, 1993).

GMH is a common complication of prematurity, occurring in 15-45% of premature infants (Kadri et al., 2006). GMH may range in severity from subependymal hemorrhage (grade 1) to intraventricular hemorrhage without (grade 2) or with (grade 3) ventricular dilatation, to periventricular venous infarction (grade 4). In survivors, neurological sequelae, particularly with higher grade GMH, include cerebral palsy, hydrocephalus requiring ventricular shunting, learning disabilities, and seizures (Levy et al., 1997; Pikus et al., 1997). Numerous factors are believed to contribute to GMH, including innate weakness of GM veins, autoregulatory dysfunction, hypoxic/ischemic tissue damage, damage due to post-ischemic reperfusion and increased venous pressure (Lou, 1993; Nakamura et al., 1990; Wei et al., 2000; Anstrom et al., 2004; Berger et al., 2002; Ghazi-Birry et al., 1997). The incidence of GMH increases with the degree of prematurity (Kadri et al., 2006), suggesting that advances in perinatal care that yield concomitant increases in the number of extremely premature infants will continue to be hampered by complications of GMH. At present, no effective prevention is available.

Hypoxia/ischemia in rodent and human CNS, both in utero (Xia et al., 1993) and in adults (Simard et al., 2006; Simard et al., 2008), results in upregulation of sulfonylurea receptor 1 (SUR1). Under pathological conditions, SUR1 upregulation is associated with formation of SUR1-regulated $NC_{Ca\text{-}ATP}$ channels, not $K_{ATP}$ channels (Simard et al., 2006; Simard et al., 2008; Simard et al., 2007). Expression of SUR1-regulated $NC_{Ca\text{-}ATP}$ channels in capillary endothelium has been causally implicated in progressive secondary hemorrhage in CNS, with block of these channels by infusion of low-dose (non-hypoglycemogenic) glibenclamide (glyburide) completely preventing secondary hemorrhage (Simard et al., 2007). Here, in certain embodiments, this channel is induced in the GM by hypoxia/ischemia, and thereby predisposes one to GMH. As an initial attempt to assess this embodiment, expression of the regulatory subunit of the channel, SUR1, and its transcriptional antecedent, hypoxia inducible factor 1 (HIF1) was studied (Bhatta, 2007) in postmortem tissues of premature infants who either were at risk for or who sustained GMH. The findings are consistent with the embodiment that the SUR1-regulated $NC_{Ca\text{-}ATP}$ channel is causally linked to GMH.

Methods

Specimens from premature infants without and with clinically diagnosed GMH were obtained from the Brain and Tissue Bank for Developmental Disorders, University of Maryland, Baltimore, with the collection protocol, including informed consent, reviewed and approved by the Institutional Review Board of the University of Maryland at Baltimore. The post-mortem interval was 3-24 hr. Cases were selected for study based either on: (i) the documented presence of GMH/IVH at autopsy or (ii) documented absence of GMH (used as "best-available" controls). Independent histological validation of presence or absence of GMH was made in all cases (see Table 1). In all but one case, the cause of prematurity was preterm rupture of membranes, with some cases also documenting chorioamnionitis by pathological examination of the placenta, and one case (without GMH) being induced for cardiac anomaly. The cause of death was extreme prematurity in all but two cases, with the others being listed as amniotic fluid aspiration syndrome or elective termination.

TABLE 1

Summary of exemplary cases examined.

| Case # | Gestational Age @ birth (weeks) | Hemorrhage clinically | Hemorrhage* in H&E section | HIF1 protein in cells** | SUR1 protein in cells[§] | SUR1 protein in veins[¶] |
|---|---|---|---|---|---|---|
| 1 | 19 | none | none | + | +++ | 0 |
| 2 | 19 | none | none | ++ | + | 0/+ |
| 3 | 22 | none | none | ++ | +++ | + |
| 4 | 22 | none | none | +++ | ++ | + |
| 5 | 22 | none | none | +++ | + | +/++ |
| 6 | 23 | none | microscopic | ++ | + | +/++ |
| 7 | 24 | none | microscopic | +++ | +++ | +/++ |
| 8 | 24 | grade 1 | grade 1 | +++ | +++ | ++++ |
| 9 | 22 | grade 1 | grade 1 | ++++ | ++++ | ++++ |
| 10 | 24 | grade 2/3 | none | ++++ | ++++ | ++++ |
| 11 | 30 | grade 2/3 | grade 1 | +++++ | +++ | ++++ |
| 12 | 23 | grade 2/3 | grade 2/3 | +++++ | ++ | +++ |

*clinical information was available only on "intraventricular hemorrhage" without differentiating further into grade, hence the designation, grade 2/3; some discrepancies in clinical vs. histological evaluation of hemorrhage may be due to histological evaluation of the GM contralateral to the side of hemorrhage, which available data were insufficient to resolve
**scale for HIF1 immunolabeling in progenitor cells within the GM: +, present in most cells, similar in intensity to some distant neurons; ++, present in most cells, somewhat more intense than in neurons; +++, present in most cells, definitely more intense than in neurons; ++++, present in all cells, more intense than in neurons; +++++, present in all cells, many with very intense labeling
[§]scale for SUR1 immunolabeling in progenitor cells within the GM: +, present in few single cells; ++, present in a moderate number of scattered cells; +++, present in patches or groups of cells; ++++ present in most cells
[¶]scale for SUR1 immunolabeling in veins within the GM: 0, none; +, in 1-2 veins; ++, in a few veins; +++, in many veins; ++++, in nearly all veins.

GM tissues and associated hemorrhages, when present, were dissected from coronal slices of formalin-fixed cerebral hemispheres. Cryosections and paraffin-embedded sections were prepared. Sections were stained with hematoxylin and eosin (H&E) or were immunolabeled using primary antibodies directed against SUR1 (C-16; Santa Cruz Biotechnology Inc.; diluted 1:200; 1 hr at room temperature (RT), 48 hr at 4° C.), or HIF-1α (SC-10790; Santa Cruz; 1:100), or von Willebrand factor (F-3520; Sigma; 1:200). CY-3 or FITC conjugated secondary antibodies (Jackson Immunoresearch, West Grove, Pa.) were used. Slides were cover slipped with Pro-Long Gold antifade reagent containing 4',6-diamino-2-phenylindole (DAPI) for nuclear staining (P36935, Invitrogen, Carlsbad, Calif.). For in situ hybridization, digoxigenin-labeled probes (antisense, 5'-TGCAGGGGTCAGGGT-CAGGGcGCTGTCGGTCCACTTGGCCAGCCAGTA-3'; SEQ ID NO:4), designed to hybridize to nucleotides 3217-3264 located within coding sequence of human Abcc8 gene (NM_000352; GenBank® Accession number for the sequence, which is incorporated by reference herein in its entirety), were supplied by GeneDetect (Brandenton, Fla.). Hybridization was performed according to the manufacturer's protocol, as previously described (Simard et al., 2006).

Results

Figure 11:
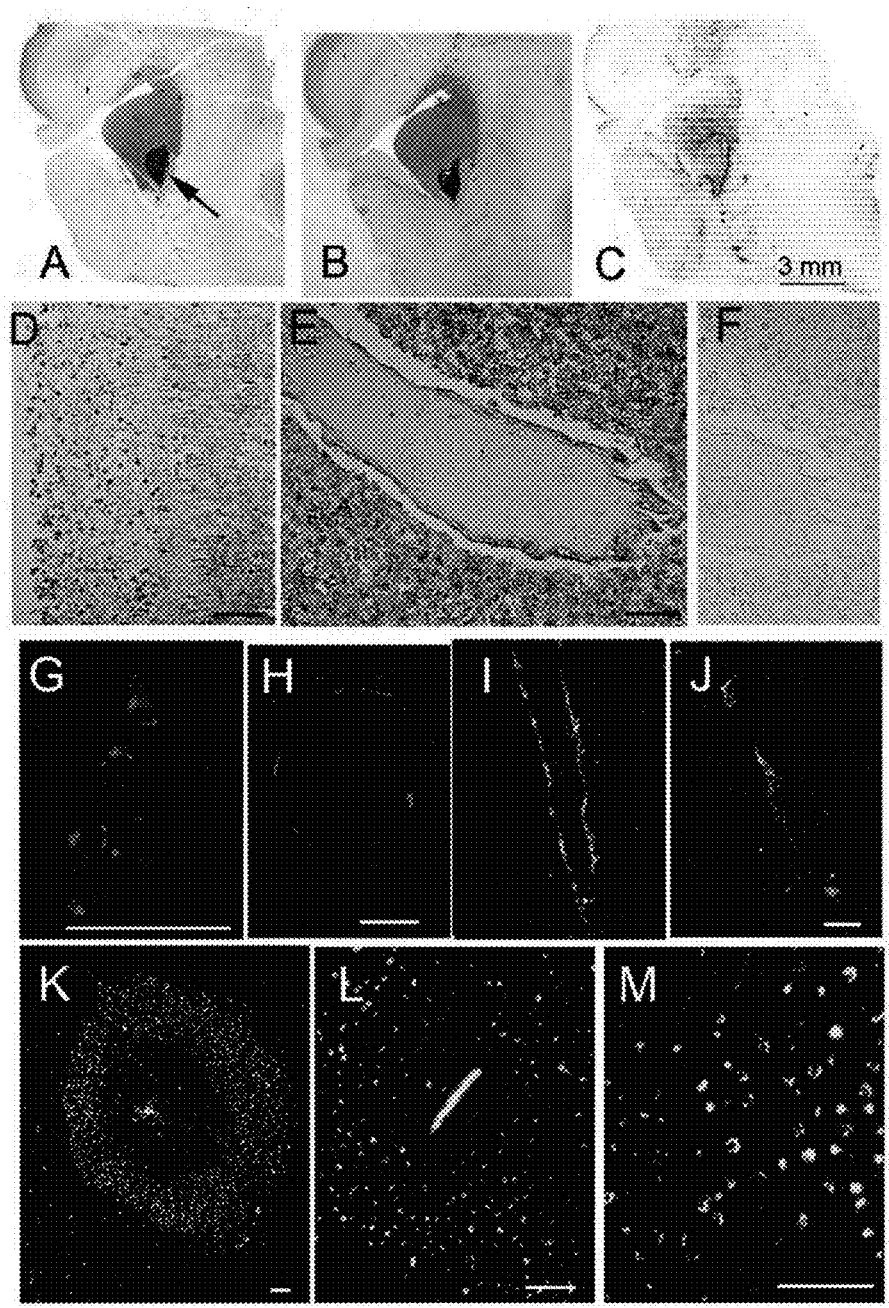
FIGS. 11A-11M show that SUR1 and HIF1 are upregulated in the germinal matrix of premature infants. A-C: Low power micrographs (A,B) or montage of micrographs (C) of periventricular tissue stained with H&E (A), showing densely packed neural progenitor cells of the GM, with an arrow pointing to a small intraparenchymal hematoma, or labeled for mRNA for Abcc8, which encodes SUR1, using in situ hybridization (B), or immunolabeled for SUR1 (C); the latter two demonstrate regionally-specific labeling for SUR1 mRNA and protein in the GM; the montage in (C) shows positive immunolabeling in black pseudocolor; case #9 in Table 1: premature infant of 22 wk gestation who lived ~12 hr and was hypoxic prior to death, necessitating intubation and mechanical ventilation; post-mortem interval, 3 hr. D-F: Micrographs of cortical tissues (D) or GM tissues (E,F) processed for in situ hybridization for mRNA for Abcc8, using antisense probe (D,E) or sense probe (F). G-J: Micrographs of GM tissues immunolabeled for SUR1 (red, CY3 for SUR1, and blue, DAPI for nuclei), and double-labeled for von Willebrand factor (green; panels I and J only); co-labeling is indicated by yellow color; SUR1 was identified in neural progenitor cells (G), and in thin-walled veins from infants with GMH (panel H, red and panel I, yellow) but not in an infant without GMH (panel J, green); panels H, I, J are from cases #11, 10, 1 in Table 1, respectively. K-M: Low (K) and high (L,M) power micrographs of sections immunolabeled for HIF1α (green, FITC for HIF1α, and blue, DAPI for nuclei), showing HIF1α in a microvessel (L) and in neural progenitor cells (M). In panels D-M, the bars represent 50 µm.

The germinal matrix appeared as a dense collection of small cells located peri-ventricularly (FIG. 11A). In some cases, evidence of a parenchymal hemorrhage was found (FIG. 11A, arrow).

In situ hybridization for mRNA for Abcc8, which encodes SUR1, showed regionally specific upregulation in the GM (FIG. 11B,E) that was noticeably more prominent than in surrounding tissues or in remote cortical tissues (FIG. 11D). Immunolabeling confirmed regionally specific upregulation of SUR1 protein in the GM (FIG. 11C), with SUR1 protein located in neural progenitor cells in all GM specimens examined (FIG. 11G). SUR1 protein was also identified in veins from infants with GMH (FIG. 11H,I), but was less likely to be found in veins from infants without GMH (FIG. 11J). Negative controls, including omission of primary antibody and use of a blocking peptide, showed no immunolabeling for SUR1 (not shown).

An important molecular antecedent of SUR1 is the transcription factor, HIF1 (Bhatta, 2007), which is upregulated by hypoxia (Wenger et al., 2005), a common condition associated with prematurity. Immunolabeling for HIF1α showed that this ubiquitous marker of hypoxia was prominently upregulated, with characteristic nuclear localization, in all GM specimens examined (FIG. 11K-M).

A semi-quantitative assessment was performed of HIF1α and SUR1 expression in specimens from 12 premature infants, some of whom had either clinical or histological evidence of GMH (Table 1). All specimens showed HIF1α expression, with all but one showing more prominent expression in progenitor cells than in remote neurons in the same tissue sections, supporting the embodiment that physiologically meaningful hypoxia was present in the GM of all of these cases. The most prominent expression of HIF1α was found in specimens from infants with frank GMH. All specimens showed SUR1 expression in progenitor cells. In 3 specimens, SUR1 was identified only in scattered cells, whereas in most specimens, SUR1 expression was evident in contiguous sheets of cells or in some cases, in nearly all cells. The clearest distinction in SUR1 expression vis-à-vis GMH was in the veins of the GM. In specimens without GMH, the veins typically exhibited little to moderate SUR1 expression, as in FIG. 1J, whereas in all specimens with frank GMH, all or nearly all veins exhibited strong SUR1 expression, as in FIG. 11H,I.

Significance of Certain Embodiments

Thus, expression of SUR1 is increased in neural progenitor cells and in vascular endothelium of the GM of premature infants who either are at risk for or who sustained GMH. Immunohistochemical analysis of post-mortem tissues can sometimes be complicated by non-specific binding of antibodies, especially if necrosis is present. However, the specimens studied showed intact cellular structures with H&E staining, as well as regionally-specific immunolabeling of cellular and vascular structures for SUR1 in the GM. Most importantly, in situ hybridization was used to confirm that SUR1 was upregulated at the mRNA level. Together, the two independent techniques using molecularly distinct probes provide important corroborative evidence that SUR1 was upregulated in GM tissues of premature infants. Additional work is performed to demonstrate concomitant upregulation of the pore-forming subunit of the channel (Simard et al., 2008).

Pathophysiology. The pathophysiological antecedents of GMH have been extensively discussed, but no fully encompassing theory has been put forth to explain it. Considerable attention has been focused on the structural weakness of GM microvessels (Wei et al., 2000; Anstrom et al., 2004). However, it is evident that any innate weakness of these vessels, by itself, would be insufficient to cause GMH, since the same weakness exists during every gestation, and most gestations are not complicated by GMH. Thus, an event must transpire to weaken these vessels further and increase the likelihood of their structural failure. In the premature brain, the GM is at the terminal end of its afferent arteriolar supply ("ventriculopetal" vascular pattern) (Nakamura et al., 1994) and therefore GM tissues and the vessels contained therein are highly susceptible to global hypoxic/ischemic events. Apart from hypoxia due to ventilatory abnormalities, one or more hypotensive episodes may contribute to the overall hypoxic/ischemic burden that adversely affects GM tissues. In addition, it is likely that yet another hemodynamic stress must be applied to structurally compromised vessels to cause an actual GMH. Because GMH most frequently arises from veins (Nakamura et al., 1990; Ghazi-Birry et al., 1997), it is thought that episodes of increased venous pressure, as can occur with mechanical ventilation or airway suctioning, may be important for triggering the actual structural failure of weakened vessels that results in GMH.

Despite the important role of hypoxia/ischemia in producing vascular changes that predispose to GMH, there is little experimental evidence to elucidate the molecular mechanism involved, either in animal models or in humans. The present invention is the first report to show that the transcription factor, HIF1, is upregulated in the GM of infants at risk. In many organs including the CNS, hypoxia results in activation of HIF1, which in turn stimulates the transcription of genes that are essential for adaptation to hypoxia/ischemia, including genes important for erythropoiesis, glycolysis and angiogenesis (Wenger et al., 2005). HIF1 plays a critical role in expression of the angiogenic factor, vascular endothelial growth factor (VEGF), which is prominently upregulated in the GM of infants at risk (Ballabh et al., 2007). Conversely, HIF1 also causes transcription of genes with seemingly maladaptive effects (Simard et al., 2007) and, in some settings, may promote ischemia-induced neuronal death (Chang and Huang, 2006). HIF1 has not been extensively studied in the premature infant brain, and a role for HIF1 has not previously been suggested in the context of GMH. However, the localization of HIF1 with two of its important transcriptional targets, VEGF (Ballabh et al., 2007) and SUR1 (Bhatta, 2007), in the GM of infants at risk reaffirms the importance of this molecular response to hypoxia.

Figure 12:
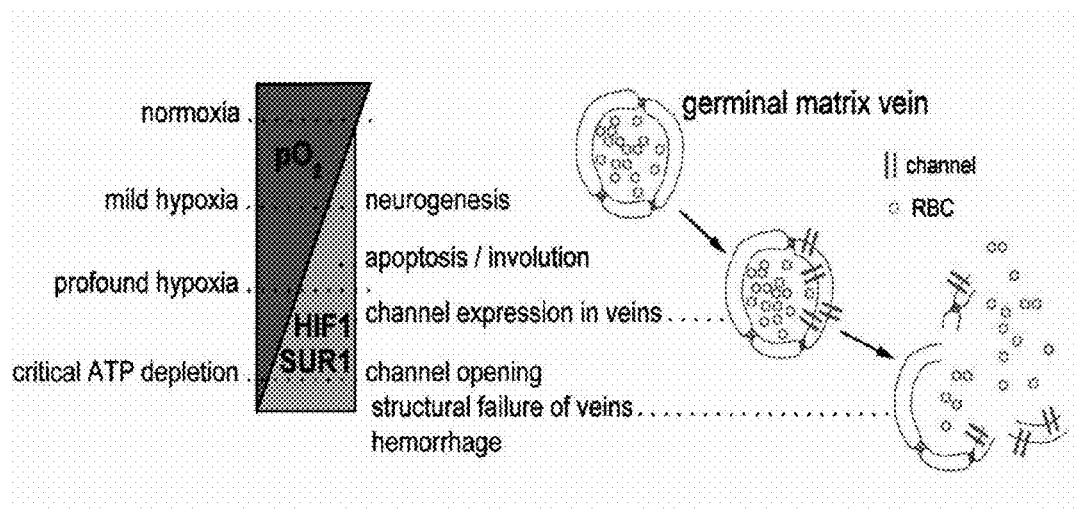
FIG. 12 illustrates exemplary events in the germinal matrix of premature infants. Scheme depicting the reciprocal relationship between $O_2$ tension on the one hand, and HIF1 activation and SUR1 expression on the other hand. Mild hypoxia, which may be the norm due to the ventriculopetal blood supply, promotes neurogenesis, whereas moderate hypoxia may promote apoptosis resulting in involution of the GM. More severe hypoxia may promote expression of SUR1-regulated $NC_{Ca-ATP}$ channels, which remain inactive until critical ATP depletion is reached (~30 µM), at which point the channels open, leading to oncotic death of cells, including endothelial cells, thereby compromising the structural integrity of veins and predisposing to GMH during episodes of venous hypertension.

Events in the GM. Mild hypoxia activates quiescent neural progenitor cells, resulting in their activation and differentiation into neurons and glia, whereas severe hypoxia induces apoptotic death in developing brain neurons (Pourie et al., 2006). Thus, mild-to-moderate hypoxia, resulting from the position of the GM as the distant-most tissue fed by a ventriculopetal blood supply (Ballabh et al., 2007), may be involved not only in stimulating neurogenesis from GM progenitor cells, but also in the normal involution of the GM (FIG. 12). HIF1, the ubiquitous sensor of hypoxia, may be a key molecular participant in both. Notably, the same hypoxic signal working via HIF1 also leads to transcriptional upregulation of SUR1 (Bhatta, 2007) and of SUR1-regulated $NC_{Ca-ATP}$ channels (Simard et al., 2007). In all of the 12 cases studied, most of the progenitor cells exhibited both HIF1 and SUR1, indicating that mild hypoxia may be a normal state in germinal matrix parenchyma, and that this tissue may be normally "primed" with SUR1. When the $NC_{Ca-ATP}$ channel is expressed in response to an hypoxic stimulus, no adverse functional consequence is expected, as long as intracellular ATP is maintained at sufficient levels (>30 µM) to keep the channel from opening (Simard et al., 2008).

Under conditions of extreme duress, a normal hypoxic signal may be magnified by one or more ischemic events, leading to more profound hypoxia. Under such conditions, HIF1 activation and SUR1 expression would become more likely, especially in veins (FIG. 12). Normally, cells of the vascular tree are less likely than parenchymal cells to experience hypoxia, but under conditions of extreme duress, when maximum extraction of $O_2$ has already occurred from hypoxic blood, venular cells will experience the strongest hypoxic challenge. In the cases we studied, veins generally were less likely to exhibit SUR1 than parenchymal cells, but in cases with GMH, SUR1 expression was reliably found in most veins the very structures that are believed to be the source of hemorrhage (Nakamura et al., 1990; Ghazi-Birry et al., 1997). When ATP is depleted to critical levels, SUR1-regulated $NC_{Ca-ATP}$ channels open, leading to oncotic cell death (Simard et al., 2006) not only of progenitor cells but of vascular endothelial cells, thereby further weakening thin walled, structurally compromised veins. In this setting, increased venous pressure would almost certainly cause extravasation of blood from damaged veins. Petechial hemorrhages may enlarge to microhemorrhages or grade 1 GMH, or worse, depending on the severity and extent of GM tissues involved. In specific embodiments, this sequence (FIG. 12), which employs critical involvement of HIF1 and SUR1, accounts for numerous observations and encompasses numerous hypotheses that have been put forth to explain GMH.

Preventing GMH. Available strategies for preventing GMH are limited. Currently, the most effective measures are those that target the respiratory system (Cools and Offringa, 2005; Wright et al., 1995). Vitamin E, phenobarbital, morphine, ibuprofen, indomethacin, agents that target coagulation, and magnesium/aminophylline have been tried, but are either ineffective or their use remains controversial. In an animal model of GMH, prenatal treatment with angiogenic inhibitors reduces the incidence of GMH (Ballabh et al., 2007), but angiogenic suppression in premature infants would be undesirable, since it could impair lung maturation (Thebaud, 2007).

Novel treatment strategies are desperately needed to combat GMH. Block of SUR1 using glibenclamide is such a treatment, in particular aspects of the invention. Glibenclamide pretreatment in humans is associated with significantly better outcomes from stroke (Simard et al., 2008; Kunte et al., 2007), and constant infusion of drug at doses below those that give hypoglycemia is highly effective in preventing progressive secondary hemorrhage in the CNS (Simard et al., 2007). The present example is consistent with the embodiment that the SUR1-regulated $NC_{Ca-ATP}$ channel is causally linked to GMH. In particular embodiments of the invention, glibenclamide and other compounds that block the expression and/or activity of the channel are useful in reducing the incidence of this devastating complication of prematurity.

Example 15

Traumatic Brain Injury Embodiments

Traumatic brain injury (TBI) causes deficits in motor, sensory, cognitive, and emotional functions. This debilitating neurological disorder is common in young adults and often requires life-long rehabilitation. A contusion injury to the brain is typically aggravated by secondary injury, resulting in expansion of the original lesion and concomitant worsening of neurological outcome. Mechanisms of secondary injury are diverse and may include cytotoxic processes, such as excitotoxicity, free radical damage, apoptosis, inflammation, etc. In addition, secondary injury may result from microvascular dysfunction, including ischemia, edema, and "progressive secondary hemorrhage", a phenomenon wherein capillaries gradually loose their structural integrity and become fragmented, resulting in extravasation of blood and formation of petechial hemorrhages. Whereas historically, ischemia and edema have been targeted for treatment, progressive secondary hemorrhage has not, simply because hemorrhage has not been viewed as being preventable. However, blood is extremely toxic to neural tissues, as it incites free radical formation and inflammatory responses that are especially damaging to myelin of white matter tracks, thereby worsening the overall neurological injury. Thus, if secondary injury is to be minimized, it is important that progressive secondary hemorrhage be reduced.

The inventor has discovered that the novel ion channel, the SUR1-regulated $NC_{Ca-ATP}$ channel is highly relevant to understanding secondary injury in TBI (Simard et al., 2008). This channel is not constitutively expressed, but is expressed only after injury to the CNS, with expression being particularly prominent in endothelial cells of penumbral capillaries surrounding the primary injury site (Simard et al., 2007). Originally, the work indicated that an ischemic/hypoxic insult was required for de novo expression (Simard et al., 2006), but recently, evidence was obtained that this channel is also newly expressed following trauma to the spinal cord (Simard et al., 2007) and brain (see below).

The $NC_{Ca-ATP}$ channel is unique (Simard et al., 2008). It conveys monovalent but not divalent cations, it requires intracellular $Ca^{2+}$, and channel opening is triggered by depletion of intracellular ATP. When opened, the channel depolarizes the cell due to influx of $Na^+$, drawing in $Cl^-$ and water, leading to oncotic cell swelling and oncotic cell death. When capillary endothelial cells undergo oncotic death, the structural integrity of capillaries is lost, resulting in formation of petechial hemorrhages. Of particular importance, this channel is regulated by sulfonylurea receptor 1 (SUR1), just like pancreatic $K_{ATP}$ channels. Unlike $K_{ATP}$ channels, whose opening leads to hyperpolarization, opening of $NC_{Ca-ATP}$ channels leads to cell depolarization. Opening of $NC_{Ca-ATP}$ channels is prevented by the sulfonylurea, glibenclamide (glyburide), which protects cells that express the channel from oncotic swelling and oncotic death. In rodent models of stroke and spinal cord injury, systemic administration of low-dose glibenclamide is highly neuroprotective (Simard et al., 2006; 2007; 2008). In human diabetics who coincidentally are taking sulfonylureas at the time of stroke, outcomes are highly favorable compared to matched controls (Kunte et al., 2007).

The inventor has obtained experimental data that indicate that: (i) progressive secondary hemorrhage is prominent following percussion-TBI, with hemorrhage doubling during the first 12-24 hr; (ii) SUR1, the regulatory subunit of the channel, and TRPM4, the pore forming subunit of the channel, are abundantly upregulated post-TBI; (iii) progressive secondary hemorrhage can be significantly reduced by low-dose glibenclamide; (iv) glibenclamide-treatment is associated with significant neurological and neurobehavioral functional improvement. Thus, in certain embodiments of the invention, glibenclamide, for example, is useful for preventing, ameliorating, and/or treating TBI.

In one embodiment, there is established a useful treatment to reduce secondary injury related to microvascular dysfunction post-TBI. Since glibenclamide (glyburide) is a safe drug that has been used for over two decades to treat type 2 diabetes in humans, providing treatment of TBI in humans that is critical to reducing secondary injury and therefore optimizing rehabilitation post-TBI.

In a specific embodiment as may be demonstrated in a rodent model of TBI, properly timed treatment with the proper dose of the SUR1 antagonist, glibenclamide, is believed to (i) minimize secondary injury (formation of edema and secondary hemorrhage); (ii) minimize lesion size, limiting it to the original site of primary injury; and/or (iii) optimize neurofunctional, cognitive and psychophysiological recovery. In another specific embodiment, the time-course is determined for upregulation of the glibenclamide-sensitive, SUR1-regulated $NC_{Ca-ATP}$ channel following percussion-TBI. In an additional specific embodiment, the time-window and optimal dose for treatment with glibenclamide is determined.

In an additional embodiment, the therapeutic efficacy is determined of glibenclamide in male and female rats using a comprehensive battery of neurofunctional, cognitive and psychophysiological tests assessed up to 6 months post-TBI, for example.

TBI—the Clinical Problem

Each year, 1.5 million Americans sustain TBI. As a result of these injuries, 50,000 people die, 230,000 people are hospitalized and survive, and 80,000-90,000 people experience the onset of long-term disability (Langlois et al., 2006; Thurman et al., 1999). TBI is the leading cause of death and disability in children and adults ages 1-44 years. As detailed above, warfighters and veterans are also highly prone to suffer from TBI and its aftereffects (Warden, 2006; Sayer et al., 2008). Overall, more than 5 million Americans—2% of the U.S. population—currently live with disabilities resulting from TBI. The consequences in terms of physical impairments, functional limitations, disabilities, societal restrictions, and economic impact are practically immeasurable.

In spite of its importance to civilian and military personnel, there is no effective therapy in clinical use that is specifically directed towards ameliorating secondary brain injury after trauma. An important reason for this unfortunate deficiency in clinical care is an incomplete understanding of cellular and molecular processes that underlie secondary brain injury. One important area of deficiency concerns mechanisms of secondary injury related to microvascular dysfunction, in particular, progressive secondary hemorrhage.

TBI—Secondary Injury and Progressive Secondary Hemorrhage (PSH)

The pathophysiology of TBI is complex and involves multiple injury mechanisms that are spatially and temporally specific, including both primary and secondary injury mechanisms. A consistent pattern of cytotoxic and microvascular abnormalities can be documented in the early posttraumatic period (Dietrich et al., 1994) with many secondary injury mechanisms remaining active for days to weeks after the primary insult. It is believed that by successfully targeting one or more mechanism of secondary injury, the burden of injury will be lessened, rehabilitation will be more successful, and the overall outcome will improve pursuant to the treatments and methods disclosed herein.

Numerous mechanisms of secondary injury have been identified, including cytotoxic mechanisms involving excitotoxicity, free radical production, apoptosis, inflammation and others, as well as microvascular abnormalities responsible for ischemia and edema (Bramlett and Dietrich, 2007; Raghupathi, 2004). Notably, one pathophysiological process that is largely unrecognized as a mechanism of secondary injury is "progressive secondary hemorrhage" (PSH). Contusion of brain often results in formation of intraparenchymal petechial hemorrhages (Dietrich et al., 1994; Cortez et al., 1898; Oertel et al., 2002; Schmidt and Grady, 1993). Formation of petechial hemorrhages has been associated with small venules (Dietrich et al., 1994), but less well appreciated is the fact that hemorrhages are frequently complicated by "blossoming" or expansion (Cortez et al., 1989; Oertel et al., 2002; Vajtr et al., 2008). Although sometimes erroneously attributed to continued bleeding of vessels fractured by the original trauma, this phenomenon actually represents a secondary pathological process, as we have shown in spinal cord injury (Simard et al., 2007). PSH occurs during the first several hours after a traumatic insult. It results from progressive catastrophic failure of the structural integrity of capillaries, and is characterized by formation of small discrete satellite (petechial) hemorrhages in tissues surrounding the site of primary injury. With time, petechial hemorrhages increase in number and eventually coalesce into a hemorrhagic lesion that encompasses the entire site of primary injury. PSH is particularly damaging because it greatly expands the volume of neural tissue destroyed by the primary injury. The capillary dysfunction implicit with PSH causes tissue ischemia and hypoxia, and the hemorrhage that characterizes PSH is exquisitely toxic to CNS cells (Regan and Guo, 1998; Wang et al., 2002), further injuring neural tissues due to oxidative stress and inflammation. Together, these processes render PSH the most destructive mechanism of secondary injury involving the CNS.

Two molecular mechanisms can potentially account for PSH: (i) upregulation of matrix metalloproteinases (Vajtr et al., 2008; Vilalta et al., 2008), (ii) upregulation of the capillary endothelial SUR1-regulated NCCa-ATP channel (see below and Simard et al., 2007). Both occur post-TBI. In general, research has identified various promising pharmacological compounds that specifically antagonize many of the commonly identified secondary mechanisms of injury that contribute to TBI. However, none explicitly targets PSH post-TBI. In certain aspects, the role of SUR1-regulated $NC_{Ca-ATP}$ channels is evaluated in PSH post-TBI it is believed that glibenclamide has utility in reducing or eliminating PSH post-TBI.

The SUR1-regulated $NC_{Ca-ATP}$ Channel

Channel properties. The properties of the SUR1-regulated $NC_{Ca-ATP}$ channel have been reviewed (Simard et al., 2007;

Simard et al., 2008; Simard et al., 2007). It is a 35 pS cation channel that conducts inorganic monovalent cations, but is impermeable to $Ca^{2+}$ and $Mg^{2+}$ (Chen and Simard, 2001). Channel opening requires nanomolar concentrations of $Ca^{2+}$ on the cytoplasmic side, and is blocked by intracellular ATP ($EC_{50}$, 0.79 µM). Like $K_{ATP}$ channels, SUR1-regulated $NC_{Ca-ATP}$ channels are blocked by first and second generation sulfonylureas, tolbutamide ($EC_{50}$, 16.1 µM) and glibenclamide ($EC_{50}$, 48 nM) (Chen et al., 2003). Recent work has shown that the pore-forming subunit of the channel is TRPM4 (see below), (Simard et al., 2007), but at present, no high affinity, high specificity drugs are available to block TRPM4.

Channel expression. The SUR1-regulated $NC_{Ca-ATP}$ channel is not constitutively expressed, but is expressed in the CNS under conditions of injury or hypoxia. The channel was first discovered in reactive astrocytes obtained from the hypoxic inner zone of the gliotic capsule post-stab injury and foreign body implantation (Chen et al., 2001; Chen et al., 2003). Since then, it has been identified using patch clamp electrophysiology in neurons from the core of an ischemic stroke (Simard et al., 2006) and in cultured human and mouse endothelial cells subjected to hypoxia (Simard et al., 2007).

Apart from patch clamp recordings to demonstrate presence of the channel, CNS tissues have been analyzed to detect the regulatory subunit of the channel, SUR1, at protein and mRNA levels. Normally, SUR1 is expressed in some neurons, but not in astrocytes or capillaries. Post-injury, SUR1 is strongly upregulated in several rodent models of CNS injury, including models of cerebral ischemia (Simard et al., 2006), penetrating brain injury with foreign body (Chen et al., 2003), and SCI (Simard et al., 2007). Upregulation of SUR1 is found in all members of the neurovascular unit, i.e., neurons, astrocytes and capillary endothelial cells.

Channel function. The consequences of opening the SUR1-regulated $NC_{Ca-ATP}$ channel have been studied in cells by depleting ATP to mimic injury conditions. ATP depletion induces a strong inward current that depolarizes the cell completely to 0 mV. Cells subsequently undergo oncotic cell swelling (cytotoxic edema). Eventually, ATP-depletion leads to cell death, predominantly by non-apoptotic, propidium iodide-positive oncotic (necrotic) cell death, which can be blocked by glibenclamide (Simard et al., 2006).

Glibenclamide Block of SUR1—In Vivo Models of CNS Injury

The effect of glibenclamide was studied in rodent models of ischemic stroke. In a model of malignant cerebral edema, glibenclamide reduced mortality and cerebral edema (excess water) by half (Simard et al., 2006). In a model of stroke induced by thromboemboli, glibenclamide reduced lesion volume by half, and its use was associated with cortical sparing that was attributed to improved leptomeningeal collateral blood flow due to reduced mass effect from edema (Simard et al., 2006).

The effect of glibenclamide was studied in a rodent model of spinal cord injury (SCI) (Simard et al., 2007). Acutely, SCI results in progressive secondary hemorrhage, characterized by a progressively expansive lesion with fragmentation of capillaries, hemorrhage that doubles in volume over 12 hr, tissue necrosis and severe neurological dysfunction. Necrotic lesions are surrounded by widespread upregulation of SUR1 in capillaries and neurons. Following SCI, block of SUR1 by glibenclamide essentially eliminates capillary fragmentation and progressive secondary hemorrhage, is associated with a 3-fold reduction in lesion volume, and results in marked neurobehavioral functional improvement.

Role of the channel in edema and hemorrhage. Edema and progressive secondary hemorrhage are key mechanisms of secondary injury post-TBI (Marmarou, 2007; Unterberg et al., 2004). Edema resulting from TBI or ischemia can lead to raised ICP and brain herniation. Early progressive hemorrhage occurs in almost 50% of head-injured patients, usually following contusion injury, and it too is associated with elevations in ICP (Oertel et al., 2002; Smith et al., 2007; Xi et al., 2006).

Molecular mechanisms involved in cerebral ischemia, including cytotoxic edema, vasogenic edema, and hemorrhagic conversion were recently reviewed (Simard et al., 2007). Although mechanisms are complex and not completely understood, evidence has accumulated that SUR1-regulated $NC_{Ca-ATP}$ channels play a critical role in each of these, and that block of the channel by glibenclamide yields significant beneficial effects. To date, most of the work has focused on brain ischemia and SCI, but strong data presented below indicate that the same mechanisms are at play in TBI.

Glibenclamide—Benefit in Human Stroke

An outcome analysis was carried out of patients with diabetes mellitus (DM) hospitalized within 24 hr of onset of acute ischemic stroke in the Neurology Clinic, Charité Hospital, Berlin, Germany, during 1994-2000 (Kunte et al., 2007). After exclusions, the cohort comprised 33 patients taking a sulfonylurea (e.g., glibenclamide) at admission through discharge (treatment group) and 28 patients not on a sulfonylurea (control group). The primary outcome was a decrease in National Institutes of Health Stroke Scale (NIHSS) of 4 points or more from admission to discharge or a discharge NIHSS score=0, which is considered a "major neurological improvement". The secondary outcome was a discharge modified Rankin Scale (mRS) score of 2 or less, which signifies functional independence. The primary outcome was reached by 36% of patients in the treatment group and 7% in the control group (odds ratio=7.5 in favor of sulfonylurea; P=0.007). The secondary outcome was reached by 81.8% vs. 57.1% (odds ratio=3.4 in favor of sulfonylurea; P=0.035).

In particular embodiments of the invention, secondary hemorrhage and lesion expansion that develops over time following percussion-TBI can be prevented by blocking $NC_{Ca-ATP}$ channels with glibenclamide, and that by doing so, a substantial improvement in neurofunctional outcome can be achieved.

Work on Rodent Model of Percussion-TBI

The model of percussion-TBI. The percussion-TBI model that has been studied is an exemplary gravity-driven, parasagittal mechanical percussion model similar to the gravity-driven, parasagittal fluid percussion model (Thompson et al., 2005; Fujimoto et al., 2004), except that the impact force is transmitted via a blunt mechanical impactor instead of a fluid column. Unlike typical weight drop devices that utilize a small diameter impactor head with restricted penetration (Bullock et al., 1995; Suh et al., 2000) in the model used by the inventor, TBI is created with an impactor rod tipped with a 5-mm Teflon ball (4 gm total) activated by vertical weight drop. Like fluid percussion, the model has unrestricted penetration, disperses the force over an area of ~20 $mm^2$ and transiently displaces a larger volume of brain tissue than a small diameter impactor with restricted penetration.

Figure 13:
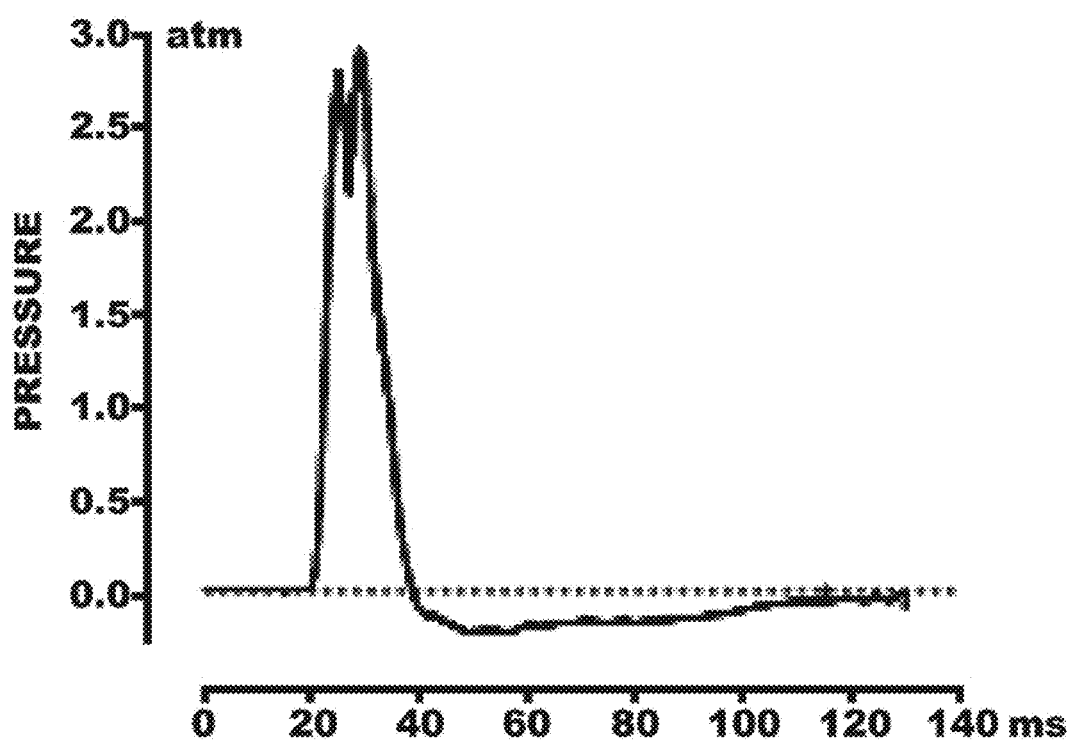
FIG. 13 shows a pressure wave produced by percussion injury model. Typical pressure wave produced by 10-cm drop of 10 gm weight to produce 2.5-3.0 atm peak pressure, resulting in moderate-to severe percussion injury.

Young adult male Long-Evans rats, 240-280 gm, were studied. Rats were anesthetized (Ketamine and Xylazine) and physiological parameters including temperature and blood gases were maintained within appropriate physiological ranges. With the head fixed in a stereotaxic frame, a 6-mm circular craniectomy was created abutting the sagittal and lambdoidal sutures. A posterior location was chosen to emphasize damage to underlying hippocampus (Vink et al., 2001; Floyd et al., 2002). The impactor was activated using a 10-gm weight dropped from 10 cm, which produced a transient impact pressure of 2.5-3 atm (FIG. 13). Sham controls underwent craniectomy without percussion.

For some studies, the effect of treatment with glibenclamide was assessed. Immediately after TBI, rats were implanted with mini-osmotic pumps (Alzet 2002, 0.5 ml/hr; Durect Corporation, Cupertino, Calif.) that delivered either vehicle (DMSO/saline) or drug (glibenclamide, Sigma, in DMSO/saline) subcutaneously (Simard et al., 2006; Simard et al., 2007). Pharmacokinetic analysis indicated that 3 hr were required to achieve 90% steady-state serum drug levels. The dose of glibenclamide delivered was 200 ng/hr, which at 3 hr, resulted in a non-significant decrease in serum glucose, from 236±15 to 201±20 (5-6 rats per group; p=0.19). The dose of DMSO delivered was 40 nl/hr, which is 300 times less than that associated with neuroprotection.

Figure 14:
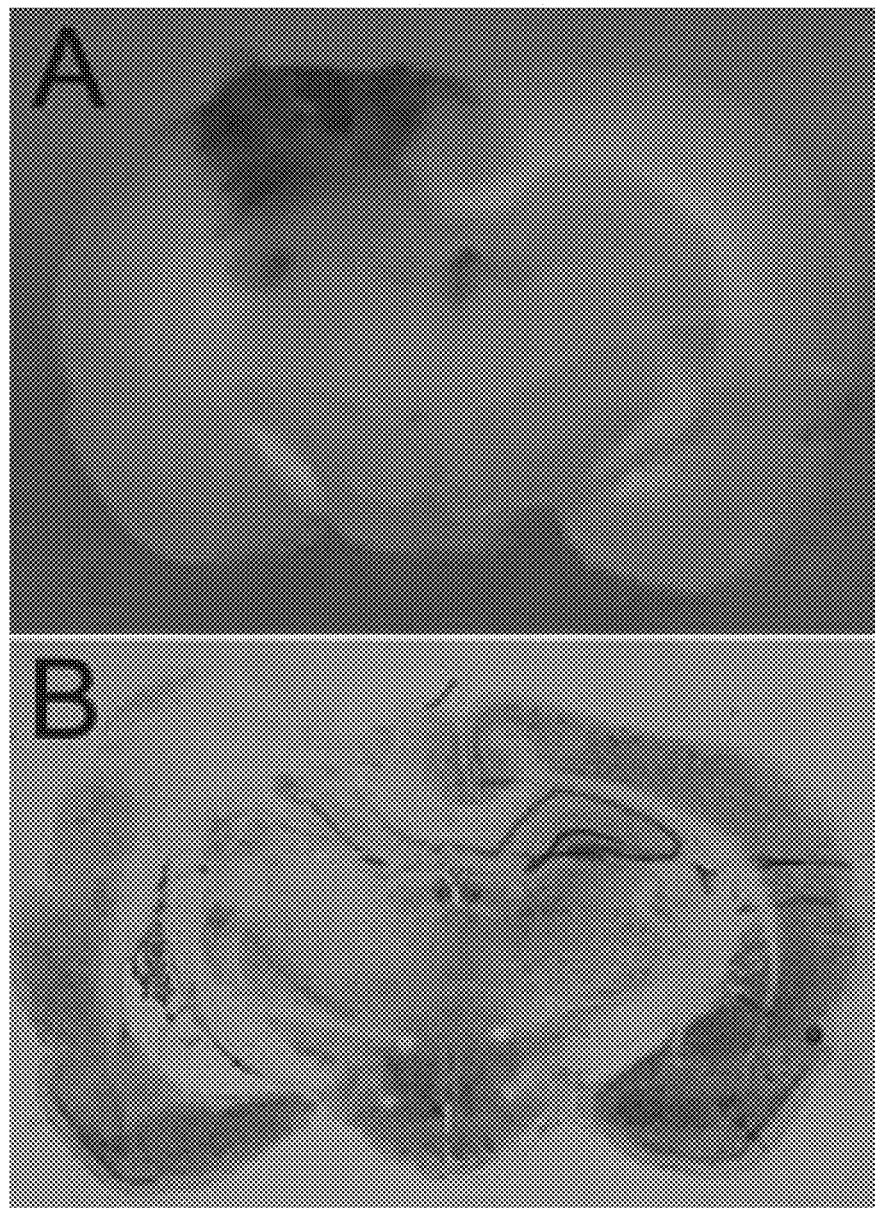
Figure 15:
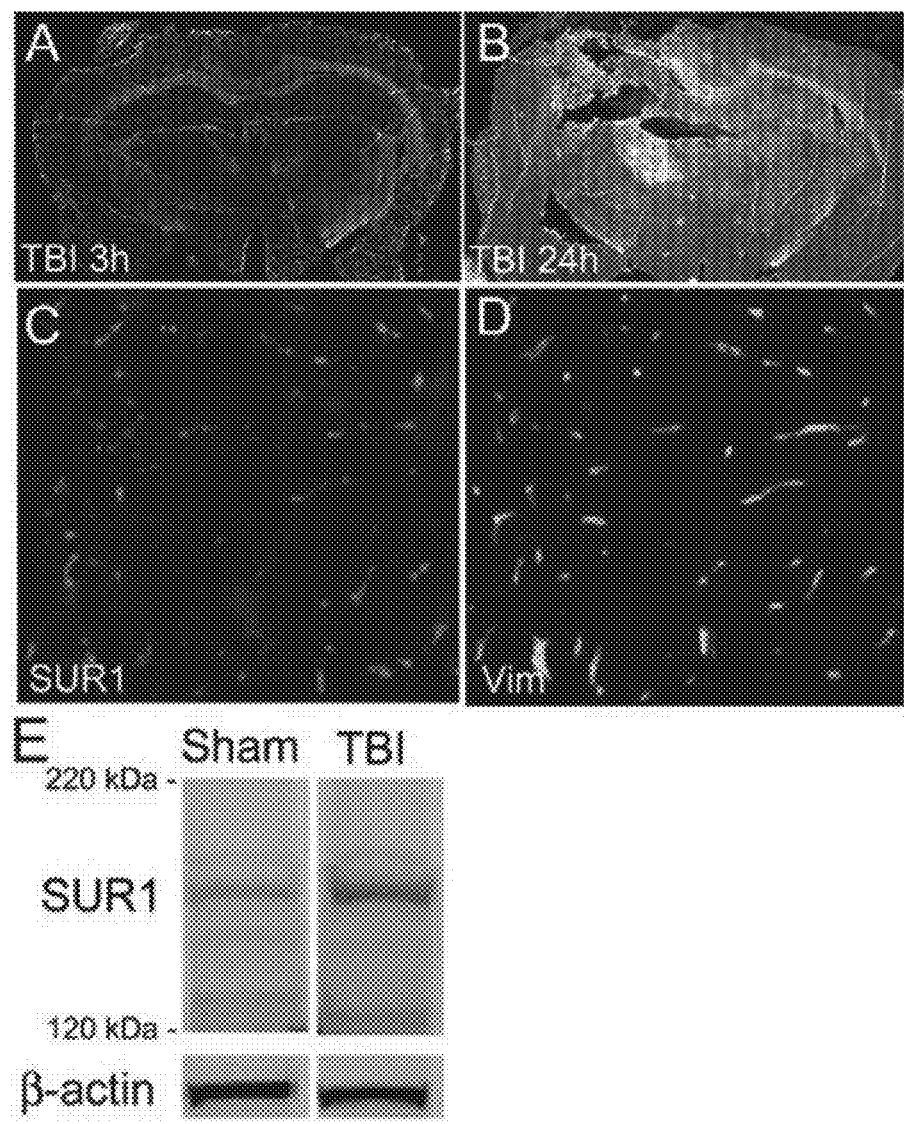
FIG. 15 demonstrates that SUR1 is upregulated in a rat model of percussion TBI. A,B: Montages of sections immunolabeled for SUR13 hr (A) and 24 hr (B) post-TBI (2.5-3 atm), showing progressive upregulation of SUR1 beyond regions of necrosis; rat in (B) same as in FIG. 14B. C,D: High power views of penumbral tissue 24-hr post-TBI immunolabeled for SUR1 (C) and colabeled for vimentin (D) to show capillaries. E: Western blots for SUR1 for uninjured rat brain, including parietal cortex and underlying hippocampus (Sham) and for the same regions 24 hr post-TBI; β-actin shown as loading control.
Figure 19:
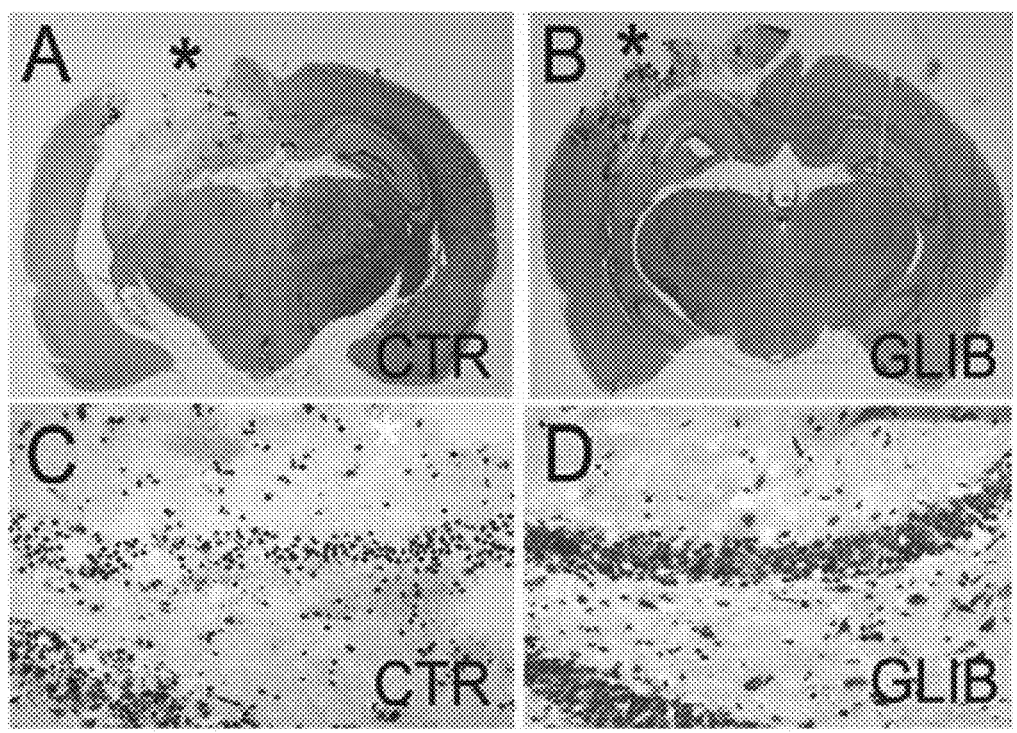
FIGS. 19A-19D demonstrate that glibenclamide reduces lesion size and spares hippocampal neurons post-TBI. A-D: Low-power (A,B) and high-power (C,D) views of Niss1-stained coronal sections 7 days post-TBI (2.5-3 atm), with high-power views showing ipsilateral hippocampus; note overall loss of neurons, with many remaining neurons pyknotic, in vehicle-treated rat (C) versus normal appearance of hippocampus in glibenclamide-treated rat (D); note hemosiderin staining (yellow discoloration) in vehicle-treated rat (C); percussion site marked by asterisk; data shown are representative of 5 rats/group.

Mortality, pathology and behavior. The acute-stage outcome (24 hr) produced in our percussion model with 2.5-3 atm transient pressure was similar to reports with fluid percussion of 2.5-3 atm (Thompson et al., 2005; Fujimoto et al., 2004; Dixon et al., 1987). The mortality of 15% was similar (Dixon et al., 1987). As with fluid percussion, a combined focal and diffuse injury was produced. A hemorrhagic contusion was apparent at the site of percussion that extended below the corpus callosum to involve much of the ipsilateral hippocampus and deeper structures (FIGS. 14, 15). There was significant cell and tissue loss in hippocampal CA2/CA3 and hilus ipsilateral to the injury site (see FIG. 19A,19C). Evidence of contralateral injury was also seen (FIG. 15B). Compared to sham controls, survivors exhibited marked reduction in spontaneous movements, in startle response, in exploratory movements in open field testing and much less frequent vertical exploration in an open cylinder test (see FIG. 20).

SUR1 is upregulated in rats post-TBI. Rats were studied for SUR1 expression. Montages of sections immunolabeled at 3 hr showed little SUR1, but by 24 hr, SUR1 was prominent both ipsilaterally and contralaterally (FIG. 15A,15B). Co-immunolabeled sections showed that newly expressed SUR1 co-localized with NeuN (neurons; not shown) and with von-Willebrand factor or vimentin (capillaries; FIG. 15C,15D). Upregulation was confirmed with Western blots (FIG. 15E).

Figure 16:
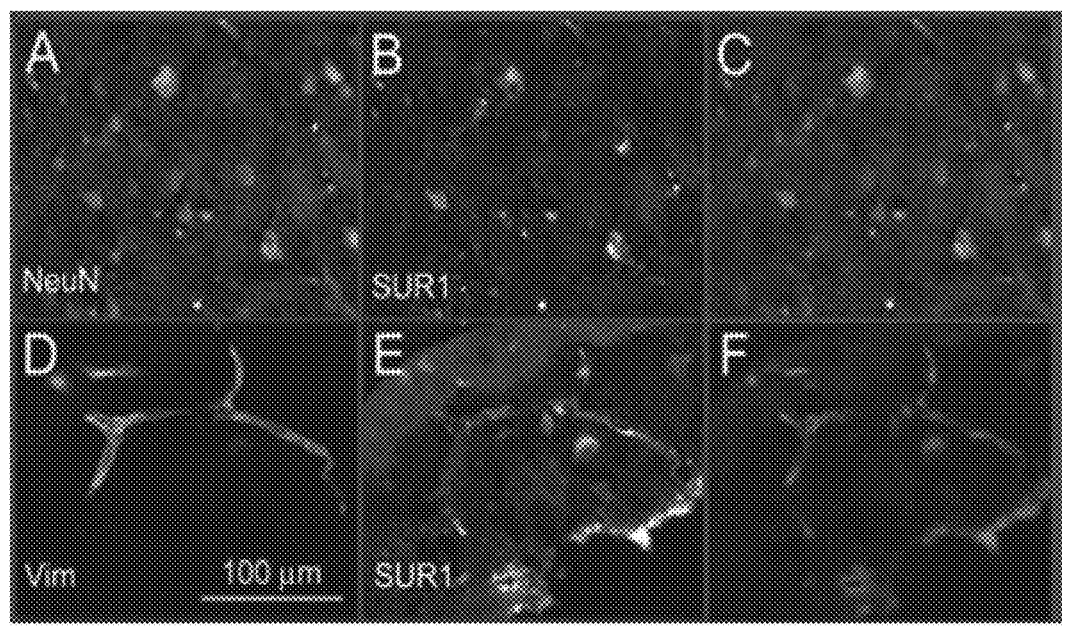
FIGS. 16A-16F demonstrate that SUR1 is upregulated in human brain following gunshot wound (GSW). A-F: High power views of neurons (A-C) and capillaries (D-F) immunolabeled for either NeuN (A) or vimentin (D) and double labeled for SUR1 (B,E); superimposed images are also shown (C,F); biopsy specimen from 24 year old male obtained at the time of decompressive craniotomy/debridement, 24 hr following GSW to the brain.

SUR1 is upregulated in humans post-TBI. To ascertain the relevance of these observations to humans, we also studied SUR1 expression in biopsy specimens from patients who required craniotomy for debridement/decompression 6-30 hr post-insult. Immunohistochemistry for SUR1 and in situ hybridization for Abcc8, which encodes SUR1, showed prominent upregulation in neurons and microvessels in 2/2 patients studied with gunshot wound to the brain (FIG. 16) and in one patient with intracerebral hematoma due to rupture of arteriovenous malformation (see Simard et al., 2008). This is consistent with the methods and treatments disclosed herein, and supports the use of SUR1 antagonists in the treatment of human TBI patients.

Figure 17:
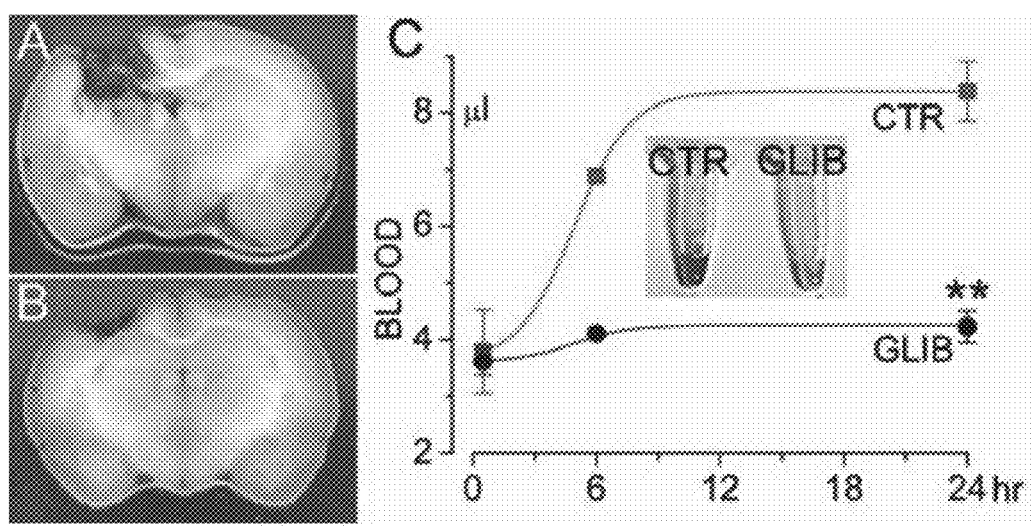
FIG. 17A-17C show that progressive secondary hemorrhage post-TBI is reduced by glibenclamide. A,B: Unprocessed coronal sections showing contusion injury in vehicle-treated control (A) and in glibenclamide-treated rat (B) 24-hr post-TBI (2.5-3 atm). C: Extravasated blood quantified at various times post-TBI in vehicle-treated and glibenclamide-treated rats, with non-linear least squares fit to Boltzman equation indicating half maximum blood at 5.2 hr; representative brain homogenates at 24 hr from both groups are also shown (insert); n=3-5/group; **, P<0.01.

In rat, progressive secondary hemorrhage manifests as an increase in extravasated blood. Using the model of percussion-TBI, data was obtained showing that the magnitude of the hemorrhage into the brain increased progressively over the first 24 hr after injury. Animals were sacrificed at ½, 6 and 24 hr after percussion-TBI (n=3-5 rats per group). They were perfused with heparinized saline to remove intravascular blood and portions of brain encompassing the lesion were homogenized and processed using Drabkin's reagent to convert hemoglobin to cyanomethemoglobin for spectrophotometric measurements (Simard et al., 2007). Values rose progressively over the first 24 hr, reaching half-maximum 5.2 hr post-injury, and maximizing only ~10 hr post-injury (FIG. 17). The fact that secondary hemorrhage is progressive over such a long period of time is seldom appreciated, but forms an underlying rationale for directly attacking this severely harmful cause of secondary injury post-TBI.

Block of SUR1 with glibenclamide reduces progressive secondary hemorrhage. We assessed the effect of glibenclamide on progressive secondary hemorrhage. As above, animals were sacrificed at ½, 6 and 24 hr after percussion-TBI. Glibenclamide treatment did not affect the volume of blood measured ½ hr post-injury, indicated a comparable magnitude of injury between groups (FIG. 17). However, glibenclamide prevented further increases in blood that were observed at later times in vehicle-treated controls (FIG. 17). At 24 hr post-injury, tissue homogenates from glibenclamide-treated animals were visibly less bloody that those from vehicle-treated animals (FIG. 17, insert). Overall, these data indicate that glibenclamide was highly effective in reducing progressive secondary hemorrhage post-TBI.

Glibenclamide effect on secondary hemorrhage is not due to an effect on coagulation or to inhibition of MMP. In uninjured rats given the same dose as above, glibenclamide had no effect on tail bleeding time (19.3±1.9 vs. 21.5±3.1 sec; n=3-5; P=0.6).

Figure 18:
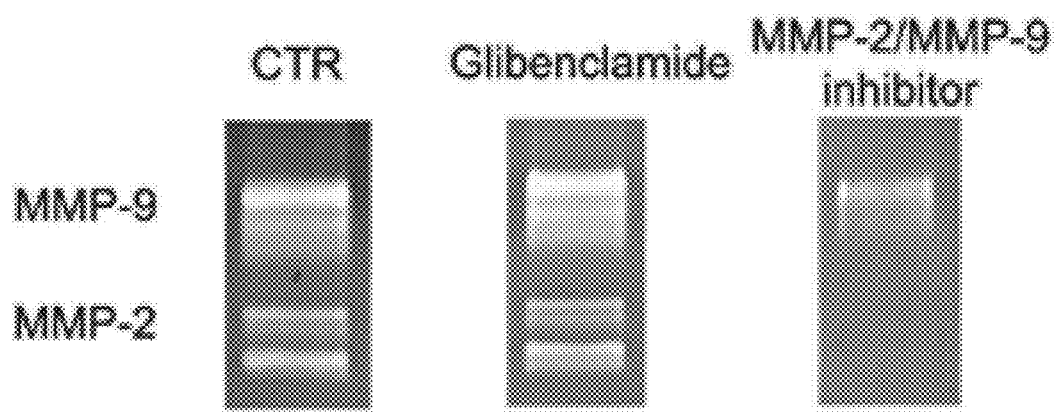
FIG. 18 demonstrates that glibenclamide does not inhibit matrix metalloproteinase (MMP) activity. Zymography showed that gelatinase activity of recombinant MMP (Chemicon) was the same under control conditions (CTR) and in the presence of glibenclamide (10 µM), but was significantly reduced by MMP-inhibitor II (300 nM; Calbiochem).

In stroke, hemorrhagic conversion has been attributed to activation of matrix metalloproteinases (MMP) (Justicia et al., 2003; Lorenzl et al., 2003; Romanic et al., 1998). It was assessed whether glibenclamide might be directly inhibiting MMPs. Zymography of recombinant MMPs showed that gelatinase activity assayed in the presence of glibenclamide was the same as that assayed without it, although gelatinase activity was strongly inhibited by commercially available MMP inhibitor II (FIG. 18). This finding makes it unlikely that glibenclamide was acting directly via MMP inhibition to decrease secondary hemorrhage post-TBI, and indicated instead that a mechanism involving SUR1-regulated $NC_{Ca\text{-}ATP}$ channels in capillary endothelium was likely to be involved, as we have shown recently for SCI (Simard et al., 2007).

Block of SUR1 with glibenclamide reduces lesion size and spares hippocampal neurons. The beneficial effect of glibenclamide on progressive secondary hemorrhage was associated with a reduction in lesion area on coronal sections at the epicenter of injury, from 8.2±1.3 to 4.4±0.8 mm$^2$ (10 rats/group; P=0.025), at 7 days post-TBI (FIG. 19A versus 19B).

Niss1 stained sections also showed that glibenclamide treatment was associated with sparing of hippocampus, including sparing of neurons in CAL CA3 and dentate gyrus regions (FIG. 19A-19D). Neuronal loss, pyknotic cells and hemorrhages observed in vehicle treated controls were much less likely to be seen with glibenclamide treatment (FIG. 19).

Figure 20:
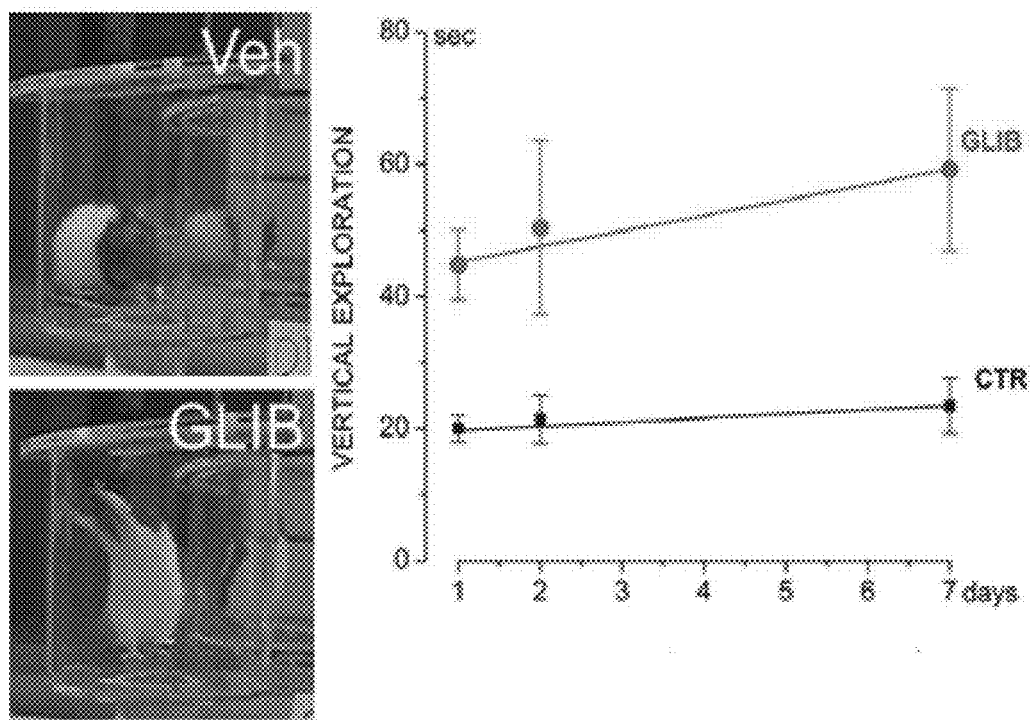
FIG. 20 demonstrates that glibenclamide improves neurobehavioral function post-TBI. Images of rats in the cylinder used to assess spontaneous forelimb use (SFU) and spontaneous vertical exploration (SVE) post-TBI (2.5-3 atm). SVE, quantified as the time (in sec) spent with both forepaws raised above shoulder-height during the first 3 min in the cylinder, was significantly greater in glibenclamide treated rats compared to vehicle-treated rats during repeated sessions over the first week post-injury; 5 rats/group; P<0.01 by repeated measures ANOVA; same rats as in FIG. 19.

Block of SUR1 with glibenclamide improves neurobehavioral function. The data included only simple testing of neurobehavioral function. Spontaneous forelimb use (SFU) was quantified and spontaneous vertical exploration (SVE) was quantified during 7 days post-TBI. SFU measures sensorimotor asymmetry (Schallert et al., 2000) whereas SVE measures not only vestibulomotor function but also time spent in exploratory activity. At 2 days post-TBI, glibenclamide treatment was associated with an increase in spontaneous use of the forelimb contralateral to the injury from 3.5±3.5% in controls to 16.5±3.4% in the treatment group (P=0.05). At 1, 2 and 7 days post-TBI, glibenclamide-treated rats consistently exhibited significantly greater SVE scores than controls (FIG. 20).

Figure 21:
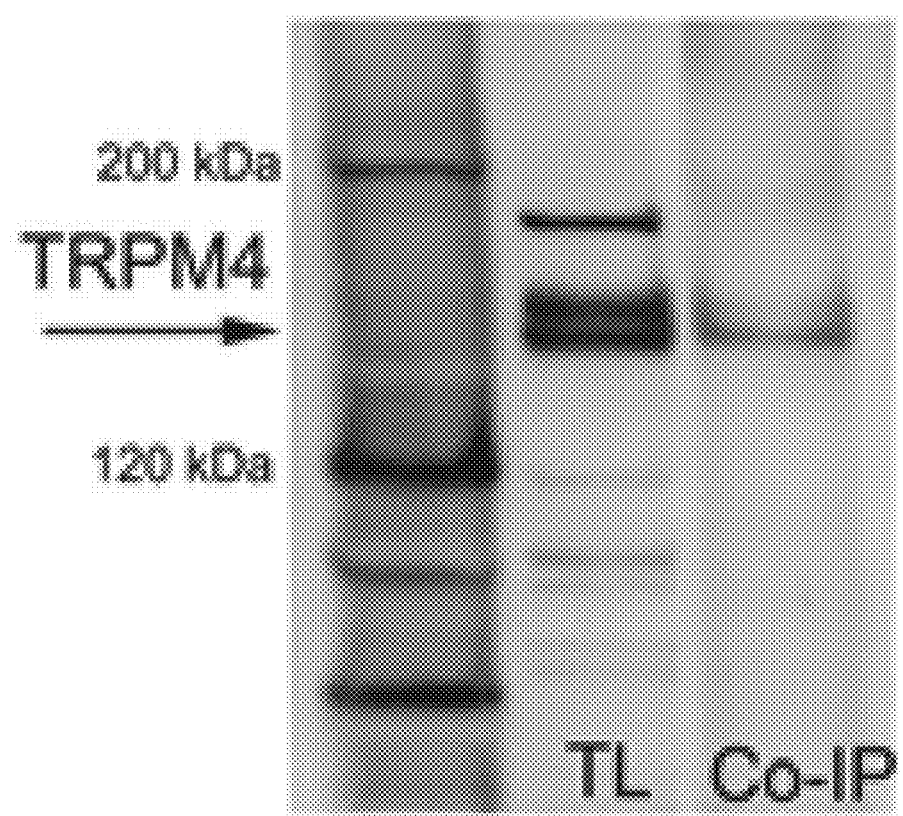
FIG. 21 shows that TRPM4 physically associates with SUR1 to form the SUR1-regulated $NC_{Ca-ATP}$ channel. Western blot for TRPM4 of total lysate (TL) of injured tissues (middle lane), and of the product of immunoprecipitation using SUR1 antibody (Co-IP) (right lane); ladder also shown (left lane) (from Simard et al., submitted).
Figure 22:
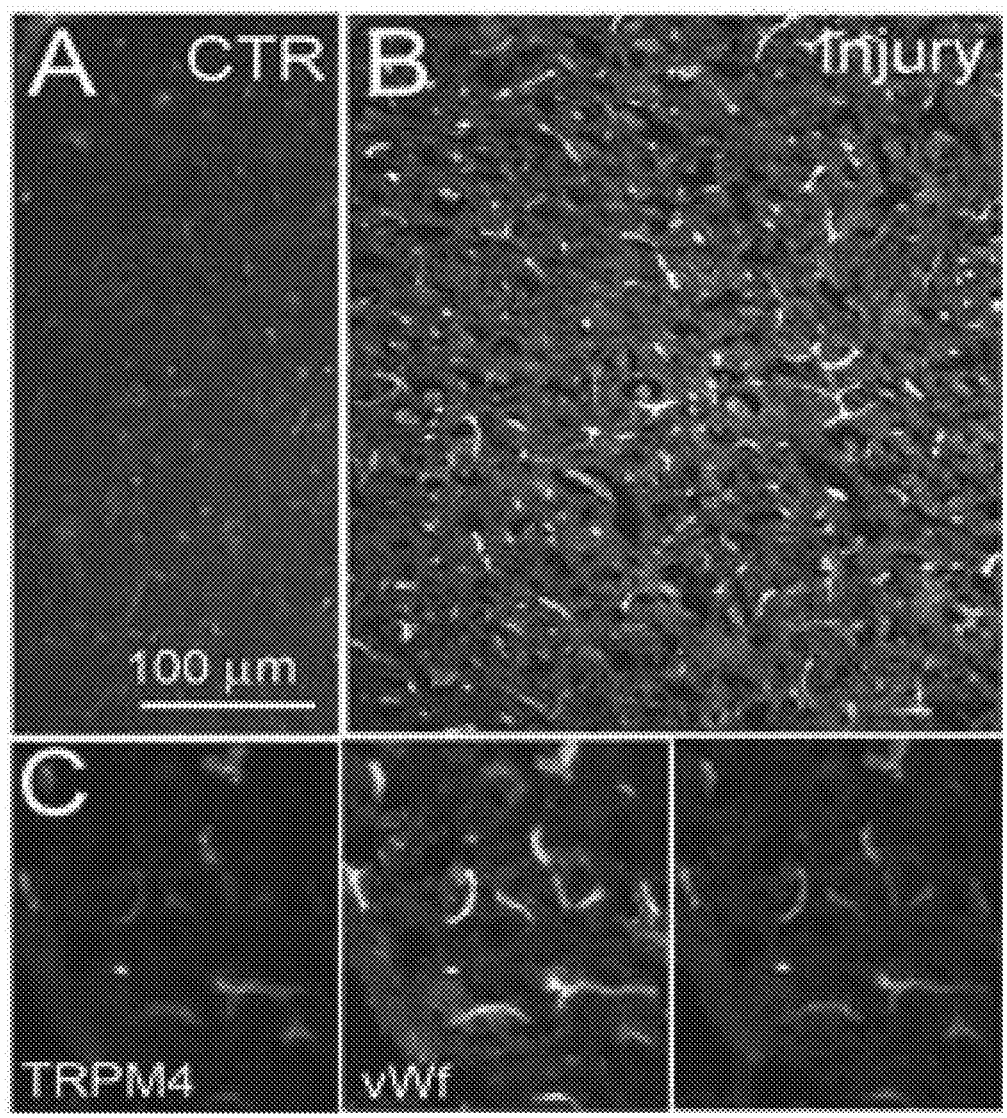
FIGS. 22A-22C demonstrate that TRPM4 is upregulated in penumbral capillaries 24 hr post-TBI. A-C: Low-power (A,B) and highpower (C) views of uninjured control (A) and post-TBI penumbral (B,C) tissues immunolabeled for TRPM4 or von-Willebrand factor (vWf), as indicated; merged images also shown (C, right panel).

Transient receptor potential M4 (TRPM4) pores physically associates with SUR1 and is upregulated in penumbral capillaries post-TBI. The SUR1-regulated $NC_{Ca-ATP}$ channel is composed of molecularly distinct regulatory and pore-forming subunits encoded by different genes. SUR1 was previously identified as the regulatory subunit (Simard et al., 2006; Chen et al., 2003) and it is considered that TRPM4 forms the pore-forming subunit, based on essentially identical biophysical properties of $NC_{Ca-ATP}$ and TRPM4 channels (Simard et al., 2007). Co-immunoprecipitation studies were carried out to examine the physical association between SUR1 and TRPM4. Western blots showed that total lysate from injured tissue exhibited abundant TRPM4 protein (FIG. 21, middle lane), and that immunoprecipitation using anti-SUR1 antibody yielded a product also identified as TRPM4 (FIG. 21, right lane), confirming physical association between SUR1 and TRPM4. Moreover, as with SUR1, TRPM4 is abundantly upregulated especially in penumbral capillaries post-TBI (FIG. 22). In certain aspects, the temporal profile for SUR1 and TRPM4 mRNA and protein expression post-TBI is determined.

Figure 23:
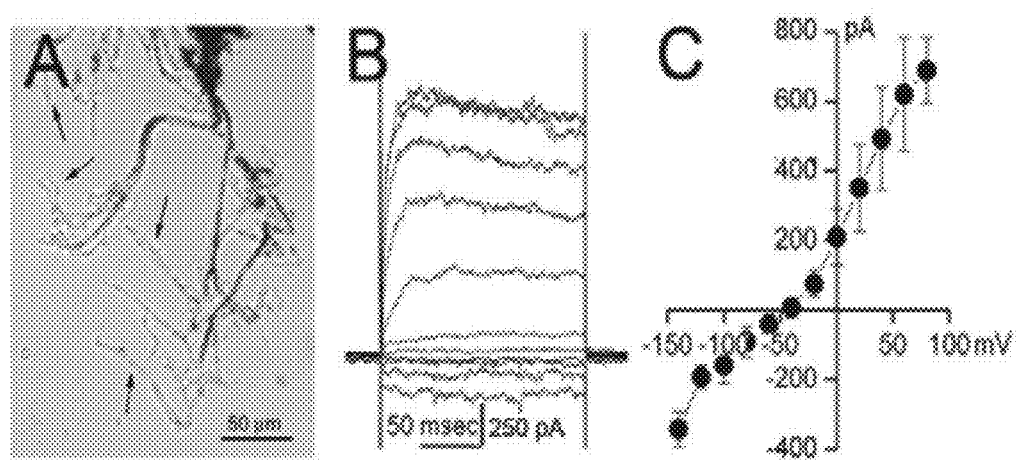
FIGS. 23A-23C show patch clamp of endothelial cells attached to freshly isolated brain capillaries. A: Micrograph of capillaries isolated using magnetic particles (black clump at top of figure); arrows point to segments targeted for patch clamp. B,C: Currents (B) and I-V curve of peak currents (C) recorded from endothelial cells still attached to capillary; standard physiological solutions inside and outside; n=5.

Studies on isolation of brain microvascular complexes and patch clamp of capillaries. Microvascular complexes were isolated from normal (uninjured) rat brain using a method based on perfusion with magnetic particles (details of method given below). Magnetic separation yielded microvascular complexes that typically included a precapillary arteriole plus attached capillaries (FIG. 23A). As is evident from the image, unambiguous identification of capillaries for precise positioning of the pipette for patch clamping attached capillary endothelial cells is readily achievable (FIG. 23A, arrows).

Capillary endothelial cells still attached to intact microvascular complexes were patch clamped using a conventional whole cell method. Cells were studied with standard physiological solutions in the bath and in the pipette, including 2 mM ATP in the pipette solution. Membrane currents showed time-dependent activation (FIG. 23B) with a weakly rectifying current-voltage (I-V) relationship that reversed near −50 mV (FIG. 23C). These recordings demonstrate the feasibility of patch clamping freshly isolated capillary endothelial cells still attached to intact microvascular complexes from brain.

In certain embodiments of the invention, SUR1, which regulates the novel $NC_{Ca-ATP}$ channel, is directly responsible for critical pathological mechanisms of secondary injury, most importantly, progressive secondary hemorrhage, and that by blocking this channel with the highly potent and safe antagonist, glibenclamide (glyburide), significant improvements in outcome can be obtained post-TBI. Demonstrating these concepts advances pharmaceutical treatments that greatly improves management of TBI and improves existing strategies for rehabilitation. Modern techniques of molecular biology, electrophysiology and neurobehavioral may be employed, for example.

In one case, the time course for upregulation of the molecular components of the channel as well as of functional channels, which is required to define the time-window for treatment, is determined. In another case, one can evaluate the effect of channel inhibition on edema and hemorrhage using various doses of glibenclamide beginning at various times post-injury, to determine the allowable time-window and the optimal dose for treatment. Finally, in an additional case, one can confirm the therapeutic efficacy of glibenclamide in male and female rats using a comprehensive battery of neurofunctional, cognitive and psychophysiological tests assessed up to 6 months post-TBI.

The model of percussion-TBI. In certain aspects data were obtained using a mechanical percussion device that was designed and built, which produced injury forces (see FIG. 13) and yielded brain damage (see FIG. 14) comparable to moderate-to-severe fluid percussion (Thompson et al., 2005). Although the device yielded quite reproducible results (FIG. 14A, 14B, 17A, 19A are from 4 different rats), fluid percussion injury (FPI) has long been used and is widely accepted in TBI research (Thompson et al., 2005). Although some injury parameters are better controlled using a controlled cortical impact (CCI) device rather than a FPI device, FPI is preferred over CCI, in certain cases, because CCI generally produces a more focused injury compared with FPI and overall, TBI is less severe with CCI compared to FPI (Obenaus et al., 2007). Injuries produced by parasagittal FPI are more diffuse and, importantly, are more likely to involve hippocampus. These differences inevitably have implications with respect to behavioral and functional outcomes (Fujimoto et al., 2004; Cernak, 2005).

Thus, a fluid percussion model, with a percussion pressure of ~3 atm may be used in studies as disclosed herein. Controls undergo sham surgery (craniectomy without percussion). Young adult (12 weeks) male (Objective 1-3) or female (Objective 3) Long-Evans rats are suitable animals for use in the studies disclosed herein.

Drug treatment following TBI. Typically, studies of drug interventions post-TBI utilize one or more injections of drug during the post-injury period. This technique yields plasma levels of drug that can fluctuate widely between peaks and troughs, depending on (usually unknown) pharmacokinetic parameters. A constant infusion of drug is utilized, with the aim of achieving constant occupancy of high-affinity receptors without potential complications inherent with transiently excessive drug levels. Thus, within 2-3 min of injury, miniosmotic pumps (Alzet) are implanted over the dorsal thorax to deliver either vehicle or drug subcutaneously, with pumps fitted with "Lynch coils" to obtain any desired delay in start of treatment. This technique has been successfully employed in previous studies (Simard et al., 2006; Simard et al., 2007).

For certain studies, glibenclamide was delivered at 200 ng/hr (no loading dose). For other studies, the effects of various doses of glibenclamide, including use of a loading dose, are characterized. The purpose is to mimic treatment that would be implemented in humans, including use of a loading dose and constant infusion, coupled with a delay in start of treatment. (One case use i.p. and s.q. routes in rats instead of i.v., as would be used in humans, for example.)

In certain embodiments of the invention, SUR1-regulated $NC_{Ca-ATP}$ channels are upregulated in neurons and capillary endothelial cells over several hours after TBI Previous work identified SUR1 as the regulatory subunit of the $NC_{Ca-ATP}$ channel (Simard et al., 2006; Simard et al., 2007; Chen et al., 2003). New work has identified transient receptor potential melastatin 4 (TRPM4) as the pore forming subunit. Thus, determining the time course for channel upregulation post-TBI employs studying expression of mRNA and protein for these two molecular components, in certain cases. However, expression of subunits does not necessarily assure expression of pathologically functional channels. Therefore, full characterization of the time course of channel expression also utilizes patch clamp experiments to document the expression of functional channels in capillary endothelial cells and neurons.

Specific embodiments on percussion-TBI indicate that SUR1 protein is upregulated 24 hr after injury in capillaries and neurons. However, the beneficial effect of glibenclamide on progressive secondary hemorrhage at 6 hr (FIG. 17) indicates that channels are upregulated much earlier than 24 hr. Indeed, previous work in stroke indicated that SUR1 itself, as well as functional SUR1-regulated $NC_{Ca-ATP}$ channels are upregulated in neurons as early as 2-3 hr after onset of ischemia (Simard et al., 2006). Channel upregulation in neurons and astrocytes is thought to be critical for cytotoxic edema, whereas channel upregulation in capillary endothelial cells is thought to be critical for ionic edema, vasogenic edema and hemorrhagic conversion (Simard et al., 2007). Understanding the time course for channel expression in different cell types is crucial for determining the treatment window for glibenclamide.

Overview of Studies

In certain cases, the time course for upregulation of $NC_{Ca-ATP}$ channels following percussion-TBI is determined. This utilizes three exemplary series of studies. First, Western blots are used to measure the increase in SUR1 and TRPM4 protein and qPCR is used to measure the increase in mRNA for SUR1 and TRPM4. The qPCR experiments provide direct confirmation of involvement of transcription, and also indirectly validate the Western blot studies. As regards specificity of antibody, it was previously shown that the anti-SUR1 antibody to be used for Westerns (and immunochemistry, see below) exhibits a high degree of specificity for SUR1, and labels only a single band (180 kDa) in the range between 116-220 kDa (simard et al., 2006). Secondly, it is determined which cells are actually upregulating transcriptional expression of SUR1 and TRPM4. This is done using double immunolabeling experiments, with validation provided at the mRNA level using in situ hybridization. Third, it is determined whether newly upregulated SUR1 and TRPM4 are associated with functional $NC_{Ca-ATP}$ channels, which employs patch clamp experiments.

Experimental Design:

Time-Course for SUR1 and TRPM4 Protein and mRNA, Using Westerns and qPCR

SUR1 and TRPM4 protein is measured in 7 groups of animals: in controls (sham surgery) and in animals with ~3 atm percussion-TBI at 6 times after injury, at ¾, 1.5, 3, 6 12, 24 hr. Blots are stripped and re-blotted for Kir6.1 and Kir6.2, to show non-involvement of $K_{ATP}$, as previously (Simard et al., 2006). Each of the seven groups requires 3 rats per group.

SUR1 and TRPM4 mRNA are measured in 7 groups of animals: in controls (sham surgery) and in animals with ~3 atm percussion-TBI at 6 times after injury, at ¾, 1.5, 3, 6 12, 24 hr. Each of the seven groups require 3 rats per group. (NB: separate groups are required for protein and mRNA because tissues are processed differently)

Specific Methods:

Preparation of tissues. After death, animals are perfused with heparinized saline to remove blood from the intravascular compartment. For the qPCR experiments, the perfusion solution includes RNAlater (Ambion, Auston Tex.), to prevent RNA degradation and optimize quantification. The injured left hemisphere is sectioned to include 5 mm rostral and 5 mm caudal to the impact site (2×impact diameter), with sampling including parietal lobe and underlying tissues, including hippocampus. Harvested tissues are flash frozen in liquid nitrogen and stored at −80° C. until processed.

Western blots. Lysates of whole tissues are prepared by homogenizing in RIPA lysis buffer, and electrophoretic gels (NuPAGE® 3-8% Tris-Acetate gels; Novex, Invitrogen, Carlsbad, Calif.) are processed as described (Perillan et al., 2002). Blots are analyzed for SUR1 (SC-5789; Santa Cruz Biotechnology), TRPM4 (SC-27540; Santa Cruz), Kir6.1 or Kir6.2 (Santa Cruz). Membranes are stripped and re-blotted for β-actin (1:5000; Sigma), which is used as loading control. Detection is carried out using the ECL system (Amersham BioTBIences, Inc.) with routine imaging (Fuji LAS-3000) and quantification (Scion Image, Scion Corp, Frederick, Md.).

The specificity of the SUR1 antibody has been documented (Simard et al., 2006). The specificity of the Kir6.x antibodies is confirmed with Western blots on insulinoma RIN-m5f cells (Kir6.2) and rat heart (Kir6.1). The specificity of the TRPM4 antibody using TRPM4 heterologously expressed in COS-7 cells is confirmed.

qPCR. Lysates of whole tissues are prepared by homogenizing in RNA lysis buffer (Promega). There is reverse transcription of 1 µg of total RNA (normalized conditions) with random hexonucleotides according to the manufacturer's protocol (Applied Biosystems) and real-time PCR reactions with an ABI PRISM 7300 Sequence Detector System (Applied Biosystems) are performed using a TaqMan based protocol in a 96-well plate format. Taq Man probes and primers are selected with Primer Express 2.0 (Applied Biosystems) software and synthesized by Applied Biosystems. Primer sequences: H1 histone family member (housekeeping gene): CGGACCACCCCAAGTATTCA (forward) (SEQ ID NO:5); GCCGGCACGGTTCTTCT (reverse) (SEQ ID NO:6); CAT-GATCGTGGCTGCTATCCAGGCA (SEQ ID NO:7) (TaqMan Probe). rSUR1 (NM_013039.1): GAGTCGGACT-TCTCGCCCT (forward) (SEQ ID NO:8); CCTTGACAGTGGACCGAACC (reverse) (SEQ ID NO:9); TTCCACATCCTGGTCACACCGCTGT (SEQ ID NO:10) (TaqMan Probe); rTRPM4 (XM_574447): AGTTGAGTTC-CCCCTGGACT (forward) (SEQ ID NO:11); AATTC-CAGTCCCTCCCACTC (reverse) (SEQ ID NO:12). Amplification reactions are performed using a TaqMan amplification kit (Applied Biosystems) according to the manufacturer's protocol, in 25 µl of reaction volume with 2 µl of cDNA. The amplification program consists of a 5-min holding period at 95° C., followed by 40 cycles of 95° C. for 30 sec, 60° C. for 30 sec and 72° C. for 30 sec. Relative quantification is performed using a standard curve method (User Bulletin #2, PE Applied Biosystems). All samples are run in triplicate.

Statistical analysis: Means will be compared using ANOVA.

Cellular Localization, Using Immunohistochemistry and In Situ Hybridization, for SUR1 and TRPM4.

In these studies, SUR1 and TRPM4 are the focus, but now with the intent of determining the cell types responsible for SUR1 and TRPM4 upregulation. For this, one can perform double immunolabeling experiments, labeling neurons with NeuN, astrocytes with GFAP, and capillary endothelial cells with vonWillebrand factor and vimentin (Schnittler et al., 1998). Also, one can perform in situ hybridization experiments to further validate the SUR1 and TRPM4 immunohistochemistry.

Immunolabeling is performed for SUR1 and TRPM4 plus double labeling for a cell-specific marker (NeuN, GFAP, vimentin, vWf) in 7 groups of animals: in controls (sham surgery) and in animals with ~3 atm percussion-TBI at 6 times after injury, at ¾, 1.5, 3, 6 12, 24 hr. Each of the seven groups may include, for example, 3 animals/group.

Confirmatory in situ hybridization studies are performed for SUR1 mRNA in 4 groups of animals: in controls (sham surgery) and in animals with ~3 atm percussion-TBI at 3 times after injury, at 1.5, 6 and 24 hr. These studies can utilize tissues from the same rats as used for immunolabeling.

Specific Methods:

Preparation of tissues. After death, animals are perfused with heparinized saline to remove blood from the intravascular compartment followed by 4% paraformaldehyde. The brain is harvested, cut to include 5 mm rostral and 5 mm caudal to the impact site. The brain is cryoprotected using 30% w/v sucrose.

Immunohistochemistry. Cryosections are used for double immunolabeling (SUR1+NeuN, SUR1+GFAP; SUR1+vWf) or (TRPM4+NeuN, TRPM4+GFAP; TRPM4+vWf), using standard techniques (Chen et al., 2003). After permeabilizing (0.3% Triton X-100 for 10 min), sections are blocked (2% donkey serum for 1 hr; Sigma D-9663), then incubated with primary antibody directed against SUR1 (1:200; 1 hr at room temperature then 48 h at 4° C.; SC-5789; Santa Cruz Biotechnology) or TRPM4 (1:200 overnight at 4° C.; Santa Cruz). After washing, sections are incubated with fluorescent secondary antibody (1:400; donkey anti-goat Alexa Fluor 555; Molecular Probes, OR). For co-labeling, one can use primary antibodies directed against NeuN (1:100; MAB377; Chemicon, CA); GFAP (1:500; CY3 conjugated; C-9205; Sigma, St. Louis, Mo.); vonWillebrand factor (1:200; F3520, Sigma) vimentin (1:200; CY3 conjugated; C-9060, Sigma) and, as needed, species-appropriate fluorescent secondary antibodies. Fluorescent signals are visualized using epifluorescence microscopy (Nikon Eclipse E1000).

In situ hybridization. Fresh-frozen sections are post-fixed in 5% formaldehyde for 5 min. Digoxigenin-labeled probes (SUR1: antisense: '5-GCCCGGGCACCCTGCTGGCTCT-GTGTGTCCTTCCGCGCCTGGGCATCG-3' (SEQ ID NO:13); TRPM4: (antisense: '5-CCAGGGCAGGCCGC-GAATGGAATTCCCGGATGAGGCTGTAGCGCTGCG-3' (SEQ ID NO:14); GeneDetect)") are designed and supplied by GeneDetect (Brandenton, Fla.) and hybridization is performed according to the manufacturer's protocol (Simard et al., 2006; Simard et al., 2007).

Channel Function Using Patch Clamp Electrophysiology on Isolated Cells

It is determined electrophysiologically whether upregulated SUR1 and TRPM4 subunits form functional $NC_{Ca-ATP}$ channels in capillary endothelial cells and neurons. The salient biophysical features of the channel (Simard et al., 2008) include: (i) the channel conducts $Cs^+$, so that recordings with $Cs^+$ as the only permeant cation unambiguously distinguish between SUR1-regulated $NC_{Ca-ATP}$ channels and SUR1-regulated $K_{ATP}$ channels; (ii) the channel is regulated by SUR1, so that block of a $Cs^+$ conductance by low concentrations of glibenclamide identifies the channel with virtual certainty.

The data on TBI indicate that glibenclamide is highly effective in reducing progressive secondary hemorrhage. In certain aspects, this high potency reflects not only the high affinity of the drug at the receptor ($EC_{50}$=48 nM at neutral pH, 6 nM at pH 6.8) (Chen et al., 2003), but also the fact that ischemic or injured tissues are at lower pH (≈6.5),42 coupled with the relatively acidic pKa of glibenclamide (6.3), resulting in greater lipid solubility and thus greater tissue concentration of the compound in ischemic regions. This is tested directly.

Cell isolation is performed twice weekly, with each batch of freshly isolated cells studied over the course of 2 days, allowing patch clamp experiments ~4 days/week.

Specific Methods:

Isolation of brain microvessels with attached capillaries. The method used (see FIG. 23) is adapted from Harder et al. (1994) Tissues are prepared at 3-5 hr post-TBI. A rat undergoes transcardiac perfusion of 50 ml of heparinized PBS containing a 1% suspension of iron oxide particles (10 μm; Aldrich Chemical Co.). The contused brain is removed, the pia and pial vessels are stripped away, the tissue is minced into pieces 1-2 mm3 with razor blades. Tissue pieces are incubated with dispase II (2.4 U/ml; Roche) for 30 min with agitation in the incubator. Tissues are dispersed by trituration with a fire-polished Pasteur pipette. Microvessels are adhered to the sides of 1.5 ml Eppendorf tubes by rocking 20 min adjacent to a magnet (Dynal MPC-S magnetic particle concentrator; Dynal Biotech, Oslo, Norway). Isolated microvessels are washed in PBS ×2 to remove cellular debris and are stored at 4° C. in physiological solution (Harder et al., 1994). For patch clamp study of capillary cells, an aliquote of microvessels is transferred to the recording chamber, and using phase contrast microscopy, capillaries near the end of the visualized microvascular tree are targeted for patch clamping.

Isolation of neurons. Neurons are isolated from vibratome cut brain sections as we described.2 Tissues are prepared at 3-5 hr post-TBI. The brain is removed and vibratome sections (300 μm) are processed as described (Hainsworth et al., 2001) to obtain single neurons for patch clamping. Selected portions of slices are incubated at 35° C. in HBSS bubbled with air. After 30 min, the pieces are transferred to HBSS containing 1.5 mg/ml protease XIV (Sigma). After 30-40 min of protease treatment, the pieces are rinsed in enzyme-free HBSS and mechanically triturated. For controls, cells were utilized from sham animals. Cells are allowed to settle in HBSS for 10-12 min in a plastic Petri dish mounted on the stage of an inverted microscope. Large and medium-sized pyramidal-shaped neurons are selected for recordings. Patch clamp electrophysiology. Numerous papers present detailed accounts of the patch clamp methodologies that may be use, including whole-cell, inside-out, outside-out and perforated patch methods (Chen et al., 2001; Chen et al., 2003; Perillan et al., 2002; Perillan et al., 1999; Perillan et al., 2000).

The overall design of the studies follows a strategy previously used with reactive astrocytes and neurons for characterizing the $NC_{Ca-ATP}$ channel (Simard et al., 2006; Chen et al., 2001; Chen et al., 2003). Initial studies are carried out using a whole-cell perforated patch configuration to characterize macroscopic currents, and to test the overall response to ATP depletion induced by exposure to the mitochondrial poisons, Na azide or Na cyanide/2-deoxyglucose, as used in previously (Simard et al., 2006; Simard et al., 2007; Chen et al., 2001). This configuration is also useful for characterizing the response to the SUR1 activators: if the cell expresses $NC_{Ca-ATP}$ channels, diazoxide activates an inward current that reverses near zero millivolts, whereas if the cell expresses $K_{ATP}$ channels, diazoxide activates an outward current that reverses near −70 mV.

Additional characterization is carried out using inside-out patches for single channel recordings. This method makes it simpler to study endothelial cell patches, which can thus be obtained from either intact isolated capillaries or from single isolated endothelial cells. In addition, this method allows precise control of $Ca^{2+}$, $H^+$ and ATP concentrations on the cytoplasmic side, and for this reason is preferable to whole-cell recordings. Also, as previously shown (Chen et al., 2003), in this configuration anti-SUR1 antibody binds to the channel and inhibits glibenclamide action, making positive, antibody-based identification of the channel readily feasible during the patch clamp study.

The single channel slope conductance is obtained by measuring single channel currents at various membrane potentials using $Na^+$, $K^+$ and $Cs^+$ as the charge carrier, at different pH's including pH 7.9, 7.4, 6.9 and 6.4.

The probability of channel opening ($nP_o$) is measured at different concentrations of intracellular calcium ($[Ca^{2+}]_i$), at different pH's including pH 7.9, 7.4, 6.9 and 6.4. The $NC_{Ca-ATP}$ channel in astrocytes is regulated by $[Ca^{2+}]_i$, a unique feature that distinguishes the $NC_{Ca-ATP}$ channel from $K_{ATP}$ channel.

The concentration-response relationship is measured for channel inhibition by AMP, ADP, ATP at pH 7.9, 7.4, 6.9 and 6.4. There is a potentially important interaction between hydrogen ion and nucleotide binding that may also be very important in the context of ischemia.

The concentration-response for channel inhibition by glibenclamide is studied. The effect of glibenclamide will be studied at different pH's (7.9, 7.4, 6.9 and 6.4). The importance of these studies is several-fold. Pharmacological data at neutral pH are critical to characterizing the channel and for comparison with the channel in astrocytes. Values for half-maximum inhibition by sulfonylureas provide useful information on involvement of SUR1 vs. other SUR isoforms and other potential targets. As discussed above, because glibenclamide and other sulfonylureas are weak acids, they are more lipid soluble at low pH and thus can be expected to access the membrane more readily at low pH. See detailed discussion and the effect of pH on channel inhibition by glibenclamide in citation (Simard et al., 2008).

Statistical analysis. Means are compared using ANOVA.

In certain embodiments of the invention, SUR1 and TRPM4 are progressively upregulated at both the protein and mRNA levels in the region of percussion during the initial few hours post-injury, that upregulation is prominent in neurons and capillary endothelial cells, and that upregulation requires several hours to reach a maximum. Moreover, in specific embodiments SUR1 and TRPM4 upregulation are associated with formation of functional $NC_{Ca-ATP}$ channels and that Kir6.x pore forming subunits are not involved.

Early treatment with the proper dose of the SUR1 antagonist, glibenclamide, minimizes formation of edema and progressive secondary hemorrhage, and glibenclamide shifts the injury-magnitude vs. response curve to the right, in specific embodiments. There is data showing a strong salutary effect of glibenclamide when treatment is begun immediately after percussion-TBI. The findings indicate that this drug is useful. Doses of drug and timing of drug administration is optimized.

The endpoints for study, edema and secondary hemorrhage, are reliably quantified by measuring extravasated sodium and hemoglobin. The choice of these measures reflects the embodiment that edema and secondary hemorrhage are reliable, quantifiable indicators of lesion severity in the acute phase, and correlate well with lesion size and neurobehavioral performance assessed at later times, in certain cases.

Overview of Studies:

In a specific embodiment the effect of glibenclamide on edema and hemorrhage is determined when dosing and timing are varied. For these studies, rats re subjected to ~3 atm percussion-TBI; 4 different time delays (0-6 hr) before administration of one dose of drug ("dose2", see below) are studied, and 4 different doses of drug when drug is administered with a 2-hr delay are studied Each animal is evaluated for edema (sodium) and hemorrhage (hemoglobin) at 24 hr post-injury, at which time hemorrhage has maximized (see FIG. 17).

Experiments useful to assess the effect and extent of glibenclamide on shifting the injury-magnitude vs. response curve for edema and for hemorrhage, separate groups of rats are studied that are injured with different percussion pressures (~1, ~2, ~3, ~4 atm), and are treated with the "best dose" of glibenclamide, as determined in the foregoing studies, with no delay in treatment.

Experimental Design:

Using edema (sodium) and hemorrhage (hemoglobin) as treatment endpoints, one can measure the effect of treatment with glibenclamide, starting at various times after injury (0-6 hr) and with various doses (4 different doses) of glibenclamide One can study 11 groups of male rats with percussion-TBI, with 8 rats/group, as follows, for example:

| | | |
|---|---|---|
| 1. | | 0-hr delay/vehicle control |
| 2. | | 0-hr delay/dose2 |
| 3. | | 2-hr delay/vehicle control |
| 4. | | 2-hr delay/dose2 |
| 5. | | 4-hr delay/vehicle control |
| 6. | | 4-hr delay/dose2 |
| 7. | | 6-hr delay/vehicle control |
| 8. | | 6-hr delay/dose2 |
| 9. | | 2-hr delay/dose1 |
| 10. | | 2-hr delay/dose3 |
| 11. | | 2-hr delay/dose4 | where:

dose1=loading dose, 2.5 µg/kg, i.p.; infusion rate, 75 ng/hr, s.q.

dose2=loading dose, 5 µg/kg, i.p.; infusion rate, 150 ng/hr, s.q.

dose3=loading dose, 10 µg/kg, i.p.; infusion rate, 300 ng/hr, s.q.

dose4=loading dose, 20 µg/kg, i.p.; infusion rate, 600 ng/hr, s.q.

vehicle control=DMSO (same amount as in dose2) in NS

These doses are calculated based on the following:

1. the volume of distribution for glibenclamide (in humans) is 0.2 L/kg.48

2. for the loading doses, the serum concentrations are 25, 50, 100, 200 nM, based on the $EC_{50}$ value for channel inhibition (6 nM at pH 6.83).

3. lacking specific pharmacokinetic data for the rat, we base our infusion doses on our previous experience with stroke (Simard et al., 2006) and data with TBI (see above), which indicate that an infusion rate of 75-200 ng/hr are an effectiverate. Overall, the data indicate that 75 ng/hr, which has definite positive effects (Simard et al., 2006; Simard et al., 2008) is a suitable low dose, and that higher doses are also suitable and may be preferred.

4. testing in uninjured rats as well as on rats with stroke and SCI to determine the effect of these doses on serum glucose; of the doses suggested above, only the highest are hypoglycemogenic, but only mildly so. Notably, the loading doses of glibenclamide are 40-400 times less than typically used to induce hypoglycemia in rats (bd Elaziz et al., 1998).

Power analysis was performed with the following assumptions: $\alpha$=0.05; tails=2; N=8/group; ratio for (raw difference between population means)/(S.D. of one population)=2/1 (a conservative assumption, as suggested by FIG. 17). These values yield a power of 96% likelihood of detecting a significant effect.

Specific Methods:

Delay of treatment: Mini-osmotic pumps are implanted within 2-3 min of TBI. The pumps are fitted with widely-used "Lynch-coil" catheters that provide a dead space that requires the designated amount of time to fill. At the designated time, animals are also given the loading dose of glibenclamide i.p.

Monitoring serum glucose: serum glucose is be monitored every 3-12 hr during the first 24 hr after injury using a tail puncture to obtain a droplet of blood, and a standard glucometer for glucose measurements, to assure that levels are near euglycemic (80-160 mg/dL).

Preparation of tissues. After death, animals are perfused with heparinized PBS to remove intravascular blood. A 10-mm thick section of the upper half of the hemisphere encompassing the contusion is harvested.

Edema and hemorrhage: Tissue sodium and hemoglobin are measured in samples from the same homogenates. Sodium content is measured by flame photometry, as described (Xi et al., 2001) Hemoglobin (Hgb) is quantified spectrophotometrically after conversion to cyanomethemoglobin using Drabkin's reagent (Choudhri et al., 1997; Pfefferkorn and Rosenberg, 2003). This method has been used by us for quantifying hemorrhage following SCI in rats (Simard et al., 2007).

Data analysis: data obtained from vehicle-treated animals are compared with data obtained from glibenclamide-treated animals. Statistical significance is assessed using ANOVA.

Using edema (sodium) and hemorrhage (hemoglobin) as treatment endpoints, the shift in the stimulus-response curve with the "best dose" of glibenclamide administered without delay post-injury is measured, in separate groups of rats injured with different impact pressures (~1, ~2, ~3, ~4 atm)

These studies are similar to those above, except that the "best dose" of glibenclamide (determined above) administered immediately after injury is used. The choice of percussion pressures (~1, ~2, ~3, ~4 atm), is based in part on the literature for fluid percussion (Thompson et al., 2005), and on experience with the magnitude of injury produced in a model with 2.5-3 atm injury levels (see elsewhere herein).

Power analysis was performed with the following assumptions: $\alpha=0.05$; tails=2; N=8/group; ratio for (raw difference between population means)/(S.D. of one population)=2/1 (a conservative assumption, as suggested by FIG. 17). These values yield a power of 96% likelihood of detecting a significant effect.

Specific Methods: Same as Above

In specific embodiments, glibenclamide is beneficial in reducing edema and hemorrhage in the area of percussion, at least for some doses and with some delay in treatment, and shifts the injury-magnitude vs. response curve to the right, i.e., converts a "severe" injury to a "moderate" injury.

In certain embodiments, serum glucose levels are monitored to assure that they do not drop too low (less than about 80 mg/dL). In embodiments, the protocols are amended to correct for hypoglycemia, in order to maintain levels between 80-160 mg/dL.

In certain embodiments, in a rodent model of TBI, treatment with the "best dose" of the sulfonylurea receptor antagonist, glibenclamide, improves early sensorimotor and later cognitive and psychophysiological performance, and reduce lesion size and hippocampal neuronal cell loss. The foregoing studies are conducted with terminal endpoints (animals sacrificed to measure edema and blood in contused brain at 24 hr). One can perform measurements of neurofunctional, cognitive and psychophysiological endpoints out to 6 months in separate groups of male and female rats. These studies determine whether early treatment-related gains in edema and hemorrhage translate into long-term functional gains. In addition, these studies assess the role of gender in the response to glibenclamide treatment.

Animal and human studies have shown that the response to CNS injury is different in females and males, and that gender affects behavioral performance (Bimonte et al., 2000; Gresack and Frick, 2003; LaBuda et al., 2002). It is ascertained whether any difference in response to glibenclamide treatment exists between male and female rats, in certain aspects of the invention.

In humans post-TBI, the goals and targets of rehabilitation differ based on time post-TBI. Early-on after injury, acute rehabilitation tends to focus on recovery of sensorimotor dysfunction, locomotion, etc. Later on, after sensorimotor abnormalities have stabilized, long term cognitive and psychophysiological effects become more important targets of rehabilitation. One can assess the animals for effects of treatment with this time-frame in mind:

1. During the early phase, the following are assessed: (i) a strength/reflex test (NEUROLOGICAL SEVERITY SCORE); (ii) vestibulomotor tests (ROTAROD TEST and SPONTANEOUS FORELIMB USE TASK).

2. Animals are then allowed to survive for 6 months, at which time one can assess: (iii) a cognitive test (MORRIS WATER MAZE LEARNING PARADIGM); (iv) fear conditioning test (SUSCEPTIBILITY TO STRESS-INDUCED NONHABITUATING STARTLE).

This comprehensive range of testing includes sensorimotor tasks, cognitive and as well as a psychophysiological outcome measure potentially related to delayed-onset PTSD, (Garrick et al., 2001; Cohen et al., 2004), a critical sequela of TBI in humans (Andrews et al., 2007; Carty et al., 2006).

Overview of Experiments:

The animals undergo ~3 atm percussion-TBI, are administered either vehicle or drug, and later reassessed for neurofunctional and neurobehavioral recovery. One can use the "best dose" of glibenclamide, as determined in studies referred to above, and one can use two different treatment times—treatment starting immediately post-injury and treatment starting with a 4-hr delay, with both treatments lasting for 1 week. However, an important purpose of the studies is to ascertain whether a 4-hr delay in treatment is effective. In certain cases the start of treatment is delayed in one group as long as possible after injury, in order to most usefully simulate the human situation.

Neurofunctional recovery is assessed using established sensorimotor tests during post-injury days 1-28 (Fujimoto et al., 2004). Cognitive and psychophysiological tests are assessed at 6 months. Body weight is measured periodically. Histological and stereological evaluation of brains, includes determining overall lesion size as well as neuronal counts in CA(1)/CA(3) hippocampal regions at 6 months." (Grady et al., 2003; Hellmich et al., 2005).

(A) NEUROLOGICAL SEVERITY SCORE (NSS). This is an aggregate neurological testing strategy (Fujimoto et al., 2004). In the Neurologic Severity Score (see Table 5 of Fujimoto et al., 2004), animals are scored on an all-or-none scale for such tests as the ability to exit from a circle, righting reflex, hemiplegia, limb reflexes, pinna reflex, corneal reflex, startle reflex, beam balance, and beam walking. An animal receives one point for the ability to successfully perform each task and no points for the inability to perform, with the overall NSS being the sum of these scores.

(B) ROTAROD TEST. (Hamm et al., 1994; Lu et al., 2003) The rotarod task is a sensitive index of injury-induced motor dysfunction. The rotarod task measures aspects of motor impairment that are not assessed by either the beam-balance or beam-walking latency, and has been found to be a more sensitive and efficient index for assessing motor impairment produced by brain injury. (Hamm et al., 1994) Frequency of evaluation can affect performance—daily assessment promotes functional recovery whereas weekly assessment does not significantly affect outcome in injured animals during a 4-week assessment. (O'Connor et al., 2003).

(C) SPONTANEOUS FORELIMB USE TASK (SFU). This task measures sensorimotor asymmetry. (Schallert et al., 2000) It involves placing the animal in a plastic cylinder and determining the amount of time the animal spends rearing with the left, right, or both forelimbs on the cylinder wall. The cylindrical shape encourages vertical exploration of the walls with the forelimbs and it allows evaluation of landing activity. This test has been shown to be effective in detecting an injury deficit up to five months after controlled cortical impact in a mouse model. (Baskin et al., 2003). In addition, quantification of time spent in vertical exploration gives an overall measure of spontaneous activity.

(D) MORRIS WATER MAZE LEARNING PARADIGM (MWM) (Thompson et al., 2006; Dixon et al., 1999; Sanders et al., 1999; Kline et al., 2002). The MWM is the most widely used test for cognitive evaluation in experimental TBI. (Fujimoto et al., 2004). Deficits in learning have been detected up to 1 year post-injury in rats. (Fujimoto et al., 2004).

(E) STRESS-INDUCED NONHABITUATING STARTLE. The interest in the startle response is two-fold. First, it is known that percussion-TBI in rats yields a depressed startle response that can persist for over 30 days (Dixon et al., 1987; Lu et al., 2003; Wiley et al., 1996) possibly reflecting the overall decrease in spontaneous activity post-TBI. Thus, in its simplest form, the startle response provides a good test of the effect of glibenclamide treatment, with treatment expected to normalize or partially normalize this response. Note that the simple startle response in part of the NSS, is assessed during the early recovery phase (first 28 days).

It is believed that TBI-induced limbic system damage observed in percussion models of TBI may predispose the animal to delayed psychophysiological abnormalities. Months after injury, maladaptive "rewiring" of limbic circuitry is believed to give rise to altered psychophysiological responses, e.g., an increase in the susceptibility to non-habituating startle induced by new, consciously-experienced stress. A link between injury to limbic structures with increased susceptibility to non-habituating or augmented sensorimotor responses, has been discussed by Harvey et al., 2003, and is based on the observation of the important role of the hippocampus in the extinction of conditioned fear. (Brewin, 2001). Thus, whereas early-on, TBI is believed to be associated with depressed startle responses, later "recovery" from TBI is surprisingly believed to be lower the threshold for the "intensity" of a new stress (strength, duration or number of repetitions) that is required to induce non-habituating startle.

The interest in non-habituating startle resides in its potential relevance to post-traumatic stress disorder (PTSD). In humans following exposure to trauma, a vulnerable subpopulation of individuals develops PTSD with characteristic persistent autonomic hyper-responsivity, increased sensory arousal, increased startle response, and altered hypothalamo-pituitary-adrenal regulation. Often, onset of these symptoms is delayed. (Andrews et al., 2007; Carty et al., 2006). Similar effects are seen in (uninjured) rats in a rodent models of PTSD, in which the (awake) animal is exposed to repeated, randomly applied, inescapable stress. The stress paradigm used by Manion et al. (2007) consisted of 2-hr sessions of immobilization and randomly applied tailshocks each day for 3 days. Seven days later, the rats developed non-habituating startle. Slightly different paradigms have been used by others (Garrick et al., 2001; Garrick et al., 1997; Rasmussen et al., 2008). The methods disclosed herein may be used to evaluate the effect of glibenclamide on this phenomenon post-TBI. one can assess this question, and evaluate the effect of glibenclamide on this phenomenon post-TBI.

Experimental Design:

The effect of the "best dose" of glibenclamide administered at two treatment times on neurofunctional, cognitive and psychophysiological recovery is assessed in animals in times extending out to 6 months after injury.

8 groups are studied in all, 4 groups of males and 4 groups of females; for each gender, there is one sham-injured group and three TBI groups; the three TBI groups include a vehicle-treated group, a group treated with the "best dose" glibenclamide given immediately after injury, and a group treated with the "best dose" glibenclamide given 4 hr after injury. The "best dose" is determined from studies described above.

On any given day, 2 rats undergo TBI and then enter into a schedule of comprehensive testing during the subsequent 4 weeks (followed by 5 month recovery and more testing). Gender and treatment group are randomly assigned.

Power analysis was performed with the following assumptions: $c'=0.05$; tails=2; $N=12$/group; ratio for (raw difference between population means)/(S.D. of one population)=3/2 (worse case scenario). These values yield a power of 94% likelihood of detecting a significant effect.

Specific Methods:

Neurological severity score (NSS). The Neurologic Severity Score is obtained as detailed in Table 5 of Fujimoto et al. (2004).

FREQUENCY OF TESTING POST-TBI: Rats are tested on days 1, 3, 7, 14, 21, 28 post-TBI.

STATISTICAL TEST: Repeated measures ANOVA.

Rotarod test. The accelerating Rotarod test has been described. Rats are trained for 3 consecutive days before TBI, measuring latency to fall off the rod (10 trials/day).

FREQUENCY OF TESTING POST-TBI: Rats are tested on days 3, 7, 14, 21, 28 post-TBI. This schedule avoids the potential confounder that frequent assessments tend to promote functional recovery whereas weekly assessments do not (O'Connor et al., 2003).

STATISTICAL TEST: Repeated measures ANOVA.

Spontaneous forelimb use task (SFU). Rats are placed in a clear cylinder (diameter, 20 cm; height, 20 cm) in front of a mirror. Activity is videotaped for 5-30 min, depending on activity levels. Scoring is done by an experimenter blind to the condition of the animal using a VCR with slow motion and frame by frame capabilities. Asymmetrical forelimb usage is counted. This consists of recording: (1) the limb (left or right) used to push off the floor prior to rearing; (2) the limb used for single forelimb support on the floor of the box; and (3) the limb used for single forelimb support against the walls of the box (Schallert et al., 2000). Usage of both forelimbs simultaneously is not counted. Data are expressed as percentage of right (unaffected by injury) forelimb use, i.e. (right forelimb use/right+left forelimb use)☐100.

FREQUENCY OF TESTING POST-TBI: Rats are tested on days 3, 7, 14, 21, 28 post-TBI, during the same session with Rotarod.

STATISTICAL TEST: Repeated measures ANOVA.

Morris water maze learning paradigm (MWM). The MWM will be used to measure acquisition of spatial learning (DeFord et al., 2001; Hamm et al., 1993). A standard apparatus is used. At each trial, rats are placed by hand in the pool at one of four start locations (north, south, east, west) facing the wall. Start locations are randomly assigned to each animal. A computerized video tracking system is used to record the animal's latency to reach the goal. The tracking program calculates the distance from the animal to the goal during each trial (at 0.2 sec intervals) and adds these distances together as a measure of how close the animal is swimming to the goal during the trial. This measure is defined as "cumulative distance from the goal." To assess for the possible confounding effect of motor impairment, swim speeds are also measured on each trial. Rats are given a maximum of 120 sec to find the hidden platform. If an animal fails to find the platform after 120 sec, it is placed on the platform by the experimenter. Rats are allowed to remain on the platform for 30 sec and then are returned to a cage with a lamp warmer between trials. There is a 4-min inter-trial interval. Animals are tested 6 months post-TBI to allow for recovery of motor deficits. Rats were given four trials per day for five consecutive days.

FREQUENCY OF TESTING POST-TBI: 4 trials/day on 5 consecutive days, beginning 6 months post-TBI).

STATISTICAL TEST: Repeated measures ANOVA.

Stress-induced non-habituating startle (SINHS) (Manion et al., 2007). Animals are acclimated to the acoustic startle equipment for 3 consecutive days, one day without sound followed by two days with sound. This acclimation is finished 3 days prior to baseline recordings in order to avoid desensitization effects. A baseline recording of acoustic startle response (details below) is taken for each animal on the day prior to beginning the stress procedure. Stress exposure consists of a 2-h per day session of immobilization and tail-shocks for three consecutive days. Stressing is done during the dark or active phase of the light-dark cycle. Animals are restrained by being wrapped in a cloth jacket and having their head and torso immobilized in a ventilated plexiglass tube. Forty electric shocks (2-3 mA, 3 s duration; programmable animal shocker, Coulbourn Instruments) are delivered to their tails at semi-random intervals of 150-210 s.

ASR testing is conducted with a Startle Response Acoustic Test System (San Diego Instruments). This system includes weight-sensitive platform(s) in a sound-attenuated chamber. The animal's movements in response to stimuli are measured as a voltage change by a strain gauge inside each platform and are converted to grams of body weight change following analog to digital conversion. These changes are recorded by an interfaced computer as the maximum response occurring within 200 ms of the onset of the startle-eliciting stimulus. All acoustic stimuli are administered by an amplified speaker mounted 24 cm above the test cage. During testing, animals are individually placed in holding cages (14.5×7×6.5 cm) that are small enough to restrict extensive locomotion but large enough to allow the subject to turn around and make other small movements.

Following placement of the animal into the chamber, the chamber lid is closed, leaving the subject in darkness. A 3 min adaptation period occurs in which no startle stimulus is presented. Startle stimuli consist of 110 dB sound pressure level (unweighted scale; re: 0.0002 dynes/cm2) noise bursts of 20 ms duration, sometimes preceded by 100 ms with 68 dB, 1 kHz pure tones (pre-pulses). Decibel levels are verified by a sound meter. Each stimulus had a 2 ms rise and decay time such that onset and offset are abrupt, a primary criterion for startle. There are four types of stimulus trials: 110 dB alone, with pre-pulse, pre-pulse alone and no stimulus. Each trial type is presented eight times. Trial types are presented in random order to avoid order effects and habituation. Inter-trial intervals range randomly from 15 to 25 s. All animals are tested 1, 4, 7 and 10 days following the final day of the stress procedure, which will begin 1 week after the MWM, 6 months post-TBI.

FREQUENCY OF TESTING POST-TBI: 1 trial/day on 13 consecutive days, starting 1 week after MWM, 6 months post-TBI.

STATISTICAL TEST: Repeated measures ANOVA.

The effect of the "best dose" of glibenclamide administered at two treatment times on lesion size and hippocampal neuronal count at 6 months post-injury is assessed.

These experiments utilize the brains of animals injured and treated in the earlier portion of this example, using tissues from 5 rats from each of the 8 treatment groups. Coronal sections (25 µm) spaced 200 µm apart throughout the injury area (5 mm rostral and 5 mm caudal to the epicentre) are stained with Nissl stain and adjacent sections are immuno-labeled for NeuN (Chemicon).

A stereological system is used for efficient, unbiased and accurate measurements of lesion volumes and of counts of surviving neurons in different treatment groups. Nissl stained sections are used to measure lesion size. NeuN-immunolabeled sections are used to count neurons in ipsilateral and contralateral hippocampus (CA1, CA3 and dentate gyrus). All quantitative analyses are performed blindly. Using the Stereoinvestigator software (Microbrightfield, Williston, Vt., USA), counts of neurons (450×450 µm grids) and neuronal profiles within 50×50 µm counting frames spaced evenly throughout the ipsilateral and contralateral hippocampus are obtained using a 20× objective. Using Stereoinvestigator software, serial reconstruction of the ipsilateral and contralateral hippocampus are performed to compute total volumes. To determine if the neurons are decreasing in size, cross-sectional areas of hippocampal neuronal profiles will be determined by outlining the perimeter of all defined neurons within 50×50 µm counting frames spaced evenly throughout the sections (450×450 µm grids).

STATISTICAL TEST: ANOVA.

In particular embodiments, glibenclamide, as an example, results in a significant improvement in standard measures neurofunctional outcome, including the neurological severity score and vestibulomotor assessments, and the beneficial effects endure during the month of repeated testing.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS AND PATENT APPLICATIONS

U.S. Pat. No. 5,399,363
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,613,308

PUBLICATIONS

Aguilar-Bryan, L., Nelson, D. A., Vu, Q. A., Humphrey, M. B., and Boyd, A. E., III 1990. Photoaffinity labeling and partial purification of the beta cell sulfonylurea receptor using a novel, biologically active glyburide analog. J. Biol. Chem. 265:8218-8224.

Andrews, B., Brewin C R, Philpott R, Stewart L. Delayed-onset posttraumatic stress disorder: a systematic review of the evidence. Am J Psychiatry 2007 September; 164(9): 1319-26.

Anstrom, J A, Brown W R, Moody D M, Thore C R, Challa V R, Block S M. Subependymal veins in premature neonates: implications for hemorrhage. Pediatr Neurol 2004 January; 30(1):46-53.

Balentine, J. D., 1978. Pathology of experimental spinal cord trauma. I. The necrotic lesion as a function of vascular injury. Lab Invest 39:236-253.

Ballabh, P., Xu H, Hu F, Braun A, Smith K, Rivera A, Lou N, Ungvari Z, Goldman S A, Csiszar A, Nedergaard M 2007 Angiogenic inhibition reduces germinal matrix hemorrhage. Nat Med 13:477-485

Baskin, Y K, Dietrich W D, Green E J. Two effective behavioral tasks for evaluating sensorimotor dysfunction following traumatic brain injury in mice. J Neurosci Methods 2003 Oct. 15; 129(1):87-93.

Basso, D. M., Beattie, M. S., and Bresnahan, J. C. 1995. A sensitive and reliable locomotor rating scale for open field testing in rats. J. Neurotrauma 12:1-21.

bd Elaziz M A, Al-Dhawailie A A, Tekle A. The effect of stress on the pharmacokinetics and pharmacodynamics of glibenclamide in diabetic rats. Eur J Drug Metab Pharmacokinet 1998 July; 23(3):371-6.

Berger, R, Garnier Y, Jensen A. Perinatal brain damage: underlying mechanisms and neuroprotective strategies. J Soc Gynecol Investig 2002 November; 9(6):319-28.

Bhatta, S., Transcriptional regulation of SUR1-regulated NC(Ca-ATP) channel by hypoxia inducible factor 1a in brain injury. Doctoral Dissertation, University of Maryland, 2007.

Bilgen, M., Abbe, R., Liu, S. J., and Narayana, P. A. 2000. Spatial and temporal evolution of hemorrhage in the hyperacute phase of experimental spinal cord injury: in vivo magnetic resonance imaging. Magn Reson. Med. 43:594-600.

Bimonte, H A, Hyde L A, Hoplight B J, Denenberg V H. In two species, females exhibit superior working memory and inferior reference memory on the water radial-arm maze. Physiol Behav 2000 August; 70(3-4):311-7.

Bracken, M. B., Shepard, M. J., Collins, W. F., Holford, T. R., Young, W., Baskin, D. S., Eisenberg, H. M., Flamm, E., Leo-Summers, L., Maroon, J. et al 1990. A randomized, controlled trial of methylprednisolone or naloxone in the treatment of acute spinal-cord injury. Results of the Second National Acute Spinal Cord Injury Study. N. Engl. J. Med. 322:1405-1411.

Bramlett, H. M., Dietrich W D. Progressive damage after brain and spinal cord injury: pathomechanisms and treatment strategies. Prog Brain Res 2007; 161:125-41.

Brewin, C R., A cognitive neuroscience account of post-traumatic stress disorder and its treatment. Behav Res Ther 2001 April; 39(4):373-93.

Bullock, R., Zauner A, Myseros J S, Marmarou A, Woodward J J, Young H F. Evidence for prolonged release of excitatory amino acids in severe human head trauma. Relationship to clinical events. Ann N Y Acad Sci 1995 Sep. 15; 765:290-7.

Carty, J., O'Donnell M L, Creamer M. Delayed-onset PTSD: a prospective study of injury survivors. J Affect Disord 2006 February; 90(2-3):257-61.

Cernak, I., Animal models of head trauma. NeuroRx 2005 July; 2(3):410-22.

Chan, T. K., Chan, V., Teng, C. S., and Yeung, R. T. 1982. Effects of gliclazide and glibenclamide on platelet function, fibrinolysis and metabolic control in diabetic patients with retinopathy. Sem. Hop. 58:1197-1200.

Chang, Y C, Huang C C 2006 Perinatal brain injury and regulation of transcription. Cur Opin Neurol 19:141-147

Chen, M., Simard J M. Cell swelling and a nonselective cation channel regulated by internal Ca2+ and ATP in native reactive astrocytes from adult rat brain. J Neurosci 2001 Sep. 1; 21(17):6512-21.

Chen, M., Dong Y, Simard J M. Functional coupling between sulfonylurea receptor type 1 and a nonselective cation channel in reactive astrocytes from adult rat brain. J Neurosci 2003 Sep. 17; 23(24):8568-77.

Choudhri, T F, Hoh, B. L., Solomon, R. A., Connolly, E. S, Jr., and Pinsky, D. J. Use of a spectrophotometric hemoglobin assay to objectively quantify intracerebral hemorrhage in mice. Stroke 1997 November; 28(11):2296-302.

Cohen H, Zohar J, Matar M A, Zeev K, Loewenthal U, Richter-Levin G. Setting apart the affected: the use of behavioral criteria in animal models of post traumatic stress disorder. Neuropsychopharmacology 2004 November; 29(11):1962-70.

Colak, A., Soy, O., Uzun, H., Aslan, O., Barut, S., Belce, A., Akyildiz, A., and Tasyurekli, M. 2003. Neuroprotective effects of GYKI 52466 on experimental spinal cord injury in rats. J. Neurosurg. 98:275-281.

Cools, F., Offringa M 2005 Neuromuscular paralysis for newborn infants receiving mechanical ventilation. Cochrane Database Syst Rev CD002773

Cortez, S C, McIntosh T K, Noble L J. Experimental fluid percussion brain injury: vascular disruption and neuronal and glial alterations. Brain Res 1989 Mar. 20; 482(2):271-82

DeFord, S M, Wilson M S, Gibson C J, Baranova A, Hamm R J. Nefiracetam improves Morris water maze performance following traumatic brain injury in rats. Pharmacol Biochem Behav 2001 July; 69(3-4):611-6.

Dietrich, W D, Alonso O, Halley M. Early microvascular and neuronal consequences of traumatic brain injury: a light and electron microscopic study in rats. J Neurotrauma 1994 June; 11(3):289-301.

Dixon, C E, Lyeth B G, Povlishock J T et al. A fluid percussion model of experimental brain injury in the rat. J Neurosurg 1987 July; 67(1):110-9.

Dixon, C E., Kochanek P M, Yan H Q et al. One-year study of spatial memory performance, brain morphology, and cholinergic markers after moderate controlled cortical impact in rats. J Neurotrauma 1999 February; 16(2):109-22.

Faden, A. I., Lemke, M., Simon, R. P., and Noble, L. J. 1988. N-methyl-D-aspartate antagonist MK801 improves outcome following traumatic spinal cord injury in rats: behavioral, anatomic, and neurochemical studies. J. Neurotrauma 5:33-45.

Fitch, M. T., Doller, C., Combs, C. K., Landreth, G. E., and Silver, J. 1999. Cellular and molecular mechanisms of glial scarring and progressive cavitation: in vivo and in vitro analysis of inflammation-induced secondary injury after CNS trauma. J. Neurosci. 19:8182-8198.

Floyd, C L, Golden K M, Black R T, Hamm R J, Lyeth B G. Craniectomy position affects morns water maze performance and hippocampal cell loss after parasagittal fluid percussion. J Neurotrauma 2002 March; 19(3):303-16.

Folkerth, R D., Neuropathologic substrate of cerebral palsy. J Child Neurol 2005 December; 20(12):940-9.

Fujimoto S T, Longhi L, Saatman K E, Conte V, Stocchetti N, McIntosh T K. Motor and cognitive function evaluation following experimental traumatic brain injury. Neurosci Biobehav Rev 2004 July; 28(4):365-78.

Galderisi, U., Cascino, A., and Giordano, A. 1999. Antisense oligonucleotides as therapeutic agents. J. Cell Physiol 181:251-257.

Garrick, T., Morrow N, Shalev A Y, Eth S. Stress-induced enhancement of auditory startle: an animal model of posttraumatic stress disorder. Psychiatry 2001; 64(4):346-54.

Garrick, T., Morrow N, Eth S, Marciano D, Shalev A. Psychophysiologic parameters of traumatic stress disorder in rats. Ann N Y Acad Sci 1997 Jun. 21; 821:533-7.

Gedeon, C., Koren G. Designing Pregnancy Centered Medications: Drugs Which Do Not Cross the Human Placenta. Placenta 2005 Nov. 25.

Gensel, J. C., Tovar, C. A., Hamers, F. P., Deibert, R. J., Beattie, M. S., and Bresnahan, J. C. 2006. Behavioral and histological characterization of unilateral cervical spinal cord contusion injury in rats. J. Neurotrauma 23:36-54.

Gerzanich, V., Ivanov, A., Ivanova, S., Yang, J. B., Zhou, H., Dong, Y., and Simard, J. M. 2003. Alternative splicing of cGMP-dependent protein kinase I in angiotensin-hypertension: novel mechanism for nitrate tolerance in vascular smooth muscle. Circ. Res. 93:805-812.

Ghazi-Birry, H S, Brown W R, Moody D M, Challa V R, Block S M, Reboussin D M. Human germinal matrix: venous origin of hemorrhage and vascular characteristics. AJNR Am J Neuroradiol 1997 February; 18(2):219-29.

Gidday, J. M., Gasche, Y. G., Copin, J. C., Shah, A. R., Perez, R. S., Shapiro, S. D., Chan, P. H., and Park, T. S. 2005. Leukocyte-derived matrix metalloproteinase-9 mediates blood-brain barrier breakdown and is proinflammatory after transient focal cerebral ischemia. Am. J. Physiol Heart Circ. Physiol 289:H558-H568.

Grady M S, Charleston J S, Maris D, Witgen B M, Lifshitz J. Neuronal and glial cell number in the hippocampus after experimental traumatic brain injury: analysis by stereological estimation. J Neurotrauma 2003 October; 20(10):929-41.

Gresack, J E, Frick K M. Male mice exhibit better spatial working and reference memory than females in a water-escape radial arm maze task. Brain Res 2003 Aug. 22; 982(1): 98-107.

Griffiths, I. R., Burns, N., and Crawford, A. R. 1978. Early vascular changes in the spinal grey matter following impact injury. Acta Neuropathol. (Berl) 41:33-39.

Hainsworth, A H, Spadoni F, Lavaroni F, Bernardi G, Stefani A. Effects of extracellular pH on the interaction of sipatrigine and lamotrigine with high-voltage-activated (HVA) calcium channels in dissociated neurones of rat cortex. Neuropharmacology 2001 May; 40(6):784-91.

Hamm, R J, Pike B R, O'Dell D M, Lyeth B G, Jenkins L W. The rotarod test: an evaluation of its effectiveness in assessing motor deficits following traumatic brain injury. J Neurotrauma 1994 April; 11(2):187-96.

Hamm, R J, Lyeth B G, Jenkins L W, O'Dell D M, Pike B R. Selective cognitive impairment following traumatic brain injury in rats. Behav Brain Res 1993 Dec. 31; 59(1-2):169-73.

Hansen, A. M., Christensen, I. T., Hansen, J. B., Carr, R. D., Ashcroft, F. M., and Wahl, P. 2002. Differential interactions of nateglinide and repaglinide on the human beta-cell sulphonylurea receptor 1. Diabetes 51:2789-2795.

Harder, D R, Gebremedhin D, Narayanan J et al. Formation and action of a P-450 4A metabolite of arachidonic acid in cat cerebral microvessels. Am J Physiol 1994 May; 266(5 Pt 2):H2098-H2107.

Harvey, A G, Brewin C R, Jones C, Kopelman M D. Coexistence of posttraumatic stress disorder and traumatic brain injury: towards a resolution of the paradox. J Int Neuropsychol Soc 2003 May; 9(4):663-76.

Haseloff, R. F., Krause, E., Bigl, M., Mikoteit, K., Stanimirovic, D., and Blasig, I. E. 2006. Differential protein expression in brain capillary endothelial cells induced by hypoxia and posthypoxic reoxygenation. Proteomics. 6:1803-1809.

Hayes, K. C., and Kakulas, B. A. 1997. Neuropathology of human spinal cord injury sustained in sports-related activities. J. Neurotrauma 14:235-248.

Hellmich H L, Capra B, Eidson K et al. Dose-dependent neuronal injury after traumatic brain injury. Brain Res 2005 May 24; 1044(2):144-54.

Jansen-Olesen, I., Mortensen, C. H., El-Bariaki, N., and Ploug, K. B. 2005. Characterization of K(ATP)-channels in rat basilar and middle cerebral arteries: studies of vasomotor responses and mRNA expression. Eur. J. Pharmacol. 523: 109-118.

Justicia, C., Panes J, Sole S et al. Neutrophil infiltration increases matrix metalloproteinase-9 in the ischemic brain after occlusion/reperfusion of the middle cerebral artery in rats. J Cereb Blood Flow Metab 2003 December; 23(12): 1430-40.

Kadri, H., Mawla A A, Kazah J. The incidence, timing, and predisposing factors of germinal matrix and intraventricular hemorrhage (GMH/IVH) in preterm neonates. Childs Nerv Syst 2006 September; 22(9):1086-90.

Kapadia, S. E., 1984. Ultrastructural alterations in blood vessels of the white matter after experimental spinal cord trauma. J. Neurosurg. 61:539-544.

Kawata, K., Morimoto, T., Ohashi, T., Tsujimoto, S., Hoshida, T., Tsunoda, S., and Sakaki, T 1993. Experimental study of acute spinal cord injury: a histopathological study. No Shinkei Geka 21:45-51.

Kline A E, Massucci J L, Marion D W, Dixon C E. Attenuation of working memory and spatial acquisition deficits after a delayed and chronic bromocriptine treatment regimen in rats subjected to traumatic brain injury by controlled cortical impact. J Neurotrauma 2002 April; 19(4):415-25.

Kraus, K. H., 1996. The pathophysiology of spinal cord injury and its clinical implications. Semin. Vet. Med. Surg. (Small Anim) 11:201-207.

Kunte, H., Schmidt S, Eliasziw Mdel Zoppo G J, Simard J M, Masuhr F, Weih M, Dirnagl U Sulfonylureas improve outcome in patients with type 2 diabetes and acute ischemic stroke. Stroke 2007 September; 38(9):2526-30.

Kwon, B. K., Tetzlaff, W., Grauer, J. N., Beiner, J., and Vaccaro, A. R. 2004. Pathophysiology and pharmacologic treatment of acute spinal cord injury. Spine J. 4:451-464.

LaBuda, C J, Mellgren R L, Hale R L. Sex differences in the acquisition of a radial maze task in the CD-1 mouse. Physiol Behav 2002 Jun. 1; 76(2):213-7.

Langlois, J A, Rutland-Brown W, Wald M M. The epidemiology and impact of traumatic brain injury: a brief overview. J Head Trauma Rehabil 2006 September; 21(5):375-8.

Levy, M L, Masri L S, McComb J G. Outcome for preterm infants with germinal matrix hemorrhage and progressive hydrocephalus. Neurosurgery 1997 November; 41(5):1111-7.

Lorenzl, S., De P G, Segal A Z, Beal M F. Dysregulation of the levels of matrix metalloproteinases and tissue inhibitors of matrix metalloproteinases in the early phase of cerebral ischemia. Stroke 2003 June; 34(6):e37-e38.

Lorrain, J., Millet, L., Lechaire, I., Lochot, S., Ferrari, P., Visconte, C., Sainte-Marie, M., Lunven, C., Berry, C. N., Schaeffer, P. et al 2003. Antithrombotic properties of SSR182289A, a new, orally active thrombin inhibitor. J. Pharmacol. Exp. Ther. 304:567-574.

Lou, H C., On the pathogenesis of germinal layer hemorrhage in the neonate. APMIS Suppl 1993; 40:97-102.

Lu, J., Moochhala S, Shirhan M et al. Neuroprotection by aminoguanidine after lateral fluid-percussive brain injury in rats: a combined magnetic resonance imaging, histopathologic and functional study. Neuropharmacology 2003 February; 44(2):253-63.

Manion, ST, Gamble E H, Li H. Prazosin administered prior to inescapable stressor blocks subsequent exaggeration of acoustic startle response in rats. Pharmacol Biochem Behav 2007 March; 86(3):559-65.

Marmarou, A. A review of progress in understanding the pathophysiology and treatment of brain edema. Neurosurg Focus 2007; 22(5):E1.

Merola, A., O'Brien, M. F., Castro, B. A., Smith, D. A., Eule, J. M., Lowe, T. G., Dwyer, A. P., Haher, T. R., and Espat, N. J. 2002. Histologic characterization of acute spinal cord injury treated with intravenous methylprednisolone. J. Orthop. Trauma 16:155-161.

Nakai, A., Shibazaki Y, Taniuchi Y, Oya A, Asakura H, Kuroda S, Koshino T, Araki T. Influence of mild hypothermia on delayed mitochondrial dysfunction after transient intrauterine ischemia in the immature rat brain. Brain Res Dev Brain Res 2001 May 31; 128(1):1-7.

Nakamura, Y., Okudera T, Fukuda S, Hashimoto T. Germinal matrix hemorrhage of venous origin in preterm neonates. Hum Pathol 1990 October; 21(10):1059-62.

Nakamura, Y., Okudera T, Hashimoto T 1994 Vascular architecture in white matter of neonates: its relationship to periventricular leukomalacia. J Neuropathol Exp Neurol 53:582-589

Nedergaard, M., Kraig R P, Tanabe J, Pulsinelli W A. Dynamics of interstitial and intracellular pH in evolving brain infarct. Am J Physiol 1991 March; 260(3 Pt 2):R581-R588.

Nelson, D. A., Bryan, J., Wechsler, S., Clement, J. P., and guilar-Bryan,L. 1996. The high-affinity sulfonylurea receptor: distribution, glycosylation, purification, and immunoprecipitation of two forms from endocrine and neuroendocrine cell lines. Biochemistry 35:14793-14799.

Nelson, E., Gertz, S. D., Rennels, M. L., Ducker, T. B., and Blaumanis, O. R. 1977. Spinal cord injury. The role of vascular damage in the pathogenesis of central hemorrhagic necrosis. Arch. Neurol. 34:332-333.

Nikulina, E., Tidwell, J. L., Dai, H. N., Bregman, B. S., and Filbin, M. T. 2004. The phosphodiesterase inhibitor rolipram delivered after a spinal cord lesion promotes axonal regeneration and functional recovery. Proc. Natl. Acad. Sci. U.S.A 101:8786-8790.

Noble, L. J., Donovan, F., Igarashi, T., Goussev, S., and Werb, Z. 2002. Matrix metalloproteinases limit functional recovery after spinal cord injury by modulation of early vascular events. J. Neurosci. 22:7526-7535.

Obenaus, A., Robbins M, Blanco G et al. Multi-modal magnetic resonance imaging alterations in two rat models of mild neurotrauma. J Neurotrauma 2007 July; 24(7):1147-60.

O'Connor, C., Heath D L, Cernak I, Nimmo A J, Vink R. Effects of daily versus weekly testing and pre-training on the assessment of neurologic impairment following diffuse traumatic brain injury in rats. J Neurotrauma 2003 October; 20(10):985-93.

Oertel, M., Kelly D F, McArthur D, Boscardin, W. J., Glenn, T. C., Lee, J. H., Gravori, T., Obukhov, D., McBride, D. Q., and Martin, N. A. Progressive hemorrhage after head trauma: predictors and consequences of the evolving injury. J Neurosurg 2002 January; 96(1):109-16.

Pannu, R., Christie, D. K., Barbosa, E., Singh, I., and Singh, A. K. 2007. Post-trauma Lipitor treatment prevents endothelial dysfunction, facilitates neuroprotection, and promotes locomotor recovery following spinal cord injury. J. Neurochem.

Park S, Yamaguchi M, Zhou C, Calvert J W, Tang J, Zhang J H. Neurovascular protection reduces early brain injury after subarachnoid hemorrhage. Stroke 2004; 35:2412-7.

Partridge, C. J., Beech, D. J., and Sivaprasadarao, A. 2001. Identification and pharmacological correction of a membrane trafficking defect associated with a mutation in the sulfonylurea receptor causing familial hyperinsulinism. J. Biol. Chem. 276:35947-35952.

Perillan, P R, Chen M, Potts E A, Simard J M. Transforming growth factor-beta 1 regulates Kir2.3 inward rectifier K+ channels via phospholipase C and protein kinase C-delta in reactive astrocytes from adult rat brain. J Biol Chem 2002 Jan. 18; 277(3):1974-80.

Perillan, P R, Li X, Simard J M. K(+) inward rectifier currents in reactive astrocytes from adult rat brain. Glia 1999 September; 27(3):213-25.

Perillan, P R, Li X, Potts E A, Chen M, Bredt D S, Simard J M. Inward rectifier K(+) channel Kir2.3 (IRK3) in reactive astrocytes from adult rat brain. Glia 2000 August; 31(2):181-92.

Pfefferkorn, T., Rosenberg G A. Closure of the blood-brain barrier by matrix metalloproteinase inhibition reduces rtPA-mediated mortality in cerebral ischemia with delayed reperfusion. Stroke 2003 August; 34(8):2025-30.

Pikus, H J, Levy M L, Gans W, Mendel E, McComb J G. Outcome, cost analysis, and long-term follow-up in preterm infants with massive grade IV germinal matrix hemorrhage and progressive hydrocephalus. Neurosurgery 1997 May; 40(5):983-8.

Pourie, G., Blaise S, Trabalon M, Nedelec E, Gueant J L, Daval J L 2006 Mild, non-lesioning transient hypoxia in the newborn rat induces delayed brain neurogenesis associated with improved memory scores. Neuroscience 140:1369-1379

Raghupathi, R., Cell death mechanisms following traumatic brain injury. Brain Pathol 2004 April; 14(2):215-22.

Rasmussen, D D, Crites N J, Burke B L. Acoustic startle amplitude predicts vulnerability to develop post-traumatic stress hyper-responsivity and associated plasma corticosterone changes in rats. Psychoneuroendocrinology 2008 April; 33(3):282-91.

Regan, R F, Guo Y. Toxic effect of hemoglobin on spinal cord neurons in culture. J Neurotrauma 1998 August; 15(8): 645-53.

Rivlin, A. S., and Tator, C. H. 1977. Objective clinical assessment of motor function after experimental spinal cord injury in the rat. J. Neurosurg. 47:577-581.

Romanic, A M, White R F, Arleth A J, Ohlstein E H, Barone F C. Matrix metalloproteinase expression increases after cerebral focal ischemia in rats: inhibition of matrix metalloproteinase-9 reduces infarct size. Stroke 1998 May; 29(5): 1020-30.

Sanders, M J, Dietrich W D, Green E J. Cognitive function following traumatic brain injury: effects of injury severity and recovery period in a parasagittal fluid-percussive injury model. J Neurotrauma 1999 October; 16(10):915-25.

Sayer, N A, SChiros C E, Sigford B et al. Characteristics and rehabilitation outcomes among patients with blast and other injuries sustained during the Global War on Terror. Arch Phys Med Rehabil 2008 January; 89(1):163-70.

Schallert, T., Fleming S M, Leasure J L, Tillerson J L, Bland S T. CNS plasticity and assessment of forelimb sensorimotor outcome in unilateral rat models of stroke, cortical ablation, parkinsonism and spinal cord injury. Neuropharmacology 2000 Mar. 3; 39(5):777-87.

Schmidt, R H, Grady M S. Regional patterns of blood-brain barrier breakdown following central and lateral fluid percussion injury in rodents. J Neurotrauma 1993; 10(4):415-30.

Schnittler, H J, Schmandra T, Drenckhahn D. Correlation of endothelial vimentin content with hemodynamic parameters. Histochem Cell Biol 1998 August; 110(2):161-7.

Schwartz, G., and Fehlings, M. G. 2001. Evaluation of the neuroprotective effects of sodium channel blockers after spinal cord injury: improved behavioral and neuroanatomical recovery with riluzole. J. Neurosurg. 94:245-256.

Seidel, M F, Simard J M, Hunter S F, Campbell G A. Isolation of arteriolar microvessels and culture of smooth muscle cells from cerebral cortex of guinea pig. Cell Tissue Res 1991 September; 265(3):579-87.

Seino, S., 1999. ATP-sensitive potassium channels: a model of heteromultimeric potassium channel/receptor assemblies. Annu. Rev. Physiol 61:337-362.

Sharma, N., Crane, A., Clement, J. P., Gonzalez, G., Babenko, A. P., Bryan, J., and guilar-Bryan, L. 1999. The C terminus of SUR1 is required for trafficking of KATP channels. J. Biol. Chem. 274:20628-20632.

Simard, J M, Chen M, Tarasov K V, Bhatta, S., Ivanova, S., MeInitchenko, L., Tsymbalyuk, N., West, G. A., and Gerzanich, V. 2006. Newly expressed SUR1-regulated NC(Ca-ATP) channel mediates cerebral edema after ischemic stroke. Nat Med 2006 April; 12(4):433-40.

Simard, J M, Kent T A, Chen M, Tarasov K V, Gerzanich V. Brain oedema in focal ischaemia: molecular pathophysiology and theoretical implications. Lancet Neurol 2007 March; 6(3):258-68.

Simard, J M, Woo S K, Bhatta S, Gerzanich V. Drugs acting on SUR1 to treat CNS ischemia and trauma. Cur Opin Pharmacol 2008; 8(1):42-9.

Simard, J M, Tsymbalyuk O, Ivanov A, Ivanova S, Bhatta S, Geng Z, Woo S K, Gerzanich V. Endothelial sulfonylurea receptor 1-regulated NC Ca-ATP channels mediate progressive hemorrhagic necrosis following spinal cord injury. J Clin Invest 2007 August; 117(8):2105-13.

Simard, J M, Tarasov K V, Gerzanich V. Non-selective cation channels, transient receptor potential channels and ischemic stroke. Biochim Biophys Acta 2007 August; 1772 (8):947-57.

Simard, J M, Woo S K, Bhatta S, Gerzanich V. Drugs acting on SUR1 to treat CNS ischemic and trauma. Cur Opin Pharmacol 2007.

Soblosky, J. S., Song, J. H., and Dinh, D. H. 2001. Graded unilateral cervical spinal cord injury in the rat: evaluation of forelimb recovery and histological effects. Behav. Brain Res. 119:1-13.

Stephan, D., Winkler, M., Kuhner, P., Russ, U., and Quast, U. 2006. Selectivity of repaglinide and glibenclamide for the pancreatic over the cardiovascular K(ATP) channels. Diabetologia 49:2039-2048.

Suh, S W, Chen J W, Motamedi M et al. Evidence that synaptically-released zinc contributes to neuronal injury after traumatic brain injury. Brain Res 2000 Jan. 10; 852(2):268-73.

Sullivan, H C, Harik S I. ATP-sensitive potassium channels are not expressed in brain microvessels. Brain Res 1993; 612:336-8.

Sumii, T., and Lo, E. H. 2002. Involvement of matrix metalloproteinase in thrombolysis-associated hemorrhagic transformation after embolic focal ischemia in rats. Stroke 33:831-836.

Sun, H. S., Feng, Z. P., Barber, P. A., Buchan, A. M., and French, R. J. 2007. Kir6.2-containing ATP-sensitive potassium channels protect cortical neurons from ischemic/anoxic injury in vitro and in vivo. Neuroscience 144:1509-1515.

Tanaka, M., Natori M, Ishimoto H, Miyazaki T, Kobayashi T, Nozawa S. Experimental growth retardation produced by transient period of uteroplacental ischemia in pregnant Sprague-Dawley rats. Am J Obstet Gynecol 1994 November; 171 (5):1231-4.

Tator, C. H., 1991. Review of experimental spinal cord injury with emphasis on the local and systemic circulatory effects. Neurochirurgie 37:291-302.

Tator, C. H., 1995. Update on the pathophysiology and pathology of acute spinal cord injury. Brain Pathol. 5:407-413.

Tator, C. H., and Fehlings, M. G. 1991. Review of the secondary injury theory of acute spinal cord trauma with emphasis on vascular mechanisms. J. Neurosurg. 75:15-26.

Tator, C. H., and Koyanagi, T. 1997. Vascular mechanisms in the pathophysiology of human spinal cord injury. J. Neurosurg. 86:483-492.

Teng, Y. D., Choi, H., Onario, R. C., Zhu, S., Desilets, F. C., Lan, S., Woodard, E. J., Snyder, E. Y., Eichler, M. E., and Friedlander, R. M. 2004. Minocycline inhibits contusion-triggered mitochondrial cytochrome c release and mitigates functional deficits after spinal cord injury. Proc. Natl. Acad. Sci. U.S. A 101:3071-3076.

Thebaud, B., 2007 Angiogenesis in lung development, injury and repair: implications for chronic lung disease of prematurity. Neonatology 91:291-297

Thompson, H J, Lifshitz J, Marklund N et al. Lateral fluid percussion brain injury: a 15-year review and evaluation. J Neurotrauma 2005 January; 22(1):42-75.

Thompson, H J, LeBold D G, Marklund N, Morales D M, Hagner A P, McIntosh T K. Cognitive evaluation of traumatically brain-injured rats using serial testing in the Morris water maze. Restor Neurol Neurosci 2006; 24(2):109-14.

Thurman, D J, Alverson C, Dunn K A, Guerrero J, Sniezek J E. Traumatic brain injury in the United States: A public health perspective. J Head Trauma Rehabil 1999 December; 14(6):602-15.

Unterberg, A W, Stover J, Kress B, Kiening K L. Edema and brain trauma. Neuroscience 2004; 129(4):1021-9.

Smith, J S, Chang E F, Rosenthal G et al. The role of early follow-up computed tomography imaging in the management of traumatic brain injury patients with intracranial hemorrhage. J Trauma 2007 July; 63(1):75-82.

Vajtr, D., Benada O, Kukacka J et al. Correlation of ultrastructural changes of endothelial cells and astrocytes occurring during blood brain barrier damage after traumatic brain injury with biochemical markers of BBB leakage and inflammatory response. Physiol Res 2008 Apr. 1.

Vergani, P., Locatelli A, Doria V, Assi F, Paterlini G, Pezzullo J C, Ghidini A. Intraventricular hemorrhage and periventricular leukomalacia in preterm infants. Obstet Gynecol 2004 August; 104(2):225-31.

Vilalta, A., Sahuquillo J, Rosell A, Poca M A, Riveiro M, Montaner J. Moderate and severe traumatic brain injury induce early overexpression of systemic and brain gelatinases. Intensive Care Med 2008 Mar. 19.

Vink, R., Mullins P G, Temple M D, Bao W, Faden A I. Small shifts in craniotomy position in the lateral fluid percussion injury model are associated with differential lesion development. J Neurotrauma 2001 August; 18(8):839-47.

Wang, X., Mori T, Sumii T, Lo E H. Hemoglobin-induced cytotoxicity in rat cerebral cortical neurons: caspase activation and oxidative stress. Stroke 2002 July; 33(7):1882-8.

Wang, X., Tsuji, K., Lee, S. R., Ning, M., Furie, K. L., Buchan, A. M., and Lo, E. H. 2004. Mechanisms of hemorrhagic transformation after tissue plasminogen activator reperfusion therapy for ischemic stroke. Stroke 35:2726-2730.

Warden, D., Military TBI during the Iraq and Afghanistan wars. J Head Trauma Rehabil 2006 September; 21(5):398-402.

Wei, W., Xin-Ya S, Cai-Dong L, Zhong-Han K, Chun-Peng C. Relationship between extracellular matrix both in choroid plexus and the wall of lateral ventricles and intraventricular hemorrhage in preterm neonates. Clin Anat 2000; 13(6):422-8.

Wenger, R H, Stiehl D P, Camenisch G 2005 Integration of oxygen signaling at the consensus HRE. Sci STKE 2005:re12

Wiley, J L, Compton A D, Pike B R, Temple M D, McElderry J W, Hamm R J. Reduced sensorimotor reactivity following traumatic brain injury in rats. Brain Res 1996 Apr. 15; 716(1-2):47-52.

Wright, L L, Horbar J D, Gunkel H, Verter J, Younes N, Andrews E B, Long W 1995 Evidence from multicenter networks on the current use and effectiveness of antenatal corticosteroids in low birth weight infants. Am J Obstet Gynecol 173:263-269

Xi, G., Keep R F, Hoff J T. Mechanisms of brain injury after intracerebral haemorrhage. Lancet Neurol 2006 January; 5(1):53-63.

Xi, G., Hua Y, Bhasin R R, Ennis S R, Keep R F, Hoff J T. Mechanisms of edema formation after intracerebral hemorrhage: effects of extravasated red blood cells on blood flow and blood-brain barrier integrity. Stroke 2001 Dec. 1; 32(12):2932-8.

Xia, Y., Eisenman D, Haddad G G. Sulfonylurea receptor expression in rat brain: effect of chronic hypoxia during development. Pediatr Res 1993 November; 34(5):634-41.

Yamashita, S., Park, J. B., Ryu, P. D., Inukai, H., Tanifuji, M., and Murase, K. 1994. Possible presence of the ATP-sensitive K+ channel in isolated spinal dorsal horn neurons of the rat. Neurosci. Lett. 170:208-212.

Yan, F F, Lin C W, Cartier E A, Shyng S L. Role of ubiquitin-proteasome degradation pathway in biogenesis efficiency of β-cell ATP-sensitive potassium channels. Am J Physiol Cell Physiol 2005; 289:C1351-C1359.

Yokoshiki, H., Sunagawa, M., Seki, T., and Sperelakis, N. 1999. Antisense oligodeoxynucleotides of sulfonylurea receptors inhibit ATP-sensitive K+ channels in cultured neonatal rat ventricular cells. Pflugers Arch. 437:400-408.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating intraventricular hemorrhage in the brain of an infant, comprising administering an effective amount of an inhibitor of $NC_{ca-ATp}$ channel to the infant following birth and the mother prior to birth, wherein the inhibitor is a sulfonylurea compound or a benzamido derivative, wherein the infant has been exposed to a global hypoxic/ischemic event.

* * * * *